(12) United States Patent
Li et al.

(10) Patent No.: US 11,970,537 B2
(45) Date of Patent: Apr. 30, 2024

(54) FUSION PROTEIN DIMER USING ANTIBODY FC REGION AS BACKBONE AND USE THEREOF

(71) Applicant: Nanjing GenScript Biotech Co., Ltd., Jiangsu (CN)

(72) Inventors: Zhongdao Li, Jiangsu (CN); Lixin Song, Jiangsu (CN); Wang Zhang, Jiangsu (CN); Yafeng Zhang, Jiangsu (CN); Dongliang Wang, Jiangsu (CN); Zhenyu Liu, Jiangsu (CN); Fangliang Zhang, Jiangsu (CN)

(73) Assignee: Nanjing GenScript Biotech Co., Ltd., Jiangsu (CN)

( * ) Notice: Subject to any disclaimer, the term of this patent is extended or adjusted under 35 U.S.C. 154(b) by 783 days.

(21) Appl. No.: 16/958,079

(22) PCT Filed: Dec. 26, 2018

(86) PCT No.: PCT/CN2018/123878
§ 371 (c)(1),
(2) Date: Jun. 25, 2020

(87) PCT Pub. No.: WO2019/129053
PCT Pub. Date: Jul. 4, 2019

(65) Prior Publication Data
US 2020/0317787 A1 Oct. 8, 2020

(30) Foreign Application Priority Data
Dec. 26, 2017 (CN) .......................... 201711431542.4

(51) Int. Cl.
| | | |
|---|---|---|
| C07K 16/28 | (2006.01) | |
| A61K 39/395 | (2006.01) | |
| A61P 35/00 | (2006.01) | |
| C07K 14/54 | (2006.01) | |

(52) U.S. Cl.
CPC ...... C07K 16/2818 (2013.01); C07K 14/5434 (2013.01); C07K 16/2827 (2013.01); C07K 2317/569 (2013.01); C07K 2319/30 (2013.01)

(58) Field of Classification Search
None
See application file for complete search history.

(56) References Cited

U.S. PATENT DOCUMENTS

| | | | | |
|---|---|---|---|---|
| 2002/0102264 A1* | 8/2002 | Cheung | ................ | C07K 16/18 530/389.1 |
| 2002/0122807 A1* | 9/2002 | Dan | ................ | C07K 16/4266 435/6.16 |
| 2002/0146750 A1* | 10/2002 | Hoogenboom | .... | A61K 47/6843 424/155.1 |
| 2003/0166163 A1* | 9/2003 | Gillies | ................ | A61P 35/00 435/325 |
| 2005/0137384 A1* | 6/2005 | Gillies | ................ | A61P 37/04 530/391.1 |
| 2007/0003514 A1* | 1/2007 | Penichet | ................ | A61K 38/208 530/391.1 |
| 2012/0201746 A1* | 8/2012 | Liu | ................ | A61P 7/00 424/1.11 |
| 2014/0249296 A1* | 9/2014 | Ploegh | ................ | C12N 9/52 435/68.1 |
| 2016/0152730 A1* | 6/2016 | Tavernier | ................ | A61P 35/00 530/351 |
| 2017/0327597 A1* | 11/2017 | Labrijn | ................ | C07K 16/00 |
| 2018/0291103 A1* | 10/2018 | Xu | ................ | A61K 39/39558 |
| 2019/0023795 A1* | 1/2019 | Tveita | ................ | C07K 16/2896 |
| 2019/0194284 A1* | 6/2019 | Kley | ................ | C12N 15/62 |
| 2019/0314455 A1* | 10/2019 | Ptacin | ................ | A61K 47/644 |
| 2019/0315864 A1* | 10/2019 | Xu | ................ | A61P 13/10 |
| 2020/0190193 A1* | 6/2020 | Pandit | ................ | C07K 16/28 |
| 2021/0002343 A1* | 1/2021 | Karow | ................ | C07K 14/54 |

FOREIGN PATENT DOCUMENTS

WO  WO 2017/165464 A1  9/2017

OTHER PUBLICATIONS

Topalian et al. (2015) Cancer Cell 27: 450-461.*
Rhodes et al. (2016) Annu. Rev. Immunol. 34: 151-172.*
Pardoll DM, "The blockade of immune checkpoints in cancer immunotherapy," *Nat Rev Cancer*, 2012, 12:252-64.
Nirschl CJ, Drake CG., "Molecular Pathways: Co-Expression of Immune Checkpoint Molecules: Signaling Pathways and Implications for Cancer Immunotherapy," *Clin Cancer Res*, 2013 19(18), 4917-24.
Zheng X et al., "The use of supercytokines, immunocytokines, engager cytokines, and other synthetic cytokines in immunotherapy." *Cell Mol Immunol.*, Feb. 2022;19(2):192-209.

* cited by examiner

*Primary Examiner* — Ilia I Ouspenski
(74) *Attorney, Agent, or Firm* — Klarquist Sparkman, LLP

(57) ABSTRACT

Provided is a fusion protein dimer using an antibody Fc region as the backbone, comprising a first and a second polypeptide chain. The first polypeptide chain comprises a first antibody Fc region and one or more single-domain antibodies fused to the first antibody Fc region. The second polypeptide chain comprises a second antibody Fc region and one or more single domain antibodies fused to the second antibody Fc region. The first polypeptide chain and/or the second polypeptide chain further comprise a cytokine fused to the Fc region of the respective antibody. Further provided is use of the fusion protein dimer in preparing an immunotherapeutic drug for treating tumors. The Fc fusion protein heterodimer not only increases the activity of a single domain antibody, but also significantly improves the biological activity of a cytokine. Further, by means of the targeting specificity of the antibody, the targeted transport of the cytokine is effectively enhanced, and cytotoxicity is attenuated, thereby obtaining better anti-tumor potential.

17 Claims, 12 Drawing Sheets

Specification includes a Sequence Listing.

FUSION PROTEIN DIMER USING ANTIBODY FC REGION AS BACKBONE AND USE THEREOF

CROSS REFERENCE TO RELATED APPLICATIONS

This is the U.S. National Stage of International Application No. PCT/CN2018/123878, filed Dec. 26, 2018, which was published in Chinese under PCT Article 21(2), which in turn claims the benefit of Chinese Patent Application No. 201711431542.4, filed Dec. 26, 2017.

INCORPORATION OF ELECTRONIC SEQUENCE LISTING

The electronic sequence listing, submitted herewith as an ASCI txt file named sequence listing.txt (240,040 bytes), created on Apr. 18, 2023, is herein incorporated by reference in its entirety.

TECHNICAL FIELD

The present invention relates to a fusion protein, and in particular to a fusion protein dimer based on an antibody Fc region.

BACKGROUND

An immune system is a set of defense system in mammals, which can resist invasion of various pathogens and eliminate tumors. An antibody molecule plays a very important role in the immune system, such as recognizing a tumor antigen and activating immune response. At the same time, a cytokine, as an immunoregulatory factor, can regulate both innate immunity and adaptive immunity, and is also of great importance in cancer immunotherapy [1-3]. Such a regulatory factor participates in almost every link of the immune system, and plays a powerful role in regulating and balancing the immune system. Interferon and IL-2 are first selected as cytokines for application in the immunotherapy. IFN-α is used for treating various cancers, such as melanoma, a kidney cancer, follicular lymphoma, and chronic myeloid leukemia. While IL-2 was approved by FDA for the treatment of advanced metastatic melanoma and metastatic kidney cancer in 1998. Other cytokines, such as IL-7, IL-10, IL-12, IL-15 and IL-21, etc., are also in the clinical testing stage [4]. Therefore, the cytokine has a certain potential for immunotherapy [5, 6].

However, cytokine-based immunotherapy is severely hindered in clinical application, mainly due to serious side effects and underperformed pharmacokinetic properties [5]. Therefore, in order to improve the therapeutic effect of the cytokine, it is often necessary to modify the cytokine. At present, the more commonly used method is adopting an antibody fusion method for targeted delivery of a cytokine to a specific site through an antibody, thereby effectively reducing cytotoxicity, improving the pharmacokinetic properties and in turn enhancing the immune regulation function [7, 8]. Nevertheless, after some cytokines are fused to an antibody, the activity of the antibody itself will be reduced, thereby affecting the overall effect. Furthermore, some cytokines need to be used in combination to give full play to their respective best effects [9, 10], while the prior art cannot meet this requirement.

At present, with the successful coming into the market of PD-1 and CTLA-4 antibodies, the immunotherapy based on immune checkpoint blocking has been rapidly developed and promoted. However, these antibodies are only effective for some patients and will produce drug resistance [11, 12]. Therefore, if the cytokine can be fused to an antibody molecule and exert the optimal overall effect, the immunotherapeutic effect will be significantly enhanced, so that more patients can be effectively treated.

SUMMARY

In an aspect, the present invention provides a fusion protein dimer using an antibody Fc region as the backbone, including a first polypeptide chain and a second polypeptide chain, wherein the first polypeptide chain includes a first antibody Fc region and one or more single-domain antibodies fused to the first antibody Fc region; the second polypeptide chain includes a second antibody Fc region and one or more single-domain antibodies fused to the second antibody Fc region; and the first polypeptide chain and/or the second polypeptide chain further include a cytokine fused to the Fc region of the respective antibody.

In some embodiments, the single-domain antibody is a single-domain antibody against an immune checkpoint molecule. Preferably, the single-domain antibody is an anti-PD-1 single-domain antibody or an anti-PD-L1 single-domain antibody. In some embodiments, the single-domain antibody is an anti-PD-1 single-domain antibody. In some other embodiments, the single-domain antibody is a PD-L1 single-domain antibody.

In some embodiments, the cytokine is selected from IL-2, IL-12, GM-CSF, an IL-2 mutant, and a combination thereof. In some embodiments, two subunits P35 and P40 of the IL-12 are linked through a linker sequence to form an IL-12 single chain protein and thus are present in the first polypeptide chain and/or the second polypeptide chain. In some specific embodiments, two subunits P35 and P40 of the IL-12 are linked through a linker sequence to form an IL-12 single chain protein and thus are present in the first polypeptide chain and/or the second polypeptide chain.

In some embodiments, the single-domain antibody, the antibody Fc region and the cytokine in the fusion protein dimer are linked through a linker sequence or directly fused. In some embodiments, the single-domain antibody and the antibody Fc region in the fusion protein dimer are linked through a linker sequence or directly linked therebetween. In some other embodiments, the antibody Fc region and the cytokine in the fusion protein dimer are linked through a linker sequence. Preferably, the linker sequence is selected from (G4S)1-3 (SEQ ID NO: 75), KRVAPELLGGPS (SEQ ID NO: 76), ASTKG (SEQ ID NO: 77), and NSPPAA (SEQ ID NO: 78).

In some embodiments, the first antibody Fc region and the second antibody Fc region are different (i.e., form an antibody Fc fusion protein heterodimer) and have asymmetric complementary structures to each other. The asymmetric complementary structure can be formed, for example, by a KiH (knobs-into-holes) technology. Preferably, the first antibody Fc region has a mutation site combination T366W/S354C, and the second antibody Fc region has a mutation site combination T366S/L368A/Y407V/Y349C. In some specific embodiments, the antibody Fc region is selected from a human IgG1 mutant and a human IgG4 mutant.

In some embodiments, the first polypeptide chain and/or the second polypeptide chain include two serially arranged anti-PD-1 single-domain antibodies. In some other embodiments, the first polypeptide chain and/or the second polypeptide chain include two serially arranged anti-PD-L1 single-domain antibodies.

In some embodiments, the cytokine contained in the first polypeptide chain is IL-12, and the cytokine contained in the second polypeptide chain is IL-2 or an IL-2 mutant. In some embodiments, the cytokine contained in the first polypeptide chain is IL-12, and the cytokine is deleted from the second polypeptide chain. In some other embodiments, the cytokine contained in the first polypeptide chain is IL-2 or an IL-2 mutant, and the cytokine is deleted from the second polypeptide chain.

In some embodiments, the one or more single-domain antibodies are linked to the N-terminus of the antibody Fc region through a linker sequence, and the cytokine is linked to the C-terminus of the antibody Fc region through a linker sequence. In another embodiment, the one or more single-domain antibodies are linked to the C-terminus of the antibody Fc region through a linker sequence, and the cytokine is linked to the N-terminus of the antibody Fc region through a linker sequence. In some other embodiments, the one or more single domain antibodies are directly linked to the N-terminus of the Fc region, and the cytokine is linked to the C-terminus of the antibody Fc region through a linker sequence. In some other embodiments, the one or more single-domain antibodies are directly linked to the C-terminus of the Fc region, and the cytokine is linked to the N-terminus of the antibody Fc region through a linker sequence.

In some embodiments, the anti-PD-1 single-domain antibody has amino acid sequences as shown in SEQ ID NO: 3 and SEQ ID NO:71. In some other embodiments, the anti-PD-L1 single-domain antibody has amino acid sequences as shown in SEQ ID NOs: 72-74.

In some embodiments, the IL-12 single chain protein has an amino acid sequence as shown in SEQ ID NO: 6.

In some embodiments, the IL-2 has an amino acid sequence as shown in SEQ ID NO: 8. In some other embodiments, the IL-2 mutant has an amino acid sequence as shown in SEQ ID NO: 10.

In some embodiments, the first polypeptide chain and the second polypeptide chain are selected from amino acid sequences as shown in SEQ ID NO: 16, 18, 20, 22, 24, 26, 28, 32, 34, 36, 38, 40, 42, 44, 46, 48, 50, 52, 54, 56, 58, 60 or 62.

In some specific embodiments, the first polypeptide chain has an amino acid sequence as shown in SEQ ID NO: 20, and the second polypeptide chain has an amino acid sequence as shown in SEQ ID NOs: 22, 24 or 28; the first polypeptide chain has an amino acid sequence as shown in SEQ ID NO: 26, and the second polypeptide chain has an amino acid sequence as shown in SEQ ID NO: 28; the first polypeptide chain has an amino acid sequence as shown in SEQ ID NO: 16, and the second polypeptide chain has an amino acid sequence as shown in SEQ ID NO: 18; the first polypeptide chain has an amino acid sequence as shown in SEQ ID NO: 32, and the second polypeptide chain has amino acid sequences as shown in SEQ ID NOs: 34 and 36; or the first polypeptide chain has an amino acid sequence as shown in SEQ ID NO: 36, and the second polypeptide chain has an amino acid sequence as shown in SEQ ID NO: 38.

In some other specific embodiments, the first polypeptide chain has an amino acid sequence as shown in SEQ ID NO: 40, and the second polypeptide chain has amino acid sequences as shown in SEQ ID NOs: 42, 44; the first polypeptide chain has an amino acid sequence as shown in SEQ ID NO: 44, and the second polypeptide chain has an amino acid sequence as shown in SEQ ID NO: 46; the first polypeptide chain has an amino acid sequence as shown in SEQ ID NO: 48, and the second polypeptide chain has amino acid sequences as shown in SEQ ID NOs: 50 and 52; the first polypeptide chain has an amino acid sequence as shown in SEQ ID NO: 52, and the second polypeptide chain has an amino acid sequence as shown in SEQ ID NO: 54; the first polypeptide chain has an amino acid sequence as shown in SEQ ID NO: 56, and the second polypeptide chain has amino acid sequences as shown in SEQ ID NOs: 58 and 60; or the first polypeptide chain has an amino acid sequence as shown in SEQ ID NO: 60, and the second polypeptide chain has an amino acid sequence as shown in SEQ ID NO: 62.

In some other embodiments, the first antibody Fc region and the second antibody Fc region are wild-type antibody Fc regions, forming an antibody Fc fusion protein homodimer.

In another aspect, the present invention provides an isolated polynucleotide encoding the first polypeptide chain or the second polypeptide chain of the fusion protein dimer.

In some specific embodiments, the polynucleotide has a nucleotide sequence as shown in SEQ ID NOs: 15, 17, 19, 21, 23, 25, 27, 29, 31, 33, 35 or 37. In some other specific embodiments, the polynucleotide has nucleotide sequences as shown in SEQ ID NOs: 39, 41, 43, 45, 47, 49, 51, 53, 55, 57, 59 and 61.

In another aspect, the present invention provides an expression vector including the polynucleotide.

In another aspect, the present invention provides a host cell including the expression vector.

In another aspect, the present invention provides use of the fusion protein dimer, the polynucleotide, the expression vector or the host cell in preparing an antitumor drug. Preferably, the tumor is melanoma or a lung cancer.

In another aspect, the present invention provides an anti-tumor pharmaceutical composition including the fusion protein dimer, and a pharmaceutically acceptable carrier.

In another aspect, the present invention provides a method of treating a tumor, including administering to a subject a therapeutically effective amount of the fusion protein dimer or a pharmaceutical composition containing the fusion protein dimer.

In some embodiments, the anti-tumor pharmaceutical composition provided by the present invention can be applied to a subject through at least one route selected from the group consisting of: parenteral, subcutaneous, intramuscular, intravenous, intra-articular, endobronchial, intra-abdominal, intravesicular, endochondral, intracavitary, intracoelomic, intracelebellar, intraventricular, intracolonic, intracervical, intragastric, intrahepatic, intramyocardial, endosseous, intrapelvic, intrapericardial, intraperitoneal, intrapleural, intraprostatic, intrapulmonic, endorectal, intrarenal, intraretinal, intraspinal, intrasynovial, intrathoracic, entotympanic, intrauterine, intravesical, intravitreous, rapid injection, subconjunctival, transvaginal, transrectal, buccal, sublingual, intranasal, intratumoral and transdermal. Preferably, the anti-tumor pharmaceutical composition is administered to a subject by intratumoral or intravenous administration.

On the other hand, the present invention also provides the anti-PD-1 single-domain antibody itself, which has the amino acid sequence as shown in SEQ ID NO: 3. The present invention also provides a polynucleotide encoding the anti-PD-1 single-domain antibody, which has the nucleotide sequence as shown in SEQ ID NO: 2. The present invention also provides the anti-PD-1 single-domain antibody itself, which has amino acid sequence as shown in SEQ ID NO: 71. The present invention also provides the anti-PD-L1 single-domain antibody itself, which has amino acid sequences as shown in SEQ ID NOs: 72-74.

The fusion protein of the present invention combines the advantages of small molecule, good permeability, high stability and the like of the single-domain antibody with the immunoregulation and the like activities of the cytokine. More importantly, the present invention uses an antibody Fc fusion protein heterodimer technology to organically fuse the two, thereby not only improving the activity of the single-domain antibody, but also obviously improving the biological activity of the cytokine; and by means of the targeting specificity of the antibody, the targeted transport of the cytokine is effectively enhanced, and cytotoxicity is attenuated, thereby obtaining better anti-tumor potential and significantly improved pharmacokinetic properties.

DETAILED DESCRIPTION

Figure 1:
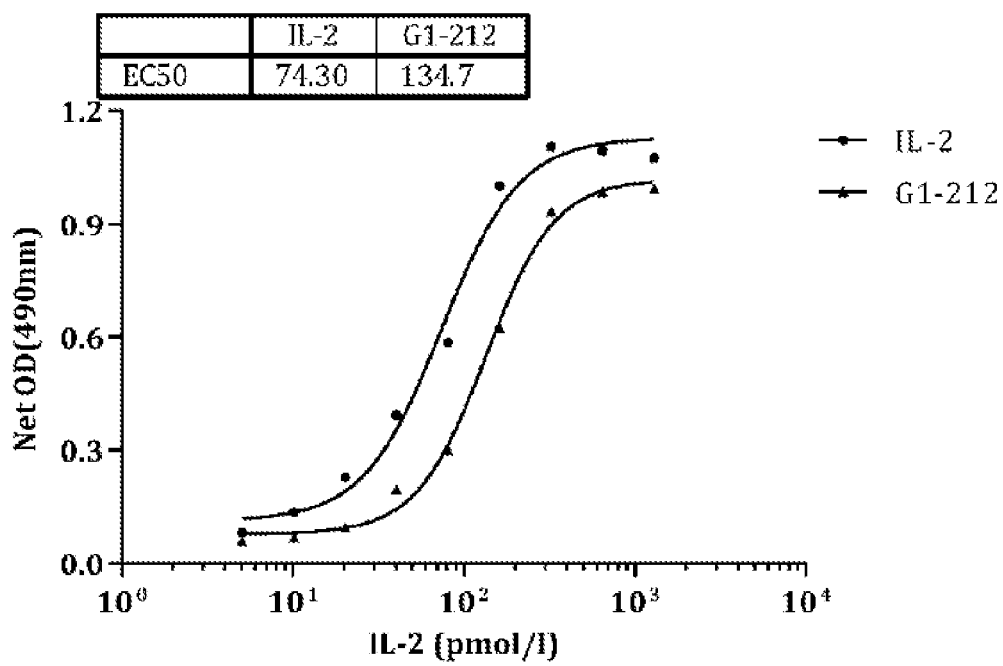
FIG. 1 shows the IL-2 activity of a G1-212 fusion protein compared with that of a control IL-2.

Unless otherwise specified, technical and scientific terms used in the present invention have the meanings commonly understood by those of ordinary skills in the art to which the present invention belongs.

The present invention provides a fusion protein with an anti-tumor activity by utilizing an antibody Fc heterodimer technology, wherein the fusion protein includes a single-domain antibody and one or more cytokines, and an antibody Fc region serving as a backbone part [13]. In the present invention, "single-domain antibody-cytokine fusion protein", "antibody/cytokine fusion protein" and "antibody-cytokine fusion protein" all refer to single-domain antibody-cytokine fusion proteins based on an antibody Fc heterodimer technology, including a fusion protein formed by connecting one or more single-domain antibodies and one or more cytokines through an antibody Fc region, and optionally, the single-domain antibodies and the cytokines are respectively linked at both ends of the antibody Fc through linker sequences.

The term "antibody" refers to a large "Y"-shaped protein secreted by plasma cells (effector B cells) and used by an immune system for identifying and neutralizing foreign substances such as bacteria, viruses, etc. Over the past 10 years, more and more monoclonal antibodies have been widely used in tumor therapy. The antibodies referred in the present invention will include, but are not limited to, being capable of specifically binding tumor-related antigens, inducing immune killing of tumor cells through antibody-dependent cytotoxicity (ADCC) and complement-dependent cytotoxicity (CDC), or blocking immune checkpoints, thereby activating immune responses. An antibody is usually a tetramer composed of two identical heavy chains and two identical light chains interlinked by disulfide bonds.

The term "antibody Fc region" or "antibody Fc" refers to a "Y"-shaped handle region, i.e., a fragment that is crystallizable (Fc), including the second and third constant domains (CH2 and CH3 domains) of the heavy chain. The antibody Fc region can be obtained by hydrolyzing an antibody molecule with a proteolytic enzyme (such as papain).

The term "using the antibody Fc region as the backbone" refers to that in the fusion protein dimer of the present invention, the single-domain antibody and the cytokine are usually located on two sides of the antibody Fc region respectively. That is, the single-domain antibody and the cytokine are linked through the antibody Fc region to form a fusion protein. "Using the antibody Fc region as the backbone" also means that the two polypeptide chains (the first and second polypeptide chains) are bound together to form a fusion protein dimer by the interaction of the Fc regions in the two polypeptide chains, for example by disulfide bonds or noncovalent interactions.

The dimer protein referred in the present invention refers to that the protein is referred to as a homodimer when two subunits/monomers are the same during the protein formation, and the protein is referred to as a heterodimer when the protein is formed by a combination of two subunits/monomers that are not exactly the same. The term "antibody Fc heterodimer" refers to a protein composed of two different subunits/monomers, and each subunit/monomer contains an antibody Fc fragment. The key lies in the fact that the two antibody Fc fragments each has a different amino acid site mutation, which can form complementary protein spatial structures, thereby enabling the two different subunits/monomers to be correctly combined together.

The term "KiH (knobs-into-holes) technology" refers to a technology that facilitates assembly between heavy chains of two heterologous antibodies. For example, a threonine (T) with a smaller volume at position 366 of a heavy chain CH3 region of an antibody can be mutated into a tyrosine (Y) with a larger volume to form a prominent "knobs"-type structure (T366Y); and at the same time, a larger tyrosine (Y) residue at position 407 of a heavy chain CH3 region of another antibody is mutated into a smaller threonine (T) to form a concave "holes"-type structure (Y407T); and using the steric-hindrance effect of this "knobs-into-holes" structure (i.e., asymmetric complementary structures) can realize the correct assembly between heavy chains of two different antibodies. According to the present invention, a better assembling effect is realized through combination of multiple site mutations in the two antibody Fc regions.

The term "single-domain antibody (sdAb or nanobody)" refers to another form of antibody fragment that contains only one antibody variable region in a monomeric form. Like an entire antibody, the single-domain antibody can also specifically bind to an antigen, but its mass is much smaller than that of a traditional antibody (about 15 kDa). More importantly, just benefited from the small size of the single-domain antibody, the single-domain antibody can penetrate a tissue or enter the interior of a tumor more conveniently, which is difficult for an entire antibody to do.

The term "cytokine (CK)" is a low molecular weight soluble protein produced by various cells as induced by immunogens, mitogens or other stimulants. It can transmit an intracellular signal in vivo by binding with a cell surface receptor specific to it, thereby changing a cell function, and it has many functions such as adjusting innate immunity and adaptive immunity, hemocytogenesis, cell growth, APSC pluripotent cells, and repair of injured tissues, etc.[4]. Interleukin (such as IL-2 or IL-12), as one group of cytokines, adjusts immune response by regulating an immune system. The cytokine can not only function independently, but also be fused with an antibody to form an antibody-cytokine fusion protein, also known as an immune cytokine. This new protein form organically combines the specific targeting ability of the antibody with the immunoregulation of the cytokine, thereby enhancing the immunotherapeutic effect of the antibody. More importantly, the fused cytokine is transported and enriched to a tumor site through the targeting ability of the antibody, thereby effectively avoiding the side effects caused by using a high dose of the cytokine alone.

The term "isolated polynucleotide" refers to a polynucleotide that is not naturally occurring in nature, including a polynucleotide isolated from nature (including organisms) by biological techniques, and also including an artificially-synthesized polynucleotide. The isolated polynucleotide may be a genomic DNA, cDNA, mRNA or other synthesized RNAs, or a combination thereof. Multiple nucleotide sequences for encoding the fusion protein dimer of the present invention and other polypeptide fragments are provided herein. It should be pointed out that those skilled in the art can design nucleotide sequences which are not exactly the same as the nucleotide sequences provided above but all encode the same amino acid sequences according to the amino acid sequences provided herein and based on codon degeneracy. These modified nucleotide sequences are also included in the scope of the present invention.

When referring to a polynucleotide, the term "vector" as used refers to any molecule (e.g., nucleic acid, plasmid, or virus, etc.) used for transferring nucleotide coding information into a host cell. The term "expression vector" refers to a vector suitable for expressing a target gene (a nucleotide sequence to be expressed) in a host cell, and generally includes a target gene, a promoter, a terminator, a marker gene and the like parts.

The term "host cell" refers to a cell that has been or can be transformed with a nucleic acid sequence to express a selected gene of interest. This term includes a progeny of a parent cell, regardless of whether the progeny is the same in morphology or gene composition as the original parent cells, as long as the progeny has the selected target gene. Commonly used host cells include bacteria, yeasts, mammalian cells, etc., such as CHO cells.

Referring to a pharmaceutical composition, the term "pharmaceutically acceptable carrier" as used refers to substances such as a solid or liquid diluent, a filler, an antioxidant, a stabilizer and the like that can be safely applied, which are suitable for administration to humans and/or animals without excessive adverse side effects, while being suitable for maintaining the vitality of drugs or active agents located therein. According to the route of administration, various carriers well known in the art can be applied, including, but not limited to, saccharides, starch, cellulose and derivatives thereof, maltose, gelatin, talc, calcium sulfate, vegetable oil, synthetic oil, polyol, alginic acid, phosphate buffer, emulsifier, isotonic saline, and/or pyrogen-free water, etc. The pharmaceutical composition provided by the present invention can be made into clinically acceptable dosage forms such as powder, injection and the like. The pharmaceutical composition of the present invention may be administered to the subject using any suitable route, for example, by oral administration, intravenous infusion, intramuscular injection, subcutaneous injection, intraperitoneal, rectal, sublingual, or by inhalation, transdermal, etc.

The term "therapeutically effective amount" refers to an amount of an active compound that is sufficient to cause a biological or medical response in a subject as desired by a clinician. The "therapeutically effective amount" of the fusion protein of the present invention can be determined by those skilled in the art according to factors such as the route of administration, the body weight, age, and disease condition of the subject, and the like factors. For example, a typical daily dosage range may be 0.01 mg to 100 mg of an active ingredient per kg of body weight.

The term "and/or" means that elements before and after the term can exist simultaneously, or only one of the elements exists. For example, "A and/or B" may be A and B, only A, or only B.

In order to utilize the advantages of the immune cytokine and the single-domain antibody to improve the immunotherapeutic effect, we fuse the cytokine onto a PD-1 single-domain antibody, to develop a single-domain antibody-cytokine fusion protein against PD-1, and evaluate the function of the fusion protein through in vitro and in vivo analysis. The cytokines referred in the present invention include interleukins, such as interleukin-2 (IL-2) and interleukin-12 (IL-12), and granulocyte-macrophage colony stimulating factors (GM-CSF), etc., wherein the interleukin-2 and the interleukin-12 participate in various links of immune regulation, thereby enhancing immune response.

The construction of the fusion protein dimer for killing tumor cells and various characteristics of the fusion protein of the present invention can be further understood from the following description.

1. Design and Construction, Expression in CHO Cells, and Purification of Fusion Protein:

The cytokine IL-2 or IL-12 can be linked to the N-terminus or C-terminus of the antibody Fc through a linker sequence (Gly4Ser)3 (i.e. (G4S)3) (SEQ ID NO: 75). Similarly, the PD-1 single-domain antibody can also be linked to the N-terminus or C-terminus of the antibody Fc through the linker sequence (Gly4Ser)3 (SEQ ID NO: 75). The formed fusion protein maintains the dual effects of the antibody and the cytokine. Since a functional IL-12 is composed of two subunits, p35 and p40, the IL-12 will be fused onto the antibody Fc separately in the form of the two subunits, or alternatively the two subunits of the IL-12 will be first fused to the antibody Fc through the linker sequence (Gly4Ser)3 to form a single chain protein, and then the single chain protein is fused onto the antibody Fc.

Figure 23:
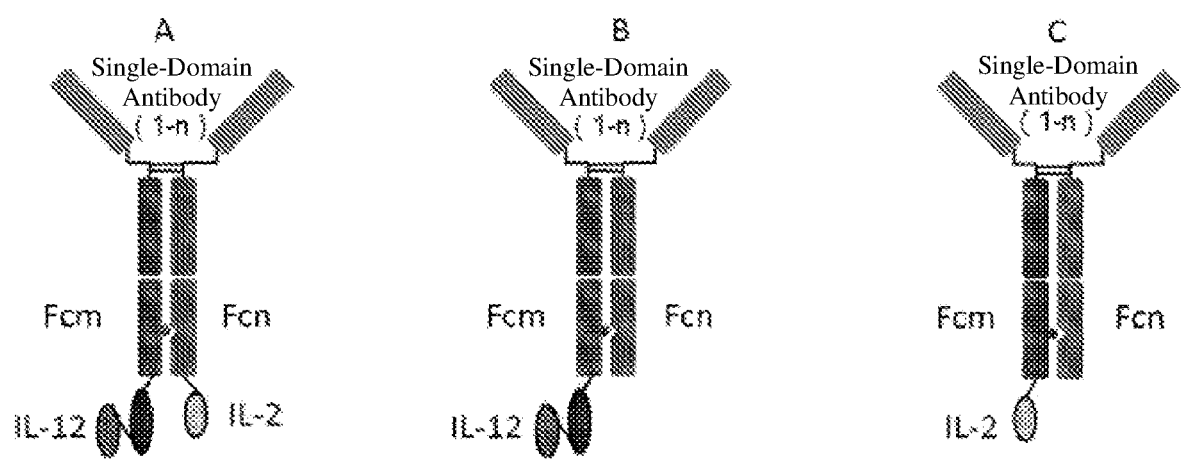
FIG. 23A shows that the cytokines IL-2 and IL-12 can each be selectively linked to the C-terminus or N-terminus of each antibody Fc chain (Fcm, Fcn respectively) through a linker sequence, and correspondingly one or more single-domain antibodies ((1-n) single-domain antibodies) can be selectively linked to the other end of each antibody Fc chain through a linker sequence.
FIG. 23B shows that the cytokine IL-12 can be selectively fused to the C-terminus or N-terminus of an antibody Fc chain (e.g. Fcm) through a linker sequence separately, the other antibody Fc chain lacks cytokines, and correspondingly one or more single-domain antibodies ((1-n) single-domain antibodies) can be selectively linked to the other end of each antibody Fc chain through a linker sequence.
FIG. 23C shows that the cytokine IL-2 can be selectively fused to the C-terminus or N-terminus of an antibody Fc chain (e.g. Fcm) through a linker sequence separately, the other antibody Fc chain lacks cytokines, and correspondingly one or more single-domain antibodies ((1-n) single-domain antibodies) can be selectively linked to the other end of each antibody Fc chain through a linker sequence.

In a traditional antibody-cytokine fusion protein structure, a cytokine is linked to two heavy chains or two light chains of an antibody simultaneously, and thus existing in the form of a homodimer. However, this immune cytokine that is fused based on an IgG platform has poor pharmacokinetic properties. In order to fuse the cytokine onto the antibody in a monomer form and change the ratio of the antibody to the cytokine at the same time, and thus enhance the targeting ability of the fusion protein, we adopt a technology based on an antibody Fc heterodimer to fuse the IL-2 or IL-12 separately to an Fc chain while the other chain lacks cytokines, such that a IL-12 or IL-2 monomer fusion protein is formed, as shown in FIGS. 23B and 23C respectively, or alternatively the IL2 and IL-12 are each linked to an Fc chain to produce a fusion protein with both IL-2 and IL-12 proteins, as shown in FIG. 23A.

The core of the antibody Fc heterodimer technology is to modify the two chains of the antibody Fc respectively to generate asymmetric complementary structures, thereby combining the two modified chains and avoiding the generation of a homodimer. The principle of modification is based on the following aspects: hydrophobic/spatial complementarity (such as KiH and ZW1), electrostatic complementarity (such as DD-KK), spatial complementarity+electrostatic interaction (such as EW-RVT), and spatial complementarity+hydrogen bonding complementarity (such as A107), etc. In this study, we adopt hydrophobic/spatial complementation to modify the Fc, to enable it to be fused to only one cytokine, thereby producing a monomeric immune cytokine. Furthermore, we also use a wild-type antibody Fc backbone to construct the immune factor of homodimer as a control.

Since the wild-type IL-2 has certain cytotoxicity, we designed a mutant of IL-2 (IL-2m) which is then fused onto the antibody Fc, in order to further reduce the toxic and side effects.

The antibody Fc-based single-domain antibody-cytokine fusion protein constructed by the aforementioned method will be expressed in CHO cells, and then subjected to Protein A affinity chromatography and molecular sieve purification to obtain a protein for in vivo and in vitro analysis.

2. In Vitro Experiment of Antibody-Cytokine Fusion Protein:

2.1: Cell-Based Target Affinity Experiment

The experiment of target affinity of the antibody/cytokine fusion protein to a PD-1 receptor is determined by Biacore, enzyme-linked adsorption assay, FACS and the like methods in cell lines expressing PD-1 and activated T cells.

Experimental Steps:

Determination of antibody affinity by the activated T cells: CD4+ T cells are isolated from human peripheral blood mononuclear cells by a positive T cell screening kit (BD Bioscience), then activated by an anti-CD3 antibody for 4 days, and determined by a fluorescence-labeled antibody and a FACS method. The parameters for the binding between the antibody/cytokine fusion protein and the PD-1 are determined by flowing a human PD-1-FC (R&D system) or FLAG-tagged monkey PD-1 protein, a labeled CM5 sensory probe, and a PD-1 receptor protein through a probe, and the affinity is determined by SPR (Biacore).

The antibody affinity is assessed by means of the cell lines expressing the PD-1 antigens: Jurkat cells (Jurkat-PD1) overexpressing the PD-1 antigens are incubated with PD-1 single-domain antibody-cytokine fusion proteins for 2 hours at 4° C., washed with PBS for 3 times, then added with fluorescently-labeled secondary antibodies (goat anti-human IgG-FITCs), mixed gently until even, and incubated at 4° C. for 1 hour. The cells are then washed for 3 times with PBS again, followed by affinity determination using a BD FACScalibur flow cytometer.

2.2: Determination of Functionality:

2.2.1: Experiments of Cell Proliferation and IFN-γ and IL-2 Secretion:

The IL-2 and IL-12 can promote the proliferation of human T cells and can also activate various lymphocytes, thereby promoting the proliferation of the T cells and the secretion of interferon-gamma (IFN-γ). By detecting T cell proliferation or IFN-γ secretion, the cytokine activity of the antibody-cytokine fusion protein can be assessed.

In this experiment, the cytokine activity of the antibody-cytokine fusion protein will be determined by employing the fusion protein to stimulate NK92 cells to release IFN-γ so as to verify the in vitro biological activity of the cytokine in the fusion protein. Specifically, since the fusion protein constructed in this experiment contains the cytokine, different fusion proteins are incubated with the NK92 cells, and then the release of IFN-γ is detected.

2.2.2: Antibody-Dependent Cell-Mediated Cytotoxicity (ADCC)

Overview: ADCC refers to the effect of NK cells, macrophages, neutrophil granulocytes and the like that express IgGFc receptors to kill target cells such as virus-infected cells and tumor cells by binding to Fc segments of IgG antibodies that have been bound to the surfaces of the target cells. The IgG antibody can mediate the ADCC functions of these cells, wherein the NK cells are the main cells that can play the ADCC role.

Process: the IgG antibody specifically binds to antigenic determinants on the surfaces of the target cells; after that, natural killer cells (NK cells) are bound to IgG Fc segments bound on the target cells by means of corresponding receptors on their surfaces; the activated NK cells release cytotoxic substances such as perforin and granzyme to kill the target cells; and the target cells undergo apoptosis and the antibody is treated by liver.

Experimental Steps:

1. Preparation of target cells: Raji cells are infected with influenza viruses for 48 hours to reach an infection rate of 80-95%; washed twice with normal saline and labelled with PKH67.

2. Preparation of effector cells: PBMC cells are isolated from healthy volunteers' blood according to normal procedures, and washed twice.

3. ADCC determination: ADCC determination will adopt a FACS method, which counts living cells and dead cells to determine the activity of the cell.

4. Brief steps: labeled target cells are inoculated on a 96-well plate; added with the antibody and kept at the temperature of 37° C. for 15 minutes; added with unlabeled PBMC effector cells and kept at the temperature of 37° C. for 2 hours; added with a fluorescently-labeled dead cell dye (7AAD) and kept at 4° C. for 20 minutes; and cell counting is conducted by FACS.

5. FACS counting analysis: a target cell (living and dead cells) interval is identified; an effector cell interval is identified; living cells (PKH67) are counted; and dead cells (7AAD) are counted.

2.2.3: PD-1 Inhibition (PD-1/PD-L1 Pathway Blocking) Experiment and Mixed Lymphocyte Reaction Experiment Overview: a PD-1 inhibition experiment (Promega) and a mixed lymphocyte reaction experiment (Genscript) will be carried out according to standard procedures. The following are brief steps of the PD-1 inhibition experiment.

Experimental Steps:

1. PD-L1 cells are melted and inoculated on a 96-well plate, and kept at the temperature of 37° C.

2. A fusion protein sample constructed based on the PD1 single-domain antibody and a reference Keytruda which are diluted by equal times are prepared. Alternatively, a fusion protein sample constructed based on the PDL1 single-domain antibody and a reference Atezolizumab which are diluted by equal times are prepared. The two references are only used as standards to measure the stability before different batches of experiments.

3. The 96-well culture plate is taken out from a carbon dioxide incubator, the culture solution is pipetted, and the diluted antibodies are added into the PD-L1 cell well.

4. PD-1 effector cells are melted and added into the 96-well plate containing the antibody, and kept at the temperature of 37° C. for 6 hours.

5. Luciferase detection: a Bio-Glo™ detection reagent is prepared, 80 μl of it is added into the 96-well plate containing the antibodies and cells, maintained at room temperature for 5-10 minutes, and detected for luminescence in a GloMax system.

6. Data analysis: the induction multiple is calculated as the induction multiple=RLU antibody dilution/RLU antibody negative control; and EC50 is calculated through GraphPad by means of RLU and Log 10 and induction multiple and Log 10.

3. Assessment of In Vivo Anti-Tumor Effect

In vivo anti-tumor efficacy will be assessed by establishing tumor models with a human IL-12 receptor, human PD-1 and knock-in mice. The humanization of the IL-12 receptor and the PD-1 respectively makes it possible to directly assess the in vivo pharmaceutical effect of the fusion protein in which the single-domain antibody and the cytokine are fused. Tumor models suitable for this assessment may include, but are not limited to, GL261 or B16 cell lines. The pharmaceutical effect will be assessed in the following aspects: (1) inhibition of tumor formation; (2) inhibition of growth of formed tumors; and (3) dose gradient test (three doses).

The antibody alone should show an anti-tumor effect, but the single-domain antibody-cytokine fusion protein will show a better anti-tumor effect, and this tumor inhibition effect is dose-dependent.

3.1 Establishment of Mouse Model and Administration Treatment $1 \times 10^6$ GL261 or B16 cells are injected subcutaneously into the abdomen or back of mice. When the average tumor volume reaches 100 mm$^3$, the mice are randomly divided into 4 groups (8 mice in each group): a control group, an anti-PD-1 group, an anti-PD-1+IL2 group, an anti-PD-1+IL-12 group and an anti-PD-1+IL2+IL12 group. Administration is conducted once every four days, for a total of three times. Each time the administration is conducted with PBS (the control group), a PD-1 (sdAb-Fc) single-domain antibody Fc fusion (anti-PD-1 group), a PD-1 sdAb-IL2 fusion protein (anti-PD-1+IL2 group), a PD-1 sdAb-IL12 fusion protein (anti-PD-1+IL12 group) and a PD-1 sdAb-IL2-IL12 fusion protein (anti-PD-1+IL2+IL12 group) through intratumoral or tail vein administration. Then the tumor growth condition is monitored for 3 times a week.

3.2 Statistical Analysis of Data

A SPSS software is employed for analysis. The data is all expressed in the form of "mean±standard deviation". Using one-way ANOVA analysis, it is statistically significant with the difference of $P<0.05$.

The antibody-cytokine fusion protein of the present invention can selectively transport a cytokine to a target cell in vivo, so the cytokine will exhibit local biological reactions, such as local inflammatory reactions, and stimulating T cell growth and activation. The PD-1 antibody can further play an anti-cancer role by binding to a receptor on a cell membrane surface. Therefore, it is feasible to treat cancer with the fused antibody and cytokine by targeted delivery of the cytokine to enhance the immune response.

Experimental Results and Analysis

1. Construction of Immune Cytokine Fusion Protein Based on Antibody Fc Heterodimer In this study, a series of single-domain antibody-cytokine fusion proteins based on the antibody Fc heterodimer are constructed. The components used for constructing the fusion proteins are a PD-1 single-domain antibody, and cytokines IL-12, IL-2 and IL-2 mutants.

The sequence of the anti-PD-1 single-domain antibody is inserted behind a polyclonal site EcoRI of a pTT5 expression vector, and meanwhile a KOZAK sequence GCCGC- CACC and a signal peptide sequence are also added in front of the fusion protein gene to help secrete the fusion protein out of a cell. A SC01 vector expressing the single-domain antibody is produced.

An antibody Fc fragment is inserted onto the pTT5 vector via the polyclonal site EcoRI, then the sequence of the PD-1 single-domain antibody is linked to the N-terminus of the Fc via Gibson assembly, and they are linked through the (G4S)3 (SEQ ID NO: 75) linker sequence therebetween. Then the IL-12 sequence is linked to the C-terminus of the Fc in a similar manner, and there is also a G4S (SEQ ID NO: 75) linker sequence between them. Finally, a vector G1-208 for expressing a PD-1 single-domain antibody and IL-12 fusion protein is formed. Meanwhile a KOZAK sequence GCCGC-CACC and a signal peptide sequence are also added in front of the fusion protein gene to help secrete the fusion protein out of a cell. In a similar manner, the PD-1 single-domain antibody and the IL-2 are fused to the N-terminus and C-terminus of the Fc respectively, to produce a vector G1-212 for expressing the PD-1 single-domain antibody and IL-2 fusion protein.

Both the G1-208 and the G1-212 are homodimers based on the antibody Fc. In order to generate a Fc-based heterodimer, the knob-into-holes technology is used for antibody Fc modification, wherein the mutation site combination of one Fc chain is T366W/S354C, and the mutation site combination of the other Fc chain is T366S/L368A/Y407V/Y349C. The sequence of the anti-PD-1 single-domain antibody is linked to the N-terminus of the Fc through Gibson assembly, and the IL-12 and the IL-2 are respectively linked to the C-terminus of the Fc in a similar manner, thereby producing an expression vector G1-405 in which the PD-1 single-domain antibody, the IL-12 and the IL-2 are fused.

G1-716 is obtained by connecting a PD-1 single-domain antibody to the N-terminus of an existing PD-1 single-domain antibody through the (G4S)3 (SEQ ID NO: 75) linker sequence based on the G1-405.

G1-723 is obtained through modification by conducting site mutation of an IL-2 gene based on the G1-716.

G1-717 is obtained through modification by deleting an IL-12 gene based on the G1-716.

G1-719 is obtained through modification by deleting the IL-2 gene based on the G1-716.

Two PD-1 single-domain antibodies are linked in series through the (G4S)3 (SEQ ID NO: 75) linker sequence, and then linked to the N-terminus of the Fc through the (G4S)3 (SEQ ID NO: 75) linker sequence, thereby forming a homodimer G1-709.

The information about the plasmids constructed in this experiment is shown in Table 1 below:

TABLE 1

| Composition of Fusion Proteins | |
|---|---|
| # | Plasmid |
| SC01 | PD1 sdAb |
| G1-208 | PD1-Fc-IL12 |
| G1-212 | PD1-Fc-IL2 |
| G1-405 | PD1-Fc-IL12 |
|  | PD1-Fc-IL2 |
| G1-709 | (PD1)2-Fc |
| G1-716 | (PD1)2-Fc-IL12 |
|  | (PD1)2-Fc-IL2 |
| G1-723 | (PD1)2-Fc-IL12 |
|  | (PD1)2-Fc-IL2m |
| G1-717 | (PD1)2-Fc-IL2 |
|  | (PD1)2-Fc |

TABLE 1-continued

| Composition of Fusion Proteins | |
|---|---|
| # | Plasmid |
| G1-719 | (PD1)2-Fc-IL12 |
|  | (PD1)2-Fc |

The fusion protein plasmid constructed onto the pTT5 expression vector is transiently transfected into CHO-3E7 cells by a PEI transfection reagent, and then cultured at 37° C. for 6 days. The supernatant of the culture solution is collected by centrifugation. The fusion protein is purified by a Protein A affinity column, and then further purified by a molecular sieve, with the purity finally reaching more than 95%.

The signal peptide DNA sequence (SEQ ID NO: 1) used in this study is as follows:

ATGGGCTGGTCCTGCATCATCCTGTTTCTGGTGGCTACCGCTACCGGCGTG

CACTCT

The DNA sequence (SEQ ID NO: 2) of the anti-PD-1 single-domain antibody SC01 used in this study is as follows:

CAAGTTCAACTGGTGGAAAGCGGTGGTGGTCTGGTTCAGCCGGGCGGTAGC

CTGCGTCTGAGCTGCGCGGCGAGCGGTGGTACCCTGGACTACTATGCGATC

GGTTGGTTCCGTCAGGCGCCGGGCAAGGAGCGTGAGGCGGTGAGCTGCATT

AGCAGCAGCGACGGTAGCACCTACTATGCGGATAGCGTTAAGGGCCGTTTT

ACCATCAGCCGTGATAACAGCAAAAACACCCTGTACCTGCAAATGAACAGC

CTGCGTGCGGAAGACACCGCGGTGTATCACTGCGCGACCGATCGTGCGTGC

GGTAGCAGCTGGCTGGGCGCGGAGAGCTGGGCGCAAGGCACCCTGGTTACC

GTGAGCAGC

The amino acid sequence of SC01 (SEQ ID NO: 3) is as follows:

QVQLVESGGGLVQPGGSLRLSCAASGGTLDYYAIGWFRQAPGKEREAVSCI

SSSDGSTYYADSVKGRFTISRDNSKNTLYLQMNSLRAEDTAVYHCATDRAC

GSSWLGAESWAQGTLVTVSS

The DNA sequence (SEQ ID NO: 4) of the G4S linker used in this study is as follows:

GGTGGAGGCGGTAGTGGCGGAGGCGGTTCAGGCGGAGGCGGATCT

The full length DNA sequence (SEQ ID NO: 5) of the cytokine IL-12 used in this study is as follows:

ATTTGGGAGCTGAAGAAAGACGTGTACGTGGTCGAGCTGGACTGGTACCCT

GATGCCCCAGGCGAGATGGTCGTGCTGACCTGCGATACACCAGAGGAAGAT

GGTATCACCTGGACACTGGATCAGTCCTCAGAGGTGCTGGGCTCTGGTAAA

ACACTGACCATTCAGGTGAAGGAGTTCGGTGACGCTGGACAGTACACTTGT

CATAAGGGCGGGGAGGTGCTGTCTCACTCCCTGCTGCTGCTGCATAAGAAG

-continued

GAGGATGGAATCTGGTCCACTGACATCCTGAAAGACCAGAAGGAGCCAAAG

AACAAAACCTTCCTGCGATGCGAGGCTAAGAACTACAGCGGCCGCTTTACA

TGCTGGTGGCTGACAACCATCAGCACCGATCTGACCTTTAGCGTGAAGTCA

TCCAGGGGCAGTTCAGACCCTCAGGGAGTCACATGTGGCGCCGCAACCCTG

TCAGCAGAGCGAGTGCGGGGAGACAATAAGGAATACGAGTACAGCGTCGAG

TGTCAGGAGGATTCCGCATGTCCAGCTGCAGAAGAATCCCTGCCTATCGAA

GTCATGGTGGACGCTGTGCATAAACTGAAGTACGAGAATTACACCAGCAGC

TTTTTCATCCGGGACATCATCAAGCCCGATCCACCTAAGAATCTGCAGCTG

AAGCCTCTGAAAAATAGCCGACAGGTCGAAGTGTCATGGGAATACCCAGAC

ACCTGGTCAACACCACACTCCTACTTCTCCCTGACCTTCTGTGTGCAGGTC

CAGGGAAAAAGCAAGCGGGAAAAGAAAGATCGGGTGTTCACCGACAAGACC

AGTGCTACAGTGATTTGCCGGAAGAATGCCAGCATTTCTGTCAGAGCTCAG

GACCGGTACTATAGCTCTTCCTGGAGCGAGTGGGCTTCAGTGCCATGTTCT

GGaGGCGGtGGATCTGGCGGAGGTGGAAGCGGAGGCGGTGGATCTAGAAAC

CTGCCCGTCGCAACCCCTGATCCAGGGATGTTCCCCTGTCTGCATCACAGC

CAGAATCTGCTGAGGGCTGTCTCCAACATGCTGCAGAAGGCTCGACAGACC

CTGGAGTTCTACCCATGTACCAGCGAAGAGATCGACCACGAGGATATCACA

AAGGATAAAACCAGCACAGTGGAAGCATGCCTGCCTCTGGAACTGACCAAG

AATGAGAGCTGCCTGAATAGCAGGGAGACCTCCTTCATCACCAACGGCTCA

TGCCTGGCTTCAAGGAAGACCAGCTTCATGATGGCTCTGTGTCTGAGCTCT

ATCTATGAGGACCTGAAGATGTACCAGGTGGAGTTCAAGACCATGAACGCC

AAGCTGCTGATGGATCCAAAGAGGCAGATCTTCCTGGATCAGAATATGCTG

GCAGTGATCGATGAGCTGATGCAGGCCCTGAATTTTAACAGTGAGACAGTG

CCTCAGAAGAGCTCTCTGGAAGAGCCAGACTTTTACAAAACTAAGATCAAG

CTGTGCATTCTGCTGCACGCTTTCCGCATCAGAGCTGTCACTATCGATAGA

GTGATGAGCTATCTGAATGCCTCA

The full-length amino acid sequence (SEQ ID NO: 6) of the IL-12 as used is as follows:

IWELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEPK

NKTFLRCEAKNYSGRFTCWWLTTISTDLTFSVKSSRGSSDPQGVTCGAATL

SAERVRGDNKEYEYSVECQEDSACPAAEESLPIEVMVDAVHKLKYENYTSS

FFIRDIIKPDPPKNLQLKPLKNSRQVEVSWEYPDTWSTPHSYFSLTFCVQV

QGKSKREKKDRVFTDKTSATVICRKNASISVRAQDRYYSSSWSEWASVPCS

GGGGSGGGGSGGGGSRNLPVATPDPGMFPCLHHSQNLLRAVSNMLQKARQT

LEFYPCTSEEIDHEDITKDKTSTVEACLPLELTKNESCLNSRETSFITNGS

CLASRKTSFMMALCLSSIYEDLKMYQVEFKTMNAKLLMDPKRQIFLDQNML

AVIDELMQALNFNSETVPQKSSLEEPDFYKTKIKLCILLHAFRIRAVTIDR

VMSYLNAS

The DNA sequence (SEQ ID NO: 7) of the cytokine human IL-2 as used in this study is as follows:

GCACCTACTTCAAGTTCTACAAAGAAAACACAGCTACAACTGGAGCATTTA

CTGCTGGATTTACAGATGATTTTGAATGGAATTAATAATTACAAGAATCCC

AAACTCACCAGGATGCTCACATTTAAGTTTTACATGCCCAAGAAGGCCACA

GAACTGAAACATCTTCAGTGTCTAGAAGAAGAACTCAAACCTCTGGAGGAA

GTGCTAAATTTAGCTCAAAGCAAAAACTTTCACTTAAGACCCAGGGACTTA

ATCAGCAATATCAACGTAATAGTTCTGGAACTAAAGGGATCTGAAACAACA

TTCATGTGTGAATATGCTGATGAGACAGCAACCATTGTAGAATTTCTGAAC

AGATGGATTACCTTTTGTCAAAGCATCATCTCAACACTGACT

The amino acid sequence (SEQ ID NO: 8) of the human IL-2 is as follows:

APTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSETT

FMCEYADETATIVEFLNRWITFCQSIISTLT

The DNA sequence (SEQ ID NO: 9) of the human IL-2 mutant as used in this study is as follows:

GCACCTACTTCAAGTTCTACAAAGAAAACACAGCTACAACTGGAGCATTTA

CTGCTGGATTTACAGATGATTTTGAATGGAATTAATAATTACAAGAATCCC

AAACTCACCAGGATGCTCACATTTAAGTTTTACATGCCCAAGAAGGCCACA

GAACTGAAACATCTTCAGTGTCTAGAAGAAGAACTCAAACCTCTGGAGGAA

GTGCTAAATTTAGCTCAAAGCAAAAACTTTCACTTCGACCCCAGGGACGTG

GTGAGCAATATCAACGTATTCGTTCTGGAACTAAAGGGATCTGAAACAACA

TTCATGTGTGAATATGCTGATGAGACAGCAACCATTGTAGAATTTCTGAAC

AGATGGATTACCTTTTGTCAAAGCATCATCTCAACACTGACT

The amino acid sequence (SEQ ID NO: 10) of the human IL-2 mutant is as follows:

APTSSSTKKTQLQLEHLLLDLQMILNGINNYKNPKLTRMLTFKFYMPKKA

TELKHLQCLEEELKPLEEVLNLAQSKNFHFDPRDVVSNINVFVLELKGSE

TTFMCEYADETATIVEFLNRWITFCQSIISTLT

The full-length DNA sequence (SEQ ID NO: 11) of the G1-208 fusion protein as used in this study is as follows:

CAAGTTCAACTGGTGGAAAGCGGTGGTGGTCTGGTTCAGCCGGGCGGTAGC

CTGCGTCTGAGCTGCGCGGCGAGCGGTGGTACCCTGGACTACTATGCGATC

GGTTGGTTCCGTCAGGCGCCGGGCAAGGAGCGTGAGGCGGTGAGCTGCATT

AGCAGCAGCGACGGTAGCACCTACTATGCGGATAGCGTTAAGGGCCGTTTT

ACCATCAGCCGTGATAACAGCAAAAACACCCTGTACCTGCAAATGAACAGC

CTGCGTGCGGAAGACACCGCGGTGTATCACTGCGCGACCGATCGTGCGTGC

GGTAGCAGCTGGCTGGGCGCGGAGAGCTGGGCGCAAGGCACCCTGGTTACC

-continued
GTGAGCAGCGGTGGaGGCGGTAGTGGCGGAGGCGGTTCAGGCGGAGGCGGA
TCTGAACCCAAGTCCTGCGACAAGACCCACACCTGTCCCCCTTGTCCTGCC
CCTGAACTGCTGGGCGGACCCAGCGTGTTCCTGTTCCCCCCAAAGCCTAAG
GACACCCTGATGATCTCCCGGACCCCCGAAGTGACCTGCGTGGTGGTGGAT
GTGTCCCACGAGGACCCTGAAGTGAAGTTCAATTGGTACGTGGACGGCGTG
GAAGTGCACAACGCCAAGACCAAGCCTAGAGAGGAACAGTACGCCTCCACC
TACCGGGTGGTGTCCGTGCTGACCGTGCTGCACCAGGATTGGCTGAACGGC
AAAGAGTACAAGTGCAAGGTGTCCAACAAGGCCCTGCCTGCCCCCATCGAA
AAGACCATCTCCAAGGCCAAGGGCCAGCCCCGGGAACCCCAGGTGTACACA
CTGCCCCCTAGCAGGGACGAGCTGACCAAGAACCAGGTGTCCCTGACCTGT
CTCGTGAAAGGCTTCTACCCCTCCGATATCGCCGTGGAATGGGAGTCCAAC
GGCCAGCCTGAGAACAACTATAAGACCACCCCCCCTGTGCTGGACTCCGAC
GGCTCATTCTTCCTGTACAGCAAGCTGACAGTGGACAAGTCCCGGTGGCAG
CAGGGCAACGTGTTCTCCTGCTCCGTGATGCACGAGGCCCTGCACAACCAC
TACACCCAGAAGTCCCTGTCCCTGAGCCCCGGCGGTGGaGGCGGTAGTGGC
GGAGGCGGTTCAGGCGGAGGCGGATCTATTTGGGAGCTGAAGAAAGACGTG
TACGTGGTCGAGCTGGACTGGTACCCTGATGCCCCAGGCGAGATGGTCGTG
CTGACCTGCGATACACCAGAGGAAGATGGTATCACCTGGACACTGGATCAG
TCCTCAGAGGTGCTGGGCTCTGGTAAAACACTGACCATTCAGGTGAAGGAG
TTCGGTGACGCTGGACAGTACACTTGTCATAAGGGCGGGGAGGTGCTGTCT
CACTCCCTGCTGCTGCTGCATAAGAAGGAGGATGGAATCTGGTCCACTGAC
ATCCTGAAAGACCAGAAGGAGCCAAAGAACAAAACCTTCCTGCGATGCGAG
GCTAAGAACTACAGCGGCCGCTTTACATGCTGGTGGCTGACAACCATCAGC
ACCGATCTGACCTTTAGCGTGAAGTCATCCAGGGGCAGTTCAGACCCTCAG
GGAGTCACATGTGGCGCCGCAACCCTGTCAGCAGAGCGAGTGCGGGGAGAC
AATAAGGAATACGAGTACAGCGTCGAGTGTCAGGAGGATTCCGCATGTCCA
GCTGCAGAAGAATCCCTGCCTATCGAAGTCATGGTGGACGCTGTGCATAAA
CTGAAGTACGAGAATTACACCAGCAGCTTTTTCATCCGGGACATCATCAAG
CCCGATCCACCTAAGAATCTGCAGCTGAAGCCTCTGAAAAATAGCCGACAG
GTCGAAGTGTCATGGGAATACCCAGACACCTGGTCAACACCACACTCCTAC
TTCTCCCTGACCTTCTGTGTGCAGGTCCAGGGAAAAAGCAAGCGGGAAAAG
AAAGATCGGGTGTTCACCGACAAGACCAGTGCTACAGTGATTTGCCGGAAG
AATGCCAGCATTTCTGTCAGAGCTCAGGACCGGTACTATAGCTCTTCCTGG
AGCGAGTGGGCTTCAGTGCCATGTTCTGGaGGCGGtGGATCTGGCGGAGGT
GGAAGCGGAGGCGGTGGATCTAGAAACCTGCCCGTCGCAACCCCTGATCCA
GGGATGTTCCCCTGTCTGCATCACAGCCAGAATCTGCTGAGGGCTGTCTCC
AACATGCTGCAGAAGGCTCGACAGACCCTGGAGTTCTACCCATGTACCAGC
GAAGAGATCGACCACGAGGATATCACAAAGGATAAAACCAGCACAGTGGAA
GCATGCCTGCCTCTGGAACTGACCAAGAATGAGAGCTGCCTGAATAGCAGG
GAGACCTCCTTCATCACCAACGGCTCATGCCTGGCTTCAAGGAAGACCAGC
TTCATGATGGCTCTGTGTCTGAGCTCTATCTATGAGGACCTGAAGATGTAC -continued
CAGGTGGAGTTCAAGACCATGAACGCCAAGCTGCTGATGGATCCAAAGAGG
CAGATCTTCCTGGATCAGAATATGCTGGCAGTGATCGATGAGCTGATGCAG
GCCCTGAATTTTAACAGTGAGACAGTGCCTCAGAAGAGCTCTCTGGAAGAG
CCAGACTTTTACAAAACTAAGATCAAGCTGTGCATTCTGCTGCACGCTTTC
CGCATCAGAGCTGTCACTATCGATAGAGTGATGAGCTATCTGAATGCCTCA The full-length amino acid sequence (SEQ ID NO: 12) of the G1-208 fusion protein as used in this study is as follows:

QVQLVESGGGLVQPGGSLRLSCAASGGTLDYYAIGWFRQAPGKEREAVSCI
SSSDGSTYYADSVKGRFTISRDNSKNTLYLQMNSLRAEDTAVYHCATDRAC
GSSWLGAESWAQGTLVTVSSGGGGSGGGGSGGGGSEPKSCDKTHTCPPCPA
PELLGGPSVFLFPPKPKDTLMISRTPEVTCVVVDVSHEDPEVKFNWYVDGV
EVHNAKTKPREEQYASTYRVVSVLTVLHQDWLNGKEYKCKVSNKALPAPIE
KTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNH
YTQKSLSLSPGGGGSGGGGSGGGGSIWELKKDVYVVELDWYPDAPGEMVV
LTCDTPEEDGITWTLDQSSEVLGSGKTLTIQVKEFGDAGQYTCHKGGEVLS
HSLLLLHKKEDGIWSTDILKDQKEPKNKTFLRCEAKNYSGRFTCWWLTTIS
TDLTFSVKSSRGSSDPQGVTCGAATLSAERVRGDNKEYEYSVECQEDSACP
AAEESLPIEVMVDAVHKLKYENYTSSFFIRDIIKPDPPKNLQLKPLKNSRQ
VEVSWEYPDTWSTPHSYFSLTFCVQVQGKSKREKKDRVFTDKTSATVICRK
NASISVRAQDRYYSSSWSEWASVPCSGGGGSGGGGSGGGGSRNLPVATPDP
GMFPCLHHSQNLLRAVSNMLQKARQTLEFYPCTSEEIDHEDITKDKTSVE
ACLPLELTKNESCLNSRETSFITNGSCLASRKTSFMMALCLSSIYEDLKMY
QVEFKTMNAKLLMDPKRQIFLDQNMLAVIDELMQALNFNSETVPQKSSLEE
PDFYKTKIKLCILLHAFRIRAVTIDRVMSYLNAS

The full-length DNA sequence (SEQ ID NO: 13) of the G1-212 fusion protein as used in this study is as follows:

CAAGTTCAACTGGTGGAAAGCGGTGGTGGTCTGGTTCAGCCGGGCGGTAGC
CTGCGTCTGAGCTGCGCGGCGAGCGGTGGTACCCTGGACTACTATGCGATC
GGTTGGTTCCGTCAGGCGCCGGGCAAGGAGCGTGAGGCGGTGAGCTGCATT
AGCAGCAGCGACGGTAGCACCTACTATGCGGATAGCGTTAAGGGCCGTTTT
ACCATCAGCCGTGATAACAGCAAAAACACCCTGTACCTGCAAATGAACAGC
CTGCGTGCGGAAGACACCGCGGTGTATCACTGCGCGACCGATCGTGCGTGC
GGTAGCAGCTGGCTGGGCGCGGAGAGCTGGGCGCAAGGCACCCTGGTTACC
GTGAGCAGCGGTGGaGGCGGTAGTGGCGGAGGCGGTTCAGGCGGAGGCGGA
TCTGAACCCAAGTCCTGCGACAAGACCCACACCTGTCCCCCTTGTCCTGCC
CCTGAACTGCTGGGCGGACCCAGCGTGTTCCTGTTCCCCCCAAAGCCTAAG
GACACCCTGATGATCTCCCGGACCCCCGAAGTGACCTGCGTGGTGGTGGAT
GTGTCCCACGAGGACCCTGAAGTGAAGTTCAATTGGTACGTGGACGGCGTG

-continued

```
GAAGTGCACAACGCCAAGACCAAGCCTAGAGAGGAACAGTACGCCTCCACC
TACCGGGTGGTGTCCGTGCTGACCGTGCTGCACCAGGATTGGCTGAACGGC
AAAGAGTACAAGTGCAAGGTGTCCAACAAGGCCCTGCCTGCCCCATCGAA
AAGACCATCTCCAAGGCCAAGGGCCAGCCCCGGGAACCCCAGGTGTACACA
CTGCCCCCTAGCAGGGACGAGCTGACCAAGAACCAGGTGTCCCTGACCTGT
CTCGTGAAAGGCTTCTACCCCTCCGATATCGCCGTGGAATGGGAGTCCAAC
GGCCAGCCTGAGAACAACTATAAGACCACCCCCCCTGTGCTGGACTCCGAC
GGCTCATTCTTCCTGTACAGCAAGCTGACAGTGGACAAGTCCCGGTGGCAG
CAGGGCAACGTGTTCTCCTGCTCCGTGATGCACGAGGCCCTGCACAACCAC
TACACCCAGAAGTCCCTGTCCCTGAGCCCCGGCGGTGGaGGCGGTAGTGGC
GGAGGCGGTTCAGGCGGAGGCGGATCTGCACCTACTTCAAGTTCTACAAAG
AAAACACAGCTACAACTGGAGCATTTACTGCTGGATTTACAGATGATTTTG
AATGGAATTAATAATTACAAGAATCCCAAACTCACCAGGATGCTCACATTT
AAGTTTTACATGCCCAAGAAGGCCACAGAACTGAAACATCTTCAGTGTCTA
GAAGAAGAACTCAAACCTCTGGAGGAAGTGCTAAATTTAGCTCAAAGCAAA
AACTTTCACTTAAGACCCAGGGACTTAATCAGCAATATCAACGTAATAGTT
CTGGAACTAAAGGGATCTGAAACAACATTCATGTGTGAATATGCTGATGAG
ACAGCAACCATTGTAGAATTTCTGAACAGATGGATTACCTTTTGTCAAAGC
ATCATCTCAACACTGACT
```

The full-length amino acid sequence (SEQ ID NO: 14) of the G1-212 fusion protein as used in this study is as follows:

```
QVQLVESGGGLVQPGGSLRLSCAASGGTLDYYAIGWFRQAPGKEREAVSCI
SSSDGSTYYADSVKGRFTISRDNSKNTLYLQMNSLRAEDTAVYHCATDRAC
GSSWLGAESWAQGTLVTVSSGGGGSGGGGSGGGGSEPKSCDKTHTCPPCPA
PELLGGPSVFLFPPKPKDTLMISRTPEVTCVVVDVSHEDPEVKFNWYVDGV
EVHNAKTKPREEQYASTYRVVSVLTVLHQDWLNGKEYKCKVSNKALPAPIE
KTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNH
YTQKSLSLSPGGGGGSGGGGSGGGGSAPTSSSTKKTQLQLEHLLLDLQMIL
NGINNYKNPKLTRMLTFKFYMPKKATELKHLQCLEEELKPLEEVLNLAQSK
NFHLRPRDLISNINIVLELKGSETTFMCEYADETATIVEFLNRWITFCQS
IISTLT
```

The fusion protein G1-405 used in this study is a heterodimer, which is formed by two Fc chains (Fc1 and Fc2) that are modified and fused with other proteins through a Knob-into-holes structure. The full-length DNA sequence (SEQ ID NO: 15) of Fc1 is as follows:

```
CAAGTTCAACTGGTGGAAAGCGGTGGTGGTCTGGTTCAGCCGGGCGGT
AGCCTGCGTCTGAGCTGCGCGGCGAGCGGTGGTACCCTGGACTACTAT
GCGATCGGTTGGTTCCGTCAGGCGCCGGGCAAGGAGCGTGAGGCGGTG
AGCTGCATTAGCAGCAGCGACGGTAGCACCTACTATGCGGATAGCGTT
AAGGGCCGTTTTACCATCAGCCGTGATAACAGCAAAAACACCCTGTAC
CTGCAAATGAACAGCCTGCGTGCGGAAGACACCGCGGTGTATCACTGC
GCGACCGATCGTGCGTGCGGTAGCAGCTGGCTGGGCGCGGAGAGCTGG
GCGCAAGGCACCCTGGTTACCGTGAGCAGCGGTGGaGGCGGTAGTGGC
GGAGGCGGTTCAGGCGGAGGCGGATCTGAACCCAAGTCCTGCGACAAG
ACCCACACCTGTCCCCCTTGTCCTGCCCCTGAACTGCTGGGCGGACCC
AGCGTGTTCCTGTTCCCCCCAAAGCCTAAGGACACCCTGATGATCTCC
CGGACCCCCGAAGTGACCTGCGTGGTGGTGGATGTGTCCCACGAGGAC
CCTGAAGTGAAGTTCAATTGGTACGTGGACGGCGTGGAAGTGCACAAC
GCCAAGACCAAGCCTAGAGAGGAACAGTACGCCTCCACCTACCGGGTG
GTGTCCGTGCTGACCGTGCTGCACCAGGATTGGCTGAACGGCAAAGAG
TACAAGTGCAAGGTGTCCAACAAGGCCCTGCCTGCCCCCATCGAAAAG
ACCATCTCCAAGGCCAAGGGCCAGCCCCGGGAACCCCAGGTGTACACA
CTGCCCCCTTGCAGGGACGAGCTGACCAAGAACCAGGTGTCCCTGTGG
TGTCTCGTGAAAGGCTTCTACCCCTCCGATATCGCCGTGGAATGGGAG
TCCAACGGCCAGCCTGAGAACAACTATAAGACCACCCCCCCTGTGCTG
GACTCCGACGGCTCATTCTTCCTGTACAGCAAGCTGACAGTGGACAAG
TCCCGGTGGCAGCAGGGCAACGTGTTCTCCTGCTCCGTGATGCACGAG
GCCCTGCACAACCACTACACCCAGAAGTCCCTGTCCCTGAGCCCCGGC
GGTGGaGGCGGTAGTGGCGGAGGCGGTTCAGGCGGAGGCGGATCTATT
TGGGAGCTGAAGAAAGACGTGTACGTGGTCGAGCTGGACTGGTACCCT
GATGCCCCAGGCGAGATGGTCGTGCTGACCTGCGATACACCAGAGGAA
GATGGTATCACCTGGACACTGGATCAGTCCTCAGAGGTGCTGGGCTCT
GGTAAAACACTGACCATTCAGGTGAAGGAGTTCGGTGACGCTGGACAG
TACACTTGTCATAAGGGCGGGGAGGTGCTGTCTCACTCCCTGCTGCTG
CTGCATAAGAAGGAGGATGGAATCTGGTCCACTGACATCCTGAAAGAC
CAGAAGGAGCCAAAGAACAAAACCTTCCTGCGATGCGAGGCTAAGAAC
TACAGCGGCCGCTTTACATGCTGGTGGCTGACAACCATCAGCACCGAT
CTGACCTTTAGCGTGAAGTCATCCAGGGGCAGTTCAGACCCTCAGGGA
GTCACATGTGGCGCCGCAACCCTGTCAGCAGAGCGAGTGCGGGGAGAC
AATAAGGAATACGAGTACAGCGTCGAGTGTCAGGAGGATTCCGCATGT
CCAGCTGCAGAAGAATCCCTGCCTATCGAAGTCATGGTGGACGCTGTG
CATAAACTGAAGTACGAGAATTACACCAGCAGCTTTTTCATCCGGGAC
ATCATCAAGCCCGATCCACCTAAGAATCTGCAGCTGAAGCCTCTGAAA
AATAGCCGACAGGTCGAAGTGTCATGGGAATACCCAGACACCTGGTCA
ACACCACACTCCTACTTCTCCCTGACCTTCTGTGTGCAGGTCCAGGGA
AAAAGCAAGCGGGAAAGAAAGATCGGGTGTTCACCGACAAGACCAGT
GCTACAGTGATTTGCCGGAAGAATGCCAGCATTTCTGTCAGAGCTCAG
GACCGGTACTATAGCTCTTCCTGGAGCGAGTGGGCTTCAGTGCCATGT
TCTGGaGGCGGtGGATCTGGCGGAGGTGGAAGCGGAGGCGGTGGATCT
AGAAACCTGCCCGTCGCAACCCCTGATCCAGGGATGTTCCCCTGTCTG
```

```
CATCACAGCCAGAATCTGCTGAGGGCTGTCTCCAACATGCTGCAGAAG

GCTCGACAGACCCTGGAGTTCTACCCATGTACCAGCGAAGAGATCGAC

CACGAGGATATCACAAAGGATAAAACCAGCACAGTGGAAGCATGCCTG

CCTCTGGAACTGACCAAGAATGAGAGCTGCCTGAATAGCAGGGAGACC

TCCTTCATCACCAACGGCTCATGCCTGGCTTCAAGGAAGACCAGCTTC

ATGATGGCTCTGTGTCTGAGCTCTATCTATGAGGACCTGAAGATGTAC

CAGGTGGAGTTCAAGACCATGAACGCCAAGCTGCTGATGGATCCAAAG

AGGCAGATCTTCCTGGATCAGAATATGCTGGCAGTGATCGATGAGCTG

ATGCAGGCCCTGAATTTTAACAGTGAGACAGTGCCTCAGAAGAGCTCT

CTGGAAGAGCCAGACTTTTACAAAACTAAGATCAAGCTGTGCATTCTG

CTGCACGCTTTCCGCATCAGAGCTGTCACTATCGATAGAGTGATGAGC

TATCTGAATGCCTCA
```

The fusion protein G1-405 used in this study is a heterodimer, which is formed by two Fc chains (Fc1 and Fc2) that are modified and fused with other proteins through a Knob-into-holes structure. The full-length amino acid sequence (SEQ ID NO: 16) of Fc1 is as follows:

```
QVQLVESGGGLVQPGGSLRLSCAASGGTLDYYAIGWFRQAPGKEREAV

SCISSSDGSTYYADSVKGRFTISRDNSKNTLYLQMNSLRAEDTAVYHC

ATDRACGSSWLGAESWAQGTLVTVSSGGGGSGGGGSGGGGSEPKSCDK

THTCPPCPAPELLGGPSVFLFPPKPKDTLMISRTPEVTCVVVDVSHED

PEVKFNWYVDGVEVHNAKTKPREEQYASTYRVVSVLTVLHQDWLNGKE

YKCKVSNKALPAPIEKTISKAKGQPREPQVYTLPPCRDELTKNQVSLW

CLVKGFYPSDIAVEWESNGQPENNYKTTPPVLDSDGSHLYSKLTVDKS

RWQQGNVFSCSVMHEALHNHYTQKSLSLSPGGGGGSGGGGSGGGGSIW

ELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGV

TCGAATLSAERVRGDNKEYEYSVECQEDSACPAAEESLPIEVMVDAVH

KLKYENYTSSFFIRDIIKPDPPKNLQLKPLKNSRQVEVSWEYPDTWST

PHSYFSLTFCVQVQGKSKREKKDRVFTDKTSATVICRKNASISVRAQD

RYYSSSWSEWASVPCSGGGGSGGGGSGGGGSRNLPVATPDPGMFPCLH

HSQNLLRAVSNMLQKARQTLEFYPCTSEEIDHEDITKDKTSTVEACLP

LELTKNESCLNSRETSFITNGSCLASRKTSFMMALCLSSIYEDLKMYQ

VEFKTMNAKLLMDPKRQIFLDQNMLAVIDELMQALNFNSETVPQKSSL

EEPDFYKTKIKLCILLHAFRIRAVTIDRVMSYLNAS
```

The fusion protein G1-405 used in this study is a heterodimer, which is formed by two Fc chains (Fc1 and Fc2) that are modified and fused with other proteins through a Knob-into-holes structure. The full-length DNA sequence (SEQ ID NO: 17) of Fc2 is as follows:

```
CAAGTTCAACTGGTGGAAAGCGGTGGTGGTCTGGTTCAGCCGGGCGGT

AGCCTGCGTCTGAGCTGCGCGGCGAGCGGTGGTACCCTGGACTACTAT

GCGATCGGTTGGTTCCGTCAGGCGCCGGGCAAGGAGCGTGAGGCGGTG

AGCTGCATTAGCAGCAGCGACGGTAGCACCTACTATGCGGATAGCGTT

AAGGGCCGTTTTACCATCAGCCGTGATAACAGCAAAAACACCCTGTAC

CTGCAAATGAACAGCCTGCGTGCGGAAGACACCGCGGTGTATCACTGC

GCGACCGATCGTGCGTGCGGTAGCAGCTGGCTGGGCGCGGAGAGCTGG

GCGCAAGGCACCCTGGTTACCGTGAGCAGCGGTGGaGGCGGTAGTGGC

GGAGGCGGTTCAGGCGGAGGCGGATCTGAACCCAAGTCCTGCGACAAG

ACCCACACCTGTCCCCCTTGTCCTGCCCCTGAACTGCTGGGCGGACCC

AGCGTGTTCCTGTTCCCCCCAAAGCCTAAGGACACCCTGATGATCTCC

CGGACCCCCGAAGTGACCTGCGTGGTGGTGGATGTGTCCCACGAGGAC

CCTGAAGTGAAGTTCAATTGGTACGTGGACGGCGTGGAAGTGCACAAC

GCCAAGACCAAGCCTAGAGAGGAACAGTACGCCTCCACCTACCGGGTG

GTGTCCGTGCTGACCGTGCTGCACCAGGATTGGCTGAACGGCAAAGAG

TACAAGTGCAAGGTGTCCAACAAGGCCCTGCCTGCCCCCATCGAAAAG

ACCATCTCCAAGGCCAAGGGCCAGCCCCGGGAACCCCAGGTGTGTACA

CTGCCCCCTAGCAGGGACGAGCTGACCAAGAACCAGGTGTCCCTGTCC

TGTGCCGTGAAAGGCTTCTACCCCTCCGATATCGCCGTGGAATGGGAG

TCCAACGGCCAGCCTGAGAACAACTATAAGACCACCCCCCCTGTGCTG

GACTCCGACGGCTCATTCTTCCTGGTGAGCAAGCTGACAGTGGACAAG

TCCCGGTGGCAGCAGGGCAACGTGTTCTCCTGCTCCGTGATGCACGAG

GCCCTGCACAACCACTACACCCAGAAGTCCCTGTCCCTGAGCCCCGGC

GGTGGaGGCGGTAGTGGCGGAGGCGGTTCAGGCGGAGGCGGATCTGCA

CCTACTTCAAGTTCTACAAAGAAAACACAGCTACAACTGGAGCATTTA

CTGCTGGATTTACAGATGATTTTGAATGGAATTAATAATTACAAGAAT

CCCAAACTCACCAGGATGCTCACATTTAAGTTTTACATGCCCAAGAAG

GCCACAGAACTGAAACATCTTCAGTGTCTAGAAGAAGAACTCAAACCT

CTGGAGGAAGTGCTAAATTTAGCTCAAAGCAAAAACTTTCACTTAAGA

CCCAGGGACTTAATCAGCAATATCAACGTAATAGTTCTGGAACTAAAG

GGATCTGAAACAACATTCATGTGTGAATATGCTGATGAGACAGCAACC

ATTGTAGAATTTCTGAACAGATGGATTACCTTTTGTCAAAGCATCATC

TCAACACTGACT
```

The fusion protein G1-405 used in this study is a heterodimer, which is formed by two Fc chains (Fc1 and Fc2) that are modified and fused with other proteins through a Knob-into-holes structure. The full-length amino acid sequence (SEQ ID NO: 18) of Fc2 is as follows:

```
QVQLVESGGGLVQPGGSLRLSCAASGGTLDYYAIGWFRQAPGKEREAV

SCISSSDGSTYYADSVKGRFTISRDNSKNTLYLQMNSLRAEDTAVYHC

ATDRACGSSWLGAESWAQGTLVTVSSGGGGSGGGGSGGGGSEPKSCDK
```

THTCPPCPAPELLGGPSVFLFPPKPKDTLMISRTPEVTCVVVDVSHED

PEVKFNWYVDGVEVHNAKTKPREEQYASTYRVVSVLTVLHQDWLNGKE

YKCKVSNKALPAPIEKTISKAKGQPREPQVCTLPPSRDELTKNQVSLS

CAVKGFYPSDIAVEWESNGQPENNYKTTPPVLDSDGSHLVSKLTVDKS

RWQQGNVFSCSVMHEALHNHYTQKSLSLSPGGGGSGGGGSGGGGSAP

TSSSTKKTQLQLEHLLLDLQMILNGINNYKNPKLTRMLTFKFYMPKKA

TELKHLQCLEEELKPLEEVLNLAQSKNFHLRPRDLISNINVIVLELKG

SETTFMCEYADETATIVEFLNRWITFCQSIISTLT

The fusion protein G1-716 used in this study is a heterodimer, which is formed by two Fc chains (Fc3 and Fc4) that are modified and fused with other proteins through a Knob-into-holes structure. The full-length DNA sequence (SEQ ID NO: 19) of Fc3 is as follows:

CAAGTTCAACTGGTGGAAAGCGGTGGTGGTCTGGTTCAGCCGGGCGGT

AGCCTGCGTCTGAGCTGCGCGGCGAGCGGTGGTACCCTGGACTACTAT

GCGATCGGTTGGTTCCGTCAGGCGCCGGGCAAGGAGCGTGAGGCGGTG

AGCTGCATTAGCAGCAGCGACGGTAGCACCTACTATGCGGATAGCGTT

AAGGGCCGTTTTACCATCAGCCGTGATAACAGCAAAAACACCCTGTAC

CTGCAAATGAACAGCCTGCGTGCGGAAGACACCGCGGTGTATCACTGC

GCGACCGATCGTGCGTGCGGTAGCAGCTGGCTGGGCGCGGAGAGCTGG

GCGCAAGGCACCCTGGTTACCGTGAGCAGCGGTGGaGGCGGTAGTGGC

GGAGGCGGTTCAGGCGGAGGCGGATCTCAAGTTCAACTGGTGGAAAGC

GGTGGTGGTCTGGTTCAGCCGGGCGGTAGCCTGCGTCTGAGCTGCGCG

GCGAGCGGTGGTACCCTGGACTACTATGCGATCGGTTGGTTCCGTCAG

GCGCCGGGCAAGGAGCGTGAGGCGGTGAGCTGCATTAGCAGCAGCGAC

GGTAGCACCTACTATGCGGATAGCGTTAAGGGCCGTTTTACCATCAGC

CGTGATAACAGCAAAAACACCCTGTACCTGCAAATGAACAGCCTGCGT

GCGGAAGACACCGCGGTGTATCACTGCGCGACCGATCGTGCGTGCGGT

AGCAGCTGGCTGGGCGCGGAGAGCTGGGCGCAAGGCACCCTGGTTACC

GTGAGCAGCGGTGGaGGCGGTAGTGGCGGAGGCGGTTCAGGCGGAGGC

GGATCTGAACCCAAGTCCTGCGACAAGACCCACACCTGTCCCCCTTGT

CCTGCCCCTGAACTGCTGGGCGGACCCAGCGTGTTCCTGTTCCCCCCA

AAGCCTAAGGACACCCTGATGATCTCCCGGACCCCCGAAGTGACCTGC

GTGGTGGTGGATGTGTCCCACGAGGACCCTGAAGTGAAGTTCAATTGG

TACGTGGACGGCGTGGAAGTGCACAACGCCAAGACCAAGCCTAGAGAG

GAACAGTACGCCTCCACCTACCGGGTGGTGTCCGTGCTGACCGTGCTG

CACCAGGATTGGCTGAACGGCAAAGAGTACAAGTGCAAGGTGTCCAAC

AAGGCCCTGCCTGCCCCCATCGAAAAGACCATCTCCAAGGCCAAGGGC

CAGCCCCGGGAACCCCAGGTGTACACACTGCCCCCTTGCAGGGACGAG

CTGACCAAGAACCAGGTGTCCCTGTGGTGTCTCGTGAAAGGCTTCTAC

CCCTCCGATATCGCCGTGGAATGGGAGTCCAACGCCAGCCTGAGAAC

AACTATAAGACCACCCCCCCTGTGCTGGACTCCGACGGCTCATTCTTC

CTGTACAGCAAGCTGACAGTGGACAAGTCCCGGTGGCAGCAGGGCAAC

GTGTTCTCCTGCTCCGTGATGCACGAGGCCCTGCACAACCACTACACC

CAGAAGTCCCTGTCCCTGAGCCCCGGCGGTGGaGGCGGTAGTGGCGGA

GGCGGTTCAGGCGGAGGCGGATCTATTTGGGAGCTGAAGAAAGACGTG

TACGTGGTCGAGCTGGACTGGTACCCTGATGCCCCAGGCGAGATGGTC

GTGCTGACCTGCGATACACCAGAGGAAGATGGTATCACCTGGACACTG

GATCAGTCCTCAGAGGTGCTGGGCTCTGGTAAAACACTGACCATTCAG

GTGAAGGAGTTCGGTGACGCTGGACAGTACACTTGTCATAAGGGCGGG

GAGGTGCTGTCTCACTCCCTGCTGCTGCTGCATAAGAAGGAGGATGGA

ATCTGGTCCACTGACATCCTGAAAGACCAGAAGGAGCCAAAGAACAAA

ACCTTCCTGCGATGCGAGGCTAAGAACTACAGCGGCCGCTTTACATGC

TGGTGGCTGACAACCATCAGCACCGATCTGACCTTTAGCGTGAAGTCA

TCCAGGGGCAGTTCAGACCCTCAGGGAGTCACATGTGGCGCCGCAACC

CTGTCAGCAGAGCGAGTGCGGGGAGACAATAAGGAATACGAGTACAGC

GTCGAGTGTCAGGAGGATTCCGCATGTCCAGCTGCAGAAGAATCCCTG

CCTATCGAAGTCATGGTGGACGCTGTGCATAAACTGAAGTACGAGAAT

TACACCAGCAGCTTTTTCATCCGGGACATCATCAAGCCCGATCCACCT

AAGAATCTGCAGCTGAAGCCTCTGAAAAATAGCCGACAGGTCGAAGTG

TCATGGGAATACCCAGACACCTGGTCAACACCACACTCCTACTTCTCC

CTGACCTTCTGTGTGCAGGTCCAGGGAAAAAGCAAGCGGGAAAAGAAA

GATCGGGTGTTCACCGACAAGACCAGTGCTACAGTGATTTGCCGGAAG

AATGCCAGCATTTCTGTCAGAGCTCAGGACCGGTACTATAGCTCTTCC

TGGAGCGAGTGGGCTTCAGTGCCATGTTCTGGaGGCGGtGGATCTGGC

GGAGGTGGAAGCGGAGGCGGTGGATCTAGAAACCTGCCCGTCGCAACC

CCTGATCCAGGGATGTTCCCCTGTCTGCATCACAGCCAGAATCTGCTG

AGGGCTGTCTCCAACATGCTGCAGAAGGCTCGACAGACCCTGGAGTTC

TACCCATGTACCAGCGAAGAGATCGACCACGAGGATATCACAAAGGAT

AAAACCAGCACAGTGGAAGCATGCCTGCCTCTGGAACTGACCAAGAAT

GAGAGCTGCCTGAATAGCAGGGAGACCTCCTTCATCACCAACGGCTCA

TGCCTGGCTTCAAGGAAGACCAGCTTCATGATGGCTCTGTGTCTGAGC

TCTATCTATGAGGACCTGAAGATGTACCAGGTGGAGTTCAAGACCATG

AACGCCAAGCTGCTGATGGATCCAAAGAGGCAGATCTTCCTGGATCAG

AATATGCTGGCAGTGATCGATGAGCTGATGCAGGCCCTGAATTTTAAC

AGTGAGACAGTGCCTCAGAAGAGCTCTCTGGAAGAGCCAGACTTTTAC

AAAACTAAGATCAAGCTGTGCATTCTGCTGCACGCTTTCCGCATCAGA

GCTGTCACTATCGATAGAGTGATGAGCTATCTGAATGCCTCA

The fusion protein G1-716 used in this study is a heterodimer, which is formed by two Fc chains (Fc3 and Fc4) that are modified and fused with other proteins through a Knob-into-holes structure. The full-length amino acid sequence (SEQ ID NO: 20) of Fc3 is as follows:

QVQLVESGGGLVQPGGSLRLSCAASGGTLDYYAIGWFRQAPGKEREAV
SCISSSDGSTYYADSVKGRFTISRDNSKNTLYLQMNSLRAEDTAVYHC
ATDRACGSSWLGAESWAQGTLVTVSSGGGGSGGGGSGGGGSQVQLVES
GGGLVQPGGSLRLSCAASGGTLDYYAIGWFRQAPGKEREAVSCISSSD
GSTYYADSVKGRFTISRDNSKNTLYLQMNSLRAEDTAVYHCATDRACG
SSWLGAESWAQGTLVTVSSGGGGSGGGGSGGGGSEPKSCDKTHTCPPC
PAPELLGGPSVFLFPPKPKDTLMISRTPEVTCVVVDVSHEDPEVKFNW
YVDGVEVHNAKTKPREEQYASTYRVVSVLTVLHQDWLNGKEYKCKVSN
KALPAPIEKTISKAKGQPREPQVYTLPPCRDELTKNQVSLWCLVKGFY
PSDIAVEWESNGQPENNYKTTPPVLDSDGSFFLYSKLTVDKSRWQQGN
VFSCSVMHEALHNHYTQKSLSLSPGGGGSGGGGSGGGGSIWELKKDV
YVVELDWYPDAPGEMVVLTCDTPEEDGITWTLDQSSEVLGSGKTLTIQ
VKEFGDAGQYTCHKGGEVLSHSLLLLHKKEDGIWSTDILKDQKEPKNK
TFLRCEAKNYSGRFTCWWLTTISTDLTFSVKSSRGSSDPQGVTCGAAT
LSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFS
LTFCVQVQGKSKREKKDRVFTDKTSATVICRKNASISVRAQDRYYSSS
WSEWASVPCSGGGGSGGGGSGGGGSRNLPVATPDPGMFPCLHHSQNLL
RAVSNMLQKARQTLEFYPCTSEEIDHEDITKDKTSTVEACLPLELTKN
ESCLNSRETSFITNGSCLASRKTSFMMALCLSSIYEDLKMYQVEFKTM
NAKLLMDPKRQIFLDQNMLAVIDELMQALNFNSETVPQKSSLEEPDFY
KTKIKLCILLHAFRIRAVTIDRVMSYLNAS

The fusion protein G1-716 used in this study is a heterodimer, which is formed by two Fc chains (Fc3 and Fc4) that are modified and fused with other proteins through a Knob-into-holes structure. The full-length DNA sequence (SEQ ID NO: 21) of Fc4 is as follows:

CAAGTTCAACTGGTGGAAAGCGGTGGTGGTCTGGTTCAGCCGGGCGGT
AGCCTGCGTCTGAGCTGCGCGGCGAGCGGTGGTACCCTGGACTACTAT
GCGATCGGTTGGTTCCGTCAGGCGCCGGGCAAGGAGCGTGAGGCGGTG
AGCTGCATTAGCAGCAGCGACGGTAGCACCTACTATGCGGATAGCGTT
AAGGGCCGTTTTACCATCAGCCGTGATAACAGCAAAAACACCCTGTAC
CTGCAAATGAACAGCCTGCGTGCGGAAGACACCGCGGTGTATCACTGC
GCGACCGATCGTGCGTGCGGTAGCAGCTGGCTGGGCGCGGAGAGCTGG
GCGCAAGGCACCCTGGTTACCGTGAGCAGCGGTGGaGGCGGTAGTGGC
GGAGGCGGTTCAGGCGGAGGCGGATCTCAAGTTCAACTGGTGGAAAGC
GGTGGTGGTCTGGTTCAGCCGGGCGGTAGCCTGCGTCTGAGCTGCGCG
GCGAGCGGTGGTACCCTGGACTACTATGCGATCGGTTGGTTCCGTCAG
GCGCCGGGCAAGGAGCGTGAGGCGGTGAGCTGCATTAGCAGCAGCGAC
GGTAGCACCTACTATGCGGATAGCGTTAAGGGCCGTTTTACCATCAGC
CGTGATAACAGCAAAAACACCCTGTACCTGCAAATGAACAGCCTGCGT

GCGGAAGACACCGCGGTGTATCACTGCGCGACCGATCGTGCGTGCGGT
AGCAGCTGGCTGGGCGCGGAGAGCTGGGCGCAAGGCACCCTGGTTACC
GTGAGCAGCGGTGGaGGCGGTAGTGGCGGAGGCGGTTCAGGCGGAGGC
GGATCTGAACCCAAGTCCTGCGACAAGACCCACACCTGTCCCCCTTGT
CCTGCCCCTGAACTGCTGGGCGGACCCAGCGTGTTCCTGTTCCCCCCA
AAGCCTAAGGACACCCTGATGATCTCCCGGACCCCCGAAGTGACCTGC
GTGGTGGTGGATGTGTCCCACGAGGACCCTGAAGTGAAGTTCAATTGG
TACGTGGACGGCGTGGAAGTGCACAACGCCAAGACCAAGCCTAGAGAG
GAACAGTACGCCTCCACCTACCGGGTGGTGTCCGTGCTGACCGTGCTG
CACCAGGATTGGCTGAACGGCAAAGAGTACAAGTGCAAGGTGTCCAAC
AAGGCCCTGCCTGCCCCCATCGAAAAGACCATCTCCAAGGCCAAGGGC
CAGCCCCGGGAACCCCAGGTGTGTACACTGCCCCCTAGCAGGGACGAG
CTGACCAAGAACCAGGTGTCCCTGTCCTGTGCCGTGAAAGGCTTCTAC
CCCTCCGATATCGCCGTGGAATGGGAGTCCAACGGCCAGCCTGAGAAC
AACTATAAGACCACCCCCCCTGTGCTGGACTCCGACGGCTCATTCTTC
CTGGTGAGCAAGCTGACAGTGGACAAGTCCCGGTGGCAGCAGGGCAAC
GTGTTCTCCTGCTCCGTGATGCACGAGGCCCTGCACAACCACTACACC
CAGAAGTCCCTGTCCCTGAGCCCCGGCGGTGGaGGCGGTAGTGGCGGA
GGCGGTTCAGGCGGAGGCGGATCTGCACCTACTTCAAGTTCTACAAAG
AAAACACAGCTACAACTGGAGCATTTACTGCTGGATTTACAGATGATT
TTGAATGGAATTAATAATTACAAGAATCCCAAACTCACCAGGATGCTC
ACATTTAAGTTTTACATGCCCAAGAAGGCCACAGAACTGAAACATCTT
CAGTGTCTAGAAGAAGAACTCAAACCTCTGGAGGAAGTGCTAAATTTA
GCTCAAAGCAAAAACTTTCACTTAAGACCCAGGGACTTAATCAGCAAT
ATCAACGTAATAGTTCTGGAACTAAAGGGATCTGAAACAACATTCATG
TGTGAATATGCTGATGAGACAGCAACCATTGTAGAATTTCTGAACAGA
TGGATTACCTTTTGTCAAAGCATCATCTCAACACTGACT

The fusion protein G1-716 used in this study is a heterodimer, which is formed by two Fc chains (Fc3 and Fc4) that are modified and fused with other proteins through a Knob-into-holes structure. The full-length amino acid sequence (SEQ ID NO: 22) of Fc4 is as follows:

QVQLVESGGGLVQPGGSLRLSCAASGGTLDYYAIGWFRQAPGKEREAV
SCISSSDGSTYYADSVKGRFTISRDNSKNTLYLQMNSLRAEDTAVYHC
ATDRACGSSWLGAESWAQGTLVTVSSGGGGSGGGGSGGGGSQVQLVES
GGGLVQPGGSLRLSCAASGGTLDYYAIGWFRQAPGKEREAVSCISSSD
GSTYYADSVKGRFTISRDNSKNTLYLQMNSLRAEDTAVYHCATDRACG
SSWLGAESWAQGTLVTVSSGGGGSGGGGSGGGGSEPKSCDKTHTCPPC
PAPELLGGPSVFLFPPKPKDTLMISRTPEVTCVVVDVSHEDPEVKFNW
YVDGVEVHNAKTKPREEQYASTYRVVSVLTVLHQDWLNGKEYKCKVSN
KALPAPIEKTISKAKGQPREPQVCTLPPSRDELTKNQVSLSCAVKGFY

-continued
PSDIAVEWESNGQPENNYKTTPPVLDSDGSHLVSKLTVDKSRWQQGNV

FSCSVMHEALHNHYTQKSLSLSPGGGGSGGGGSGGGGSAPTSSSTKK

TQLQLEHLLLDLQMILNGINNYKNPKLTRMLTFKFYMPKKATELKHLQ

CLEEELKPLEEVLNLAQSKNFHLRPRDLISNINVIVLELKGSETTFMC

EYADETATIVEFLNRWITFCQSIISTLT

The fusion protein G1-723 used in this study is a heterodimer, which is formed by two Fc chains (Fc3 and Fc5) that are modified and fused with other proteins through a Knob-into-holes structure. The full-length DNA sequence (SEQ ID NO: 23) of Fc5 is as follows:

CAAGTTCAACTGGTGGAAAGCGGTGGTGGTCTGGTTCAGCCGGGCGGT

AGCCTGCGTCTGAGCTGCGCGGCGAGCGGTGGTACCCTGGACTACTAT

GCGATCGGTTGGTTCCGTCAGGCGCCGGGCAAGGAGCGTGAGGCGGTG

AGCTGCATTAGCAGCAGCGACGGTAGCACCTACTATGCGGATAGCGTT

AAGGGCCGTTTTACCATCAGCCGTGATAACAGCAAAAACACCCTGTAC

CTGCAAATGAACAGCCTGCGTGCGGAAGACACCGCGGTGTATCACTGC

GCGACCGATCGTGCGTGCGGTAGCAGCTGGCTGGGCGCGGAGAGCTGG

GCGCAAGGCACCCTGGTTACCGTGAGCAGCGGTGGaGGCGGTAGTGGC

GGAGGCGGTTCAGGCGGAGGCGGATCTCAAGTTCAACTGGTGGAAAGC

GGTGGTGGTCTGGTTCAGCCGGGCGGTAGCCTGCGTCTGAGCTGCGCG

GCGAGCGGTGGTACCCTGGACTACTATGCGATCGGTTGGTTCCGTCAG

GCGCCGGGCAAGGAGCGTGAGGCGGTGAGCTGCATTAGCAGCAGCGAC

GGTAGCACCTACTATGCGGATAGCGTTAAGGGCCGTTTTACCATCAGC

CGTGATAACAGCAAAAACACCCTGTACCTGCAAATGAACAGCCTGCGT

GCGGAAGACACCGCGGTGTATCACTGCGCGACCGATCGTGCGTGCGGT

AGCAGCTGGCTGGGCGCGGAGAGCTGGGCGCAAGGCACCCTGGTTACC

GTGAGCAGCGGTGGaGGCGGTAGTGGCGGAGGCGGTTCAGGCGGAGGC

GGATCTGAACCCAAGTCCTGCGACAAGACCCACACCTGTCCCCCTTGT

CCTGCCCCTGAACTGCTGGGCGGACCCAGCGTGTTCCTGTTCCCCCCA

AAGCCTAAGGACACCCTGATGATCTCCCGGACCCCCGAAGTGACCTGC

GTGGTGGTGGATGTGTCCCACGAGGACCCTGAAGTGAAGTTCAATTGG

TACGTGGACGGCGTGGAAGTGCACAACGCCAAGACCAAGCCTAGAGAG

GAACAGTACGCCTCCACCTACCGGGTGGTGTCCGTGCTGACCGTGCTG

CACCAGGATTGGCTGAACGGCAAGGAGTACAAGTGCAAGGTGTCCAAC

AAGGCCCTGCCTGCCCCCATCGAAAAGACCATCTCCAAGGCCAAGGGC

CAGCCCCGGGAACCCCAGGTGTGTACACTGCCCCCTAGCAGGGACGAG

CTGACCAAGAACCAGGTGTCCCTGTCCTGTGCCGTGAAAGGCTTCTAC

CCCTCCGATATCGCCGTGGAATGGGAGTCCAACGGCCAGCCTGAGAAC

AACTATAAGACCACCCCCCCTGTGCTGGACTCCGACGGCTCATTCTTC

CTGGTGAGCAAGCTGACAGTGGACAAGTCCCGGTGGCAGCAGGGCAAC

GTGTTCTCCTGCTCCGTGATGCACGAGGCCCTGCACAACCACTACACC

-continued
CAGAAGTCCCTGTCCCTGAGCCCCGGCGGTGGaGGCGGTAGTGGCGGA

GGCGGTTCAGGCGGAGGCGGATCTGCACCTACTTCAAGTTCTACAAAG

AAAACACAGCTACAACTGGAGCATTTACTGCTGGATTTACAGATGATT

TTGAATGGAATTAATAATTACAAGAATCCCAAACTCACCAGGATGCTC

ACATTTAAGTTTTACATGCCCAAGAAGGCCACAGAACTGAAACATCTT

CAGTGTCTAGAAGAAGAACTCAAACCTCTGGAGGAAGTGCTAAATTTA

GCTCAAAGCAAAAACTTTCACTTCGACCCCAGGGACGTGGTGAGCAAT

ATCAACGTATTCGTTCTGGAACTAAAGGGATCTGAAACAACATTCATG

TGTGAATATGCTGATGAGACAGCAACCATTGTAGAATTTCTGAACAGA

TGGATTACCTTTTGTCAAAGCATCATCTCAACACTGACT

The fusion protein G1-723 used in this study is a heterodimer, which is formed by two Fc chains (Fc3 and Fc5) that are modified and fused with other proteins through a Knob-into-holes structure. The full-length amino acid sequence (SEQ ID NO: 24) of Fc5 is as follows:

QVQLVESGGGLVQPGGSLRLSCAASGGTLDYYAIGWFRQAPGKEREAV

SCISSSDGSTYYADSVKGRFTISRDNSKNTLYLQMNSLRAEDTAVYHC

ATDRACGSSWLGAESWAQGTLVTVSSGGGGSGGGGSGGGGSQVQLVES

GGGLVQPGGSLRLSCAASGGTLDYYAIGWFRQAPGKEREAVSCISSSD

GSTYYADSVKGRFTISRDNSKNTLYLQMNSLRAEDTAVYHCATDRACG

SSWLGAESWAQGTLVTVSSGGGGSGGGGSGGGGSEPKSCDKTHTCPPC

PAPELLGGPSVFLFPPKPKDTLMISRTPEVTCVVVDVSHEDPEVKFNW

YVDGVEVHNAKTKPREEQYASTYRVVSVLTVLHQDWLNGKEYKCKVSN

KALPAPIEKTISKAKGQPREPQVCTLPPSRDELTKNQVSLSCAVKGFY

PSDIAVEWESNGQPENNYKTTPPVLDSDGSHLVSKLTVDKSRWQQGNV

FSCSVMHEALHNHYTQKSLSLSPGGGGSGGGGSGGGGSAPTSSSTKK

TQLQLEHLLLDLQMILNGINNYKNPKLTRMLTFKFYMPKKATELKHLQ

CLEEELKPLEEVLNLAQSKNFHFDPRDVVSNINVFVLELKGSETTFMC

EYADETATIVEFLNRWITFCQSIISTLT

The fusion protein G1-717 used in this study is a heterodimer, which is formed by two Fc chains (Fc6 and Fc7) that are modified and fused with other proteins through a Knob-into-holes structure. The full-length DNA sequence (SEQ ID NO: 25) of Fc6 is as follows:

CAAGTTCAACTGGTGGAAAGCGGTGGTGGTCTGGTTCAGCCGGGCGGT

AGCCTGCGTCTGAGCTGCGCGGCGAGCGGTGGTACCCTGGACTACTAT

GCGATCGGTTGGTTCCGTCAGGCGCCGGGCAAGGAGCGTGAGGCGGTG

AGCTGCATTAGCAGCAGCGACGGTAGCACCTACTATGCGGATAGCGTT

AAGGGCCGTTTTACCATCAGCCGTGATAACAGCAAAAACACCCTGTAC

CTGCAAATGAACAGCCTGCGTGCGGAAGACACCGCGGTGTATCACTGC

GCGACCGATCGTGCGTGCGGTAGCAGCTGGCTGGGCGCGGAGAGCTGG

GCGCAAGGCACCCTGGTTACCGTGAGCAGCGGTGGaGGCGGTAGTGGC

```
GGAGGCGGTTCAGGCGGAGGCGGATCTCAAGTTCAACTGGTGGAAAGC
GGTGGTGGTCTGGTTCAGCCGGGCGGTAGCCTGCGTCTGAGCTGCGCG
GCGAGCGGTGGTACCCTGGACTACTATGCGATCGGTTGGTTCCGTCAG
GCGCCGGGCAAGGAGCGTGAGGCGGTGAGCTGCATTAGCAGCAGCGAC
GGTAGCACCTACTATGCGGATAGCGTTAAGGGCCGTTTTACCATCAGC
CGTGATAACAGCAAAAACACCCTGTACCTGCAAATGAACAGCCTGCGT
GCGGAAGACACCGCGGTGTATCACTGCGCGACCGATCGTGCGTGCGGT
AGCAGCTGGCTGGGCGCGGAGAGCTGGGCGCAAGGCACCCTGGTTACC
GTGAGCAGCGGTGGaGGCGGTAGTGGCGGAGGCGGTTCAGGCGGAGGC
GGATCTGAACCCAAGTCCTGCGACAAGACCCACACCTGTCCCCCTTGT
CCTGCCCCTGAACTGCTGGGCGGACCCAGCGTGTTCCTGTTCCCCCCA
AAGCCTAAGGACACCCTGATGATCTCCCGGACCCCCGAAGTGACCTGC
GTGGTGGTGGATGTGTCCCACGAGGACCCTGAAGTGAAGTTCAATTGG
TACGTGGACGGCGTGGAAGTGCACAACGCCAAGACCAAGCCTAGAGAG
GAACAGTACGCCTCCACCTACCGGGTGGTGTCCGTGCTGACCGTGCTG
CACCAGGATTGGCTGAACGGCAAAGAGTACAAGTGCAAGGTGTCCAAC
AAGGCCCTGCCTGCCCCCATCGAAAAGACCATCTCCAAGGCCAAGGGC
CAGCCCCGGGAACCCCAGGTGTACACACTGCCCCCTTGCAGGGACGAG
CTGACCAAGAACCAGGTGTCCCTGTGGTGTCTCGTGAAAGGCTTCTAC
CCCTCCGATATCGCCGTGGAATGGGAGTCCAACGGCCAGCCTGAGAAC
AACTATAAGACCACCCCCCCTGTGCTGGACTCCGACGGCTCATTCTTC
CTGTACAGCAAGCTGACAGTGGACAAGTCCCGGTGGCAGCAGGGCAAC
GTGTTCTCCTGCTCCGTGATGCACGAGGCCCTGCACAACCACTACACC
CAGAAGTCCCTGTCCCTGAGCCCCGGCGGTGGaGGCGGTAGTGGCGGA
GGCGGTTCAGGCGGAGGCGGATCTGCACCTACTTCAAGTTCTACAAAG
AAAACACAGCTACAACTGGAGCATTTACTGCTGGATTTACAGATGATT
TTGAATGGAATTAATAATTACAAGAATCCCAAACTCACCAGGATGCTC
ACATTTAAGTTTTACATGCCCAAGAAGGCCACAGAACTGAAACATCTT
CAGTGTCTAGAAGAAGAACTCAAACCTCTGGAGGAAGTGCTAAATTTA
GCTCAAAGCAAAAACTTTCACTTAAGACCCAGGGACTTAATCAGCAAT
ATCAACGTAATAGTTCTGGAACTAAAGGGATCTGAAACAACATTCATG
TGTGAATATGCTGATGAGACAGCAACCATTGTAGAATTTCTGAACAGA
TGGATTACCTTTTGTCAAAGCATCATCTCAACACTGACT
```

The fusion protein G1-717 used in this study is a heterodimer, which is formed by two Fc chains (Fc6 and Fc7) that are modified and fused with other proteins through a Knob-into-holes structure. The full-length amino acid sequence (SEQ ID NO: 26) of Fc6 is as follows:

```
QVQLVESGGGLVQPGGSLRLSCAASGGTLDYYAIGWFRQAPGKEREAV
SCISSSDGSTYYADSVKGRFTISRDNSKNTLYLQMNSLRAEDTAVYHC
ATDRACGSSWLGAESWAQGTLVTVSSGGGGSGGGGSGGGGSQVQLVES
GGGLVQPGGSLRLSCAASGGTLDYYAIGWFRQAPGKEREAVSCISSSD
GSTYYADSVKGRFTISRDNSKNTLYLQMNSLRAEDTAVYHCATDRACG
SSWLGAESWAQGTLVTVSSGGGGSGGGGSGGGGSEPKSCDKTHTCPPC
PAPELLGGPSVFLFPPKPKDTLMISRTPEVTCVVVDVSHEDPEVKFNW
YVDGVEVHNAKTKPREEQYASTYRVVSVLTVLHQDWLNGKEYKCKVSN
KALPAPIEKTISKAKGQPREPQVYTLPPCRDELTKNQVSLWCLVKGFY
PSDIAVEWESNGQPENNYKTTPPVLDSDGSFFLYSKLTVDKSRWQQGN
VFSCSVMHEALHNHYTQKSLSLSPGGGGGSGGGGSGGGGSAPTSSSTK
KTQLQLEHLLLDLQMILNGINNYKNPKLTRMLTFKFYMPKKATELKHL
QCLEEELKPLEEVLNLAQSKNFHLRPRDLISNINVIVLELKGSETTFM
CEYADETATIVEFLNRWITFCQSIISTLT
```

The fusion protein G1-717 used in this study is a heterodimer, which is formed by two Fc chains (Fc6 and Fc7) that are modified and fused with other proteins through a Knob-into-holes structure. The full-length DNA sequence (SEQ ID NO: 27) of Fc7 is as follows:

```
CAAGTTCAACTGGTGGAAAGCGGTGGTGGTCTGGTTCAGCCGGGCGGT
AGCCTGCGTCTGAGCTGCGCGGCGAGCGGTGGTACCCTGGACTACTAT
GCGATCGGTTGGTTCCGTCAGGCGCCGGGCAAGGAGCGTGAGGCGGTG
AGCTGCATTAGCAGCAGCGACGGTAGCACCTACTATGCGGATAGCGTT
AAGGGCCGTTTTACCATCAGCCGTGATAACAGCAAAAACACCCTGTAC
CTGCAAATGAACAGCCTGCGTGCGGAAGACACCGCGGTGTATCACTGC
GCGACCGATCGTGCGTGCGGTAGCAGCTGGCTGGGCGCGGAGAGCTGG
GCGCAAGGCACCCTGGTTACCGTGAGCAGCGGTGGaGGCGGTAGTGGC
GGAGGCGGTTCAGGCGGAGGCGGATCTCAAGTTCAACTGGTGGAAAGC
GGTGGTGGTCTGGTTCAGCCGGGCGGTAGCCTGCGTCTGAGCTGCGCG
GCGAGCGGTGGTACCCTGGACTACTATGCGATCGGTTGGTTCCGTCAG
GCGCCGGGCAAGGAGCGTGAGGCGGTGAGCTGCATTAGCAGCAGCGAC
GGTAGCACCTACTATGCGGATAGCGTTAAGGGCCGTTTTACCATCAGC
CGTGATAACAGCAAAAACACCCTGTACCTGCAAATGAACAGCCTGCGT
GCGGAAGACACCGCGGTGTATCACTGCGCGACCGATCGTGCGTGCGGT
AGCAGCTGGCTGGGCGCGGAGAGCTGGGCGCAAGGCACCCTGGTTACC
GTGAGCAGCGGTGGaGGCGGTAGTGGCGGAGGCGGTTCAGGCGGAGGC
GGATCTGAACCCAAGTCCTGCGACAAGACCCACACCTGTCCCCCTTGT
CCTGCCCCTGAACTGCTGGGCGGACCCAGCGTGTTCCTGTTCCCCCCA
AAGCCTAAGGACACCCTGATGATCTCCCGGACCCCCGAAGTGACCTGC
GTGGTGGTGGATGTGTCCCACGAGGACCCTGAAGTGAAGTTCAATTGG
TACGTGGACGGCGTGGAAGTGCACAACGCCAAGACCAAGCCTAGAGAG
GAACAGTACGCCTCCACCTACCGGGTGGTGTCCGTGCTGACCGTGCTG
CACCAGGATTGGCTGAACGGCAAAGAGTACAAGTGCAAGGTGTCCAAC
AAGGCCCTGCCTGCCCCCATCGAAAAGACCATCTCCAAGGCCAAGGGC
```

```
CAGCCCCGGGAACCCCAGGTGTGTACACTGCCCCCTAGCAGGGACGAG

CTGACCAAGAACCAGGTGTCCCTGTCCTGTGCCGTGAAAGGCTTCTAC

CCCTCCGATATCGCCGTGGAATGGGAGTCCAACGGCCAGCCTGAGAAC

AACTATAAGACCACCCCCCCTGTGCTGGACTCCGACGGCTCATTCTTC

CTGGTGAGCAAGCTGACAGTGGACAAGTCCCGGTGGCAGCAGGGCAAC

GTGTTCTCCTGCTCCGTGATGCACGAGGCCCTGCACAACCACTACACC

CAGAAGTCCCTGTCCCTGAGCCCCGGC
```

The fusion protein G1-717 used in this study is a heterodimer, which is formed by two Fc chains (Fc6 and Fc7) that are modified and fused with other proteins through a Knob-into-holes structure. The full-length amino acid sequence (SEQ ID NO: 28) of Fc7 is as follows:

```
QVQLVESGGGLVQPGGSLRLSCAASGGTLDYYAIGWFRQAPGKEREAV

SCISSSDGSTYYADSVKGRFTISRDNSKNTLYLQMNSLRAEDTAVYHC

ATDRACGSSWLGAESWAQGTLVTVSSGGGGSGGGGSGGGGSQVQLVES

GGGLVQPGGSLRLSCAASGGTLDYYAIGWFRQAPGKEREAVSCISSSD

GSTYYADSVKGRFTISRDNSKNTLYLQMNSLRAEDTAVYHCATDRACG

SSWLGAESWAQGTLVTVSSGGGGSGGGGSGGGGSEPKSCDKTHTCPPC

PAPELLGGPSVFLFPPKPKDTLMISRTPEVTCVVVDVSHEDPEVKFNW

YVDGVEVHNAKTKPREEQYASTYRVVSVLTVLHQDWLNGKEYKCKVSN

KALPAPIEKTISKAKGQPREPQVCTLPPSRDELTKNQVSLSCAVKGFY

PSDIAVEWESNGQPENNYKTTPPVLDSDGSHLVSKLTVDKSRWQQGNV

FSCSVMHEALHNHYTQKSLSLSPG
```

The fusion protein G1-719 used in this study is a heterodimer, which is formed by two Fc chains (Fc3 and Fc7) that are modified and fused with other proteins through a Knob-into-holes structure. The full-length DNA and amino acid sequences of the Fc3 and Fc7 have been shown hereabove.

The fusion protein G1-709 used in this study is a homodimer, and the full-length DNA sequence (SEQ ID NO: 29) is as follows:

```
CAAGTTCAACTGGTGGAAAGCGGTGGTGGTCTGGTTCAGCCGGGCGGT

AGCCTGCGTCTGAGCTGCGCGGCGAGCGGTGGTACCCTGGACTACTAT

GCGATCGGTTGGTTCCGTCAGGCGCCGGGCAAGGAGCGTGAGGCGGTG

AGCTGCATTAGCAGCAGCGACGGTAGCACCTACTATGCGGATAGCGTT

AAGGGCCGTTTTACCATCAGCCGTGATAACAGCAAAAACACCCTGTAC

CTGCAAATGAACAGCCTGCGTGCGGAAGACACCGCGGTGTATCACTGC

GCGACCGATCGTGCGTGCGGTAGCAGCTGGCTGGGCGCGGAGAGCTGG

GCGCAAGGCACCCTGGTTACCGTGAGCAGCGGTGGaGGCGGTAGTGGC

GGAGGCGGTTCAGGCGGAGGCGGATCTCAAGTTCAACTGGTGGAAAGC

GGTGGTGGTCTGGTTCAGCCGGGCGGTAGCCTGCGTCTGAGCTGCGCG

GCGAGCGGTGGTACCCTGGACTACTATGCGATCGGTTGGTTCCGTCAG

GCGCCGGGCAAGGAGCGTGAGGCGGTGAGCTGCATTAGCAGCAGCGAC

GGTAGCACCTACTATGCGGATAGCGTTAAGGGCCGTTTTACCATCAGC

CGTGATAACAGCAAAAACACCCTGTACCTGCAAATGAACAGCCTGCGT

GCGGAAGACACCGCGGTGTATCACTGCGCGACCGATCGTGCGTGCGGT

AGCAGCTGGCTGGGCGCGGAGAGCTGGGCGCAAGGCACCCTGGTTACC

GTGAGCAGCGGTGGaGGCGGTAGTGGCGGAGGCGGTTCAGGCGGAGGC

GGATCTGAACCCAAGTCCTGCGACAAGACCCACACCTGTCCCCCTTGT

CCTGCCCCTGAACTGCTGGGCGGACCCAGCGTGTTCCTGTTCCCCCCA

AAGCCTAAGGACACCCTGATGATCTCCCGGACCCCCGAAGTGACCTGC

GTGGTGGTGGATGTGTCCCACGAGGACCCTGAAGTGAAGTTCAATTGG

TACGTGGACGGCGTGGAAGTGCACAACGCCAAGACCAAGCCTAGAGAG

GAACAGTACGCCTCCACCTACCGGGTGGTGTCCGTGCTGACCGTGCTG

CACCAGGATTGGCTGAACGGCAAAGAGTACAAGTGCAAGGTGTCCAAC

AAGGCCCTGCCTGCCCCCATCGAAAAGACCATCTCCAAGGCCAAGGGC

CAGCCCCGGGAACCCCAGGTGTACACACTGCCCCCTAGCAGGGACGAG

CTGACCAAGAACCAGGTGTCCCTGACCTGTCTCGTGAAAGGCTTCTAC

CCCTCCGATATCGCCGTGGAATGGGAGTCCAACGGCCAGCCTGAGAAC

AACTATAAGACCACCCCCCCTGTGCTGGACTCCGACGGCTCATTCTTC

CTGTACAGCAAGCTGACAGTGGACAAGTCCCGGTGGCAGCAGGGCAAC

GTGTTCTCCTGCTCCGTGATGCACGAGGCCCTGCACAACCACTACACC

CAGAAGTCCCTGTCCCTGAGCCCCGGC
```

The fusion protein G1-709 used in this study is a homodimer, and the full-length amino acid sequence (SEQ ID NO: 30) of the polypeptide chain is as follows:

```
QVQLVESGGGLVQPGGSLRLSCAASGGTLDYYAIGWFRQAPGKEREAVSC

ISSSDGSTYYADSVKGRFTISRDNSKNTLYLQMNSLRAEDTAVYHCATDR

ACGSSWLGAESWAQGTLVTVSSGGGGSGGGGSGGGGSQVQLVESGGGLVQ

PGGSLRLSCAASGGTLDYYAIGWFRQAPGKEREAVSCISSSDGSTYYADS

VKGRFTISRDNSKNTLYLQMNSLRAEDTAVYHCATDRACGSSWLGAESWA

QGTLVTVSSGGGGSGGGGSGGGGSEPKSCDKTHTCPPCPAPELLGGPSVF

LFPPKPKDTLMISRTPEVTCVVVDVSHEDPEVKFNWYVDGVEVHNAKTKP

REEQYASTYRVVSVLTVLHQDWLNGKEYKCKVSNKALPAPIEKTISKAKG

QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPG
```

2. Analysis of Experimental Results of IFN-γ Release

In this experiment, the in vitro biological activities of the cytokines IL-12 and IL-2 in the fusion protein are verified by employing the cytokines to stimulate the NK92 cells to release the interferon-gamma (IFN-γ). Since the fusion protein constructed in this experiment contains the cytokine, different fusion proteins are incubated with the NK92 cells, and then the release of IFN-γ is detected.

Figure 2:
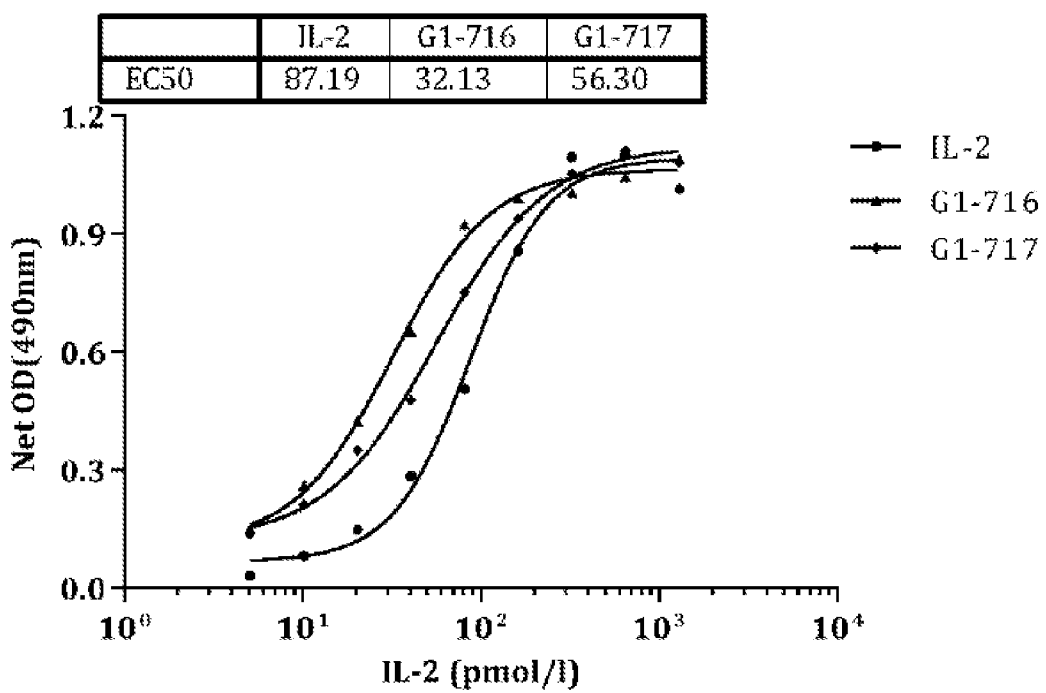
FIG. 2 shows the IL-2 activities of G1-716 and G1-717 fusion proteins compared with that of a control IL-2.
Figure 3:
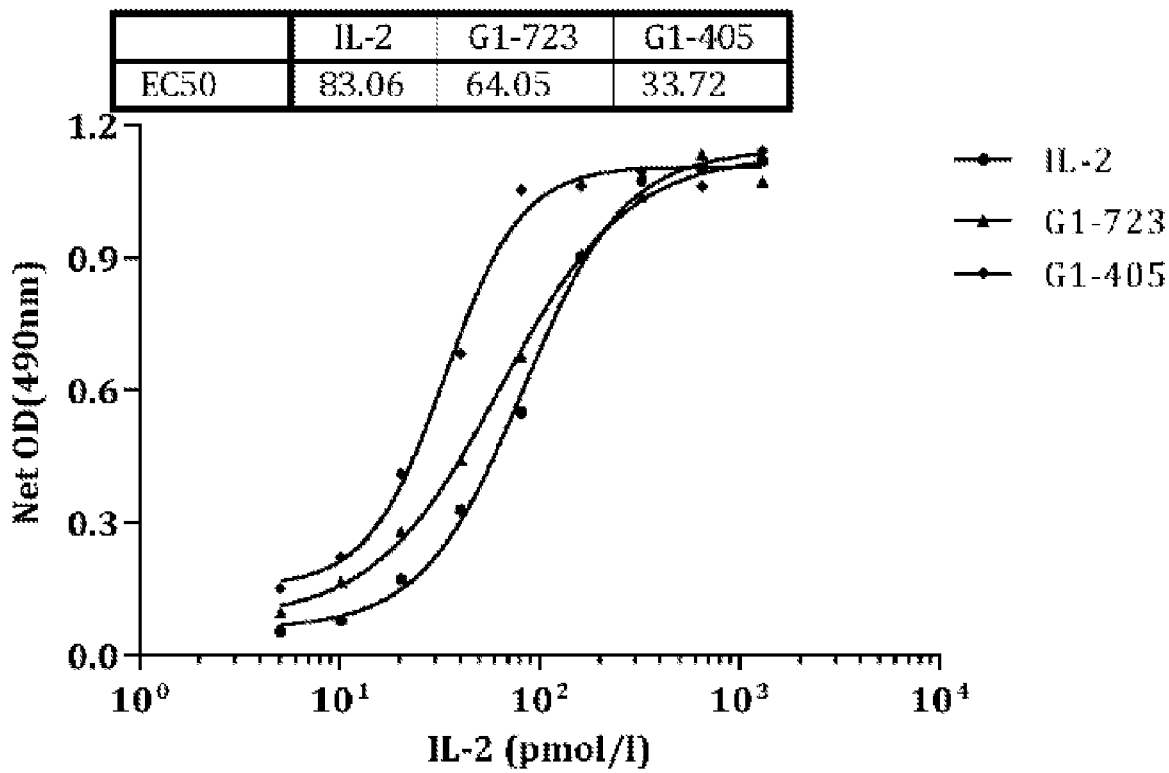
FIG. 3 shows the IL-2 activities of G1-723 and G1-405 fusion proteins compared with that of a control IL-2.

For the fusion protein in which the IL-2 is fused, compared with the biological activity of the free IL-2, the IL-2 activities of other heterodimers are enhanced except that the IL-2 activity of the homodimer fusion protein G1-212 is decreased by 0.8 times (FIG. 1), wherein the IL-2 activities of the fusion proteins G1-405 and G1-716 are increased by more than 1.5 times (FIGS. 2 and 3), and the IL-2 activities of the fusion proteins G1-723 and G1-717 are increased by about 0.5 times (FIGS. 2 and 3). Theoretically, quantitatively speaking, the homodimer fusion protein has two fused cytokines IL-2, and thus its IL-2 activity should be stronger than that of the heterodimer fusion protein in which only one IL-2 is fused, but the actual result is just the opposite. The possible reason is that the two IL-2s in the homodimer form steric hindrance to each other, which leads to the decrease of the IL-2 activity. Therefore, in general, the cytokine activity of the fusion protein in which only one IL-2 is fused based on the antibody Fc heterodimer technology will be better than that of the homodimer fusion protein in which two IL-2s are fused. Moreover, the IL-2 cytokine activity of the fusion protein in which the IL-12 and the IL-2 are fused at the same time is stronger than that of the fusion protein in which only the IL-2 is fused, which indicates the synergistic effect of the IL-12 and the IL-2.

Figure 4:
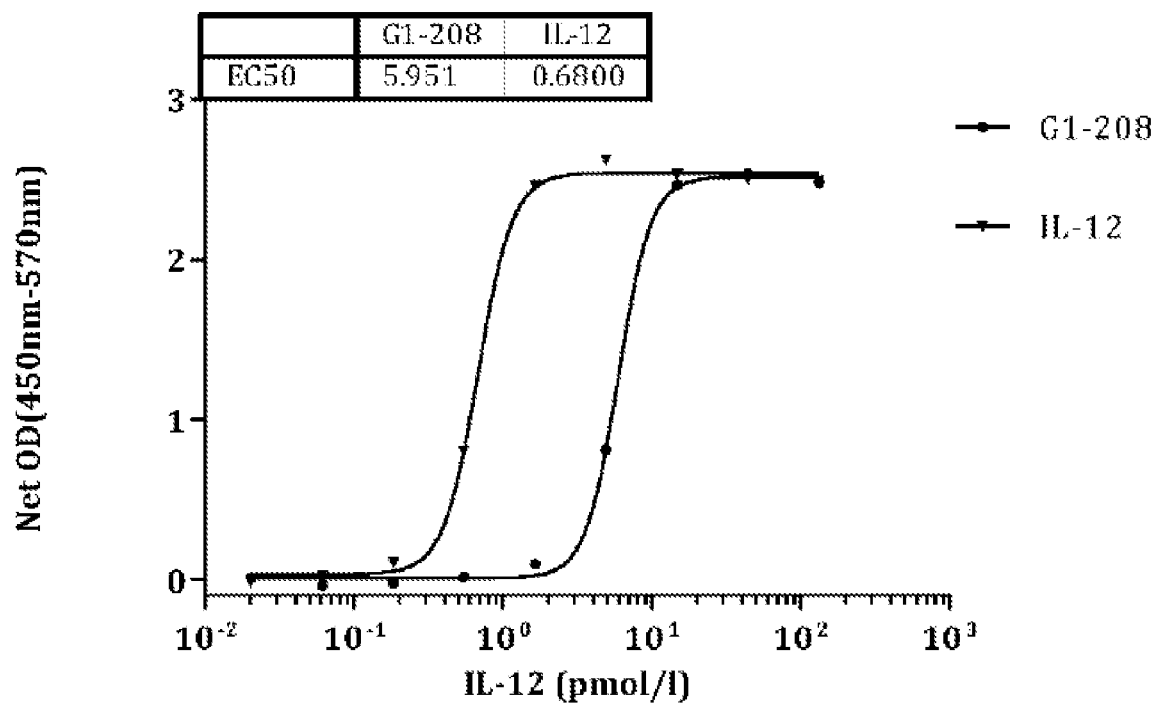
FIG. 4 shows the IL-12 activity of a G1-208 fusion protein compared with that of a control IL-12.
Figure 5:
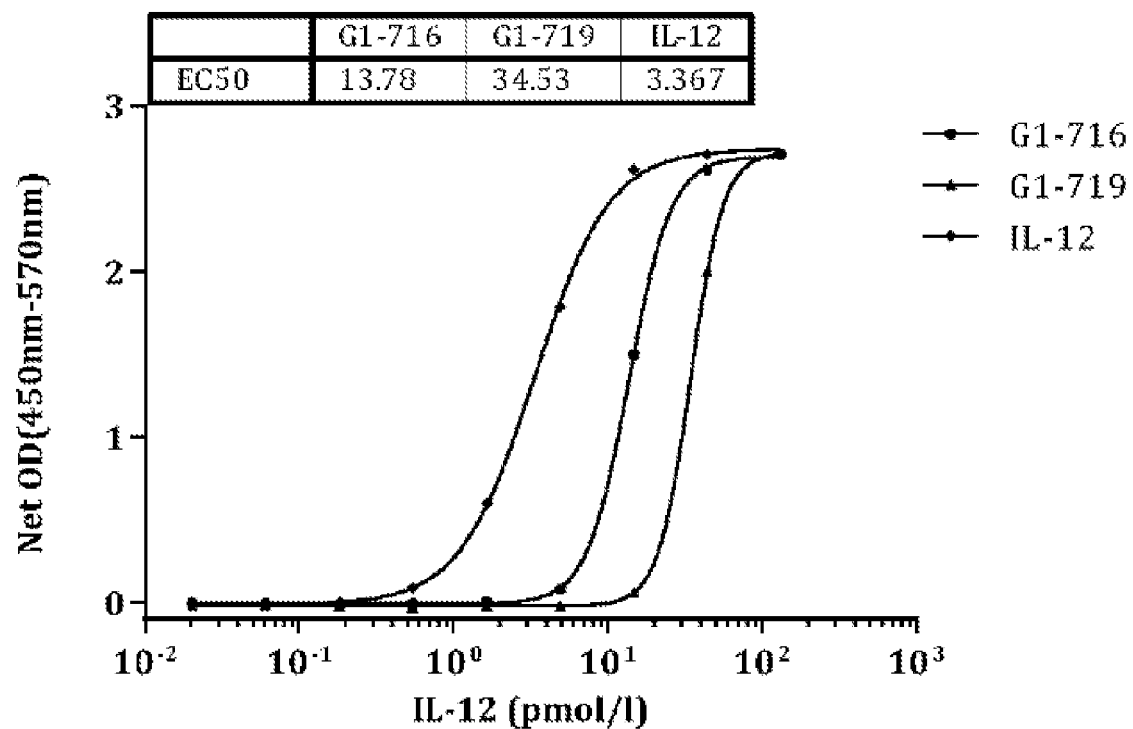
FIG. 5 shows the IL-12 activities of G1-716 and G1-719 fusion proteins compared with that of a control IL-12.
Figure 6:
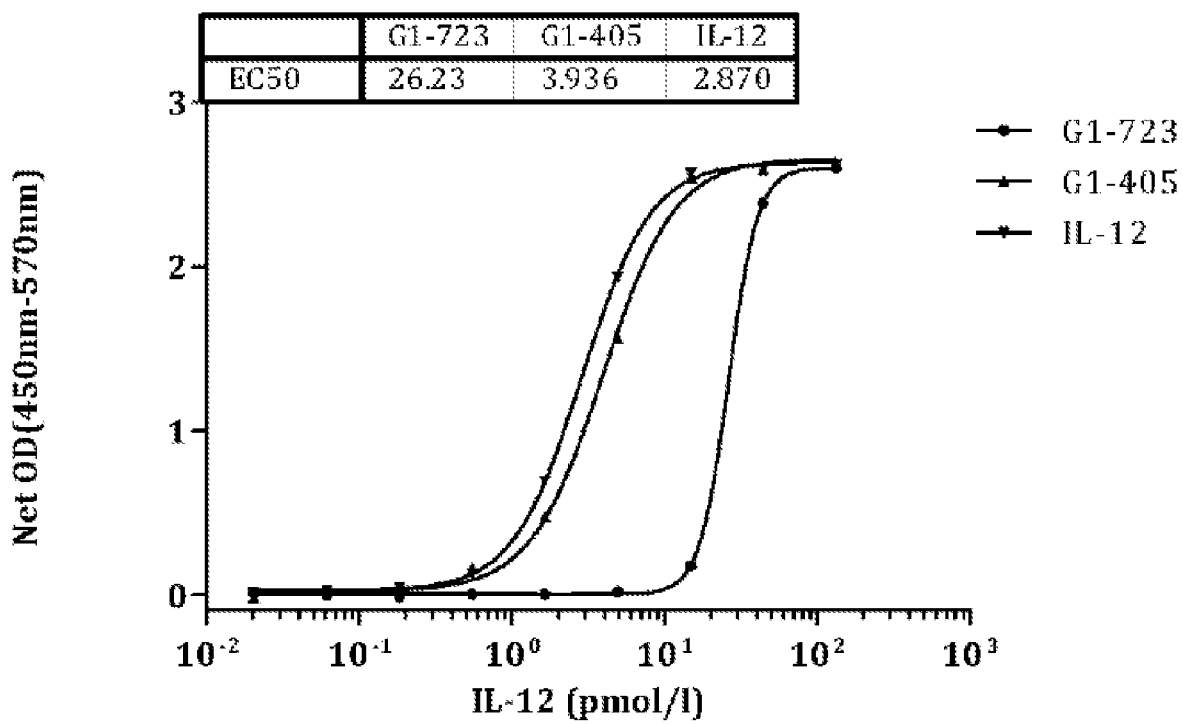
FIG. 6 shows the IL-12 activities of G1-723 and G1-405 fusion proteins compared with that of a control IL-12.

For the fusion protein in which the IL-12 is fused, compared with the biological activity of the free IL-12, the cytokine activity of the homodimer fusion protein G1-208 is decreased by 9 times (FIG. 4), while the IL-12 activity of the fusion protein G1-405 is only decreased by more than 0.3 times (FIG. 6), and also the IL-12 activity of the fusion protein G1-716 is only decreased by 3 times (FIG. 5). This shows that similar to the asymmetric fusion of the IL-2, the asymmetric fusion structure of the IL-12 will also enhance the cytokine activity to some extent. However, compared with the biological activity of the free IL-12, the cytokine activities of the heterodimer fusion proteins G1-719 (FIG. 5) and G1-723 (FIG. 6) are decreased by 8-9 times. For the sharp decline in the cytokine activity of the G1-719, the possible reason is that the IL-12 and the IL-2 have a synergistic effect, and their co-existence can promote their respective functions, while in the G1-719 only the IL-12 is fused and the IL-2 is lacked, so the cytokine activity of the G1-719 is lower than that of the fusion protein G1-716 in which the IL-12 and the IL-2 are fused at the same time. The only difference between the G1-723 and the G1-716 is that in the G1-723 the IL-2 has undergone site mutation. According to the analysis of existing studies, the IL-2 mutant can reduce the in vitro biological activity of the cytokine to a certain extent, but significantly improve the toxicity in animals Therefore, the decrease in the in vitro IL-12 activity of the G1-723 is related to the decrease in the synergistic effect of the IL-2 with the IL-12 as caused by the decrease in the IL-2 activity due to the site mutation of the IL-2. This also further verifies the synergistic effect of the IL-12 and the IL-2. In summary, the cytokine activity of the fusion protein in which only one IL-12 is fused based on the antibody Fc heterodimer technology will be better than that of the homodimer fusion protein in which two IL-12s are fused. Moreover, the IL-12 cytokine activity of the fusion protein in which the IL-12 and the IL-2 are fused at the same time is stronger than that of the fusion protein in which only the IL-12 is fused, which further indicates the synergistic effect of the IL-12 and the IL-2.

3. Analysis of PD-1 Inhibition Experiment Results

The bioassay of the PD-1/PD-L1 pathway blocking is a detection analysis based on biologically relevant action mechanisms, which can be used for measuring the efficacy and stability of antibodies and other biological formulations that can block the PD-1/PD-L1 interaction. This detection system includes the following two gene-edited cell lines: cells that can stably express human derived PD-1 and cells that stably express the human derived PD-L1.

When the two cells are co-cultured, the PD-1/PD-L1 interaction will inhibit a T cell receptor (TCR) signaling pathway and a NFAT-regulated luciferase activity. When a corresponding PD-1 or PD-L1 antibody is added to block the PD-1/PD-L1 interaction, the inhibition signal will be cleared, thereby activating the T cell receptor (TCR) signaling pathway and the NFAT-induced luciferase activity. The antibody activity is then analyzed by detecting fluorescence signals.

Figure 7:
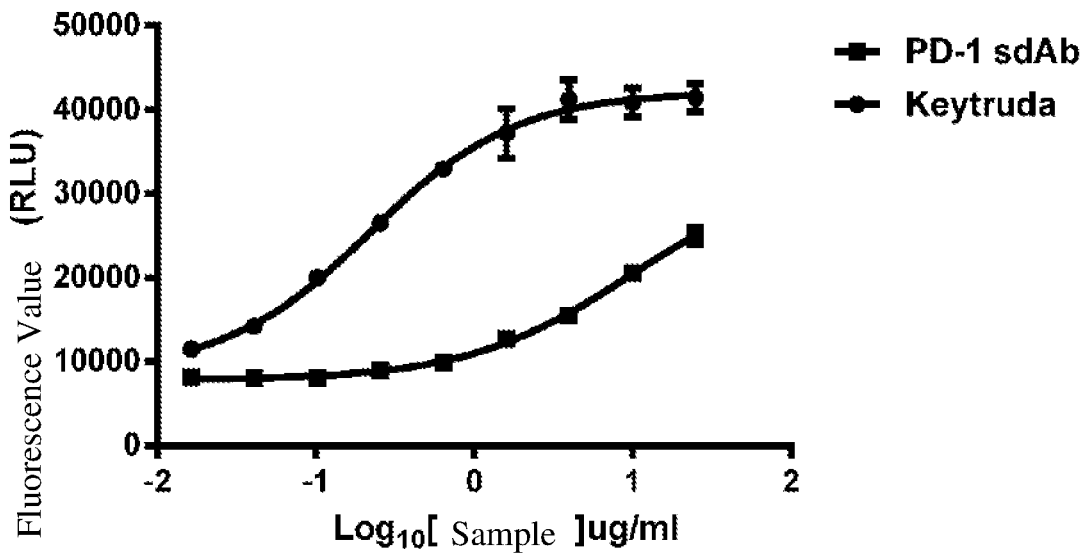
FIG. 7 shows the PD-1/PD-L1 pathway blocking activity of the PD-1 single-domain antibody compared with that of control Keytruda.
Figure 8:
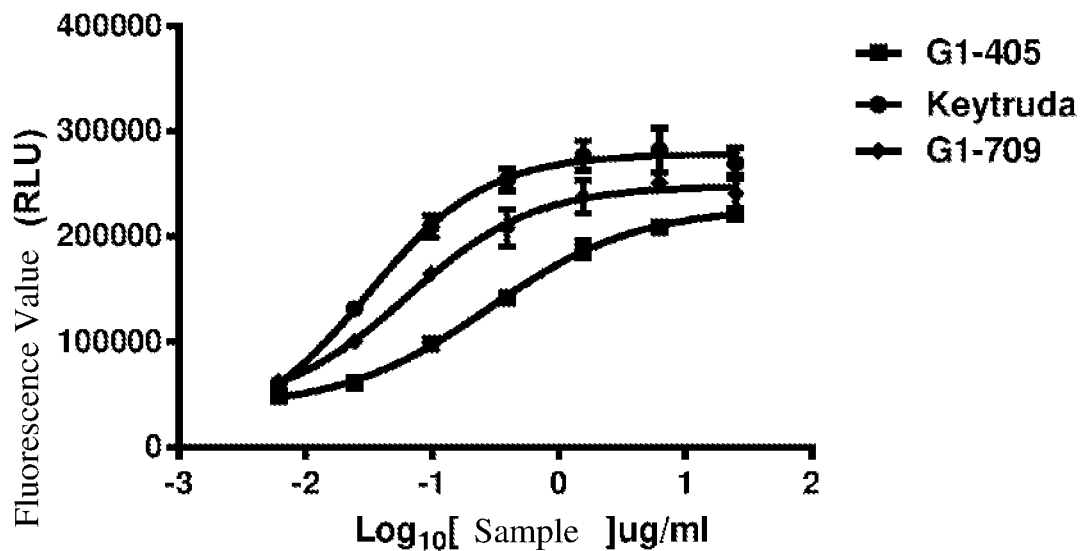
FIG. 8 shows the PD-1/PD-L1 pathway blocking activities of the fusion proteins G1-405 and G1-709 compared with that of the control Keytruda.

In this experiment, various fusion proteins bearing the PD-1 single-domain antibody are incubated with cells to detect the antibody activities of the fusion proteins. The results show that the activity of the free PD-1 single-domain antibody SC01 is very weak compared with that of the traditional IgG antibody Keytruda (FIG. 7). However, after the single-domain antibody is fused onto the antibody Fc chain, the antibody activity of the generated fusion protein, such as G1-405, is greatly enhanced, although there is still a certain gap compared with the Keytruda antibody (FIG. 8).

Figure 9:
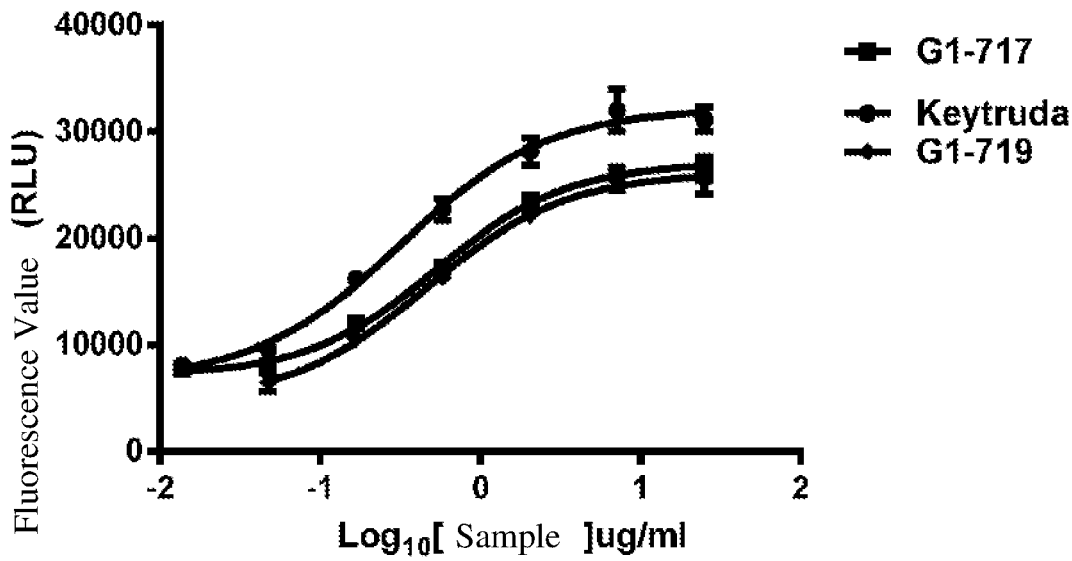
FIG. 9 shows the PD-1/PD-L1 pathway blocking activities of the fusion proteins G1-717 and G1-719 compared with that of the control Keytruda.
Figure 10:
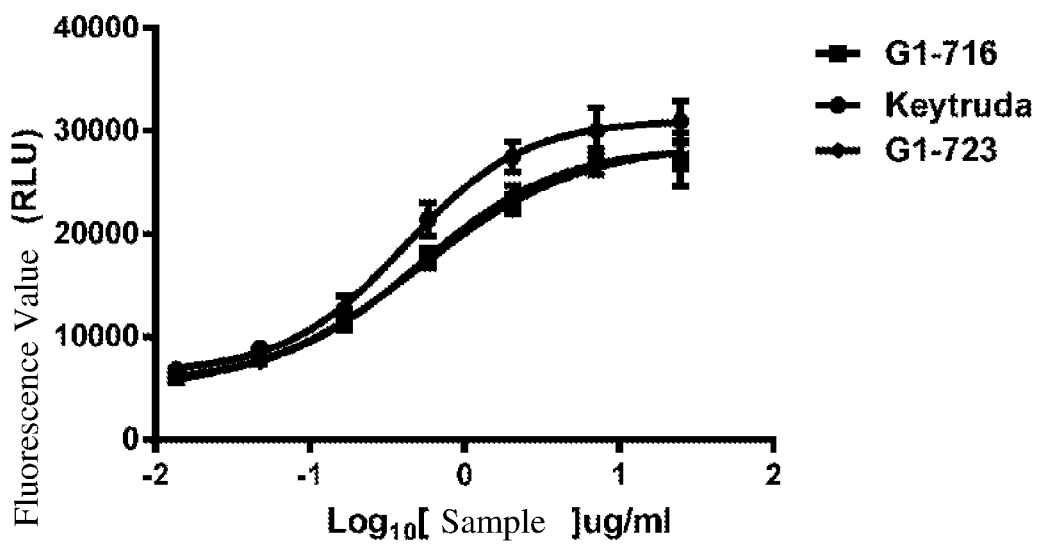
FIG. 10 shows the PD-1/PD-L1 pathway blocking activities of the fusion proteins G1-716 and G1-723 compared with that of the control Keytruda.

In order to further enhance the antibody activity of the fusion protein, we construct a fusion protein including two tandem single-domain antibodies, and the fusion protein is fused to the N-terminus of the antibody Fc chain. Taking the G1-709 single-domain antibody Fc fusion protein as an example, its PD-1 antibody activity is enhanced significantly compared with that of the fusion protein G1-405 without the tandem single-domain antibodies (FIG. 8). Furthermore, the antibody activities of the fusion proteins G1-717 and G1-719 in which the antibody and the cytokine are fused, as constructed by us based on the antibody Fc heterodimer technology, are not far from that of the Keytruda antibody (FIG. 9). However, the antibody activities of the fusion proteins G1-716 and G1-723 in which the IL-12 and the IL-2 are fused at the same time, are almost close to that of the Keytruda antibody (FIG. 10). This not only shows that the Fc chain enhances the activity of the single-domain antibody, but also shows that the cytokine further promotes the activity of the antibody to a certain extent.

4. Construction of Other Single-Domain Antibody-Cytokine Fusion Proteins Based on Antibody Fc Heterodimer The aforementioned experimental results show the superiority of the single-domain antibody-cytokine based on the antibody Fc heterodimer. In order to further verify the applicability and broad spectrum of this technology platform, we use more single-domain antibodies of different molecules to construct a series of single-domain antibody-cytokine fusion proteins based on the antibody Fc heterodimer in the following researches. Among them, the cytokines used for constructing the fusion proteins are still the IL-12 and the IL-2, and the single-domain antibody is one new PD-1 single-domain antibody or three new PD-L1 single-domain antibodies. Unlike the aforementioned antibody Fc fragment based on human IgG1 mutants, the new antibody Fc fragment is based on human IgG4 mutation.

The sequences of the new anti-PD-1 single-domain antibody or the new anti-PD-L1 single-domain antibody are respectively inserted behind the polyclonal site EcoRI of the pTT5 expression vector, and meanwhile the KOZAK sequence GCCGCCACC and the signal peptide sequence are also added in front of the fusion protein gene to help secrete the fusion protein out of a cell. A vector expressing the single-domain antibody is produced.

Similar to the aforementioned vector construction method, in order to generate a Fc-based heterodimer, the knob-into-holes technology is used for antibody Fc modification, wherein the mutation site combination of one Fc chain is T366W/S354C, and the mutation site combination of the other Fc chain is T366S/L368A/Y407V/Y349C. The two Fc chains also have other mutation sites S228P and L235E. The Fc fragment of the antibody IgG4 is inserted onto the pTT5 vector through the polyclonal site EcoRI, then four new single-domain antibody sequences are respectively linked to the N-terminus of the Fc via Gibson assembly, and there is no linker sequence between them. Then the IL-12 or IL-2 sequence is also linked to the C-terminus of the Fc in a similar manner, and there is the G4S (SEQ ID NO: 75) linker sequence between them. Finally, expression vectors for fusion proteins of different single-domain antibodies and different cytokines are formed. Meanwhile a KOZAK sequence GCCGCCACC and a signal peptide sequence are also added in front of the fusion protein gene to help secrete the fusion protein out of a cell.

At the same time, site mutations S228P and L235E are carried out based on the Fc fragment of the wild-type human IgG4, and then different single-domain antibodies are directly linked to the N-terminus of the Fc of the mutated IgG4, thereby forming a homodimer.

The information about the plasmids constructed in this experiment is shown in Table 2 below:

TABLE 2

Composition of Fusion Proteins

| Fusion Protein | Plasmid |
| --- | --- |
| sPD1a01 | pTT5-pd1a-IgG4Fc-il12 |
| | pTT5-pd1a-IgG4Fc-il2 |
| sPD1a02 | pTT5-pd1a-IgG4Fc-il12 |
| | pTT5-pd1a-IgG4Fc |
| sPD1a03 | pTT5-pd1a-IgG4Fc-il2 |
| | pTT5-pd1a-IgG4Fc |
| sPDL1a01 | pTT5-pdl1a-IgG4Fc-il12 |
| | pTT5-pdl1a-IgG4Fc-il2 |
| sPDL1a02 | pTT5-pdl1a-IgG4Fc-il12 |
| | pTT5-pdl1a-IgG4Fc |
| sPDL1a03 | pTT5-pdl1a-IgG4Fc-il2 |
| | pTT5-pdl1a-IgG4Fc |
| sPDL1b01 | pTT5-pdl1b-IgG4Fc-il12 |
| | pTT5-pdl1b-IgG4Fc-il2 |
| sPDL1b02 | pTT5-pdl1b-IgG4Fc-il12 |
| | pTT5-pdl1b-IgG4Fc |
| sPDL1b03 | pTT5-pdl1b-IgG4Fc-il2 |
| | pTT5-pdl1b-IgG4Fc |
| sPDL1c01 | pTT5-pdl1c-IgG4Fc-il12 |
| | pTT5-pdl1c-IgG4Fc-il2 |
| sPDL1c02 | pTT5-pdl1c-IgG4Fc-il12 |
| | pTT5-pdl1c-IgG4Fc |
| sPDL1c03 | pTT5-pdl1c-IgG4Fc-il2 |
| | pTT5-pdl1c-IgG4Fc |
| sPD1a00 | pTT5-pd1a-IgG4Fc |
| sPDL1a00 | pTT5-pdl1a-IgG4Fc |
| sPDL1b00 | pTT5-pdl1b-IgG4Fc |
| sPDL1c00 | pTT5-pdl1c-IgG4Fc |

The fusion protein plasmid constructed onto the pTT5 expression vector is transiently transfected into CHO-3E7 cells by a PEI transfection reagent, and then cultured at 37° C. for 6 days. The supernatant of the culture solution is collected by centrifugation. The fusion protein is purified by a Protein A affinity column, and then further purified by a molecular sieve, with the purity finally reaching more than 95%.

The sequences of the new anti-PD-1 single-domain antibody and the new anti-PD-L1 single-domain antibody in this study are as follows:
the amino acid sequence (SEQ ID NO: 71) of the anti-PD1a single-domain antibody:

EVQLVESGGGLVQPGGSLRLSCAVSGNIYNRNFMGWFRQAPGKGLEGVSA

IYTGTSRTYYADSVKGRFTISRDNSKNTVYLQMNSLRAEDTAVYYCAADL

RDGFWDTGVWNTWGQGTLVTVSS the amino acid sequence (SEQ ID NO: 72) of the anti-PD-L1a single-domain antibody:

EVQLVESGGGLVQPGGSLRLSCAASGRTFVTYGMGWFRQAPGKGREFVSA

ISWSGSMTSYGDSVKGRFTISRDNAKNTLYLQMNSLRPEDTAVYYCAAAL

GAVVYTTREPYTYWGQGTLVTVSS the amino acid sequence (SEQ ID NO: 73) of the anti-PD-L1b single-domain antibody:

EVQLVESGGGLVQPGGSLRLSCAASGRTFVTYGMGWFRQAPGKGREFVSA

ISWSGSSTSYGDSVKGRFTISRDNAKNTLYLQMNSLRPEDTAVYYCAAAL

GAVVYTTREPYTYWGQGTLVTVSS the amino acid sequence (SEQ ID NO: 74) of the anti-PD-L1c single-domain antibody:

EVQLVESGGGLVQPGGSLRLSCAASGRTFITYAIGWFRQAPGKGREFVSA

ISWSGSMTSYADSVKGRFTISRDNAKNTLYLQMNSLRPEDTAVYYCAAHR

GAIAPIAQSVYTNWGQGTLVTVSS

The fusion protein sPD1a01 used in this study is a heterodimer, which is formed by two Fc chains (Fc8 and Fc9) that are modified and fused with other proteins through a Knob-into-holes structure. The full-length DNA sequence (SEQ ID NO: 31) of Fc8 is as follows:

GAAGTGCAGCTGGTTGAGTCCGGCGGCGGCCTGGTGCAGCCTGGCGGTTC

TCTGCGGCTGTCTTGCGCCGTGAGCGGAAATATCTACAACCGGAACTTCA

TGGGCTGGTTTCGGCAGGCTCCAGGCAAAGGACTGGAAGGCGTGTCCGCC

ATCTACACCGGCACCTCTCGGACCTACTACGCCGACTCTGTCAAAGGCAG

ATTCACCATCTCCCGCGACAACAGCAAAAACACCGTGTACCTGCAGATGA

ACAGCCTGAGAGCTGAAGATACAGCTGTGTACTATTGCGCCGCCGATCTG

AGAGACGGCTTCTGGGACACAGGCGTGTGGAACACCTGGGGCCAGGGCAC

ACTTGTGACCGTGTCCTCTGAGTCTAAGTACGGCCCTCCCTGTCCTCCTT

GCCCTGCTCCTGAGTTCgaGGGCGGCCCCTCCGTGTTTCTCTTCCCACCC

AAGCCTAAGGACACCCTGATGATCTCCAGAACCCCTGAGGTGACCTGCGT

GGTGGTTGACGTGTCTCAGGAGGATCCCGAAGTGCAGTTTAATTGGTACG

TGGACGGCGTCGAAGTGCACAATGCTAAAACCAAGCCTCGGGAGGAACAG

TTCAATAGCACCTACAGAGTGGTGAGCGTTCTGACAGTGCTGCACCAGGA

CTGGCTGAACGGCAAAGAGTACAAGTGCAAGGTGTCCAACAAGGGCCTGC

CATCCTCCATCGAGAAGACCATCTCCAAGGCCAAGGGACAACCTAGAGAG

CCTCAGGTGTACACCCTGCCTCCCTgTCAGGAGGAGATGACCAAGAACCA

GGTGTCTCTGtggTGCCTGGTGAAGGGCTTCTACCCTTCCGACATCGCCG

```
TGGAATGGGAAAGCAACGGCCAACCTGAGAACAACTACAAGACCACCCCT

CCTGTGCTGGACTCCGATGGATCTTTCTTCCTGTACTCTCGGCTGACCGT

CGACAAGTCTAGATGGCAGGAGGGCAACGTGTTCAGCTGCTCCGTCATGC

ACGAGGCCCTGCATAACCACTACACCCAGAAGTCCCTGTCCTTATCTCTG

GGCtcaGGTGGaGGCGGTAGTGGCGGAGGCGGTTCAGGCGGAGGCGGATC

TATTTGGGAGCTGAAGAAAGACGTGTACGTGGTCGAGCTGGACTGGTACC

CTGATGCCCCAGGCGAGATGGTCGTGCTGACCTGCGATACACCAGAGGAA

GATGGTATCACCTGGACACTGGATCAGTCCTCAGAGGTGCTGGGCTCTGG

TAAAACACTGACCATTCAGGTGAAGGAGTTCGGTGACGCTGGACAGTACA

CTTGTCATAAGGGCGGGGAGGTGCTGTCTCACTCCCTGCTGCTGCTGCAT

AAGAAGGAGGATGGAATCTGGTCCACTGACATCCTGAAAGACCAGAAGGA

GCCAAAGAACAAAACCTTCCTGCGATGCGAGGCTAAGAACTACAGCGGCC

GCTTTACATGCTGGTGGCTGACAACCATCAGCACCGATCTGACCTTTAGC

GTGAAGTCATCCAGGGGCAGTTCAGACCCTCAGGGAGTCACATGTGGCGC

CGCAACCCTGTCAGCAGAGCGAGTGCGGGGAGACAATAAGGAATACGAGT

ACAGCGTCGAGTGTCAGGAGGATTCCGCATGTCCAGCTGCAGAAGAATCC

CTGCCTATCGAAGTCATGGTGGACGCTGTGCATAAACTGAAGTACGAGAA

TTACACCAGCAGCTTTTTCATCCGGGACATCATCAAGCCCGATCCACCTA

AGAATCTGCAGCTGAAGCCTCTGAAAAATAGCCGACAGGTCGAAGTGTCA

TGGGAATACCCAGACACCTGGTCAACACCACACTCCTACTTCTCCCTGAC

CTTCTGTGTGCAGGTCCAGGGAAAAAGCAAGCGGGAAAAGAAAGATCGGG

TGTTCACCGACAAGACCAGTGCTACAGTGATTTGCCGGAAGAATGCCAGC

ATTTCTGTCAGAGCTCAGGACCGGTACTATAGCTCTTCCTGGAGCGAGTG

GGCTTCAGTGCCATGTTCTGGaGGCGGtGGATCTGGCGGAGGTGGAAGCG

GAGGCGGTGGATCTAGAAACCTGCCCGTCGCAACCCCTGATCCAGGGATG

TTCCCCTGTCTGCATCACAGCCAGAATCTGCTGAGGGCTGTCTCCAACAT

GCTGCAGAAGGCTCGACAGACCCTGGAGTTCTACCCATGTACCAGCGAAG

AGATCGACCACGAGGATATCACAAAGGATAAAACCAGCACAGTGGAAGCA

TGCCTGCCTCTGGAACTGACCAAGAATGAGAGCTGCCTGAATAGCAGGGA

GACCTCCTTCATCACCAACGGCTCATGCCTGGCTTCAAGGAAGACCAGCT

TCATGATGGCTCTGTGTCTGAGCTCTATCTATGAGGACCTGAAGATGTAC

CAGGTGGAGTTCAAGACCATGAACGCCAAGCTGCTGATGGATCCAAAGAG

GCAGATCTTCCTGGATCAGAATATGCTGGCAGTGATCGATGAGCTGATGC

AGGCCCTGAATTTTAACAGTGAGACAGTGCCTCAGAAGAGCTCTCTGGAA

GAGCCAGACTTTTACAAAACTAAGATCAAGCTGTGCATTCTGCTGCACGC

TTTCCGCATCAGAGCTGTCACTATCGATAGAGTGATGAGCTATCTGAATG

CCTCA
```

The fusion protein sPD1a01 used in this study is a heterodimer, which is formed by two Fc chains (Fc8 and Fc9) that are modified and fused with other proteins through a Knob-into-holes structure. The full-length amino acid sequence (SEQ ID NO: 32) of Fc8 is as follows:

```
EVQLVESGGGLVQPGGSLRLSCAVSGNIYNRNFMGWFRQAPGKGLEGVSA

IYTGTSRTYYADSVKGRFTISRDNSKNTVYLQMNSLRAEDTAVYYCAADL

RDGFWDTGVWNTWGQGTLVTVSSESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPCQEEMTKNQVSLWCLVKGFYPSDIAVEWESNGQPENNYKTTP

PVLDSDGSFFLYSRLTVDKSRWQEGNVFSCSVMHEALHNHYTQKSLSLSL

GSGGGGSGGGGSGGGGSIWELKKDVYVVELDWYPDAPGEMVVLTCDTPEE

DGITWTLDQSSEVLGSGKTLTIQVKEFGDAGQYTCHKGGEVLSHSLLLLH

KKEDGIWSTDILKDQKEPKNKTFLRCEAKNYSGRFTCWWLTTISTDLTFS

VKSSRGSSDPQGVTCGAATLSAERVRGDNKEYEYSVECQEDSACPAAEES

LPIEVMVDAVHKLKYENYTSSFFIRDIIKPDPPKNLQLKPLKNSRQVEVS

WEYPDTWSTPHSYFSLTFCVQVQGKSKREKKDRVFTDKTSATVICRKNAS

ISVRAQDRYYSSSWSEWASVPCSGGGGSGGGGSGGGGSRNLPVATPDPGM

FPCLHHSQNLLRAVSNMLQKARQTLEFYPCTSEEIDHEDITKDKTSTVEA

CLPLELTKNESCLNSRETSFITNGSCLASRKTSFMMALCLSSIYEDLKMY

QVEFKTMNAKLLMDPKRQIFLDQNMLAVIDELMQALNFNSETVPQKSSLE

EPDFYKTKIKLCILLHAFRIRAVTIDRVMSYLNAS
```

The fusion protein sPD1a01 used in this study is a heterodimer, which is formed by two Fc chains (Fc8 and Fc9) that are modified and fused with other proteins through a Knob-into-holes structure. The full-length DNA sequence (SEQ ID NO: 33) of Fc9 is as follows:

```
GAAGTGCAGCTGGTTGAGTCCGGCGGCGGCCTGGTGCAGCCTGGCGGTTC

TCTGCGGCTGTCTTGCGCCGTGAGCGGAAATATCTACAACCGGAACTTCA

TGGGCTGGTTTCGGCAGGCTCCAGGCAAAGGACTGGAAGGCGTGTCCGCC

ATCTACACCGGCACCTCTCGGACCTACTACGCCGACTCTGTCAAAGGCAG

ATTCACCATCTCCCGCGACAACAGCAAAAACACCGTGTACCTGCAGATGA

ACAGCCTGAGAGCTGAAGATACAGCTGTGTACTATTGCGCCGCCGATCTG

AGAGACGGCTTCTGGGACACAGGCGTGTGGAACACCTGGGGCCAGGGCAC

ACTTGTGACCGTGTCCTCTGAGTCTAAGTACGGCCCTCCCTGTCCTCCTT

GCCCTGCTCCTGAGTTCgaGGGCGGCCCCTCCGTGTTTCTCTTCCCACCC

AAGCCTAAGGACACCCTGATGATCTCCAGAACCCCTGAGGTGACCTGCGT

GGTGGTTGACGTGTCTCAGGAGGATCCCGAAGTGCAGTTTAATTGGTACG

TGGACGGCGTCGAAGTGCACAATGCTAAAACCAAGCCTCGGGAGGAACAG

TTCAATAGCACCTACAGAGTGGTGAGCGTTCTGACAGTGCTGCACCAGGA

CTGGCTGAACGGCAAAGAGTACAAGTGCAAGGTGTCCAACAAGGGCCTGC

CATCCTCCATCGAGAAGACCATCTCCAAGGCCAAGGGACAACCTAGAGAG

CCTCAGGTGTgCACCCTGCCTCCCTCTCAGGAGGAGATGACCAAGAACCA

GGTGTCTCTGtCCTGCgctGTGAAGGGCTTCTACCCTTCCGACATCGCCG

TGGAATGGGAAAGCAACGGCCAACCTGAGAACAACTACAAGACCACCCCT
```

```
CCTGTGCTGGACTCCGATGGATCTTTCTTCCTGgttTCTCGGCTGACCGT
CGACAAGTCTAGATGGCAGGAGGGCAACGTGTTCAGCTGCTCCGTCATGC
ACGAGGCCCTGCATAACCACTACACCCAGAAGTCCCTGTCCTTATCTCTG
GGCtcaGGTGGaGGCGGTAGTGGCGGAGGCGGTTCAGGCGGAGGCGGATC
TGCACCTACTTCAAGTTCTACAAAGAAAACACAGCTACAACTGGAGCATT
TACTGCTGGATTTACAGATGATTTTGAATGGAATTAATAATTACAAGAAT
CCCAAACTCACCAGGATGCTCACATTTAAGTTTTACATGCCCAAGAAGGC
CACAGAACTGAAACATCTTCAGTGTCTAGAAGAAGAACTCAAACCTCTGG
AGGAAGTGCTAAATTTAGCTCAAAGCAAAAACTTTCACTTAAGACCCAGG
GACTTAATCAGCAATATCAACGTAATAGTTCTGGAACTAAAGGGATCTGA
AACAACATTCATGTGTGAATATGCTGATGAGACAGCAACCATTGTAGAAT
TTCTGAACAGATGGATTACCTTTTGTCAAAGCATCATCTCAACACTGACT
```

The fusion protein sPD1a01 used in this study is a heterodimer, which is formed by two Fc chains (Fc8 and Fc9) that are modified and fused with other proteins through a Knob-into-holes structure. The full-length amino acid sequence (SEQ ID NO: 34) of Fc9 is as follows:

```
EVQLVESGGGLVQPGGSLRLSCAVSGNIYNRNFMGWFRQAPGKGLEGVSA
IYTGTSRTYYADSVKGRFTISRDNSKNTVYLQMNSLRAEDTAVYYCAADL
RDGFWDTGVWNTWGQGTLVTVSSESKYGPPCPPCPAPEFEGGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVCTLPPSQEEMTKNQVSLSCAVKGFYPSDIAVEWESNGQPENNYKTTP
PVLDSDGSFFLVSRLTVDKSRWQEGNVFSCSVMHEALHNHYTQKSLSLSL
GSGGGGSGGGGSGGGGSAPTSSSTKKTQLQLEHLLLDLQMILNGINNYKN
PKLTRMLTFKFYMPKKATELKHLQCLEEELKPLEEVLNLAQSKNFHLRPR
DLISNINVIVLELKGSETTFMCEYADETATIVEFLNRWITFCQSIISTLT
```

The fusion protein sPD1a02 used in this study is a heterodimer, which is formed by two Fc chains (Fc8 and Fc10) that are modified and fused with other proteins through a Knob-into-holes structure. The full-length DNA and amino acid sequences of the Fc8 have been shown hereabove.

The fusion protein sPD1a02 used in this study is a heterodimer, which is formed by two Fc chains (Fc8 and Fc10) that are modified and fused with other proteins through a Knob-into-holes structure. The full-length DNA sequence (SEQ ID NO: 35) of Fc10 is as follows:

```
GAAGTGCAGCTGGTTGAGTCCGGCGGCGGCCTGGTGCAGCCTGGCGGTTC
TCTGCGGCTGTCTTGCGCCGTGAGCGGAAATATCTACAACCGGAACTTCA
TGGGCTGGTTTCGGCAGGCTCCAGGCAAAGGACTGGAAGGCGTGTCCGCC
ATCTACACCGGCACCTCTCGGACCTACTACGCCGACTCTGTCAAAGGCAG
ATTCACCATCTCCCGCGACAACAGCAAAAACACCGTGTACCTGCAGATGA
ACAGCCTGAGAGCTGAAGATACAGCTGTGTACTATTGCGCCGCCGATCTG
AGAGACGGCTTCTGGGACACAGGCGTGTGGAACACCTGGGGCCAGGGCAC
ACTTGTGACCGTGTCCTCTGAGTCTAAGTACGGCCCTCCCTGTCCTCCTT
GCCCTGCTCCTGAGTTCgaGGGCGGCCCCTCCGTGTTTCTCTTCCCACCC
AAGCCTAAGGACACCCTGATGATCTCCAGAACCCCTGAGGTGACCTGCGT
GGTGGTTGACGTGTCTCAGGAGGATCCCGAAGTGCAGTTTAATTGGTACG
TGGACGGCGTCGAAGTGCACAATGCTAAAACCAAGCCTCGGGAGGAACAG
TTCAATAGCACCTACGAGTGGTGAGCGTTCTGACAGTGCTGCACCAGGA
CTGGCTGAACGGCAAAGAGTACAAGTGCAAGGTGTCCAACAAGGGCCTGC
CATCCTCCATCGAGAAGACCATCTCCAAGGCCAAGGGACAACCTAGAGAG
CCTCAGGTGTgCACCCTGCCTCCCTCTCAGGAGGAGATGACCAAGAACCA
GGTGTCTCTGtCCTGCgctGTGAAGGGCTTCTACCCTTCCGACATCGCCG
TGGAATGGGAAAGCAACGGCCAACCTGAGAACAACTACAAGACCACCCCT
CCTGTGCTGGACTCCGATGGATCTTTCTTCCTGgttTCTCGGCTGACCGT
CGACAAGTCTAGATGGCAGGAGGGCAACGTGTTCAGCTGCTCCGTCATGC
ACGAGGCCCTGCATAACCACTACACCCAGAAGTCCCTGTCCTTATCTCTG
GGC
```

The fusion protein sPD1a02 used in this study is a heterodimer, which is formed by two Fc chains (Fc8 and Fc10) that are modified and fused with other proteins through a Knob-into-holes structure. The full-length amino acid sequence (SEQ ID NO: 36) of Fc10 is as follows:

```
EVQLVESGGGLVQPGGSLRLSCAVSGNIYNRNFMGWFRQAPGKGLEGVSA
IYTGTSRTYYADSVKGRFTISRDNSKNTVYLQMNSLRAEDTAVYYCAADL
RDGFWDTGVWNTWGQGTLVTVSSESKYGPPCPPCPAPEFEGGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVCTLPPSQEEMTKNQVSLSCAVKGFYPSDIAVEWESNGQPENNYKTTP
PVLDSDGSFFLVSRLTVDKSRWQEGNVFSCSVMHEALHNHYTQKSLSLSL
G
```

The fusion protein sPD1a03 used in this study is a heterodimer, which is formed by two Fc chains (Fc10 and Fc11) that are modified and fused with other proteins through a Knob-into-holes structure. The full-length DNA and amino acid sequences of the Fc10 have been shown hereabove.

The fusion protein sPD1a03 used in this study is a heterodimer, which is formed by two Fc chains (Fc10 and Fc11) that are modified and fused with other proteins through a Knob-into-holes structure. The full-length DNA sequence (SEQ ID NO: 37) of Fc11 is as follows:

```
GAAGTGCAGCTGGTTGAGTCCGGCGGCGGCCTGGTGCAGCCTGGCGGTTC
TCTGCGGCTGTCTTGCGCCGTGAGCGGAAATATCTACAACCGGAACTTCA
TGGGCTGGTTTCGGCAGGCTCCAGGCAAAGGACTGGAAGGCGTGTCCGCC
ATCTACACCGGCACCTCTCGGACCTACTACGCCGACTCTGTCAAAGGCAG
```

-continued

ATTCACCATCTCCCGCGACAACAGCAAAAACACCGTGTACCTGCAGATGA
ACAGCCTGAGAGCTGAAGATACAGCTGTGTACTATTGCGCCGCCGATCTG
AGAGACGGCTTCTGGGACACAGGCGTGTGGAACACCTGGGGCCAGGGCAC
ACTTGTGACCGTGTCCTCTGAGTCTAAGTACGGCCCTCCCTGTCCTCCTT
GCCCTGCTCCTGAGTTCgaGGGCGGCCCCTCCGTGTTTCTCTTCCCACCC
AAGCCTAAGGACACCCTGATGATCTCCAGAACCCCTGAGGTGACCTGCGT
GGTGGTTGACGTGTCTCAGGAGGATCCCGAAGTGCAGTTTAATTGGTACG
TGGACGGCGTCGAAGTGCACAATGCTAAAACCAAGCCTCGGGAGGAACAG
TTCAATAGCACCTACAGAGTGGTGAGCGTTCTGACAGTGCTGCACCAGGA
CTGGCTGAACGGCAAAGAGTACAAGTGCAAGGTGTCCAACAAGGGCCTGC
CATCCTCCATCGAGAAGACCATCTCCAAGGCCAAGGGACAACCTAGAGAG
CCTCAGGTGTACACCCTGCCTCCCTgTCAGGAGGAGATGACCAAGAACCA
GGTGTCTCTGtggTGCCTGGTGAAGGGCTTCTACCCTTCCGACATCGCCG
TGGAATGGGAAAGCAACGGCCAACCTGAGAACAACTACAAGACCACCCCT
CCTGTGCTGGACTCCGATGGATCTTTCTTCCTGTACTCTCGGCTGACCGT
CGACAAGTCTAGATGGCAGGAGGGCAACGTGTTCAGCTGCTCCGTCATGC
ACGAGGCCCTGCATAACCACTACACCCAGAAGTCCCTGTCCTTATCTCTG
GGCtcaGGTGGaGGCGGTAGTGGCGGAGGCGGTTCAGGCGGAGGCGGATC
TGCACCTACTTCAAGTTCTACAAAGAAAACACAGCTACAACTGGAGCATT
TACTGCTGGATTTACAGATGATTTTGAATGGAATTAATAATTACAAGAAT
CCCAAACTCACCAGGATGCTCACATTTAAGTTTTACATGCCCAAGAAGGC
CACAGAACTGAAACATCTTCAGTGTCTAGAAGAAGAACTCAAACCTCTGG
AGGAAGTGCTAAATTTAGCTCAAAGCAAAAACTTTCACTTAAGACCCAGG
GACTTAATCAGCAATATCAACGTAATAGTTCTGGAACTAAAGGGATCTGA
AACAACATTCATGTGTGAATATGCTGATGAGACAGCAACCATTGTAGAAT
TTCTGAACAGATGGATTACCTTTTGTCAAAGCATCATCTCAACACTGACT

The fusion protein sPD1a03 used in this study is a heterodimer, which is formed by two Fc chains (Fc10 and Fc11) that are modified and fused with other proteins through a Knob-into-holes structure. The full-length amino acid sequence (SEQ ID NO: 38) of Fc11 is as follows:

EVQLVESGGGLVQPGGSLRLSCAVSGNIYNRNFMGWFRQAPGKGLEGVSA

IYTGTSRTYYADSVKGRFTISRDNSKNTVYLQMNSLRAEDTAVYYCAADL

RDGFWDTGVWNTWGQGTLVTVSSESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPCQEEMTKNQVSLWCLVKGFYPSDIAVEWESNGQPENNYKTTP

PVLDSDGSFFLYSRLTVDKSRWQEGNVFSCSVMHEALHNHYTQKSLSLSL

GSGGGGSGGGGSGGGGSAPTSSSTKKTQLQLEHLLLDLQMILNGINNYKN

PKLTRMLTFKFYMPKKATELKHLQCLEEELKPLEEVLNLAQSKNFHLRPR

DLISNINVIVLELKGSETTFMCEYADETATIVEFLNRWITFCQSIISTLT

The fusion protein sPDL1a01 used in this study is a heterodimer, which is formed by two Fc chains (Fc12 and Fc13) that are modified and fused with other proteins through a Knob-into-holes structure. The full-length DNA sequence (SEQ ID NO: 39) of Fc12 is as follows:

GAGGTGCAGCTGGTGGAATCCGGCGGAGGCCTGGTCCAGCCTGGCGGCTC

TCTGCGGCTGTCCTGCGCCGCTTCTGGCAGAACCTTCGTGACCTACGGCA

TGGGCTGGTTCCGGCAGGCTCCTGGCAAGGGCAGAGAGTTCGTGTCCGCC

ATCTCCTGGTCCGGCTCCATGACCTCTTACGGCGACTCTGTGAAGGGCAG

ATTCACCATCAGCCGGGATAACGCCAAGAACACACTGTACCTGCAGATGA

ACTCCCTGCGGCCTGAGGACACCGCCGTGTACTACTGCGCCGCTGCCCTG

GGCGCTGTCGTGTACACCACCAGAGAACCCTATACCTACTGGGGACAGGG

CACCCTGGTGACCGTGTCCTCTGAGTCTAAGTACGGCCCTCCCTGTCCTC

CTTGCCCTGCTCCTGAGTTCgaGGGCGGCCCCTCCGTGTTTCTCTTCCCA

CCCAAGCCTAAGGACACCCTGATGATCTCCAGAACCCCTGAGGTGACCTG

CGTGGTGGTTGACGTGTCTCAGGAGGATCCCGAAGTGCAGTTTAATTGGT

ACGTGGACGGCGTCGAAGTGCACAATGCTAAAACCAAGCCTCGGGAGGAA

CAGTTCAATAGCACCTACAGAGTGGTGAGCGTTCTGACAGTGCTGCACCA

GGACTGGCTGAACGGCAAAGAGTACAAGTGCAAGGTGTCCAACAAGGGCC

TGCCATCCTCCATCGAGAAGACCATCTCCAAGGCCAAGGGACAACCTAGA

GAGCCTCAGGTGTACACCCTGCCTCCCTgTCAGGAGGAGATGACCAAGAA

CCAGGTGTCTCTGtggTGCCTGGTGAAGGGCTTCTACCCTTCCGACATCG

CCGTGGAATGGGAAAGCAACGGCCAACCTGAGAACAACTACAAGACCACC

CCTCCTGTGCTGGACTCCGATGGATCTTTCTTCCTGTACTCTCGGCTGAC

CGTCGACAAGTCTAGATGGCAGGAGGGCAACGTGTTCAGCTGCTCCGTCA

TGCACGAGGCCCTGCATAACCACTACACCCAGAAGTCCCTGTCCTTATCT

CTGGGCtcaGGTGGaGGCGGTAGTGGCGGAGGCGGTTCAGGCGGAGGCGG

ATCTATTTGGGAGCTGAAGAAAGACGTGTACGTGGTCGAGCTGGACTGGT

ACCCTGATGCCCCAGGCGAGATGGTCGTGCTGACCTGCGATACACCAGAG

GAAGATGGTATCACCTGGACACTGGATCAGTCCTCAGAGGTGCTGGGCTC

TGGTAAAACACTGACCATTCAGGTGAAGGAGTTCGGTGACGCTGGACAGT

ACACTTGTCATAAGGGCGGGGAGGTGCTGTCTCACTCCCTGCTGCTGCTG

CATAAGAAGGAGGATGGAATCTGGTCCACTGACATCCTGAAAGACCAGAA

GGAGCCAAAGAACAAAACCTTCCTGCGATGCGAGGCTAAGAACTACAGCG

GCCGCTTTACATGCTGGTGGCTGACAACCATCAGCACCGATCTGACCTTT

AGCGTGAAGTCATCCAGGGGCAGTTCAGACCCTCAGGGAGTCACATGTGG

CGCCGCAACCCTGTCAGCAGAGCGAGTGCGGGGAGACAATAAGGAATACG

AGTACAGCGTCGAGTGTCAGGAGGATTCCGCATGTCCAGCTGCAGAAGAA

TCCCTGCCTATCGAAGTCATGGTGGACGCTGTGCATAAACTGAAGTACGA

GAATTACACCAGCAGCTTTTTCATCCGGGACATCATCAAGCCCGATCCAC

CTAAGAATCTGCAGCTGAAGCCTCTGAAAAATAGCCGACAGGTCGAAGTG

TCATGGGAATACCCAGACACCTGGTCAACACCACACTCCTACTTCTCCCT

GACCTTCTGTGTGCAGGTCCAGGGAAAAAGCAAGCGGGAAAAGAAAGATC

-continued

```
GGGTGTTCACCGACAAGACCAGTGCTACAGTGATTTGCCGGAAGAATGCC
AGCATTTCTGTCAGAGCTCAGGACCGGTACTATAGCTCTTCCTGGAGCGA
GTGGGCTTCAGTGCCATGTTCTGGaGGCGGtGGATCTGGCGGAGGTGGAA
GCGGAGGCGGTGGATCTAGAAACCTGCCCGTCGCAACCCCTGATCCAGGG
ATGTTCCCCTGTCTGCATCACAGCCAGAATCTGCTGAGGGCTGTCTCCAA
CATGCTGCAGAAGGCTCGACAGACCCTGGAGTTCTACCCATGTACCAGCG
AAGAGATCGACCACGAGGATATCACAAAGGATAAAACCAGCACAGTGGAA
GCATGCCTGCCTCTGGAACTGACCAAGAATGAGAGCTGCCTGAATAGCAG
GGAGACCTCCTTCATCACCAACGGCTCATGCCTGGCTTCAAGGAAGACCA
GCTTCATGATGGCTCTGTGTCTGAGCTCTATCTATGAGGACCTGAAGATG
TACCAGGTGGAGTTCAAGACCATGAACGCCAAGCTGCTGATGGATCCAAA
GAGGCAGATCTTCCTGGATCAGAATATGCTGGCAGTGATCGATGAGCTGA
TGCAGGCCCTGAATTTTAACAGTGAGACAGTGCCTCAGAAGAGCTCTCTG
GAAGAGCCAGACTTTTACAAAACTAAGATCAAGCTGTGCATTCTGCTGCA
CGCTTTCCGCATCAGAGCTGTCACTATCGATAGAGTGATGAGCTATCTGA
ATGCCTCA
```

The fusion protein sPDL1a01 used in this study is a heterodimer, which is formed by two Fc chains (Fc12 and Fc13) that are modified and fused with other proteins through a Knob-into-holes structure. The full-length amino acid sequence (SEQ ID NO: 40) of Fc12 is as follows:

```
EVQLVESGGGLVQPGGSLRLSCAASGRTFVTYGMGWFRQAPGKGREFVSA
ISWSGSMTSYGDSVKGRFTISRDNAKNTLYLQMNSLRPEDTAVYYCAAAL
GAVVYTTREPYTYWGQGTLVTVSSESKYGPPCPPCPAPEFEGGPSVFLFP
PKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPR
EPQVYTLPPCQEEMTKNQVSLWCLVKGFYPSDIAVEWESNGQPENNYKTT
PPVLDSDGSFFLYSRLTVDKSRWQEGNVFSCSVMHEALHNHYTQKSLSLS
LGSGGGGSGGGGSGGGGSIWELKKDVYVVELDWYPDAPGEMVVLTCDTPE
EDGITWTLDQSSEVLGSGKTLTIQVKEFGDAGQYTCHKGGEVLSHSLLLL
HKKEDGIWSTDILKDQKEPKNKTFLRCEAKNYSGRFTCWWLTTISTDLTF
SVKSSRGSSDPQGVTCGAATLSAERVRGDNKEYEYSVECQEDSACPAAEE
SLPIEVMVDAVHKLKYENYTSSFFIRDIIKPDPPKNLQLKPLKNSRQVEV
SWEYPDTWSTPHSYFSLTFCVQVQGKSKREKKDRVFTDKTSATVICRKNA
SISVRAQDRYYSSSWSEWASVPCSGGGSGGGGSGGGGSRNLPVATPDPG
MFPCLHHSQNLLRAVSNMLQKARQTLEFYPCTSEEIDHEDITKDKTSTVE
ACLPLELTKNESCLNSRETSFITNGSCLASRKTSFMMALCLSSIYEDLKM
YQVEFKTMNAKLLMDPKRQIFLDQNMLAVIDELMQALNFNSETVPQKSSL
EEPDFYKTKIKLCILLHAFRIRAVTIDRVMSYLNAS
```

The fusion protein sPDL1a01 used in this study is a heterodimer, which is formed by two Fc chains (Fc12 and Fc13) that are modified and fused with other proteins through a Knob-into-holes structure. The full-length DNA sequence (SEQ ID NO: 41) of Fc13 is as follows:

```
GAGGTGCAGCTGGTGGAATCCGGCGGAGGCCTGGTCCAGCCTGGCGGC
TCTCTGCGGCTGTCCTGCGCCGCTTCGGCAGAACCTTCGTGACCTAC
GGCATGGGCTGGTTCCGGCAGGCTCCTGGCAAGGGCAGAGAGTTCGTG
TCCGCCATCTCCTGGTCCGGCTCCATGACCTCTTACGGCGACTCTGTG
AAGGGCAGATTCACCATCAGCCGGGATAACGCCAAGAACACACTGTAC
CTGCAGATGAACTCCCTGCGGCCTGAGGACACCGCCGTGTACTACTGC
GCCGCTGCCCTGGGCGCTGTCGTGTACACCACCAGAGAACCCTATACC
TACTGGGGACAGGGCACCCTGGTGACCGTGTCCTCTGAGTCTAAGTAC
GGCCCTCCCTGTCCTCCTTGCCCTGCTCCTGAGTTCgaGGGCGGCCCC
TCCGTGTTTCTCTTCCCACCCAAGCCTAAGGACACCCTGATGATCTCC
AGAACCCCTGAGGTGACCTGCGTGGTGGTTGACGTGTCTCAGGAGGAT
CCCGAAGTGCAGTTTAATTGGTACGTGGACGGCGTCGAAGTGCACAAT
GCTAAAACCAAGCCTCGGGAGGAACAGTTCAATAGCACCTACAGAGTG
GTGAGCGTTCTGACAGTGCTGCACCAGGACTGGCTGAACGGCAAAGAG
TACAAGTGCAAGGTGTCCAACAAGGGCCTGCCATCCTCCATCGAGAAG
ACCATCTCCAAGGCCAAGGGACAACCTAGAGAGCCTCAGGTGTgCACC
CTGCCTCCCTCTCAGGAGGAGATGACCAAGAACCAGGTGTCTCTGtCC
TGCgctGTGAAGGGCTTCTACCCTTCCGACATCGCCGTGGAATGGGAA
AGCAACGGCCAACCTGAGAACAACTACAAGACCACCCCTCCTGTGCTG
GACTCCGATGGATCTTTCTTCCTGgttTCTCGGCTGACCGTCGACAAG
TCTAGATGGCAGGAGGGCAACGTGTTCAGCTGCTCCGTCATGCACGAG
GCCCTGCATAACCACTACACCCAGAAGTCCCTGTCCTTATCTCTGGGC
tcaGGTGGaGGCGGTAGTGGCGGAGGCGGTTCAGGCGGAGGCGGATCT
GCACCTACTTCAAGTTCTACAAAGAAAACACAGCTACAACTGGAGCAT
TTACTGCTGGATTTACAGATGATTTTGAATGGAATTAATAATTACAAG
AATCCCAAACTCACCAGGATGCTCACATTTAAGTTTTACATGCCCAAG
AAGGCCACAGAACTGAAACATCTTCAGTGTCTAGAAGAAGAACTCAAA
CCTCTGGAGGAAGTGCTAAATTTAGCTCAAAGCAAAAACTTTCACTTA
AGACCCAGGGACTTAATCAGCAATATCAACGTAATAGTTCTGGAACTA
AAGGGATCTGAAACAACATTCATGTGTGAATATGCTGATGAGACAGCA
ACCATTGTAGAATTTCTGAACAGATGGATTACCTTTTGTCAAAGCATC
ATCTCAACACTGACT
```

The fusion protein sPDL1a01 used in this study is a heterodimer, which is formed by two Fc chains (Fc12 and Fc13) that are modified and fused with other proteins through a Knob-into-holes structure. The full-length amino acid sequence (SEQ ID NO: 42) of Fc13 is as follows:

```
EVQLVESGGGLVQPGGSLRLSCAASGRTFVTYGMGWFRQAPGKGREFV
SAISWSGSMTSYGDSVKGRFTISRDNAKNTLYLQMNSLRPEDTAVYYC
AAALGAVVYTTREPYTYWGQGTLVTVSSESKYGPPCPPCPAPEFEGGP
SVFLFPPKPKDTLMISRTPEVTCVVVDVSQEDPEVQFNWYVDGVEVHN
```

-continued
```
AKTKPREEQFNSTYRVVSVLTVLHQDWLNGKEYKCKVSNKGLPSSIEK

TISKAKGQPREPQVCTLPPSQEEMTKNQVSLSCAVKGFYPSDIAVEWE

SNGQPENNYKTTPPVLDSDGSFFLVSRLTVDKSRWQEGNVFSCSVMHE

ALHNHYTQKSLSLSLGSGGGGSGGGGSGGGGSAPTSSSTKKTQLQEH

LLLDLQMILNGINNYKNPKLTRMLTFKFYMPKKATELKHLQCLEEELK

PLEEVLNLAQSKNFHLRPRDLISNINVIVLELKGSETTFMCEYADETA

TIVEFLNRWITFCQSIISTLT
```

The fusion protein sPDL1a02 used in this study is a heterodimer, which is formed by two Fc chains (Fc12 and Fc14) that are modified and fused with other proteins through a Knob-into-holes structure. The full-length DNA and amino acid sequences of the Fc13 have been shown hereabove.

The fusion protein sPDL1a02 used in this study is a heterodimer, which is formed by two Fc chains (Fc12 and Fc14) that are modified and fused with other proteins through a Knob-into-holes structure. The full-length DNA sequence (SEQ ID NO: 43) of Fc14 is as follows:

```
GAGGTGCAGCTGGTGGAATCCGGCGGAGGCCTGGTCCAGCCTGGCGGC

TCTCTGCGGCTGTCCTGCGCCGCTTCTGGCAGAACCTTCGTGACCTAC

GGCATGGGCTGGTTCCGGCAGGCTCCTGGCAAGGGCAGAGAGTTCGTG

TCCGCCATCTCCTGGTCCGGCTCCATGACCTCTTACGGCGACTCTGTG

AAGGGCAGATTCACCATCAGCCGGGATAACGCCAAGAACACACTGTAC

CTGCAGATGAACTCCCTGCGGCCTGAGGACACCGCCGTGTACTACTGC

GCCGCTGCCCTGGGCGCTGTCGTGTACACCACCAGAGAACCCTATACC

TACTGGGGACAGGGCACCCTGGTGACCGTGTCCTCTGAGTCTAAGTAC

GGCCCTCCCTGTCCTCCTTGCCCTGCTCCTGAGTTCGAGGGCGGCCCC

TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCATCCTCCATCGAGAAG

ACCATCTCCAAGGCCAAGGGACAACCTAGAGAGCCTCAGGTGTGCACC

CTGCCTCCCTCTCAGGAGGAGATGACCAAGAACCAGGTGTCTCTGTCC

TGCGCTGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGGTTTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC
```

The fusion protein sPDL1a02 used in this study is a heterodimer, which is formed by two Fc chains (Fc12 and Fc14) that are modified and fused with other proteins through a Knob-into-holes structure. The full-length amino acid sequence (SEQ ID NO: 44) of Fc14 is as follows:

```
EVQLVESGGGLVQPGGSLRLSCAASGRTFVTYGMGWFRQAPGKGREFV

SAISWSGSMTSYGDSVKGRFTISRDNAKNTLYLQMNSLRPEDTAVYYC

AAALGAVVYTTREPYTYWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVCTLPPSQEEMTKNQVSLSCAVKGFYPSDIAVEWE

SNGQPENNYKTTPPVLDSDGSFFLVSRLTVDKSRWQEGNVFSCSVMHE

ALHNHYTQKSLSLSLG
```

The fusion protein sPDL1a03 used in this study is a heterodimer, which is formed by two Fc chains (Fc14 and Fc15) that are modified and fused with other proteins through a Knob-into-holes structure. The full-length DNA and amino acid sequences of the Fc14 have been shown hereabove.

The fusion protein sPDL1a03 used in this study is a heterodimer, which is formed by two Fc chains (Fc14 and Fc15) that are modified and fused with other proteins through a Knob-into-holes structure. The full-length DNA sequence (SEQ ID NO: 45) of Fc15 is as follows:

```
GAGGTGCAGCTGGTGGAATCCGGCGGAGGCCTGGTCCAGCCTGGCGGC

TCTCTGCGGCTGTCCTGCGCCGCTTCTGGCAGAACCTTCGTGACCTAC

GGCATGGGCTGGTTCCGGCAGGCTCCTGGCAAGGGCAGAGAGTTCGTG

TCCGCCATCTCCTGGTCCGGCTCCATGACCTCTTACGGCGACTCTGTG

AAGGGCAGATTCACCATCAGCCGGGATAACGCCAAGAACACACTGTAC

CTGCAGATGAACTCCCTGCGGCCTGAGGACACCGCCGTGTACTACTGC

GCCGCTGCCCTGGGCGCTGTCGTGTACACCACCAGAGAACCCTATACC

TACTGGGGACAGGGCACCCTGGTGACCGTGTCCTCTGAGTCTAAGTAC

GGCCCTCCCTGTCCTCCTTGCCCTGCTCCTGAGTTCgaGGGCGGCCCC

TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCATCCTCCATCGAGAAG

ACCATCTCCAAGGCCAAGGGACAACCTAGAGAGCCTCAGGTGTACACC

CTGCCTCCCTgTCAGGAGGAGATGACCAAGAACCAGGTGTCTCTGtgg

TGCCTGGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGTACTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC tcaGGTGGaGGCGGTAGTGGCGGAGGCGGTTCAGGCGGAGGCGGATCT

GCACCTACTTCAAGTTCTACAAAGAAAACACAGCTACAACTGGAGCAT

TTACTGCTGGATTTACAGATGATTTTGAATGGAATTAATAATTACAAG
```

AATCCCAAACTCACCAGGATGCTCACATTTAAGTTTTACATGCCCAAG

AAGGCCACAGAACTGAAACATCTTCAGTGTCTAGAAGAAGAACTCAAA

CCTCTGGAGGAAGTGCTAAATTTAGCTCAAAGCAAAAACTTTCACTTA

AGACCCAGGGACTTAATCAGCAATATCAACGTAATAGTTCTGGAACTA

AAGGGATCTGAAACAACATTCATGTGTGAATATGCTGATGAGACAGCA

ACCATTGTAGAATTTCTGAACAGATGGATTACCTTTTGTCAAAGCATC

ATCTCAACACTGACT

The fusion protein sPDL1a03 used in this study is a heterodimer, which is formed by two Fc chains (Fc14 and Fc15) that are modified and fused with other proteins through a Knob-into-holes structure. The full-length amino acid sequence (SEQ ID NO: 46) of Fc15 is as follows:

EVQLVESGGGLVQPGGSLRLSCAASGRTFVTYGMGWFRQAPGKGREFV

SAISWSGSMTSYGDSVKGRFTISRDNAKNTLYLQMNSLRPEDTAVYYC

AAALGAVVYTTREPYTYWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVYTLPPCQEEMTKNQVSLWCLVKGFYPSDIAVEWE

SNGQPENNYKTTPPVLDSDGSFFLYSRLTVDKSRWQEGNVFSCSVMHE

ALHNHYTQKSLSLSLGSGGGGSGGGGSGGGGSAPTSSSTKKTQLQLEH

LLLDLQMILNGINNYKNPKLTRMLTFKFYMPKKATELKHLQCLEEELK

PLEEVLNLAQSKNFHLRPRDLISNINVIVLELKGSETTFMCEYADETA

TIVEFLNRWITFCQSIISTLT

The fusion protein sPDL1b01 used in this study is a heterodimer, which is formed by two Fc chains (Fc16 and Fc17) that are modified and fused with other proteins through a Knob-into-holes structure. The full-length DNA sequence (SEQ ID NO: 47) of Fc16 is as follows:

GAGGTGCAGCTGGTGGAATCCGGCGGAGGCCTGGTCCAGCCTGGCGGC

TCTCTGCGGCTGTCCTGCGCCGCTTCTGGCAGAACCTTCGTGACCTAC

GGCATGGGCTGGTTCCGGCAGGCTCCTGGCAAGGGCAGAGAGTTCGTG

TCCGCCATCTCCTGGTCCGGCTCCAgcACCTCTTACGGCGACTCTGTG

AAGGGCAGATTCACCATCAGCCGGGATAACGCCAAGAACACACTGTAC

CTGCAGATGAACTCCCTGCGGCCTGAGGACACCGCCGTGTACTACTGC

GCCGCTGCCCTGGGCGCTGTCGTGTACACCACCAGAGAACCCTATACC

TACTGGGGACAGGGCACCCTGGTGACCGTGTCCTCTGAGTCTAAGTAC

GGCCCTCCCTGTCCTCCTTGCCCTGCTCCTGAGTTCGaGGGCGGCCCC

TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCCATCCTCCATCGAGAAG

ACCATCTCCAAGGCCAAGGGACAACCTAGAGAGCCTCAGGTGTACACC

CTGCCTCCCTgTCAGGAGGAGATGACCAAGAACCAGGTGTCTCTGtgg

TGCCTGGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGTACTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC tcaGGTGGaGGCGGTAGTGGCGGAGGCGGTTCAGGCGGAGGCGGATCT

ATTTGGGAGCTGAAGAAAGACGTGTACGTGGTCGAGCTGGACTGGTAC

CCTGATGCCCCAGGCGAGATGGTCGTGCTGACCTGCGATACACCAGAG

GAAGATGGTATCACCTGGACACTGGATCAGTCCTCAGAGGTGCTGGGC

TCTGGTAAAACACTGACCATTCAGGTGAAGGAGTTCGGTGACGCTGGA

CAGTACACTTGTCATAAGGGCGGGAGGTGCTGTCTCACTCCCTGCTG

CTGCTGCATAAGAAGGAGGATGGAATCTGGTCCACTGACATCCTGAAA

GACCAGAAGGAGCCAAAGAACAAAACCTTCCTGCGATGCGAGGCTAAG

AACTACAGCGGCCGCTTTACATGCTGGTGGCTGACAACCATCAGCACC

GATCTGACCTTTAGCGTGAAGTCATCCAGGGGCAGTTCAGACCCTCAG

GGAGTCACATGTGGCGCCGCAACCCTGTCAGCAGAGCGAGTGCGGGGA

GACAATAAGGAATACGAGTACAGCGTCGAGTGTCAGGAGGATTCCGCA

TGTCCAGCTGCAGAAGAATCCCTGCCTATCGAAGTCATGGTGGACGCT

GTGCATAAACTGAAGTACGAGAATTACACCAGCAGCTTTTTCATCCGG

GACATCATCAAGCCCGATCCACCTAAGAATCTGCAGCTGAAGCCTCTG

AAAAATAGCCGACAGGTCGAAGTGTCATGGGAATACCCAGACACCTGG

TCAACACCACACTCCTACTTCTCCCTGACCTTCTGTGTGCAGGTCCAG

GGAAAAAGCAAGCGGGAAAAGAAAGATCGGGTGTTCACCGACAAGACC

AGTGCTACAGTGATTTGCCGGAAGAATGCCAGCATTTCTGTCAGAGCT

CAGGACCGGTACTATAGCTCTTCCTGGAGCGAGTGGGCTTCAGTGCCA

TGTTCTGGaGGCGGtGGATCTGGCGGAGGTGGAAGCGGAGGCGGTGGA

TCTAGAAACCTGCCCGTCGCAACCCCTGATCCAGGGATGTTCCCCTGT

CTGCATCACAGCCAGAATCTGCTGAGGGCTGTCTCCAACATGCTGCAG

AAGGCTCGACAGACCCTGGAGTTCTACCCATGTACCAGCGAAGAGATC

GACCACGAGGATATCACAAAGGATAAAACCAGCACAGTGGAAGCATGC

CTGCCTCTGGAACTGACCAAGAATGAGAGCTGCCTGAATAGCAGGGAG

ACCTCCTTCATCACCAACGGCTCATGCCTGGCTTCAAGGAAGACCAGC

TTCATGATGGCTCTGTGTCTGAGCTCTATCTATGAGGACCTGAAGATG

TACCAGGTGGAGTTCAAGACCATGAACGCCAAGCTGCTGATGGATCCA

AAGAGGCAGATCTTCCTGGATCAGAATATGCTGGCAGTGATCGATGAG

CTGATGCAGGCCCTGAATTTTAACAGTGAGACAGTGCCTCAGAAGAGC

TCTCTGGAAGAGCCAGACTTTTACAAAACTAAGATCAAGCTGTGCATT

-continued

CTGCTGCACGCTTTCCGCATCAGAGCTGTCACTATCGATAGAGTGATG

AGCTATCTGAATGCCTCA

The fusion protein sPDL1b01 used in this study is a heterodimer, which is formed by two Fc chains (Fc16 and Fc17) that are modified and fused with other proteins through a Knob-into-holes structure. The full-length amino acid sequence (SEQ ID NO: 48) of Fc16 is as follows:

EVQLVESGGGLVQPGGSLRLSCAASGRTFVTYGMGWFRQAPGKGREFV

SAISWSGSSTSYGDSVKGRFTISRDNAKNTLYLQMNSLRPEDTAVYYC

AAALGAVVYTTREPYTYWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVYTLPPCQEEMTKNQVSLWCLVKGFYPSDIAVEWE

SNGQPENNYKTTPPVLDSDGSFFLYSRLTVDKSRWQEGNVFSCSVMHE

ALHNHYTQKSLSLSLGSGGGGSGGGGSGGGGSIWELKKDVYVVELDWY

PDAPGEMVVLTCDTPEEDGITWTLDQSSEVLGSGKTLTIQVKEFGDAG

QYTCHKGGEVLSHSLLLLHKKEDGIWSTDILKDQKEPKNKTFLRCEAK

NYSGRFTCWWLTTISTDLTFSVKSSRGSSDPQGVTCGAATLSAERVRG

DNKEYEYSVECQEDSACPAAEESLPIEVMVDAVHKLKYENYTSSFFIR

DIIKPDPPKNLQLKPLKNSRQVEVSWEYPDTWSTPHSYFSLTFCVQVQ

GKSKREKKDRVFTDKTSATVICRKNASISVRAQDRYYSSSWSEWASVP

CSGGGGSGGGGSGGGGSRNLPVATPDPGMFPCLHHSQNLLRAVSNMLQ

KARQTLEFYPCTSEEIDHEDITKDKTSTVEACLPLELTKNESCLNSRE

TSFITNGSCLASRKTSFMMALCLSSIYEDLKMYQVEFKTMNAKLLMDP

KRQIFLDQNMLAVIDELMQALNFNSETVPQKSSLEEPDFYKTKIKLCI

LLHAFRIRAVTIDRVMSYLNAS

The fusion protein sPDL1b01 used in this study is a heterodimer, which is formed by two Fc chains (Fc16 and Fc17) that are modified and fused with other proteins through a Knob-into-holes structure. The full-length DNA sequence (SEQ ID NO: 49) of Fc17 is as follows:

GAGGTGCAGCTGGTGGAATCCGGCGGAGGCCTGGTCCAGCCTGGCGGC

TCTCTGCGGCTGTCCTGCGCCGCTTCTGGCAGAACCTTCGTGACCTAC

GGCATGGGCTGGTTCCGGCAGGCTCCTGGCAAGGGCAGAGAGTTCGTG

TCCGCCATCTCCTGGTCCGGCTCCAGcACCTCTTACGGCGACTCTGTG

AAGGGCAGATTCACCATCAGCCGGGATAACGCCAAGAACACACTGTAC

CTGCAGATGAACTCCCTGCGGCCTGAGGACACCGCCGTGTACTACTGC

GCCGCTGCCCTGGGCGCTGTCGTGTACACCACCAGAGAACCCTATACC

TACTGGGGACAGGGCACCCTGGTGACCGTGTCCTCTGAGTCTAAGTAC

GGCCCTCCCTGTCCTCCTTGCCCTGCTCCTGAGTTCGaGGGCGGCCCC

TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCATCCTCCATCGAGAAG

ACCATCTCCAAGGCCAAGGGACAACCTAGAGAGCCTCAGGTGTgCACC

CTGCCTCCCTCTCAGGAGGAGATGACCAAGAACCAGGTGTCTCTGtCC

TGCgctGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGgttTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC tcaGGTGGaGGCGGTAGTGGCGGAGGCGGTTCAGGCGGAGGCGGATCT

GCACCTACTTCAAGTTCTACAAAGAAAACACAGCTACAACTGGAGCAT

TTACTGCTGGATTTACAGATGATTTTGAATGGAATTAATAATTACAAG

AATCCCAAACTCACCAGGATGCTCACATTTAAGTTTTACATGCCCAAG

AAGGCCACAGAACTGAAACATCTTCAGTGTCTAGAAGAAGAACTCAAA

CCTCTGGAGGAAGTGCTAAATTTAGCTCAAAGCAAAAACTTTCACTTA

AGACCCAGGGACTTAATCAGCAATATCAACGTAATAGTTCTGGAACTA

AAGGGATCTGAAACAACATTCATGTGTGAATATGCTGATGAGACAGCA

ACCATTGTAGAATTTCTGAACAGATGGATTACCTTTTGTCAAAGCATC

ATCTCAACACTGACT

The fusion protein sPDL1b01 used in this study is a heterodimer, which is formed by two Fc chains (Fc16 and Fc17) that are modified and fused with other proteins through a Knob-into-holes structure. The full-length amino acid sequence (SEQ ID NO: 50) of Fc17 is as follows:

EVQLVESGGGLVQPGGSLRLSCAASGRTFVTYGMGWFRQAPGKGREFV

SAISWSGSSTSYGDSVKGRFTISRDNAKNTLYLQMNSLRPEDTAVYYC

AAALGAVVYTTREPYTYWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVCTLPPSQEEMTKNQVSLSCAVKGFYPSDIAVEWE

SNGQPENNYKTTPPVLDSDGSFFLVSRLTVDKSRWQEGNVFSCSVMHE

ALHNHYTQKSLSLSLGSGGGGSGGGGSGGGGSAPTSSSTKKTQLQLEH

LLLDLQMILNGINNYKNPKLTRMLTFKFYMPKKATELKHLQCLEEELK

PLEEVLNLAQSKNFHLRPRDLISNINVIVLELKGSETTFMCEYADETA

TIVEFLNRWITFCQSIISTLT

The fusion protein sPDL1b02 used in this study is a heterodimer, which is formed by two Fc chains (Fc16 and Fc18) that are modified and fused with other proteins through a Knob-into-holes structure. The full-length DNA and amino acid sequences of the Fc16 have been shown hereabove.

The fusion protein sPDL1b02 used in this study is a heterodimer, which is formed by two Fc chains (Fc16 and Fc18) that are modified and fused with other proteins through a Knob-into-holes structure. The full-length DNA sequence (SEQ ID NO: 51) of Fc18 is as follows:

```
GAGGTGCAGCTGGTGGAATCCGGCGGAGGCCTGGTCCAGCCTGGCGGC
TCTCTGCGGCTGTCCTGCGCCGCTTCTGGCAGAACCTTCGTGACCTAC
GGCATGGGCTGGTTCCGGCAGGCTCCTGGCAAGGGCAGAGAGTTCGTG
TCCGCCATCTCCTGGTCCGGCTCCAgcACCTCTTACGGCGACTCTGTG
AAGGGCAGATTCACCATCAGCCGGGATAACGCCAAGAACACACTGTAC
CTGCAGATGAACTCCCTGCGGCCTGAGGACACCGCCGTGTACTACTGC
GCCGCTGCCCTGGGCGCTGTCGTGTACACCACCAGAGAACCCTATACC
TACTGGGGACAGGGCACCCTGGTGACCGTGTCCTCTGAGTCTAAGTAC
GGCCCTCCCTGTCCTCCTTGCCCTGCTCCTGAGTTCgaGGGCGGCCCC
TCCGTGTTTCTCTTCCCACCCAAGCCTAAGGACACCCTGATGATCTCC
AGAACCCCTGAGGTGACCTGCGTGGTGGTTGACGTGTCTCAGGAGGAT
CCCGAAGTGCAGTTTAATTGGTACGTGGACGGCGTCGAAGTGCACAAT
GCTAAAACCAAGCCTCGGGAGGAACAGTTCAATAGCACCTACAGAGTG
GTGAGCGTTCTGACAGTGCTGCACCAGGACTGGCTGAACGGCAAAGAG
TACAAGTGCAAGGTGTCCAACAAGGGCCTGCCATCCTCCATCGAGAAG
ACCATCTCCAAGGCCAAGGGACAACCTAGAGAGCCTCAGGTGTgCACC
CTGCCTCCCTCTCAGGAGGAGATGACCAAGAACCAGGTGTCTCTGtCC
TGCgctGTGAAGGGCTTCTACCCTTCCGACATCGCCGTGGAATGGGAA
AGCAACGGCCAACCTGAGAACAACTACAAGACCACCCCTCCTGTGCTG
GACTCCGATGGATCTTTCTTCCTGgttTCTCGGCTGACCGTCGACAAG
TCTAGATGGCAGGAGGGCAACGTGTTCAGCTGCTCCGTCATGCACGAG
GCCCTGCATAACCACTACACCCAGAAGTCCCTGTCCTTATCTCTGGGC
```

The fusion protein sPDL1b02 used in this study is a heterodimer, which is formed by two Fc chains (Fc16 and Fc18) that are modified and fused with other proteins through a Knob-into-holes structure. The full-length amino acid sequence (SEQ ID NO: 52) of Fc18 is as follows:

```
EVQLVESGGGLVQPGGSLRLSCAASGRTFVTYGMGWFRQAPGKGREFV
SAISWSGSSTSYGDSVKGRFTISRDNAKNTLYLQMNSLRPEDTAVYYC
AAALGAVVYTTREPYTYWGQGTLVTVSSESKYGPPCPPCPAPEFEGGP
SVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEK
TISKAKGQPREPQVCTLPPSQEEMTKNQVSLSCAVKGFYPSDIAVEWE
SNGQPENNYKTTPPVLDSDGSFFLVSRLTVDKSRWQEGNVFSCSVMHE
ALHNHYTQKSLSLSLG
```

The fusion protein sPDL1b03 used in this study is a heterodimer, which is formed by two Fc chains (Fc18 and Fc19) that are modified and fused with other proteins through a Knob-into-holes structure. The full-length DNA and amino acid sequences of the Fc18 have been shown hereabove.

The fusion protein sPDL1b03 used in this study is a heterodimer, which is formed by two Fc chains (Fc18 and Fc19) that are modified and fused with other proteins through a Knob-into-holes structure. The full-length DNA sequence (SEQ ID NO: 53) of Fc19 is as follows:

```
GAGGTGCAGCTGGTGGAATCCGGCGGAGGCCTGGTCCAGCCTGGCGGC
TCTCTGCGGCTGTCCTGCGCCGCTTCTGGCAGAACCTTCGTGACCTAC
GGCATGGGCTGGTTCCGGCAGGCTCCTGGCAAGGGCAGAGAGTTCGTG
TCCGCCATCTCCTGGTCCGGCTCCAgcACCTCTTACGGCGACTCTGTG
AAGGGCAGATTCACCATCAGCCGGGATAACGCCAAGAACACACTGTAC
CTGCAGATGAACTCCCTGCGGCCTGAGGACACCGCCGTGTACTACTGC
GCCGCTGCCCTGGGCGCTGTCGTGTACACCACCAGAGAACCCTATACC
TACTGGGGACAGGGCACCCTGGTGACCGTGTCCTCTGAGTCTAAGTAC
GGCCCTCCCTGTCCTCCTTGCCCTGCTCCTGAGTTCgaGGGCGGCCCC
TCCGTGTTTCTCTTCCCACCCAAGCCTAAGGACACCCTGATGATCTCC
AGAACCCCTGAGGTGACCTGCGTGGTGGTTGACGTGTCTCAGGAGGAT
CCCGAAGTGCAGTTTAATTGGTACGTGGACGGCGTCGAAGTGCACAAT
GCTAAAACCAAGCCTCGGGAGGAACAGTTCAATAGCACCTACAGAGTG
GTGAGCGTTCTGACAGTGCTGCACCAGGACTGGCTGAACGGCAAAGAG
TACAAGTGCAAGGTGTCCAACAAGGGCCTGCCATCCTCCATCGAGAAG
ACCATCTCCAAGGCCAAGGGACAACCTAGAGAGCCTCAGGTGTACACC
CTGCCTCCCTgTCAGGAGGAGATGACCAAGAACCAGGTGTCTCTGtgg
TGCCTGGTGAAGGGCTTCTACCCTTCCGACATCGCCGTGGAATGGGAA
AGCAACGGCCAACCTGAGAACAACTACAAGACCACCCCTCCTGTGCTG
GACTCCGATGGATCTTTCTTCCTGTACTCTCGGCTGACCGTCGACAAG
TCTAGATGGCAGGAGGGCAACGTGTTCAGCTGCTCCGTCATGCACGAG
GCCCTGCATAACCACTACACCCAGAAGTCCCTGTCCTTATCTCTGGGC
tcaGGTGGaGGCGGTAGTGGCGGAGGCGGTTCAGGCGGAGGCGGATCT
GCACCTACTTCAAGTTCTACAAAGAAAACACAGCTACAACTGGAGCAT
TTACTGCTGGATTTACAGATGATTTTGAATGGAATTAATAATTACAAG
AATCCCAAACTCACCAGGATGCTCACATTTAAGTTTTACATGCCCAAG
AAGGCCACAGAACTGAAACATCTTCAGTGTCTAGAAGAAGAACTCAAA
CCTCTGGAGGAAGTGCTAAATTTAGCTCAAAGCAAAAACTTTCACTTA
AGACCCAGGGACTTAATCAGCAATATCAACGTAATAGTTCTGGAACTA
AAGGGATCTGAAACAACATTCATGTGTGAATATGCTGATGAGACAGCA
ACCATTGTAGAATTTCTGAACAGATGGATTACCTTTTGTCAAAGCATC
ATCTCAACACTGACT
```

The fusion protein sPDL1b03 used in this study is a heterodimer, which is formed by two Fc chains (Fc18 and Fc19) that are modified and fused with other proteins through a Knob-into-holes structure. The full-length amino acid sequence (SEQ ID NO: 54) of Fc19 is as follows:

```
EVQLVESGGGLVQPGGSLRLSCAASGRTFVTYGMGWFRQAPGKGREFV
SAISWSGSSTSYGDSVKGRFTISRDNAKNTLYLQMNSLRPEDTAVYYC
```

-continued
```
AAALGAVVYTTREPYTYWGQGTLVTVSSESKYGPPCPPCPAPEFEGGP
SVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEK
TISKAKGQPREPQVYTLPPCQEEMTKNQVSLWCLVKGFYPSDIAVEWE
SNGQPENNYKTTPPVLDSDGSFFLYSRLTVDKSRWQEGNVFSCSVMHE
ALHNHYTQKSLSLSLGSGGGGSGGGGSGGGGSAPTSSSTKKTQLQLEH
LLLDLQMILNGINNYKNPKLTRMLTFKFYMPKKATELKHLQCLEEELK
PLEEVLNLAQSKNFHLRPRDLISNINVIVLELKGSETTFMCEYADETA
TIVEFLNRWITFCQSIISTLT
```

The fusion protein sPDL1c01 used in this study is a heterodimer, which is formed by two Fc chains (Fc20 and Fc21) that are modified and fused with other proteins through a Knob-into-holes structure. The full-length DNA sequence (SEQ ID NO: 55) of Fc20 is as follows:

```
GAGGTGCAGCTGGTGGAATCCGGCGGAGGCCTGGTGCAGCCTGGCGGC
TCTCTGAGACTGTCCTGCGCCGCTTCTGGCCGGACCTTCATCACCTAC
GCCATCGGCTGGTTCAGACAGGCCCCTGGCAAGGGCAGAGAGTTCGTG
TCCGCCATCTCCTGGTCCGGCTCTATGACCAGCTACGCCGACTCTGTG
AAGGGCAGATTCACCATCTCCCGGGATAACGCCAAGAACACCCTGTAC
CTGCAGATGAATTCCCTGAGACCTGAGGACACAGCTGTGTATTACTGC
GCCGCTCACCGGGGCGCCATCGCTCCCATCGCTCAGAGCGTGTACACC
AACTGGGGCCAGGGAACCCTGGTCACCGTGTCCAGCGAGTCTAAGTAC
GGCCCTCCCTGTCCTCCTTGCCCTGCTCCTGAGTTCgaGGGCGGCCCC
TCCGTGTTTCTCTTCCCACCCAAGCCTAAGGACACCCTGATGATCTCC
AGAACCCCTGAGGTGACCTGCGTGGTGGTTGACGTGTCTCAGGAGGAT
CCCGAAGTGCAGTTTAATTGGTACGTGGACGGCGTCGAAGTGCACAAT
GCTAAAACCAAGCCTCGGGAGGAACAGTTCAATAGCACCTACAGAGTG
GTGAGCGTTCTGACAGTGCTGCACCAGGACTGGCTGAACGGCAAAGAG
TACAAGTGCAAGGTGTCCAACAAGGGCCTGCCATCCTCCATCGAGAAG
ACCATCTCCAAGGCCAAGGGACAACCTAGAGAGCCTCAGGTGTACACC
CTGCCTCCCTgTCAGGAGGAGATGACCAAGAACCAGGTGTCTCTGtgg
TGCCTGGTGAAGGGCTTCTACCCTTCCGACATCGCCGTGGAATGGGAA
AGCAACGGCCAACCTGAGAACAACTACAAGACCACCCCTCCTGTGCTG
GACTCCGATGGATCTTTCTTCCTGTACTCTCGGCTGACCGTCGACAAG
TCTAGATGGCAGGAGGGCAACGTGTTCAGCTGCTCCGTCATGCACGAG
GCCCTGCATAACCACTACACCCAGAAGTCCCTGTCCTTATCTCTGGGC
tcaGGTGGaGGCGGTAGTGGCGGAGGCGGTTCAGGCGGAGGCGGATCT
ATTTGGGAGCTGAAGAAAGACGTGTACGTGGTCGAGCTGGACTGGTAC
CCTGATGCCCCAGGCGAGATGGTCGTGCTGACCTGCGATACACCAGAG
GAAGATGGTATCACCTGGACACTGGATCAGTCCTCAGAGGTGCTGGGC
TCTGGTAAAACACTGACCATTCAGGTGAAGGAGTTCGGTGACGCTGGA
CAGTACACTTGTCATAAGGGCGGGGAGGTGCTGTCTCACTCCCTGCTG
CTGCTGCATAAGAAGGAGGATGGAATCTGGTCCACTGACATCCTGAAA
GACCAGAAGGAGCCAAAGAACAAAACCTTCCTGCGATGCGAGGCTAAG
AACTACAGCGGCCGCTTTACATGCTGGTGGCTGACAACCATCAGCACC
GATCTGACCTTTAGCGTGAAGTCATCCAGGGGCAGTTCAGACCCTCAG
GGAGTCACATGTGGCGCCGCAACCCTGTCAGCAGAGCGAGTGCGGGGA
GACAATAAGGAATACGAGTACAGCGTCGAGTGTCAGGAGGATTCCGCA
TGTCCAGCTGCAGAAGAATCCCTGCCTATCGAAGTCATGGTGGACGCT
GTGCATAAACTGAAGTACGAGAATTACACCAGCAGCTTTTTCATCCGG
GACATCATCAAGCCCGATCCACCTAAGAATCTGCAGCTGAAGCCTCTG
AAAAATAGCCGACAGGTCGAAGTGTCATGGGAATACCCAGACACCTGG
TCAACACCACACTCCTACTTCTCCCTGACCTTCTGTGTGCAGGTCCAG
GGAAAAAGCAAGCGGGAAAAGAAAGATCGGGTGTTCACCGACAAGACC
AGTGCTACAGTGATTTGCCGGAAGAATGCCAGCATTTCTGTCAGAGCT
CAGGACCGGTACTATAGCTCTTCCTGGAGCGAGTGGGCTTCAGTGCCA
TGTTCTGGaGGCGGtGGATCTGGCGGAGGTGGAAGCGGAGGCGGTGGA
TCTAGAAACCTGCCCGTCGCAACCCCTGATCCAGGGATGTTCCCCTGT
CTGCATCACAGCCAGAATCTGCTGAGGGCTGTCTCCAACATGCTGCAG
AAGGCTCGACAGACCCTGGAGTTCTACCCATGTACCAGCGAAGAGATC
GACCACGAGGATATCACAAAGGATAAAACCAGCACAGTGGAAGCATGC
CTGCCTCTGGAACTGACCAAGAATGAGAGCTGCCTGAATAGCAGGGAG
ACCTCCTTCATCACCAACGGCTCATGCCTGGCTTCAAGGAAGACCAGC
TTCATGATGGCTCTGTGTCTGAGCTCTATCTATGAGGACCTGAAGATG
TACCAGGTGGAGTTCAAGACCATGAACGCCAAGCTGCTGATGGATCCA
AAGAGGCAGATCTTCCTGGATCAGAATATGCTGGCAGTGATCGATGAG
CTGATGCAGGCCCTGAATTTTAACAGTGAGACAGTGCCTCAGAAGAGC
TCTCTGGAAGAGCCAGACTTTTACAAAACTAAGATCAAGCTGTGCATT
CTGCTGCACGCTTTCCGCATCAGAGCTGTCACTATCGATAGAGTGATG
AGCTATCTGAATGCCTCA
```

The fusion protein sPDL1c01 used in this study is a heterodimer, which is formed by two Fc chains (Fc20 and Fc21) that are modified and fused with other proteins through a Knob-into-holes structure. The full-length amino acid sequence (SEQ ID NO: 56) of Fc20 is as follows:

```
EVQLVESGGGLVQPGGSLRLSCAASGRTFITYAIGWFRQAPGKGREFV
SAISWSGSMTSYADSVKGRFTISRDNAKNTLYLQMNSLRPEDTAVYYC
AAHRGAIAPIAQSVYTNWGQGTLVTVSSESKYGPPCPPCPAPEFEGGP
SVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEK
TISKAKGQPREPQVYTLPPCQEEMTKNQVSLWCLVKGFYPSDIAVEWE
SNGQPENNYKTTPPVLDSDGSFFLYSRLTVDKSRWQEGNVFSCSVMHE
```

-continued
```
ALHNHYTQKSLSLSLGSGGGGSGGGGSGGGGSIWELKKDVYVVELDWY

PDAPGEMVVLTCDTPEEDGITWTLDQSSEVLGSGKTLTIQVKEFGDAG

QYTCHKGGEVLSHSLLLLHKKEDGIWSTDILKDQKEPKNKTFLRCEAK

NYSGRFTCWWLTTISTDLTFSVKSSRGSSDPQGVTCGAATLSAERVRG

DNKEYEYSVECQEDSACPAAEESLPIEVMVDAVHKLKYENYTSSFFIR

DIIKPDPPKNLQLKPLKNSRQVEVSWEYPDTWSTPHSYFSLTFCVQVQ

GKSKREKKDRVFTDKTSATVICRKNASISVRAQDRYYSSSWSEWASVP

CSGGGGSGGGGSGGGGSRNLPVATPDPGMFPCLHHSQNLLRAVSNMLQ

KARQTLEFYPCTSEEIDHEDITKDKTSTVEACLPLELTKNESCLNSRE

TSFITNGSCLASRKTSFMMALCLSSIYEDLKMYQVEFKTMNAKLLMDP

KRQIFLDQNMLAVIDELMQALNFNSETVPQKSSLEEPDFYKTKIKLCI

LLHAFRIRAVTIDRVMSYLNAS
```

The fusion protein sPDL1c01 used in this study is a heterodimer, which is formed by two Fc chains (Fc20 and Fc21) that are modified and fused with other proteins through a Knob-into-holes structure. The full-length DNA sequence (SEQ ID NO: 57) of Fc21 is as follows:

```
GAGGTGCAGCTGGTGGAATCCGGCGGAGGCCTGGTGCAGCCTGGCGGC

TCTCTGAGACTGTCCTGCGCCGCTTCTGGCCGGACCTTCATCACCTAC

GCCATCGGCTGGTTCAGACAGGCCCCTGGCAAGGGCAGAGAGTTCGTG

TCCGCCATCTCCTGGTCCGGCTCTATGACCAGCTACGCCGACTCTGTG

AAGGGCAGATTCACCATCTCCCGGGATAACGCCAAGAACACCCTGTAC

CTGCAGATGAATTCCCTGAGACCTGAGGACACAGCTGTGTATTACTGC

GCCGCTCACCGGGGCGCCATCGCTCCCATCGCTCAGAGCGTGTACACC

AACTGGGGCCAGGGAACCCTGGTCACCGTGTCCAGCGAGTCTAAGTAC

GGCCCTCCCTGTCCTCCTTGCCCTGCTCCTGAGTTCGaGGGCGGCCCC

TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCATCCTCCATCGAGAAG

ACCATCTCCAAGGCCAAGGGACAACCTAGAGAGCCTCAGGTGTgCACC

CTGCCTCCCTCTCAGGAGGAGATGACCAAGAACCAGGTGTCTCTGtCC

TGCgctGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGgttTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC tcaGGTGGaGGCGGTAGTGGCGGAGGCGGTTCAGGCGGAGGCGGATCT

GCACCTACTTCAAGTTCTACAAAGAAAACACAGCTACAACTGGAGCAT

TTACTGCTGGATTTACAGATGATTTTGAATGGAATTAATAATTACAAG

AATCCCAAACTCACCAGGATGCTCACATTTAAGTTTTACATGCCCAAG

AAGGCCACAGAACTGAAACATCTTCAGTGTCTAGAAGAAGAACTCAAA

CCTCTGGAGGAAGTGCTAAATTTAGCTCAAAGCAAAAACTTTCACTTA

AGACCCAGGGACTTAATCAGCAATATCAACGTAATAGTTCTGGAACTA

AAGGGATCTGAAACAACATTCATGTGTGAATATGCTGATGAGACAGCA

ACCATTGTAGAATTTCTGAACAGATGGATTACCTTTTGTCAAAGCATC

ATCTCAACACTGACT
```

The fusion protein sPDL1c01 used in this study is a heterodimer, which is formed by two Fc chains (Fc20 and Fc21) that are modified and fused with other proteins through a Knob-into-holes structure. The full-length amino acid sequence (SEQ ID NO: 58) of Fc21 is as follows:

```
EVQLVESGGGLVQPGGSLRLSCAASGRTFITYAIGWFRQAPGKGREFV

SAISWSGSMTSYADSVKGRFTISRDNAKNTLYLQMNSLRPEDTAVYYC

AAHRGAIAPIAQSVYTNWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVCTLPPSQEEMTKNQVSLSCAVKGFYPSDIAVEWE

SNGQPENNYKTTPPVLDSDGSFFLVSRLTVDKSRWQEGNVFSCSVMHE

ALHNHYTQKSLSLSLGSGGGGSGGGGSGGGGSAPTSSSTKKTQLQLEH

LLLDLQMILNGINNYKNPKLTRMLTFKFYMPKKATELKHLQCLEEELK

PLEEVLNLAQSKNFHLRPRDLISNINVIVLELKGSETTFMCEYADETA

TIVEFLNRWITFCQSIISTLT
```

The fusion protein sPDL1c02 used in this study is a heterodimer, which is formed by two Fc chains (Fc20 and Fc22) that are modified and fused with other proteins through a Knob-into-holes structure. The full-length DNA and amino acid sequences of the Fc20 have been shown hereabove.

The fusion protein sPDL1c02 used in this study is a heterodimer, which is formed by two Fc chains (Fc20 and Fc22) that are modified and fused with other proteins through a Knob-into-holes structure. The full-length DNA sequence (SEQ ID NO: 59) of Fc22 is as follows:

```
GAGGTGCAGCTGGTGGAATCCGGCGGAGGCCTGGTGCAGCCTGGCGGC

TCTCTGAGACTGTCCTGCGCCGCTTCTGGCCGGACCTTCATCACCTAC

GCCATCGGCTGGTTCAGACAGGCCCCTGGCAAGGGCAGAGAGTTCGTG

TCCGCCATCTCCTGGTCCGGCTCTATGACCAGCTACGCCGACTCTGTG

AAGGGCAGATTCACCATCTCCCGGGATAACGCCAAGAACACCCTGTAC

CTGCAGATGAATTCCCTGAGACCTGAGGACACAGCTGTGTATTACTGC

GCCGCTCACCGGGGCGCCATCGCTCCCATCGCTCAGAGCGTGTACACC

AACTGGGGCCAGGGAACCCTGGTCACCGTGTCCAGCGAGTCTAAGTAC

GGCCCTCCCTGTCCTCCTTGCCCTGCTCCTGAGTTCGaGGGCGGCCCC
```

```
TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCATCCTCCATCGAGAAG

ACCATCTCCAAGGCCAAGGGACAACCTAGAGAGCCTCAGGTGTgCACC

CTGCCTCCCTCTCAGGAGGAGATGACCAAGAACCAGGTGTCTCTGtCC

TGCgctGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGgttTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC
```

The fusion protein sPDL1c02 used in this study is a heterodimer, which is formed by two Fc chains (Fc20 and Fc22) that are modified and fused with other proteins through a Knob-into-holes structure. The full-length amino acid sequence (SEQ ID NO: 60) of Fc22 is as follows:

```
EVQLVESGGGLVQPGGSLRLSCAASGRTFITYAIGWFRQAPGKGREFV

SAISWSGSMTSYADSVKGRFTISRDNAKNTLYLQMNSLRPEDTAVYYC

AAHRGAIAPIAQSVYTNWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVCTLPPSQEEMTKNQVSLSCAVKGFYPSDIAVEWE

SNGQPENNYKTTPPVLDSDGSFFLVSRLTVDKSRWQEGNVFSCSVMHE

ALHNHYTQKSLSLSLG
```

The fusion protein sPDL1c03 used in this study is a heterodimer, which is formed by two Fc chains (Fc22 and Fc23) that are modified and fused with other proteins through a Knob-into-holes structure. The full-length DNA and amino acid sequences of the Fc22 have been shown hereabove.

The fusion protein sPDL1c03 used in this study is a heterodimer, which is formed by two Fc chains (Fc22 and Fc23) that are modified and fused with other proteins through a Knob-into-holes structure. The full-length DNA sequence (SEQ ID NO: 61) of Fc23 is as follows:

```
GAGGTGCAGCTGGTGGAATCCGGCGGAGGCCTGGTGCAGCCTGGCGGC

TCTCTGAGACTGTCCTGCGCCGCTTCTGGCCGGACCTTCATCACCTAC

GCCATCGGCTGGTTCAGACAGGCCCCTGGCAAGGGCAGAGAGTTCGTG

TCCGCCATCTCCTGGTCCGGCTCTATGACCAGCTACGCCGACTCTGTG

AAGGGCAGATTCACCATCTCCCGGGATAACGCCAAGAACACCCTGTAC

CTGCAGATGAATTCCCTGAGACCTGAGGACACAGCTGTGTATTACTGC

GCCGCTCACCGGGGCGCCATCGCTCCCATCGCTCAGAGCGTGTACACC
```

```
AACTGGGGCCAGGGAACCCTGGTCACCGTGTCCAGCGAGTCTAAGTAC

GGCCCTCCCTGTCCTCCTTGCCCTGCTCCTGAGTTCgaGGGCGGCCCC

TCCGTGTTTCTCTTCCCACCCAAGCCTAAGGACACCCTGATGATCTCC

AGAACCCCTGAGGTGACCTGCGTGGTGGTTGACGTGTCTCAGGAGGAT

CCCGAAGTGCAGTTTAATTGGTACGTGGACGGCGTCGAAGTGCACAAT

GCTAAAACCAAGCCTCGGGAGGAACAGTTCAATAGCACCTACAGAGTG

GTGAGCGTTCTGACAGTGCTGCACCAGGACTGGCTGAACGGCAAAGAG

TACAAGTGCAAGGTGTCCAACAAGGGCCTGCCATCCTCCATCGAGAAG

ACCATCTCCAAGGCCAAGGGACAACCTAGAGAGCCTCAGGTGTACACC

CTGCCTCCCTgTCAGGAGGAGATGACCAAGAACCAGGTGTCTCTGtgg

TGCCTGGTGAAGGGCTTCTACCCTTCCGACATCGCCGTGGAATGGGAA

AGCAACGGCCAACCTGAGAACAACTACAAGACCACCCCTCCTGTGCTG

GACTCCGATGGATCTTTCTTCCTGTACTCTCGGCTGACCGTCGACAAG

TCTAGATGGCAGGAGGGCAACGTGTTCAGCTGCTCCGTCATGCACGAG

GCCCTGCATAACCACTACACCCAGAAGTCCCTGTCCTTATCTCTGGGC tcaGGTGGaGGCGGTAGTGGCGGAGGCGGTTCAGGCGGAGGCGGATCT

GCACCTACTTCAAGTTCTACAAAGAAAACACAGCTACAACTGGAGCAT

TTACTGCTGGATTTACAGATGATTTTGAATGGAATTAATAATTACAAG

AATCCCAAACTCACCAGGATGCTCACATTTAAGTTTTACATGCCCAAG

AAGGCCACAGAACTGAAACATCTTCAGTGTCTAGAAGAAGAACTCAAA

CCTCTGGAGGAAGTGCTAAATTTAGCTCAAAGCAAAAACTTTCACTTA

AGACCCAGGGACTTAATCAGCAATATCAACGTAATAGTTCTGGAACTA

AAGGGATCTGAAACAACATTCATGTGTGAATATGCTGATGAGACAGCA

ACCATTGTAGAATTTCTGAACAGATGGATTACCTTTTGTCAAAGCATC

ATCTCAACACTGACT
```

The fusion protein sPDL1c03 used in this study is a heterodimer, which is formed by two Fc chains (Fc22 and Fc23) that are modified and fused with other proteins through a Knob-into-holes structure. The full-length amino acid sequence (SEQ ID NO: 62) of Fc23 is as follows:

```
EVQLVESGGGLVQPGGSLRLSCAASGRTFITYAIGWFRQAPGKGREFV

SAISWSGSMTSYADSVKGRFTISRDNAKNTLYLQMNSLRPEDTAVYYC

AAHRGAIAPIAQSVYTNWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVYTLPPCQEEMTKNQVSLWCLVKGFYPSDIAVEWE

SNGQPENNYKTTPPVLDSDGSFFLYSRLTVDKSRWQEGNVFSCSVMHE

ALHNHYTQKSLSLSLGSGGGGSGGGGSGGGGSAPTSSSTKKTQLQEH

LLLDLQMILNGINNYKNPKLTRMLTFKFYMPKKATELKHLQCLEEELK

PLEEVLNLAQSKNFHLRPRDLISNINVIVLELKGSETTFMCEYADETA

TIVEFLNRWITFCQSIISTLT
```

The fusion protein sPD1a00 used in this study is a homodimer, and the full-length DNA sequence (SEQ ID NO: 63) of the polypeptide chain is as follows:

GAAGTGCAGCTGGTTGAGTCCGGCGGCGGCCTGGTGCAGCCTGGCGGT
TCTCTGCGGCTGTCTTGCGCCGTGAGCGGAAATATCTACAACCGGAAC
TTCATGGGCTGGTTTCGGCAGGCTCCAGGCAAAGGACTGGAAGGCGTG
TCCGCCATCTACACCGGCACCTCTCGGACCTACTACGCCGACTCTGTC
AAAGGCAGATTCACCATCTCCCGCGACAACAGCAAAAACACCGTGTAC
CTGCAGATGAACAGCCTGAGAGCTGAAGATACAGCTGTGTACTATTGC
GCCGCCGATCTGAGAGACGGCTTCTGGGACACAGGCGTGTGGAACACC
TGGGGCCAGGGCACACTTGTGACCGTGTCCTCTGAGAGCAAGTACGGA
CCACCTTGCCCACCATGTCCAGCTCCTGAGTTTGAGGGAGGACCATCC
GTGTTCCTGTTTCCTCCAAAGCCTAAGGACACCCTGATGATCAGCCGG
ACACCTGAGGTGACCTGCGTGGTGGTGGACGTGTCTCAGGAGGATCCA
GAGGTGCAGTTCAACTGGTACGTGGATGGCGTGGAGGTGCACAATGCT
AAGACCAAGCCAAGAGAGGAGCAGTTTAATTCCACATACCGCGTGGTG
AGCGTGCTGACCGTGCTGCATCAGGATTGGCTGAACGGCAAGGAGTAT
AAGTGCAAGGTGTCCAATAAGGGCCTGCCCAGCTCTATCGAAGACA
ATCAGCAAGGCTAAGGGACAGCCTAGGGAGCCACAGGTGTACACCCTG
CCCCCTTCTCAGGAGGAGATGACAAAGAACCAGGTGTCCCTGACCTGT
CTGGTGAAGGGCTTCTATCCAAGCGACATCGCTGTGGAGTGGGAGTCT
AATGGCCAGCCCGAGAACAATTACAAGACCACACCACCCGTGCTGGAC
TCTGATGGCTCCTTCTTTCTGTATTCTAGGCTGACAGTGGATAAGTCC
CGGTGGCAGGAGGGCAACGTGTTTAGCTGCTCTGTGATGCACGAGGCC
CTGCACAATCATTATACCCAGAAGTCCCTGAGCCTGTCTCTGGGCAAG

The fusion protein sPD1a00 used in this study is a homodimer, and the full-length amino acid sequence (SEQ ID NO: 64) of the polypeptide chain is as follows:

EVQLVESGGGLVQPGGSLRLSCAVSGNIYNRNFMGWFRQAPGKGLEGV
SAIYTGTSRTYYADSVKGRFTISRDNSKNTVYLQMNSLRAEDTAVYYC
AADLRDGFWDTGVWNTWGQGTLVTVSSESKYGPPCPPCPAPEFEGGPS
VFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEA
LHNHYTQKSLSLSLGK

The fusion protein sPDL1a00 used in this study is a homodimer, and the full-length DNA sequence (SEQ ID NO: 65) of the polypeptide chain is as follows:

GAGGTGCAGCTGGTGGAATCCGGCGGAGGCCTGGTCCAGCCTGGCGGC
TCTCTGCGGCTGTCCTGCGCCGCTTCTGGCAGAACCTTCGTGACCTAC
GGCATGGGCTGGTTCCGGCAGGCTCCTGGCAAGGGCAGAGAGTTCGTG
TCCGCCATCTCCTGGTCCGGCTCCATGACCTCTTACGGCGACTCTGTG
AAGGGCAGATTCACCATCAGCCGGGATAACGCCAAGAACACACTGTAC
CTGCAGATGAACTCCCTGCGGCCTGAGGACACCGCCGTGTACTACTGC
GCCGCTGCCCTGGGCGCTGTCGTGTACACCACCAGAGAACCCTATACC
TACTGGGGACAGGGCACCCTGGTGACCGTGTCCTCTGAGAGCAAGTAC
GGACCACCTTGCCCACCATGTCCAGCTCCTGAGTTTGAGGGAGGACCA
TCCGTGTTCCTGTTTCCTCCAAAGCCTAAGGACACCCTGATGATCAGC
CGGACACCTGAGGTGACCTGCGTGGTGGTGGACGTGTCTCAGGAGGAT
CCAGAGGTGCAGTTCAACTGGTACGTGGATGGCGTGGAGGTGCACAAT
GCTAAGACCAAGCCAAGAGAGGAGCAGTTTAATTCCACATACCGCGTG
GTGAGCGTGCTGACCGTGCTGCATCAGGATTGGCTGAACGGCAAGGAG
TATAAGTGCAAGGTGTCCAATAAGGGCCTGCCCAGCTCTATCGAGAAG
ACAATCAGCAAGGCTAAGGGACAGCCTAGGGAGCCACAGGTGTACACC
CTGCCCCCTTCTCAGGAGGAGATGACAAAGAACCAGGTGTCCCTGACC
TGTCTGGTGAAGGGCTTCTATCCAAGCGACATCGCTGTGGAGTGGGAG
TCTAATGGCCAGCCCGAGAACAATTACAAGACCACACCACCCGTGCTG
GACTCTGATGGCTCCTTCTTTCTGTATTCTAGGCTGACAGTGGATAAG
TCCCGGTGGCAGGAGGGCAACGTGTTTAGCTGCTCTGTGATGCACGAG
GCCCTGCACAATCATTATACCCAGAAGTCCCTGAGCCTGTCTCTGGGC
AAG

The fusion protein sPDL1a00 used in this study is a homodimer, and the full-length amino acid sequence (SEQ ID NO: 66) of the polypeptide chain is as follows:

EVQLVESGGGLVQPGGSLRLSCAASGRTFVTYGMGWFRQAPGKGREFV
SAISWSGSMTSYGDSVKGRFTISRDNAKNTLYLQMNSLRPEDTAVYYC
AAALGAVVYTTREPYTYWGQGTLVTVSSESKYGPPCPPCPAPEFEGGP
SVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHE
ALHNHYTQKSLSLSLGK

The fusion protein sPDL1b00 used in this study is a homodimer, and the full-length DNA sequence (SEQ ID NO: 67) of the polypeptide chain is as follows:

GAGGTGCAGCTGGTGGAATCCGGCGGAGGCCTGGTCCAGCCTGGCGGC
TCTCTGCGGCTGTCCTGCGCCGCTTCTGGCAGAACCTTCGTGACCTAC
GGCATGGGCTGGTTCCGGCAGGCTCCTGGCAAGGGCAGAGAGTTCGTG
TCCGCCATCTCCTGGTCCGGCTCCAgcACCTCTTACGGCGACTCTGTG
AAGGGCAGATTCACCATCAGCCGGGATAACGCCAAGAACACACTGTAC
CTGCAGATGAACTCCCTGCGGCCTGAGGACACCGCCGTGTACTACTGC

```
GCCGCTGCCCTGGGCGCTGTCGTGTACACCACCAGAGAACCCTATACC

TACTGGGGACAGGGCACCCTGGTGACCGTGTCCTCTGAGAGCAAGTAC

GGACCACCTTGCCCACCATGTCCAGCTCCTGAGTTTGAGGGAGGACCA

TCCGTGTTCCTGTTTCCTCCAAAGCCTAAGGACACCCTGATGATCAGC

CGGACACCTGAGGTGACCTGCGTGGTGGTGGACGTGTCTCAGGAGGAT

CCAGAGGTGCAGTTCAACTGGTACGTGGATGGCGTGGAGGTGCACAAT

GCTAAGACCAAGCCAAGAGAGGAGCAGTTTAATTCCACATACCGCGTG

GTGAGCGTGCTGACCGTGCTGCATCAGGATTGGCTGAACGGCAAGGAG

TATAAGTGCAAGGTGTCCAATAAGGGCCTGCCCAGCTCTATCGAGAAG

ACAATCAGCAAGGCTAAGGGACAGCCTAGGGAGCCACAGGTGTACACC

CTGCCCCCTTCTCAGGAGGAGATGACAAAGAACCAGGTGTCCCTGACC

TGTCTGGTGAAGGGCTTCTATCCAAGCGACATCGCTGTGGAGTGGGAG

TCTAATGGCCAGCCCGAGAACAATTACAAGACCACACCACCCGTGCTG

GACTCTGATGGCTCCTTCTTTCTGTATTCTAGGCTGACAGTGGATAAG

TCCCGGTGGCAGGAGGGCAACGTGTTTAGCTGCTCTGTGATGCACGAG

GCCCTGCACAATCATTATACCCAGAAGTCCCTGAGCCTGTCTCTGGGC

AAG
```

The fusion protein sPDL1b00 used in this study is a homodimer, and the full-length amino acid sequence (SEQ ID NO: 68) of the polypeptide chain is as follows:

```
EVQLVESGGGLVQPGGSLRLSCAASGRTFVTYGMGWFRQAPGKGREFV

SAISWSGSSTSYGDSVKGRFTISRDNAKNTLYLQMNSLRPEDTAVYYC

AAALGAVVYTTREPYTYWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHE

ALHNHYTQKSLSLSLGK
```

The fusion protein sPDL1c00 used in this study is a homodimer, and the full-length DNA sequence (SEQ ID NO: 69) of the polypeptide chain is as follows:

```
GAGGTGCAGCTGGTGGAATCCGGCGGAGGCCTGGTGCAGCCTGGCGGC

TCTCTGAGACTGTCCTGCGCCGCTTCTGGCCGGACCTTCATCACCTAC

GCCATCGGCTGGTTCAGACAGGCCCCTGGCAAGGGCAGAGAGTTCGTG

TCCGCCATCTCCTGGTCCGGCTCTATGACCAGCTACGCCGACTCTGTG

AAGGGCAGATTCACCATCTCCCGGGATAACGCCAAGAACACCCTGTAC

CTGCAGATGAATTCCCTGAGACCTGAGGACACAGCTGTGTATTACTGC

GCCGCTCACCGGGGCGCCATCGCTCCCATCGCTCAGAGCGTGTACACC

AACTGGGGCCAGGGAACCCTGGTCACCGTGTCCAGCGAGAGCAAGTAC

GGACCACCTTGCCCACCATGTCCAGCTCCTGAGTTTGAGGGAGGACCA

TCCGTGTTCCTGTTTCCTCCAAAGCCTAAGGACACCCTGATGATCAGC

CGGACACCTGAGGTGACCTGCGTGGTGGTGGACGTGTCTCAGGAGGAT

CCAGAGGTGCAGTTCAACTGGTACGTGGATGGCGTGGAGGTGCACAAT

GCTAAGACCAAGCCAAGAGAGGAGCAGTTTAATTCCACATACCGCGTG

GTGAGCGTGCTGACCGTGCTGCATCAGGATTGGCTGAACGGCAAGGAG

TATAAGTGCAAGGTGTCCAATAAGGGCCTGCCCAGCTCTATCGAGAAG

ACAATCAGCAAGGCTAAGGGACAGCCTAGGGAGCCACAGGTGTACACC

CTGCCCCCTTCTCAGGAGGAGATGACAAAGAACCAGGTGTCCCTGACC

TGTCTGGTGAAGGGCTTCTATCCAAGCGACATCGCTGTGGAGTGGGAG

TCTAATGGCCAGCCCGAGAACAATTACAAGACCACACCACCCGTGCTG

GACTCTGATGGCTCCTTCTTTCTGTATTCTAGGCTGACAGTGGATAAG

TCCCGGTGGCAGGAGGGCAACGTGTTTAGCTGCTCTGTGATGCACGAG

GCCCTGCACAATCATTATACCCAGAAGTCCCTGAGCCTGTCTCTGGGC

AAG
```

The fusion protein sPDL1c00 used in this study is a homodimer, and the full-length amino acid sequence (SEQ ID NO: 70) of the polypeptide chain is as follows:

```
EVQLVESGGGLVQPGGSLRLSCAASGRTFITYAIGWFRQAPGKGREFV

SAISWSGSMTSYADSVKGRFTISRDNAKNTLYLQMNSLRPEDTAVYYC

AAHRGAIAPIAQSVYTNWGQGTLVTVSSESKYGPPCPPCPAPEFEGGP

SVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHE

ALHNHYTQKSLSLSLGK
```

5. Broad-Spectrum Validation: Analysis of Experimental Results of IFN-γ Release

In this experiment, the in vitro biological activities of the cytokines IL-12 and IL-2 in the fusion protein are verified by employing the cytokines to stimulate the NK92 cells to release the interferon-gamma (IFN-γ). Since the fusion protein constructed in this experiment contains the cytokine, different fusion proteins are incubated with the NK92 cells, and then the release of IFN-γ is detected.

Figure 13:
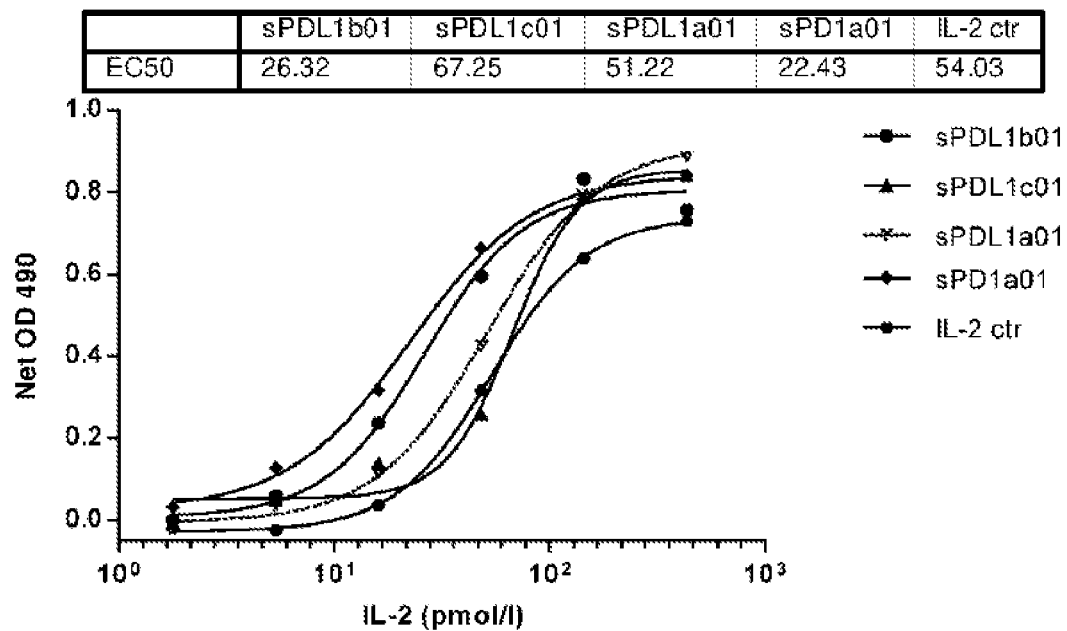
FIG. 13 shows the IL-2 activities of heterodimer fusion proteins sPDL1a01, sPDL1b01, sPDL1c01 and sPD1a01 compared with that of a control IL-2.
Figure 14:
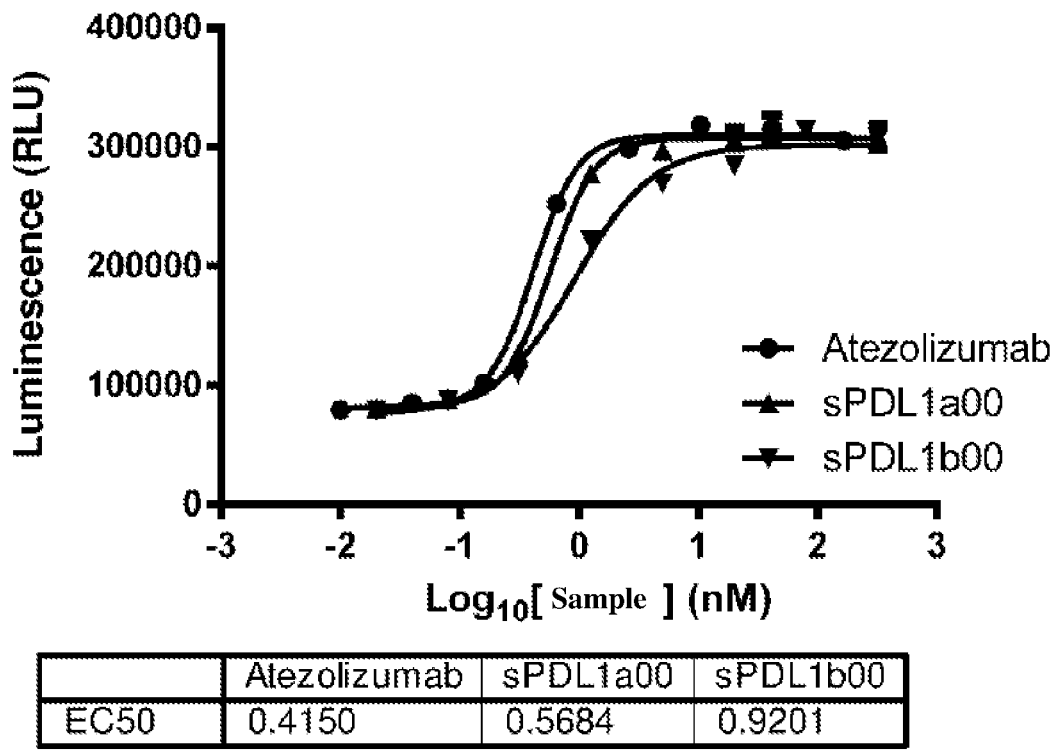
FIG. 14 shows the PD-1/PD-L1 pathway blocking activities of homodimer fusion proteins sPDL1a00 and sPDL1b00 without linked cytokine, compared with that of control Atezolizumab.
Figure 15:
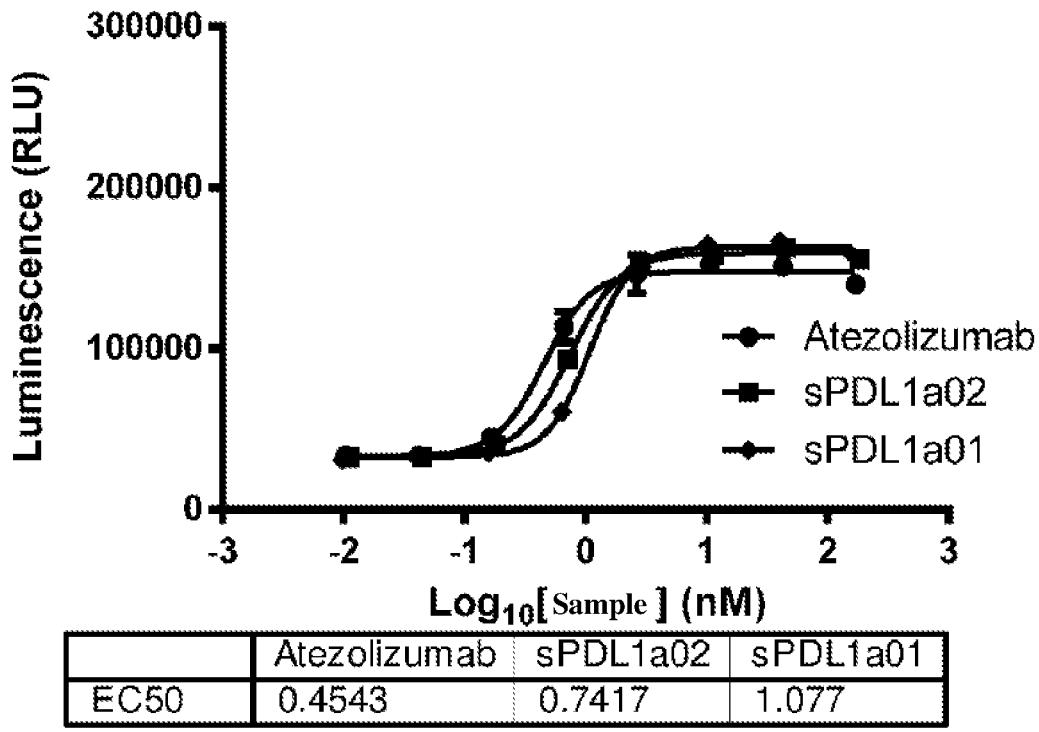
FIG. 15 shows the PD-1/PD-L1 pathway blocking activities of heterodimeric fusion proteins sPDL1a01 and sPDL1a02 compared with that of the control Atezolizumab.
Figure 16:
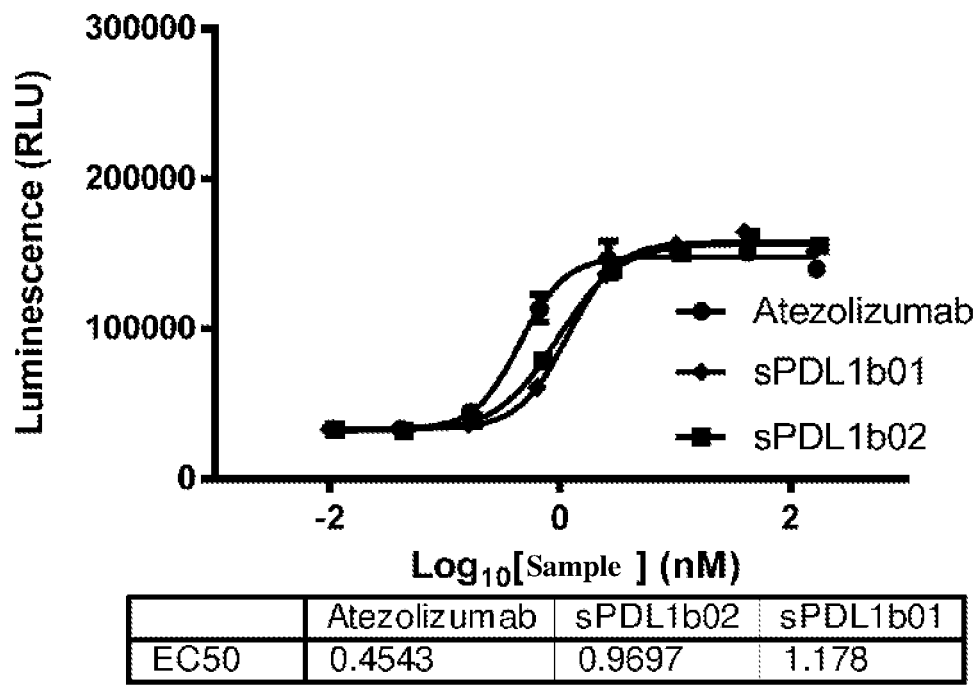
FIG. 16 shows the PD-1/PD-L1 pathway blocking activities of heterodimeric fusion proteins sPDL1b01 and sPDL1b02 compared with that of the control Atezolizumab.
Figure 17:
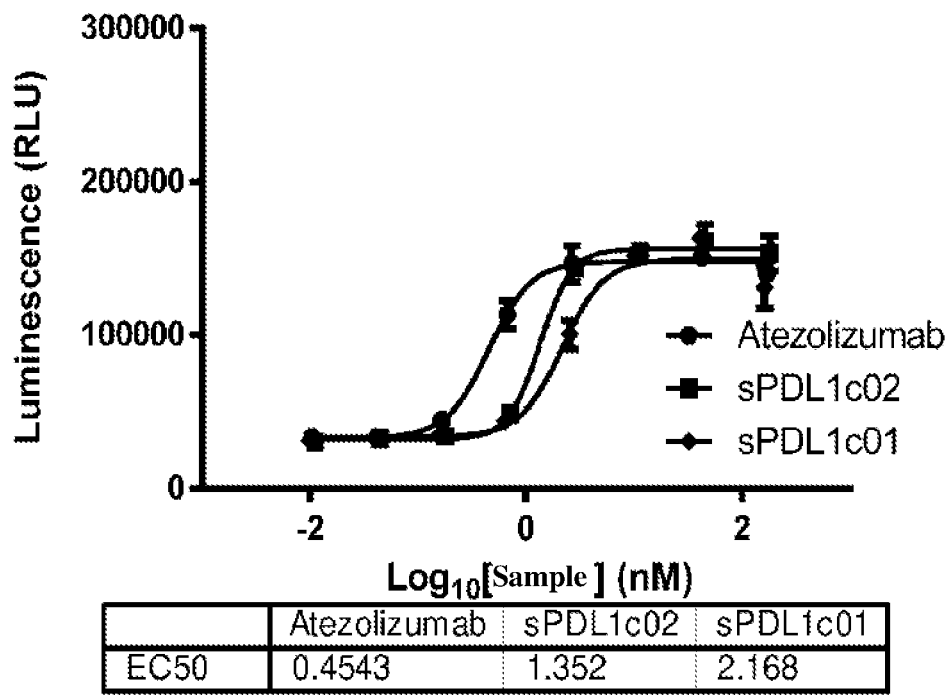
FIG. 17 shows the PD-1/PD-L1 pathway blocking activities of heterodimeric fusion proteins sPDL1c01 and sPDL1c02 compared with that of the control Atezolizumab.
Figure 18:
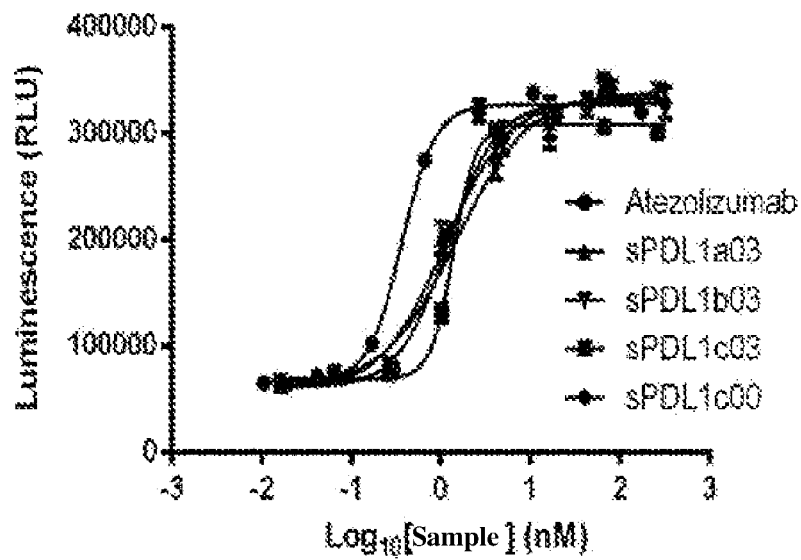
FIG. 18 not only shows the PD-1/PD-L1 pathway blocking activity of heterodimeric fusion proteins sPDL1a03, sPDL1b03, sPDL1c03, and homodimer fusion protein sPDL1c00 without linked cytokine, compared with that of the control Atezolizumab.
Figure 19:
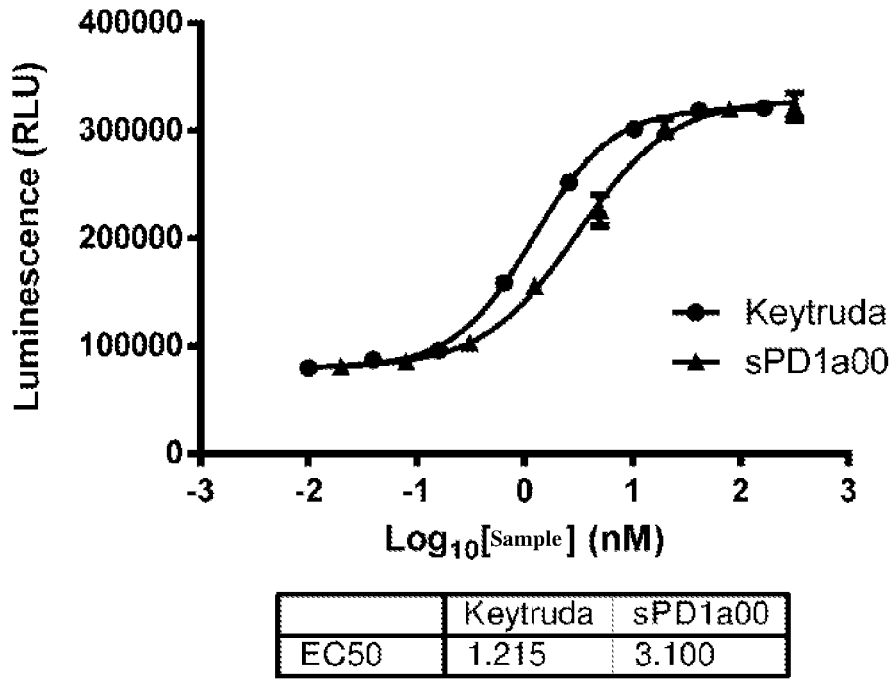
FIG. 19 shows the PD-1/PD-L1 pathway blocking activity of a homodimer fusion protein sPD1a00 without linked cytokine, compared with that of the control Keytruda.
Figure 20:
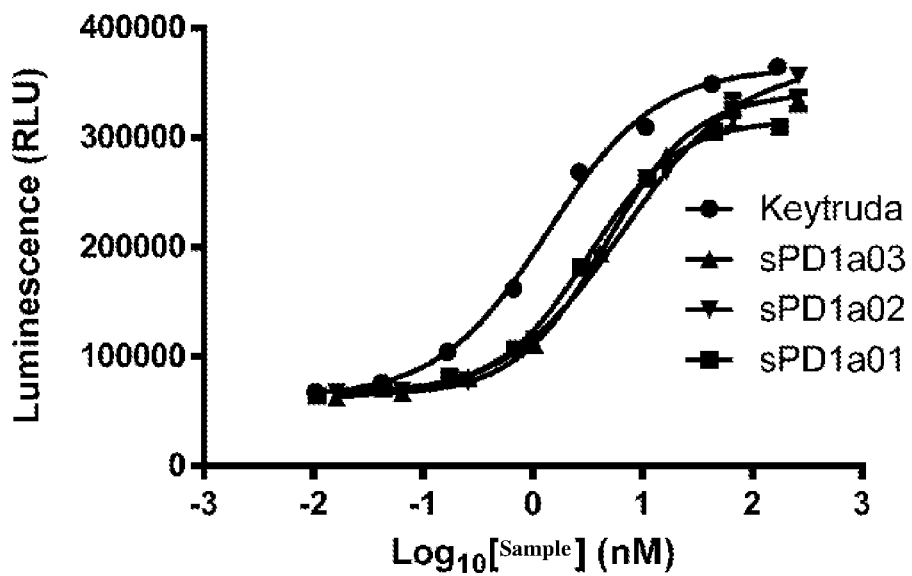
FIG. 20 shows the PD-1/PD-L1 pathway blocking activities of heterodimeric fusion proteins sPD1a01, sPD1a02 and sPD1a03 compared with that of the control Keytruda.
Figure 21:
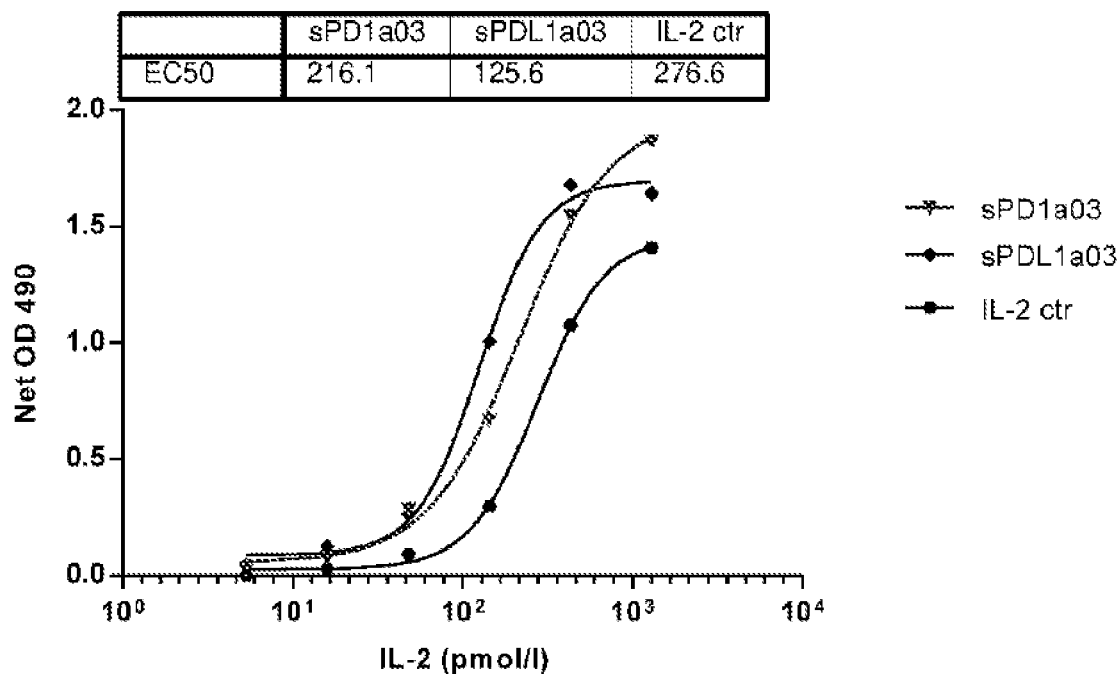
FIG. 21 shows the IL-2 activities of heterodimer fusion proteins sPD1a03 and sPDL1a03 compared with that of the control IL-2.
Figure 22:
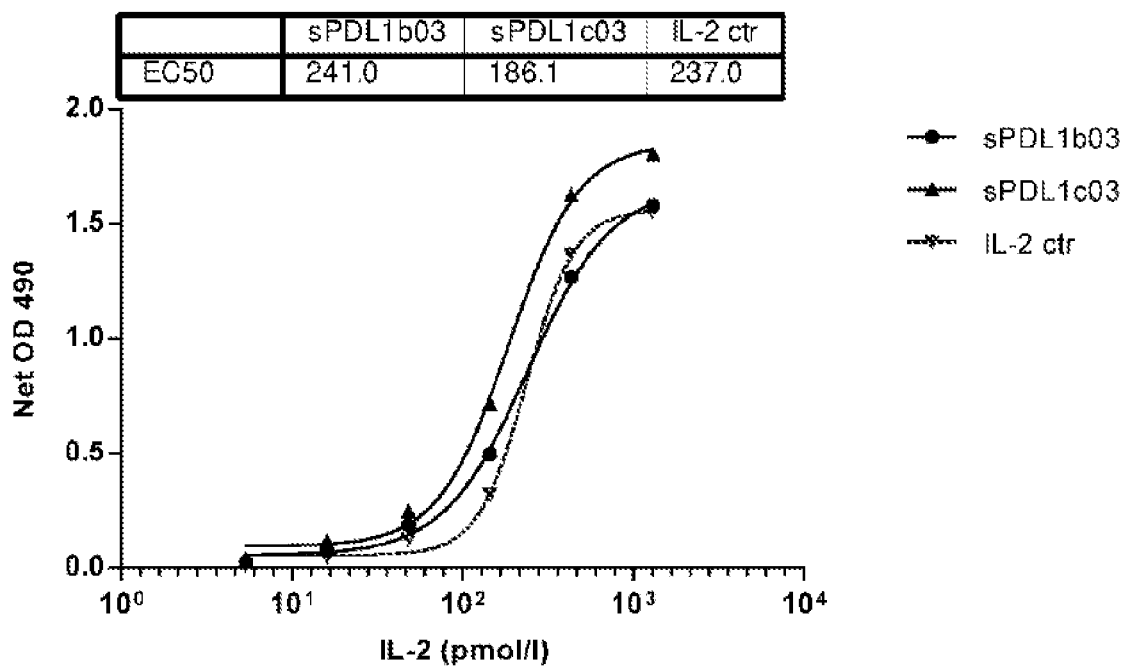
FIG. 22 shows the IL-2 activities of heterodimer fusion proteins sPDL1b03 and sPDL1c03 compared with that of the control IL-2.

For the fusion protein in which the IL-2 is fused, the IL-2 activities of the newly constructed series of heterodimers are all enhanced (FIGS. 13 and 21) or similar (FIG. 22) compared with the biological activity of the free IL-2, which is consistent with the aforementioned experimental results, thereby indicating that the fusion protein based on the antibody Fc heterodimer technology can significantly improve or maintain the IL-2 activity.

Figure 11:
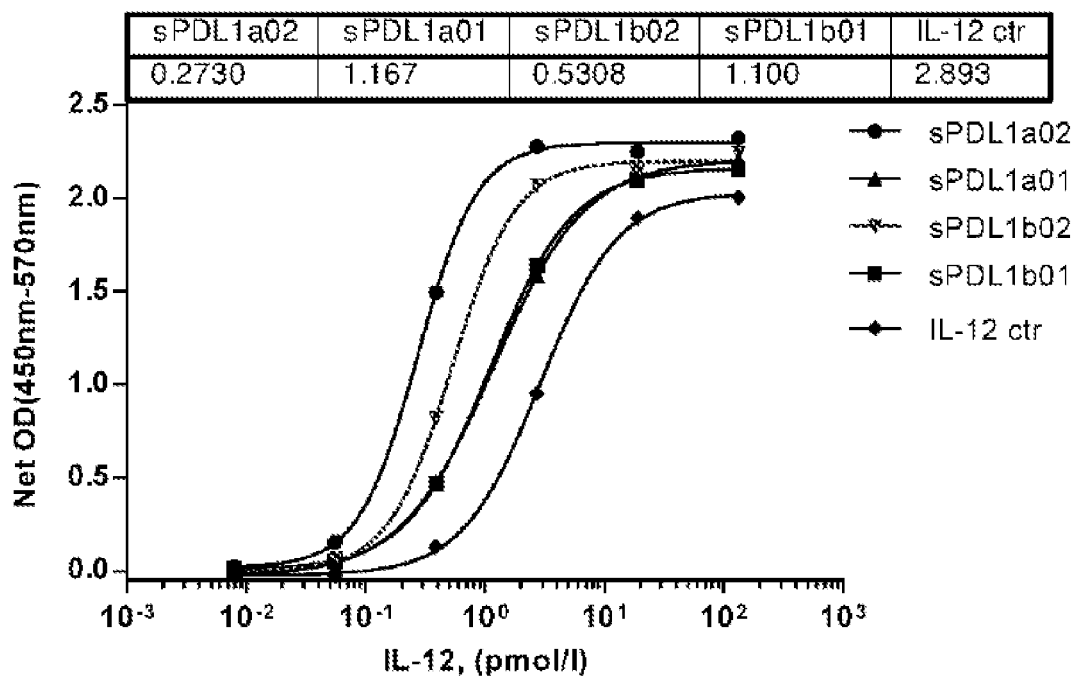
FIG. 11 shows the IL-12 activities of heterodimer fusion proteins sPDL1a01, sPDL1a02, sPDL1b01 and sPDL1b02 compared with that of a control IL-12.
Figure 12:
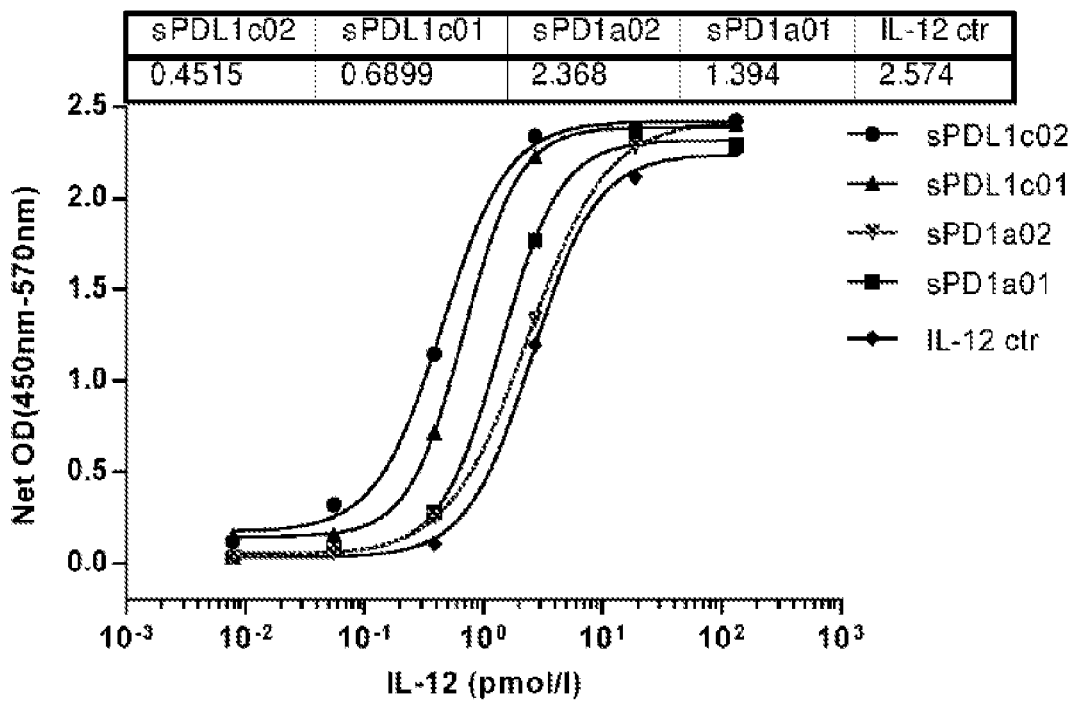
FIG. 12 shows the IL-12 activities of heterodimer fusion proteins sPDL1c01, sPDL1c02, sPD1a01 and sPD1a02 compared with that of the control IL-12.

For the fusion protein in which the IL-12 is fused, the IL-12 activities of the newly constructed series of heterodimers are all enhanced (FIGS. 11 and 12) compared with the biological activity of the free IL-12, which demonstrates again that the fusion protein based on the antibody Fc heterodimer technology can also significantly improve the IL-12 activity.

6. Broad-Spectrum Verification: Analysis of Experimental Results of PD-1/PD-L1 Pathway Blocking The bioassay of the PD-1/PD-L1 pathway blocking is a detection analysis based on biologically relevant action mechanisms, which can be used for measuring the efficacy and stability of antibodies and other biological formulations that can block the PD-1/PD-L1 interaction. This detection system includes the following two gene-edited cell lines: cells that can stably express human derived PD-1 and cells that stably express the human derived PD-L1.

When the two cells are co-cultured, the PD-1/PD-L1 interaction will inhibit a T cell receptor (TCR) signaling pathway and a NFAT-regulated luciferase activity. When a corresponding PD-1 or PD-L1 antibody is added to block the PD-1/PD-L1 interaction, the inhibition signal will be cleared, thereby activating the T cell receptor (TCR) signaling pathway and the NFAT-induced luciferase activity. The antibody activity is then analyzed by detecting fluorescence signals.

The PD-1 inhibition experiment results that are already available hereabove show that, the antibody activity of the heterodimer is not affected by the fusion of the cytokine. In order to further verify whether this structure is also applicable to other single-domain antibodies, we further construct a series of new fusion proteins based on a new batch of single-domain antibody sequences, including heterodimeric fusion proteins based on the PD-1 single-domain antibody and the PD-L1 single-domain antibody. Then the various fusion proteins bearing the single-domain antibodies are incubated with cells to detect the antibody activities of the fusion proteins. See Example 2.2.3 for specific experimental steps. The results show that, the newly constructed series of heterodimeric fusion proteins have little difference in antibody activity compared with the single-domain homodimers bearing the Fc fragments without cytokine fusion (FIGS. 14-20). This shows that the single-domain antibody-cytokine fusion protein based on the antibody Fc heterodimer technology will not affect the antibody activity.

Those skilled in the art to which the present invention belongs should understand that the methods and materials described above are merely exemplary, and should not be considered as limiting the scope of the present invention.

REFERENCES

[1] Waldmann T A. Cytokines in Cancer Immunotherapy. Cold Spring Harb Perspect Biol. 2017.
[2] Yeku O O, Brentjens R J. Armored CAR T-cells: utilizing cytokines and pro-inflammatory ligands to enhance CAR T-cell anti-tumour efficacy. Biochem Soc Trans. 2016; 44:412-8.
[3] Petrozziello E, Sturmheit T, Mondino A. Exploiting cytokines in adoptive T-cell therapy of cancer. Immunotherapy. 2015; 7:573-84.
[4] Floros T, Tarhini A A. Anticancer Cytokines: Biology and Clinical Effects of Interferon-alpha2, Interleukin (IL)-2, IL-15, IL-21, and IL-12. Semin Oncol. 2015; 42:539-48.
[5] Dhupkar P, Gordon N. Interleukin-2: Old and New Approaches to Enhance Immune-Therapeutic Efficacy. Adv Exp Med Biol. 2017; 995:33-51.
[6] Lu X. Impact of IL-12 in Cancer. Curr Cancer Drug Targets. 2017; 17:682-97.
[7] Bootz F, Neri D. Immunocytokines: a novel class of products for the treatment of chronic inflammation and autoimmune conditions. Drug Discov Today. 2016; 21:180-9.
[8] Helguera G, Morrison S L, Penichet M L. Antibody-cytokine fusion proteins: harnessing the combined power of cytokines and antibodies for cancer therapy. Clin Immunol. 2002; 105:233-46.
[9] Helguera G, Rodriguez J A, Penichet M L. Cytokines fused to antibodies and their combinations as therapeutic agents against different peritoneal HER2/neu expressing tumors. Mol Cancer Ther. 2006; 5:1029-40.
[10] Dela Cruz J S, Trinh K R, Chen H W, Ribas A, Morrison S L, Penichet M L. Anti-HER2/neu IgG3-(IL-2) and anti-HER2/neu IgG3-(GM-CSF) promote HER2/neu processing and presentation by dendritic cells: implications in immunotherapy and vaccination strategies. Mol Immunol. 2006; 43:667-76.
[11] Wang D Y, Eroglu Z, Ozgun A, Leger P D, Zhao S, Ye F, et al. Clinical Features of Acquired Resistance to Anti-PD-1 Therapy in Advanced Melanoma. Cancer Immunol Res. 2017; 5:357-62.
[12] Zaretsky J M, Garcia-Diaz A, Shin D S, Escuin-Ordinas H, Hugo W, Hu-Lieskovan S, et al. Mutations Associated with Acquired Resistance to PD-1 Blockade in Melanoma. N Engl J Med. 2016; 375:819-29.
[13] Liu H, Saxena A, Sidhu S S, Wu D. Fc Engineering for Developing Therapeutic Bispecific Antibodies and Novel Scaffolds. Front Immunol. 2017; 8:38.

The invention claimed is:

1. A fusion protein dimer comprising:
a first polypeptide chain comprising a first antibody Fc region, one or more single-domain antibodies fused to the first antibody Fc region, and a first cytokine fused to the first antibody Fc region; and
a second polypeptide chain comprising a second antibody Fc region, one or more single-domain antibodies fused to the second antibody Fc region, and a second cytokine fused to the second antibody Fc region;
wherein the first cytokine is IL-12, and the second cytokine is IL-2 or an IL-2 mutant.

2. The fusion protein dimer of claim 1, wherein the one or more single-domain antibodies comprise an anti-PD-1 single-domain antibody or an anti-PD-L1 single-domain antibody.

3. The fusion protein dimer of claim 1, wherein subunits P35 and P40 of the IL-12 are linked through a linker sequence to form an IL-12 single chain protein.

4. The fusion protein dimer of claim 1, wherein the first antibody Fc region and the second antibody Fc region are different and have asymmetric complementary structures to each other.

5. The fusion protein dimer of claim 2, wherein the first polypeptide chain and/or the second polypeptide chain comprise two serially arranged anti-PD-1 single-domain antibodies or anti-PD-L1 single-domain antibodies.

6. The fusion protein dimer of claim 2, wherein: the anti-PD-1 single-domain antibody has an amino acid sequence as shown in SEQ ID NO: 3 or SEQ ID NO: 71.

7. The fusion protein dimer of claim 2, wherein the anti-PD-L1 single-domain antibody has amino acid sequences as shown in SEQ ID NOs: 72-74.

8. The fusion protein dimer of claim 3, wherein the IL-12 single-chain protein has an amino acid sequence as shown in SEQ ID NO: 6.

9. The fusion protein dimer of claim 1 wherein:
the first polypeptide chain comprises an amino acid sequence as shown in SEQ ID NO: 20, and the second polypeptide chain has amino acid sequences as shown in SEQ ID NO: 22, 24 or 28;
the first polypeptide chain comprises an amino acid sequence as shown in SEQ ID NO: 26, and the second polypeptide chain comprises an amino acid sequence as shown in SEQ ID NO: 28;
the first polypeptide chain comprises an amino acid sequence as shown in SEQ ID NO: 16, and the second polypeptide chain comprises an amino acid sequence as shown in SEQ ID NO: 18;
the first polypeptide chain comprises an amino acid sequence as shown in SEQ ID NO: 32, and the second polypeptide chain comprises amino acid sequences as shown in SEQ ID NOs: 34, 36;
the first polypeptide chain comprises an amino acid sequence as shown in SEQ ID NO: 38, and the second polypeptide chain comprises an amino acid sequence as shown in SEQ ID NO: 36;
the first polypeptide chain comprises an amino acid sequence as shown in SEQ ID NO: 40, and the second polypeptide chain comprises amino acid sequences as shown in SEQ ID NOs: 42, 44;
the first polypeptide chain comprises an amino acid sequence as shown in SEQ ID NO: 46, and the second polypeptide chain comprises an amino acid sequence as shown in SEQ ID NO: 44;
the first polypeptide chain comprises an amino acid sequence as shown in SEQ ID NO: 48, and the second polypeptide chain comprises amino acid sequences as shown in SEQ ID NOs: 50, and 52;
the first polypeptide chain comprises an amino acid sequence as shown in SEQ ID NO: 54, and the second polypeptide chain comprises an amino acid sequence as shown in SEQ ID NO: 52;
the first polypeptide chain comprises an amino acid sequence as shown in SEQ ID NO: 56, and the second polypeptide chain comprises amino acid sequences as shown in SEQ ID NOs: 58, and 60; or
the first polypeptide chain comprises an amino acid sequence as shown in SEQ ID NO: 62, and the second polypeptide chain comprises an amino acid sequence as shown in SEQ ID NO: 60.

10. The fusion protein dimer of claim 1, wherein the one or more single-domain antibodies, the first and second antibody Fc regions, and the first and second cytokines are linked through a linker sequence or directly linked.

11. The fusion protein dimer of claim 10, wherein the linker sequence is selected from (G4S)1-3 (SEQ ID NO: 75), KRVAPELLGGPS (SEQ ID NO: 76), ASTKG (SEQ ID NO: 77), and NSPPAA (SEQ ID NO: 78).

12. The fusion protein dimer of claim 11, wherein the one or more single-domain antibodies are linked through a linker sequence or directly linked to the N-terminus of the first or second antibody Fc region, and the first or second cytokine is linked to the C-terminus of the first or second antibody Fc region through a linker sequence; or
the one or more single-domain antibodies are linked through a linker sequence or directly linked to the C-terminus of the first or second antibody Fc region, and the first or second cytokine is linked to the N-terminus of the first or second antibody Fc regions through a linker sequence.

13. The fusion protein dimer of claim 1, wherein the first antibody Fc region and the second antibody Fc region are wild-type antibody Fc regions, thereby forming an antibody Fc fusion protein homodimer.

14. Isolated polynucleotides encoding the first polypeptide chain and the second polypeptide chain of the fusion protein dimer of claim 1.

15. The polynucleotides of claim 14, comprising:
a nucleotide sequence as shown in SEQ ID NO: 19 and a nucleotide sequence as shown in SEQ ID NO: 21, 23 or 27;
a nucleotide sequence as shown in SEQ ID NO: 25 and a nucleotide sequence as shown in SEQ ID NO: 27;
a nucleotide sequence as shown in SEQ ID NO: 15 and a nucleotide sequence as shown in SEQ ID NO: 17;
a nucleotide sequence as shown in SEQ ID NO: 31 and a nucleotide sequence as shown in SEQ ID NO: 33 or 35;
a nucleotide sequence as shown in SEQ ID NO: 37 and a nucleotide sequence as shown in SEQ ID NO: 35;
a nucleotide sequence as shown in SEQ ID NO: 39 and a nucleotide sequence as shown in SEQ ID NO: 41 or 43;
a nucleotide sequence as shown in SEQ ID NO: 45 and a nucleotide sequence as shown in SEQ ID NO: 43;
a nucleotide sequence as shown in SEQ ID NO: 47 and a nucleotide sequence as shown in SEQ ID NO: 49 or 51;
a nucleotide sequence as shown in SEQ ID NO: 53 and a nucleotide sequence as shown in SEQ ID NO: 51;
a nucleotide sequence as shown in SEQ ID NO: 55 and a nucleotide sequence as shown in SEQ ID NO: 57 or 59; or
a nucleotide sequence as shown in SEQ ID NO: 61 and a nucleotide sequence as shown in SEQ ID NO: 59.

16. A method of treating a tumor, comprising administering to a subject a therapeutically effective amount of the fusion protein dimer of claim 2 or a pharmaceutical composition containing the fusion protein dimer.

17. The method of claim 16, wherein the tumor is melanoma or a lung cancer.

* * * * *

SEQUENCE LISTING

<160> NUMBER OF SEQ ID NOS: 78

<210> SEQ ID NO 1
<211> LENGTH: 57
<212> TYPE: DNA
<213> ORGANISM: Artificial Sequence
<220> FEATURE:
<223> OTHER INFORMATION: Synthetic sequence

<400> SEQUENCE: 1
atgggctggt cctgcatcat cctgtttctg gtggctaccg ctaccggcgt gcactct        57

<210> SEQ ID NO 2
<211> LENGTH: 366
<212> TYPE: DNA
<213> ORGANISM: Artificial Sequence
<220> FEATURE:
<223> OTHER INFORMATION: Synthetic sequence

<400> SEQUENCE: 2

```
caagttcaac tggtggaaag cggtggtggt ctggttcagc cgggcggtag cctgcgtctg    60
agctgcgcgg cgagcggtgg taccctggac tactatgcga tcggttggtt ccgtcaggcg   120
ccgggcaagg agcgtgaggc ggtgagctgc attagcagca gcgacggtag cacctactat   180
gcggatagcg ttaagggccg ttttaccatc agccgtgata acagcaaaaa caccctgtac   240
ctgcaaatga acagcctgcg tgcggaagac accgcggtgt atcactgcgc gaccgatcgt   300
gcgtgcggta gcagctggct gggcgcggag agctgggcgc aaggcaccct ggttaccgtg   360
agcagc                                                              366
```

<210> SEQ ID NO 3
<211> LENGTH: 122
<212> TYPE: PRT
<213> ORGANISM: Artificial Sequence
<220> FEATURE:
<223> OTHER INFORMATION: Synthetic sequence

<400> SEQUENCE: 3

```
Gln Val Gln Leu Val Glu Ser Gly Gly Gly Leu Val Gln Pro Gly Gly
  1               5                  10                  15
Ser Leu Arg Leu Ser Cys Ala Ala Ser Gly Gly Thr Leu Asp Tyr Tyr
             20                  25                  30
Ala Ile Gly Trp Phe Arg Gln Ala Pro Gly Lys Glu Arg Glu Ala Val
         35                  40                  45
Ser Cys Ile Ser Ser Ser Asp Gly Ser Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr His Cys
                 85                  90                  95
Ala Thr Asp Arg Ala Cys Gly Ser Ser Trp Leu Gly Ala Glu Ser Trp
            100                 105                 110
Ala Gln Gly Thr Leu Val Thr Val Ser Ser
        115                 120
```

<210> SEQ ID NO 4
<211> LENGTH: 45
<212> TYPE: DNA
<213> ORGANISM: Artificial Sequence
<220> FEATURE:
<223> OTHER INFORMATION: Synthetic sequence

<400> SEQUENCE: 4

```
ggtggaggcg gtagtggcgg aggcggttca ggcggaggcg gatct                    45
```

<210> SEQ ID NO 5
<211> LENGTH: 1554
<212> TYPE: DNA
<213> ORGANISM: Homo sapiens

<400> SEQUENCE: 5

```
atttgggagc tgaagaaaga cgtgtacgtg gtcgagctgg actggtaccc tgatgcccca    60
ggcgagatgg tcgtgctgac ctgcgataca ccagaggaag atggtatcac ctggacactg   120
gatcagtcct cagaggtgct gggctctggt aaaacactga ccattcaggt gaaggagttc   180
```

```
ggtgacgctg  gacagtacac  ttgtcataag  ggcggggagg  tgctgtctca  ctccctgctg    240
ctgctgcata  agaaggagga  tggaatctgg  tccactgaca  tcctgaaaga  ccagaaggag    300
ccaaagaaca  aaaccttcct  gcgatgcgag  gctaagaact  acagcggccg  ctttacatgc    360
tggtggctga  caaccatcag  caccgatctg  acctttagcg  tgaagtcatc  caggggcagt    420
tcagaccctc  agggagtcac  atgtggcgcc  gcaaccctgt  cagcagagcg  agtgcgggga    480
gacaataagg  aatacgagta  cagcgtcgag  tgtcaggagg  attccgcatg  tccagctgca    540
gaagaatccc  tgcctatcga  agtcatggtg  gacgctgtgc  ataaactgaa  gtacgagaat    600
tacaccagca  gcttttttcat  ccgggacatc  atcaagcccg  atccacctaa  gaatctgcag    660
ctgaagcctc  tgaaaaatag  ccgacaggtc  gaagtgtcat  gggaataccc  agacacctgg    720
tcaacaccac  actcctactt  ctccctgacc  ttctgtgtgc  aggtccaggg  aaaaagcaag    780
cgggaaaaga  aagatcgggt  gttcaccgac  aagaccagtg  ctacagtgat  tgccggaag    840 aatgccagca  tttctgtcag  agctcaggac  cggtactata  gctcttcctg  agcgagtgg    900 gcttcagtgc  catgttctgg  aggcggtgga  tctggcggag  gtggaagcgg  aggcggtgga    960
tctagaaacc  tgcccgtcgc  aacccctgat  ccagggatgt  tcccctgtct  gcatcacagc   1020
cagaatctgc  tgagggctgt  ctccaacatg  ctgcagaagg  ctcgacagac  cctggagttc   1080
tacccatgta  ccagcgaaga  gatcgaccac  gaggatatca  caaaggataa  accagcaca   1140 gtggaagcat  gcctgcctct  ggaactgacc  aagaatgaga  gctgcctgaa  tagcaggag   1200 acctccttca  tcaccaacgg  ctcatgcctg  gcttcaagga  agaccagctt  catgatggct   1260
ctgtgtctga  gctctatcta  tgaggacctg  aagatgtacc  aggtggagtt  caagaccatg   1320
aacgccaagc  tgctgatgga  tccaaagagg  cagatcttcc  tggatcagaa  tatgctggca   1380
gtgatcgatg  agctgatgca  ggccctgaat  tttaacagtg  acacagtgcc  tcagaagagc   1440
tctctggaag  agccagactt  ttacaaaact  aagatcaagc  tgtgcattct  gctgcacgct   1500
ttccgcatca  gagctgtcac  tatcgataga  gtgatgagct  atctgaatgc  ctca         1554

<210> SEQ ID NO 6
<211> LENGTH: 518
<212> TYPE: PRT
<213> ORGANISM: Homo sapiens

<400> SEQUENCE: 6
```

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln

```
                     130                 135                 140
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                    180                 185                 190

Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                    245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
290                 295                 300

Cys Ser Gly Gly Gly Ser Gly Gly Gly Ser Gly Gly Gly Gly
305                 310                 315                 320

Ser Arg Asn Leu Pro Val Ala Thr Pro Asp Pro Gly Met Phe Pro Cys
                    325                 330                 335

Leu His His Ser Gln Asn Leu Leu Arg Ala Val Ser Asn Met Leu Gln
                340                 345                 350

Lys Ala Arg Gln Thr Leu Glu Phe Tyr Pro Cys Thr Ser Glu Glu Ile
            355                 360                 365

Asp His Glu Asp Ile Thr Lys Asp Lys Thr Ser Thr Val Glu Ala Cys
370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                    405                 410                 415

Phe Met Met Ala Leu Cys Leu Ser Ser Ile Tyr Glu Asp Leu Lys Met
                420                 425                 430

Tyr Gln Val Glu Phe Lys Thr Met Asn Ala Lys Leu Leu Met Asp Pro
            435                 440                 445

Lys Arg Gln Ile Phe Leu Asp Gln Asn Met Leu Ala Val Ile Asp Glu
            450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                    485                 490                 495

Leu Leu His Ala Phe Arg Ile Arg Ala Val Thr Ile Asp Arg Val Met
                500                 505                 510

Ser Tyr Leu Asn Ala Ser
            515

<210> SEQ ID NO 7
<211> LENGTH: 399
<212> TYPE: DNA
<213> ORGANISM: Homo sapiens
```

<400> SEQUENCE: 7

```
gcacctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180
gaagaactca aacctctgga ggaagtgcta aatttagctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct tttgtcaaag catcatctca acactgact                          399
```

<210> SEQ ID NO 8
<211> LENGTH: 133
<212> TYPE: PRT
<213> ORGANISM: Homo sapiens

<400> SEQUENCE: 8

```
Ala Pro Thr Ser Ser Thr Lys Lys Thr Gln Leu Gln Leu Glu His
 1               5                  10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
    130
```

<210> SEQ ID NO 9
<211> LENGTH: 399
<212> TYPE: DNA
<213> ORGANISM: Artificial Sequence
<220> FEATURE:
<223> OTHER INFORMATION: Synthetic sequence

<400> SEQUENCE: 9

```
gcacctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180
gaagaactca aacctctgga ggaagtgcta aatttagctc aaagcaaaaa ctttcacttc   240
gaccccaggg acgtggtgag caatatcaac gtattcgttc tggaactaaa gggatctgaa   300
acaacattca tgtgtgaata tgctgatgag acagcaacca ttgtagaatt tctgaacaga   360
tggattacct tttgtcaaag catcatctca acactgact                          399
```

<210> SEQ ID NO 10
<211> LENGTH: 133

```
<212> TYPE: PRT
<213> ORGANISM: Artificial Sequence
<220> FEATURE:
<223> OTHER INFORMATION: Synthetic sequence

<400> SEQUENCE: 10

Ala Pro Thr Ser Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 11
<211> LENGTH: 2703
<212> TYPE: DNA
<213> ORGANISM: Artificial Sequence
<220> FEATURE:
<223> OTHER INFORMATION: Synthetic sequence

<400> SEQUENCE: 11
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca cgacggtag cacctactat      180 gcggatagcg ttaagggccg ttttaccatc agccgtgata cagcaaaaa cacccctgtac     240 ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tgaacccaag     420
tcctgcgaca agacccacac ctgtccccct tgtcctgccc tgaactgct gggcggaccc      480 agcgtgttcc tgttccccccc aaagcctaag acaccctga tgatctcccg gacccccgaa      540
gtgacctgcg tggtggtgga tgtgtcccac gaggaccctg aagtgaagtt caattggtac      600
gtggacggcg tggaagtgca acgccaag accaagccta gagaggaaca gtacgcctcc        660
acctaccggg tggtgtccgt gctgaccgtg ctgcaccagg attggctgaa cggcaaagag     720
tacaagtgca aggtgtccaa caaggccctg cctgccccca tcgaaaagac catctccaag     780 gccagggcc agccccggga accccaggtg tacacactgc ccctagcag ggacgagctg        840 accaagaacc aggtgtccct gacctgtctc gtgaaaggct ctaccccctc cgatatcgcc     900
gtggaatggg agtccaacgg ccagcctgag aacaactata agaccacccc cctgtgctg      960 gactccgacg gctcattctt cctgtacagc aagctgacag tggacaagtc ccggtggcag    1020
cagggcaacg tgttctcctg ctcgtgatg cacgaggccc tgcacaacca ctacacccag     1080
```

```
aagtccctgt ccctgagccc cggcggtgga ggcggtagtg gcggaggcgg ttcaggcgga    1140
ggcggatcta tttgggagct gaagaaagac gtgtacgtgg tcgagctgga ctggtaccct    1200
gatgccccag gcgagatggt cgtgctgacc tgcgatacac agaggaaga tggtatcacc     1260 tggacactgg atcagtcctc agaggtgctg ggctctggta aaacactgac cattcaggtg    1320
aaggagttcg gtgacgctgg acagtacact tgtcataagg gcggggaggt gctgtctcac    1380
tccctgctgc tgctgcataa gaaggaggat ggaatctggt ccactgacat cctgaaagac    1440
cagaaggagc caaagaacaa aaccttcctg cgatgcgagg ctaagaacta cagcggccgc    1500
tttacatgct ggtggctgac aaccatcagc accgatctga cctttagcgt gaagtcatcc    1560
aggggcagtt cagaccctca gggagtcaca tgtggcgccg caaccctgtc agcagagcga    1620
gtgcggggag acaataagga atacgagtac agcgtcgagt gtcaggagga ttccgcatgt    1680
ccagctgcag aagaatccct gcctatcgaa gtcatggtgg acgctgtgca taaactgaag    1740
tacgagaatt acaccagcag cttttttcatc cgggacatca tcaagcccga tccacctaag    1800
aatctgcagc tgaagcctct gaaaaatagc cgacaggtcg aagtgtcatg ggaatacccca   1860 gacacctggt caacaccaca ctcctacttc tccctgacct tctgtgtgca ggtccaggga    1920
aaaagcaagc gggaaaagaa agatcgggtg ttcaccgaca agaccagtgc tacagtgatt    1980
tgccggaaga atgccagcat ttctgtcaga gctcaggacc ggtactatag ctcttcctgg    2040
agcgagtggg cttcagtgcc atgttctgga ggcggtggat ctggcggagg tggaagcgga   2100
ggcggtggat ctagaaacct gcccgtcgca accctgatc cagggatgtt ccctgtctg     2160 catcacagcc agaatctgct gagggctgtc tccaacatgc tgcagaaggc tcgacagacc    2220
ctggagttct acccatgtac cagcgaagag atcgaccacg aggatatcac aaaggataaa    2280
accagcacag tggaagcatg cctgcctctg gaactgacca gaatgagag ctgcctgaat    2340 agcagggaga cctccttcat caccaacggc tcatgcctgg cttcaaggaa gaccagcttc    2400
atgatggctc tgtgtctgag ctctatctat gaggacctga gatgtacca ggtggagttc    2460 aagaccatga acgccaagct gctgatggat ccaaagaggc agatcttcct ggatcagaat    2520
atgctggcag tgatcgatga gctgatgcag gccctgaatt ttaacagtga gacagtgcct    2580
cagaagagct ctctggaaga gccagacttt tacaaaacta agatcaagct gtgcattctg    2640
ctgcacgctt ccgcatcag agctgtcact atcgatagag tgatgagcta tctgaatgcc    2700
tca                                                                   2703
```

<210> SEQ ID NO 12
<211> LENGTH: 901
<212> TYPE: PRT
<213> ORGANISM: Artificial Sequence
<220> FEATURE:
<223> OTHER INFORMATION: Synthetic sequence

<400> SEQUENCE: 12

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

Gly Gly Gly Ser Gly Gly Gly Gly Ser Glu Pro Lys Ser Cys Asp Lys
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Ala Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Gly Gly Gly Ser Gly Gly Gly Gly Ser Gly Gly Gly Gly Ser Ser Ile
    370                 375                 380

Trp Glu Leu Lys Lys Asp Val Tyr Val Val Glu Leu Asp Trp Tyr Pro
385                 390                 395                 400

Asp Ala Pro Gly Glu Met Val Val Leu Thr Cys Asp Thr Pro Glu Glu
                405                 410                 415

Asp Gly Ile Thr Trp Thr Leu Asp Gln Ser Ser Glu Val Leu Gly Ser
            420                 425                 430

Gly Lys Thr Leu Thr Ile Gln Val Lys Glu Phe Gly Asp Ala Gly Gln
        435                 440                 445

Tyr Thr Cys His Lys Gly Gly Glu Val Leu Ser His Ser Leu Leu Leu
    450                 455                 460

Leu His Lys Lys Glu Asp Gly Ile Trp Ser Thr Asp Ile Leu Lys Asp
465                 470                 475                 480

Gln Lys Glu Pro Lys Asn Lys Thr Phe Leu Arg Cys Glu Ala Lys Asn
```

```
            485                 490                 495
Tyr Ser Gly Arg Phe Thr Cys Trp Trp Leu Thr Thr Ile Ser Thr Asp
            500                 505                 510

Leu Thr Phe Ser Val Lys Ser Ser Arg Gly Ser Ser Asp Pro Gln Gly
            515                 520                 525

Val Thr Cys Gly Ala Ala Thr Leu Ser Ala Glu Arg Val Arg Gly Asp
            530                 535                 540

Asn Lys Glu Tyr Glu Tyr Ser Val Glu Cys Gln Glu Asp Ser Ala Cys
545                 550                 555                 560

Pro Ala Ala Glu Glu Ser Leu Pro Ile Glu Val Met Val Asp Ala Val
            565                 570                 575

His Lys Leu Lys Tyr Glu Asn Tyr Thr Ser Ser Phe Phe Ile Arg Asp
            580                 585                 590

Ile Ile Lys Pro Asp Pro Pro Lys Asn Leu Gln Leu Lys Pro Leu Lys
            595                 600                 605

Asn Ser Arg Gln Val Glu Val Ser Trp Glu Tyr Pro Asp Thr Trp Ser
            610                 615                 620

Thr Pro His Ser Tyr Phe Ser Leu Thr Phe Cys Val Gln Val Gln Gly
625                 630                 635                 640

Lys Ser Lys Arg Glu Lys Lys Asp Arg Val Phe Thr Asp Lys Thr Ser
            645                 650                 655

Ala Thr Val Ile Cys Arg Lys Asn Ala Ser Ile Ser Val Arg Ala Gln
            660                 665                 670

Asp Arg Tyr Tyr Ser Ser Ser Trp Ser Glu Trp Ala Ser Val Pro Cys
            675                 680                 685

Ser Gly Gly Gly Ser Gly Gly Gly Ser Gly Gly Gly Ser
            690                 695                 700

Arg Asn Leu Pro Val Ala Thr Pro Asp Pro Gly Met Phe Pro Cys Leu
705                 710                 715                 720

His His Ser Gln Asn Leu Leu Arg Ala Val Ser Asn Met Leu Gln Lys
            725                 730                 735

Ala Arg Gln Thr Leu Glu Phe Tyr Pro Cys Thr Ser Glu Glu Ile Asp
            740                 745                 750

His Glu Asp Ile Thr Lys Asp Lys Thr Ser Thr Val Glu Ala Cys Leu
            755                 760                 765

Pro Leu Glu Leu Thr Lys Asn Glu Ser Cys Leu Asn Ser Arg Glu Thr
            770                 775                 780

Ser Phe Ile Thr Asn Gly Ser Cys Leu Ala Ser Arg Lys Thr Ser Phe
785                 790                 795                 800

Met Met Ala Leu Cys Leu Ser Ser Ile Tyr Glu Asp Leu Lys Met Tyr
            805                 810                 815

Gln Val Glu Phe Lys Thr Met Asn Ala Lys Leu Leu Met Asp Pro Lys
            820                 825                 830

Arg Gln Ile Phe Leu Asp Gln Asn Met Leu Ala Val Ile Asp Glu Leu
            835                 840                 845

Met Gln Ala Leu Asn Phe Asn Ser Glu Thr Val Pro Gln Lys Ser Ser
            850                 855                 860

Leu Glu Glu Pro Asp Phe Tyr Lys Thr Lys Ile Lys Leu Cys Ile Leu
865                 870                 875                 880

Leu His Ala Phe Arg Ile Arg Ala Val Thr Ile Asp Arg Val Met Ser
            885                 890                 895

Tyr Leu Asn Ala Ser
            900
```

<210> SEQ ID NO 13
<211> LENGTH: 1548
<212> TYPE: DNA
<213> ORGANISM: Artificial Sequence
<220> FEATURE:
<223> OTHER INFORMATION: Synthetic sequence

<400> SEQUENCE: 13

```
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg ttttaccatc agccgtgata cagcaaaaaa caccctgtac     240
ctgcaaatga acagcctgcg tgcggaagac accgcggtgt atcactgcgc gaccgatcgt     300
gcgtgcggta gcagctggct gggcgcggag agctgggcgc aaggcacccct ggttaccgtg     360
agcagcggtg gaggcggtag tggcggaggc ggttcaggcg gaggcggatc tgaacccaag     420
tcctgcgaca gacccacac ctgtcccccct tgtcctgccc ctgaactgct gggcggaccc     480
agcgtgttcc tgttcccccc aaagcctaag gacaccctga tgatctcccg gacccccgaa     540
gtgacctgcg tggtggtgga tgtgtcccac gaggaccctg aagtgaagtt caattggtac     600
gtggacggcg tggaagtgca caacgccaag accaagccta gagaggaaca gtacgcctcc     660
acctaccggg tggtgtccgt gctgaccgtg ctgcaccagg attggctgaa cggcaaagag     720
tacaagtgca aggtgtccaa caaggccctg cctgccccca tcgaaaagac catctccaag     780
gccaagggcc agccccggga accccaggtg tacacactgc cccctagcag ggacgagctg     840
accaagaacc aggtgtccct gacctgtctc gtgaaaggct tctacccctc cgatatcgcc     900
gtggaatggg agtccaacgg ccagcctgag aacaactata agaccaccccc cctgtgctg      960
gactccgacg gctcattctt cctgtacagc aagctgacag tggacaagtc cggtggcag     1020
cagggcaacg tgttctcctg ctccgtgatg cacgaggccc tgcacaacca ctacacccag    1080
aagtccctgt ccctgagccc cggcggtgga ggcggtagtg gcggaggcgg ttcaggcgga    1140
ggcggatctg cacctactc aagttctaca agaaaaacac agctacaact ggagcattta    1200
ctgctggatt tacagatgat tttgaatgga attaataatt acaagaatcc caaactcacc    1260
aggatgctca catttaagtt ttacatgccc aagaaggcca cagaactgaa acatcttcag    1320
tgtctagaag aagaactcaa acctctggag gaagtgctaa atttagctca aagcaaaaac    1380
tttcacttaa gacccaggga cttaatcagc aatatcaacg taatagttct ggaactaaag    1440
ggatctgaaa caacattcat gtgtgaatat gctgatgaga cagcaaccat tgtagaattt    1500
ctgaacagat ggattacctt ttgtcaaagc atcatctcaa cactgact                 1548
```

<210> SEQ ID NO 14
<211> LENGTH: 516
<212> TYPE: PRT
<213> ORGANISM: Artificial Sequence
<220> FEATURE:
<223> OTHER INFORMATION: Synthetic sequence

<400> SEQUENCE: 14

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30
```

-continued

```
Ala Ile Gly Trp Phe Arg Gln Ala Pro Gly Lys Glu Arg Glu Ala Val
         35                  40                  45

Ser Cys Ile Ser Ser Ser Asp Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Thr Asp Arg Ala Cys Gly Ser Ser Trp Leu Gly Ala Glu Ser Trp
             100                 105                 110

Ala Gln Gly Thr Leu Val Thr Val Ser Ser Gly Gly Gly Ser Gly
         115                 120                 125

Gly Gly Gly Ser Gly Gly Gly Ser Glu Pro Lys Ser Cys Asp Lys
 130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                 165                 170                 175

Arg Thr Pro Glu Val Thr Cys Val Val Val Asp Val Ser His Glu Asp
             180                 185                 190

Pro Glu Val Lys Phe Asn Trp Tyr Val Asp Gly Val Glu Val His Asn
         195                 200                 205

Ala Lys Thr Lys Pro Arg Glu Glu Gln Tyr Ala Ser Thr Tyr Arg Val
 210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                 245                 250                 255

Thr Ile Ser Lys Ala Lys Gly Gln Pro Arg Glu Pro Gln Val Tyr Thr
             260                 265                 270

Leu Pro Pro Ser Arg Asp Glu Leu Thr Lys Asn Gln Val Ser Leu Thr
         275                 280                 285

Cys Leu Val Lys Gly Phe Tyr Pro Ser Asp Ile Ala Val Glu Trp Glu
 290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                 325                 330                 335

Ser Arg Trp Gln Gln Gly Asn Val Phe Ser Cys Ser Val Met His Glu
             340                 345                 350

Ala Leu His Asn His Tyr Thr Gln Lys Ser Leu Ser Leu Ser Pro Gly
         355                 360                 365

Gly Gly Gly Ser Gly Gly Gly Gly Ser Gly Gly Gly Ser Ala
 370                 375                 380

Pro Thr Ser Ser Ser Thr Lys Lys Thr Gln Leu Gln Leu Glu His Leu
385                 390                 395                 400

Leu Leu Asp Leu Gln Met Ile Leu Asn Gly Ile Asn Asn Tyr Lys Asn
                 405                 410                 415

Pro Lys Leu Thr Arg Met Leu Thr Phe Lys Phe Tyr Met Pro Lys Lys
             420                 425                 430

Ala Thr Glu Leu Lys His Leu Gln Cys Leu Glu Glu Glu Leu Lys Pro
         435                 440                 445

Leu Glu Glu Val Leu Asn Leu Ala Gln Ser Lys Asn Phe His Leu Arg
```

```
                450             455             460
Pro Arg Asp Leu Ile Ser Asn Ile Asn Val Ile Val Leu Glu Leu Lys
465                 470                 475                 480

Gly Ser Glu Thr Thr Phe Met Cys Glu Tyr Ala Asp Glu Thr Ala Thr
                485                 490                 495

Ile Val Glu Phe Leu Asn Arg Trp Ile Thr Phe Cys Gln Ser Ile Ile
                500                 505                 510

Ser Thr Leu Thr
        515

<210> SEQ ID NO 15
<211> LENGTH: 2703
<212> TYPE: DNA
<213> ORGANISM: Artificial Sequence
<220> FEATURE:
<223> OTHER INFORMATION: Synthetic sequence

<400> SEQUENCE: 15
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca cgacggtag cacctactat      180 gcggatagcg ttaagggccg ttttaccatc agccgtgata acagcaaaaa caccctgtac     240
ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tgaacccaag     420
tcctgcgaca gacccacac ctgtcccct tgtcctgcc ctgaactgct gggcggaccc        480
agcgtgttcc tgttccccc aaagcctaag gacaccctga tctcccg gaccccgaa          540 gtgacctgcg tggtggtgga tgtgtcccac gaggaccctg aagtgaagtt caattggtac     600
gtggacggcg tggaagtgca caacgccaag accaagccta gagaggaaca gtacgcctcc     660
acctaccggg tggtgtccgt gctgaccgtg ctgcaccagg attggctgaa cggcaagag      720 tacaagtgca aggtgtccaa caaggccctg cctgccccca tcgaaaagac catctccaag     780
gccaagggcc agccccggga accccaggtg tacacactgc cccttgcag ggacgagctg      840 accaagaacc aggtgtccct gtggtgtctc gtgaaaggct tctacccctc cgatatcgcc     900
gtggaatggg agtccaacgg ccagcctgag aacaactata agaccacccc ccctgtgctg     960
gactccgacg gctcattctt cctgtacagc aagctgacag tggacaagtc ccggtggcag    1020
cagggcaacg tgttctcctg ctccgtgatg cacgaggccc tgcacaacca ctacacccag    1080
aagtccctgt ccctgagccc cggcggtgga ggcggtagtg gcggaggcgg ttcaggcgga    1140
ggcggatcta tttgggagct gaagaaagac gtgtacgtgg tcgagctgga ctggtaccct    1200
gatgccccag cgagatggt cgtgctgacc tgcgatacac agaggaaga tggtatcacc      1260 tggacactgg atcagtcctc agaggtgctg ggctctggta aaacactgac cattcaggtg    1320
aaggagttcg gtgacgctgg acagtacact tgtcataagg gcgggaggt gctgtctcac     1380 tccctgctgc tgctgcataa gaaggaggat ggaatctggt ccactgacat cctgaaagac    1440
cagaaggagc caagaacaa accttcctg cgatgcgagg ctaagaacta cagcggccgc      1500
tttacatgct ggtggctgac aaccatcagc accgatctga cctttagcgt gaagtcatcc    1560 agggggcagtt cagaccctca gggagtcaca tgtgcgcccg caaccctgtc agcagagcga    1620
gtgcggggag acaataagga atacgagtac agcgtcgagt gtcaggagga ttccgcatgt    1680
```

-continued

```
ccagctgcag aagaatccct gcctatcgaa gtcatggtgg acgctgtgca taaactgaag    1740
tacgagaatt acaccagcag cttttcatc cgggacatca tcaagcccga tccacctaag    1800
aatctgcagc tgaagcctct gaaaaatagc cgacaggtcg aagtgtcatg ggaataccca    1860
gacacctggt caacaccaca ctcctacttc tccctgacct tctgtgtgca ggtccaggga    1920
aaaagcaagc gggaaaagaa agatcgggtg ttcaccgaca agaccagtgc tacagtgatt    1980
tgccggaaga atgccagcat ttctgtcaga gctcaggacc ggtactatag ctcttcctgg    2040
agcgagtggg cttcagtgcc atgttctgga ggcggtggat ctggcggagg tggaagcgga    2100
ggcggtggat ctagaaacct gcccgtcgca acccctgatc cagggatgtt ccctgtctg    2160 catcacagcc agaatctgct gagggctgtc tccaacatgc tgcagaaggc tcgacagacc    2220
ctggagttct acccatgtac cagcgaagag atcgaccacg aggatatcac aaaggataaa    2280
accagcacag tggaagcatg cctgcctctg gaactgacca agaatgagag ctgcctgaat    2340
agcagggaga cctccttcat caccaacggc tcatgcctgg cttcaaggaa gaccagcttc    2400
atgatggctc tgtgtctgag ctctatctat gaggacctga agatgtacca ggtggagttc    2460
aagaccatga acgccaagct gctgatggat ccaaagaggc agatcttcct ggatcagaat    2520
atgctggcag tgatcgatga gctgatgcag gccctgaatt ttaacagtga acagtgcct    2580 cagaagagct ctctggaaga gccagacttt tacaaaacta agatcaagct gtgcattctg    2640
ctgcacgctt tccgcatcag agctgtcact atcgatagag tgatgagcta tctgaatgcc    2700
tca                                                                 2703
```

<210> SEQ ID NO 16
<211> LENGTH: 901
<212> TYPE: PRT
<213> ORGANISM: Artificial Sequence
<220> FEATURE:
<223> OTHER INFORMATION: Synthetic sequence

<400> SEQUENCE: 16

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

Gly Gly Gly Ser Gly Gly Gly Gly Ser Glu Pro Lys Ser Cys Asp Lys
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175
```

-continued

```
Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Ala Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Cys Arg Asp Glu Leu Thr Lys Asn Gln Val Ser Leu Trp
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Gly Gly Gly Gly Ser Gly Gly Gly Ser Gly Gly Gly Gly Ser Ile
    370                 375                 380

Trp Glu Leu Lys Lys Asp Val Tyr Val Val Glu Leu Asp Trp Tyr Pro
385                 390                 395                 400

Asp Ala Pro Gly Glu Met Val Val Leu Thr Cys Asp Thr Pro Glu Glu
                405                 410                 415

Asp Gly Ile Thr Trp Thr Leu Asp Gln Ser Ser Glu Val Leu Gly Ser
            420                 425                 430

Gly Lys Thr Leu Thr Ile Gln Val Lys Glu Phe Gly Asp Ala Gly Gln
        435                 440                 445

Tyr Thr Cys His Lys Gly Gly Glu Val Leu Ser His Ser Leu Leu Leu
    450                 455                 460

Leu His Lys Lys Glu Asp Gly Ile Trp Ser Thr Asp Ile Leu Lys Asp
465                 470                 475                 480

Gln Lys Glu Pro Lys Asn Lys Thr Phe Leu Arg Cys Glu Ala Lys Asn
                485                 490                 495

Tyr Ser Gly Arg Phe Thr Cys Trp Trp Leu Thr Thr Ile Ser Thr Asp
            500                 505                 510

Leu Thr Phe Ser Val Lys Ser Ser Arg Gly Ser Ser Asp Pro Gln Gly
        515                 520                 525

Val Thr Cys Gly Ala Ala Thr Leu Ser Ala Glu Arg Val Arg Gly Asp
    530                 535                 540

Asn Lys Glu Tyr Glu Tyr Ser Val Glu Cys Gln Glu Asp Ser Ala Cys
545                 550                 555                 560

Pro Ala Ala Glu Glu Ser Leu Pro Ile Glu Val Met Val Asp Ala Val
                565                 570                 575

His Lys Leu Lys Tyr Glu Asn Tyr Thr Ser Ser Phe Phe Ile Arg Asp
            580                 585                 590
```

```
Ile Ile Lys Pro Asp Pro Pro Lys Asn Leu Gln Leu Lys Pro Leu Lys
            595                 600                 605

Asn Ser Arg Gln Val Glu Val Ser Trp Glu Tyr Pro Asp Thr Trp Ser
    610                 615                 620

Thr Pro His Ser Tyr Phe Ser Leu Thr Phe Cys Val Gln Val Gln Gly
625                 630                 635                 640

Lys Ser Lys Arg Glu Lys Lys Asp Arg Val Phe Thr Asp Lys Thr Ser
                645                 650                 655

Ala Thr Val Ile Cys Arg Lys Asn Ala Ser Ile Ser Val Arg Ala Gln
                660                 665                 670

Asp Arg Tyr Tyr Ser Ser Ser Trp Ser Glu Trp Ala Ser Val Pro Cys
            675                 680                 685

Ser Gly Gly Gly Ser Gly Gly Gly Ser Gly Gly Gly Gly Ser
690                 695                 700

Arg Asn Leu Pro Val Ala Thr Pro Asp Pro Gly Met Phe Pro Cys Leu
705                 710                 715                 720

His His Ser Gln Asn Leu Leu Arg Ala Val Ser Asn Met Leu Gln Lys
                725                 730                 735

Ala Arg Gln Thr Leu Glu Phe Tyr Pro Cys Thr Ser Glu Glu Ile Asp
            740                 745                 750

His Glu Asp Ile Thr Lys Asp Lys Thr Ser Thr Val Glu Ala Cys Leu
        755                 760                 765

Pro Leu Glu Leu Thr Lys Asn Glu Ser Cys Leu Asn Ser Arg Glu Thr
    770                 775                 780

Ser Phe Ile Thr Asn Gly Ser Cys Leu Ala Ser Arg Lys Thr Ser Phe
785                 790                 795                 800

Met Met Ala Leu Cys Leu Ser Ser Ile Tyr Glu Asp Leu Lys Met Tyr
                805                 810                 815

Gln Val Glu Phe Lys Thr Met Asn Ala Lys Leu Leu Met Asp Pro Lys
            820                 825                 830

Arg Gln Ile Phe Leu Asp Gln Asn Met Leu Ala Val Ile Asp Glu Leu
        835                 840                 845

Met Gln Ala Leu Asn Phe Asn Ser Glu Thr Val Pro Gln Lys Ser Ser
    850                 855                 860

Leu Glu Glu Pro Asp Phe Tyr Lys Thr Lys Ile Lys Leu Cys Ile Leu
865                 870                 875                 880

Leu His Ala Phe Arg Ile Arg Ala Val Thr Ile Asp Arg Val Met Ser
                885                 890                 895

Tyr Leu Asn Ala Ser
            900

<210> SEQ ID NO 17
<211> LENGTH: 1548
<212> TYPE: DNA
<213> ORGANISM: Artificial Sequence
<220> FEATURE:
<223> OTHER INFORMATION: Synthetic sequence

<400> SEQUENCE: 17
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg tttaccatc agccgtgata acagcaaaaa caccctgtac     240
ctgcaaatga acagcctgcg tgcggaagac accgcggtgt atcactgcgc gaccgatcgt     300
```

```
gcgtgcggta gcagctggct gggcgcggag agctgggcgc aaggcaccct ggttaccgtg    360
agcagcggtg gaggcggtag tggcggaggc ggttcaggcg gaggcggatc tgaacccaag    420
tcctgcgaca agacccacac ctgtccccct tgtcctgccc ctgaactgct gggcggaccc    480
agcgtgttcc tgttcccccc aaagcctaag gacaccctga tgatctcccg acccccgaa    540 gtgacctgcg tggtggtgga tgtgtcccac gaggaccctg aagtgaagtt caattggtac    600
gtggacggcg tggaagtgca caacgccaag accaagccta gagaggaaca gtacgcctcc    660
acctaccggg tggtgtccgt gctgaccgtg ctgcaccagg attggctgaa cggcaaagag    720
tacaagtgca aggtgtccaa caaggccctg cctgccccca tcgaaaagac catctccaag    780
gccaagggcc agccccggga acccaggtg tgtacactgc ccctagcag ggacgagctg      840 accaagaacc aggtgtccct gtcctgtgcc gtgaaaggct tctaccctc cgatatcgcc      900 gtggaatggg agtccaacgg ccagcctgag aacaactata agaccacccc ccctgtgctg    960
gactccgacg gctcattctt cctggtgagc aagctgacag tggacaagtc ccggtggcag   1020
cagggcaacg tgttctcctg ctccgtgatg cacgaggccc tgcacaacca ctacacccag   1080
aagtccctgt ccctgagccc cggcggtgga ggcggtagtg gcggaggcgg ttcaggcgga   1140
ggcggatctg cacctacttc aagttctaca agaaaacac agctacaact ggagcattta    1200
ctgctggatt tacagatgat tttgaatgga attaataatt acaagaatcc caaactcacc   1260
aggatgctca catttaagtt ttacatgccc aagaaggcca cagaactgaa acatcttcag   1320
tgtctagaag aagaactcaa acctctggag gaagtgctaa atttagctca aagcaaaaac   1380
tttcacttaa gacccaggga cttaatcagc aatatcaacg taatagttct ggaactaaag   1440
ggatctgaaa caacattcat gtgtgaatat gctgatgaga cagcaaccat tgtagaattt   1500
ctgaacagat ggattacctt ttgtcaaagc atcatctcaa cactgact                1548

<210> SEQ ID NO 18
<211> LENGTH: 516
<212> TYPE: PRT
<213> ORGANISM: Artificial Sequence
<220> FEATURE:
<223> OTHER INFORMATION: Synthetic sequence

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

Gly Gly Gly Ser Gly Gly Gly Gly Ser Glu Pro Lys Ser Cys Asp Lys
130                 135                 140
```

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Ala Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Cys Thr
            260                 265                 270

Leu Pro Pro Ser Arg Asp Glu Leu Thr Lys Asn Gln Val Ser Leu Ser
        275                 280                 285

Cys Ala Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Val Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Gly Gly Gly Gly Ser Gly Gly Gly Ser Gly Gly Gly Gly Ser Ala
370                 375                 380

Pro Thr Ser Ser Ser Thr Lys Lys Thr Gln Leu Gln Leu Glu His Leu
385                 390                 395                 400

Leu Leu Asp Leu Gln Met Ile Leu Asn Gly Ile Asn Asn Tyr Lys Asn
                405                 410                 415

Pro Lys Leu Thr Arg Met Leu Thr Phe Lys Phe Tyr Met Pro Lys Lys
            420                 425                 430

Ala Thr Glu Leu Lys His Leu Gln Cys Leu Glu Glu Glu Leu Lys Pro
        435                 440                 445

Leu Glu Glu Val Leu Asn Leu Ala Gln Ser Lys Asn Phe His Leu Arg
450                 455                 460

Pro Arg Asp Leu Ile Ser Asn Ile Asn Val Ile Val Leu Glu Leu Lys
465                 470                 475                 480

Gly Ser Glu Thr Thr Phe Met Cys Glu Tyr Ala Asp Glu Thr Ala Thr
                485                 490                 495

Ile Val Glu Phe Leu Asn Arg Trp Ile Thr Phe Cys Gln Ser Ile Ile
            500                 505                 510

Ser Thr Leu Thr
        515

<210> SEQ ID NO 19
<211> LENGTH: 3114
<212> TYPE: DNA
<213> ORGANISM: Artificial Sequence
<220> FEATURE:

<223> OTHER INFORMATION: Synthetic sequence

<400> SEQUENCE: 19

```
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg ttttaccatc agccgtgata acagcaaaaa caccctgtac     240
ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tcaagttcaa     420
ctggtggaaa gcggtggtgg tctggttcag ccgggcggta gcctgcgtct gagctgcgcg     480
gcgagcggtg gtaccctgga ctactatgcg atcggttggt tccgtcaggc gccgggcaag     540
gagcgtgagg cggtgagctg cattagcagc agcgacggta gcacctacta tgcggatagc     600
gttaagggcc gttttaccat cagccgtgat aacagcaaaa acaccctgta cctgcaaatg     660
aacagcctgc gtgcggaaga caccgcggtg tatcactgcg cgaccgatcg tgcgtgcggt     720
agcagctggc tgggcgcgga gagctgggcg caaggcaccc tggttaccgt gagcagcggt     780
ggaggcggta gtggcggagg cggttcaggc ggaggcggat ctgaacccaa gtcctgcgac     840
aagacccaca cctgtccccc ttgtcctgcc ctgaactgc tgggcggacc cagcgtgttc     900
ctgttccccc caaagcctaa ggacaccctg atgatctccc ggacccccga agtgacctgc     960
gtggtggtgg atgtgtccca cgaggaccct gaagtgaagt tcaattggta cgtggacggc    1020
gtggaagtgc acaacgccaa gaccaagcct agagaggaac agtacgcctc cacctaccgg    1080
gtggtgtccg tgctgaccgt gctgcaccag gattggctga cggcaaaga gtacaagtgc    1140
aaggtgtcca acaaggccct gcctgccccc atcgaaaaga ccatctccaa ggccaagggc    1200
cagccccggg aacccaggt gtacacactg cccccttgca gggacgagct gaccaagaac    1260
caggtgtccc tgtggtgtct cgtgaaaggc ttctacccct ccgatatcgc cgtggaatgg    1320
gagtccaacg gccagcctga gaacaactat aagaccaccc cccctgtgct ggactccgac    1380
ggctcattct tcctgtacag caagctgaca gtggacaagt cccggtggca gcagggcaac    1440
gtgttctcct gctccgtgat gcacgaggcc ctgcacaacc actacaccca gaagtccctg    1500
tccctgagcc ccggcggtgg aggcggtagt ggcggaggcg gttcaggcgg aggcggatct    1560
atttgggagc tgaagaaaga cgtgtacgtg gtcgagctgg actggtaccc tgatgcccca    1620
ggcgagatgg tcgtgctgac ctgcgataca ccagaggaag atggtatcac ctggacactg    1680
gatcagtcct cagaggtgct gggctctggt aaaacactga ccattcaggt gaaggagttc    1740
ggtgacgctg gacagtacac ttgtcataag ggcggggagg tgctgtctca ctccctgctg    1800
ctgctgcata gaaggagga tggaatctgg tccactgaca tcctgaaaga ccagaaggag    1860
ccaaagaaca aaaccttcct gcgatgcgag gctaagaact acagcggccg ctttacatgc    1920
tggtggctga caaccatcag caccgatctg acctttagcg tgaagtcatc caggggcagt    1980
tcagaccctc agggagtcac atgtggcgcc gcaaccctgt cagcagagcg agtgcgggga    2040
gacaataagg aatacgagta cagcgtcgag tgtcaggagg attccgcatg tccagctgca    2100
gaagaatccc tgcctatcga agtcatggtg gacgctgtgc ataaactgaa gtacgagaat    2160
tacaccagca gcttttttcat ccgggacatc atcaagcccg atccacctaa gaatctgcag    2220
ctgaagcctc tgaaaaatag ccgacaggtc gaagtgtcat gggaataccc agacacctgg    2280
```

```
tcaacaccac actcctactt ctccctgacc ttctgtgtgc aggtccaggg aaaaagcaag    2340
cgggaaaaga aagatcgggt gttcaccgac aagaccagtg ctacagtgat ttgccggaag    2400
aatgccagca tttctgtcag agctcaggac cggtactata gctcttcctg gagcgagtgg    2460
gcttcagtgc catgttctgg aggcggtgga tctggcggag gtggaagcgg aggcggtgga    2520
tctagaaacc tgcccgtcgc aaccctgat ccagggatgt tcccctgtct gcatcacagc     2580
cagaatctgc tgagggctgt ctccaacatg ctgcagaagg ctcgacagac cctggagttc    2640
tacccatgta ccagcgaaga gatcgaccac gaggatatca caaaggataa aaccagcaca    2700
gtggaagcat gcctgcctct ggaactgacc aagaatgaga gctgcctgaa tagcagggag    2760
acctccttca tcaccaacgg ctcatgcctg gcttcaagga agaccagctt catgatggct    2820
ctgtgtctga gctctatcta tgaggacctg aagatgtacc aggtggagtt caagaccatg    2880
aacgccaagc tgctgatgga tccaaagagg cagatcttcc tggatcagaa tatgctggca    2940
gtgatcgatg agctgatgca ggccctgaat tttaacagtg agacagtgcc tcagaagagc    3000
tctctggaag agccagactt ttacaaaact aagatcaagc tgtgcattct gctgcacgct    3060
ttccgcatca gagctgtcac tatcgataga gtgatgagct atctgaatgc ctca          3114
```

<210> SEQ ID NO 20
<211> LENGTH: 1038
<212> TYPE: PRT
<213> ORGANISM: Artificial Sequence
<220> FEATURE:
<223> OTHER INFORMATION: Synthetic sequence

<400> SEQUENCE: 20

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

Gly Gly Gly Ser Gly Gly Gly Ser Gln Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Gly Thr Leu Asp Tyr Tyr Ala Ile Gly Trp Phe Arg Gln
                165                 170                 175

Ala Pro Gly Lys Glu Arg Glu Ala Val Ser Cys Ile Ser Ser Ser Asp
            180                 185                 190

Gly Ser Thr Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
```

```
            210                 215                 220
Ala Glu Asp Thr Ala Val Tyr His Cys Ala Thr Asp Arg Ala Cys Gly
225                 230                 235                 240

Ser Ser Trp Leu Gly Ala Glu Ser Trp Ala Gln Gly Thr Leu Val Thr
                245                 250                 255

Val Ser Ser Gly Gly Gly Gly Ser Gly Gly Gly Ser Gly Gly Gly Gly
            260                 265                 270

Gly Ser Glu Pro Lys Ser Cys Asp Lys Thr His Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Ala Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Cys Arg Asp Glu
                405                 410                 415

Leu Thr Lys Asn Gln Val Ser Leu Trp Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Gly Gly Gly Ser Gly Gly Gly
            500                 505                 510

Gly Gly Ser Gly Gly Gly Gly Ser Ile Trp Glu Leu Lys Lys Asp Val
        515                 520                 525

Tyr Val Val Glu Leu Asp Trp Tyr Pro Asp Ala Pro Gly Glu Met Val
    530                 535                 540

Val Leu Thr Cys Asp Thr Pro Glu Glu Asp Gly Ile Thr Trp Thr Leu
545                 550                 555                 560

Asp Gln Ser Ser Glu Val Leu Gly Ser Gly Lys Thr Leu Thr Ile Gln
                565                 570                 575

Val Lys Glu Phe Gly Asp Ala Gly Gln Tyr Thr Cys His Lys Gly Gly
            580                 585                 590

Glu Val Leu Ser His Ser Leu Leu Leu His Lys Lys Glu Asp Gly
        595                 600                 605

Ile Trp Ser Thr Asp Ile Leu Lys Asp Gln Lys Glu Pro Lys Asn Lys
    610                 615                 620

Thr Phe Leu Arg Cys Glu Ala Lys Asn Tyr Ser Gly Arg Phe Thr Cys
625                 630                 635                 640
```

```
Trp Trp Leu Thr Thr Ile Ser Thr Asp Leu Thr Phe Ser Val Lys Ser
                645                 650                 655

Ser Arg Gly Ser Ser Asp Pro Gln Gly Val Thr Cys Gly Ala Ala Thr
            660                 665                 670

Leu Ser Ala Glu Arg Val Arg Gly Asp Asn Lys Glu Tyr Glu Tyr Ser
            675                 680                 685

Val Glu Cys Gln Glu Asp Ser Ala Cys Pro Ala Ala Glu Glu Ser Leu
690                 695                 700

Pro Ile Glu Val Met Val Asp Ala Val His Lys Leu Lys Tyr Glu Asn
705                 710                 715                 720

Tyr Thr Ser Ser Phe Phe Ile Arg Asp Ile Ile Lys Pro Asp Pro Pro
                725                 730                 735

Lys Asn Leu Gln Leu Lys Pro Leu Lys Asn Ser Arg Gln Val Glu Val
                740                 745                 750

Ser Trp Glu Tyr Pro Asp Thr Trp Ser Thr Pro His Ser Tyr Phe Ser
            755                 760                 765

Leu Thr Phe Cys Val Gln Val Gln Gly Lys Ser Lys Arg Glu Lys Lys
            770                 775                 780

Asp Arg Val Phe Thr Asp Lys Thr Ser Ala Thr Val Ile Cys Arg Lys
785                 790                 795                 800

Asn Ala Ser Ile Ser Val Arg Ala Gln Asp Arg Tyr Tyr Ser Ser Ser
                805                 810                 815

Trp Ser Glu Trp Ala Ser Val Pro Cys Ser Gly Gly Gly Ser Gly
            820                 825                 830

Gly Gly Gly Ser Gly Gly Gly Ser Arg Asn Leu Pro Val Ala Thr
            835                 840                 845

Pro Asp Pro Gly Met Phe Pro Cys Leu His His Ser Gln Asn Leu Leu
850                 855                 860

Arg Ala Val Ser Asn Met Leu Gln Lys Ala Arg Gln Thr Leu Glu Phe
865                 870                 875                 880

Tyr Pro Cys Thr Ser Glu Glu Ile Asp His Glu Asp Ile Thr Lys Asp
                885                 890                 895

Lys Thr Ser Thr Val Glu Ala Cys Leu Pro Leu Glu Leu Thr Lys Asn
                900                 905                 910

Glu Ser Cys Leu Asn Ser Arg Glu Thr Ser Phe Ile Thr Asn Gly Ser
            915                 920                 925

Cys Leu Ala Ser Arg Lys Thr Ser Phe Met Met Ala Leu Cys Leu Ser
930                 935                 940

Ser Ile Tyr Glu Asp Leu Lys Met Tyr Gln Val Glu Phe Lys Thr Met
945                 950                 955                 960

Asn Ala Lys Leu Leu Met Asp Pro Lys Arg Gln Ile Phe Leu Asp Gln
                965                 970                 975

Asn Met Leu Ala Val Ile Asp Glu Leu Met Gln Ala Leu Asn Phe Asn
            980                 985                 990

Ser Glu Thr Val Pro Gln Lys Ser  Ser Leu Glu Glu Pro Asp Phe Tyr
            995                 1000                1005

Lys Thr Lys Ile Lys Leu Cys Ile Leu Leu His Ala Phe Arg Ile
    1010                1015                1020

Arg Ala Val Thr Ile Asp Arg Val Met Ser Tyr Leu Asn Ala Ser
    1025                1030                1035

<210> SEQ ID NO 21
<211> LENGTH: 1959
```

<212> TYPE: DNA
<213> ORGANISM: Artificial Sequence
<220> FEATURE:
<223> OTHER INFORMATION: Synthetic sequence

<400> SEQUENCE: 21

```
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg ttttaccatc agccgtgata acagcaaaaa caccctgtac     240
ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tcaagttcaa     420
ctggtggaaa gcggtggtgg tctggttcag ccgggcggta gcctgcgtct gagctgcgcg     480
gcgagcggtg gtaccctgga ctactatgcg atcggttggt tccgtcaggc gccgggcaag     540
gagcgtgagg cggtgagctg cattagcagc agcgacggta gcacctacta tgcggatagc     600
gttaagggcc gttttaccat cagccgtgat aacagcaaaa acaccctgta cctgcaaatg     660
aacagcctgc gtgcggaaga caccgcggtg tatcactgcg cgaccgatcg tgcgtgcggt     720
agcagctggc tgggcgcgga gagctgggcg caaggcaccc tggttaccgt gagcagcggt     780
ggaggcggta gtggcggagg cggttcaggc ggaggcggat ctgaacccaa gtcctgcgac     840
aagacccaca cctgtccccc ttgtcctgcc cctgaactgc tgggcggacc cagcgtgttc     900
ctgttccccc caaagcctaa ggacaccctg atgatctccc ggacccccga agtgacctgc    960
gtggtggtgg atgtgtccca cgaggaccct gaagtgaagt tcaattggta cgtggacggc    1020
gtggaagtgc acaacgccaa gaccaagcct agagaggaac agtacgcctc cacctaccgg    1080
gtggtgtccg tgctgaccgt gctgcaccag gattggctga acggcaaaga gtacaagtgc    1140
aaggtgtcca acaaggccct gcctgccccc atcgaaaaga ccatctccaa ggccaagggc    1200
cagccccggg aaccccaggt gtgtacactg cccccctagca gggacgagct gaccaagaac    1260
caggtgtccc tgtcctgtgc cgtgaaaggc ttctaccccc ccgatatcgc cgtggaatgg    1320
gagtccaacg gccagcctga gaacaactat aagaccaccc ccctgtgct ggactccgac    1380
ggctcattct cctggtgag caagctgaca gtggacaagt cccggtggca gcagggcaac    1440
gtgttctcct gctccgtgat gcacgaggcc ctgcacaacc actacaccca gaagtccctg    1500
tccctgagcc ccggcggtgg aggcggtagt ggcggaggcg gttcaggcgg aggcggatct    1560
gcacctactt caagttctac aaagaaaaca cagctacaac tggagcattt actgctggat    1620
ttacagatga ttttgaatgg aattaataat tacaagaatc ccaaactcac caggatgctc    1680
acatttaagt tttacatgcc caagaaggcc acagaactga acatcttca gtgtctagaa    1740
gaagaactca aacctctgga ggaagtgcta aatttagctc aaagcaaaaa ctttcactta    1800
agacccaggg acttaatcag caatatcaac gtaatagttc tggaactaaa gggatctgaa    1860
acaacattca tgtgtgaata tgctgatgag acagcaacca ttgtagaatt tctgaacaga    1920
tggattacct tttgtcaaag catcatctca acactgact                          1959
```

<210> SEQ ID NO 22
<211> LENGTH: 653
<212> TYPE: PRT
<213> ORGANISM: Artificial Sequence
<220> FEATURE:

<223> OTHER INFORMATION: Synthetic sequence

<400> SEQUENCE: 22

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

Gly Gly Gly Ser Gly Gly Gly Ser Gln Val Gln Leu Val Glu Ser
130                 135                 140

Gly Gly Gly Leu Val Gln Pro Gly Gly Ser Leu Arg Leu Ser Cys Ala
145                 150                 155                 160

Ala Ser Gly Gly Thr Leu Asp Tyr Tyr Ala Ile Gly Trp Phe Arg Gln
            165                 170                 175

Ala Pro Gly Lys Glu Arg Glu Ala Val Ser Cys Ile Ser Ser Ser Asp
        180                 185                 190

Gly Ser Thr Tyr Tyr Ala Asp Ser Val Lys Gly Arg Phe Thr Ile Ser
            195                 200                 205

Arg Asp Asn Ser Lys Asn Thr Leu Tyr Leu Gln Met Asn Ser Leu Arg
210                 215                 220

Ala Glu Asp Thr Ala Val Tyr His Cys Ala Thr Asp Arg Ala Cys Gly
225                 230                 235                 240

Ser Ser Trp Leu Gly Ala Glu Ser Trp Ala Gln Gly Thr Leu Val Thr
            245                 250                 255

Val Ser Ser Gly Gly Gly Gly Ser Gly Gly Gly Gly Ser Gly Gly Gly
        260                 265                 270

Gly Ser Glu Pro Lys Ser Cys Asp Lys Thr His Thr Cys Pro Pro Cys
    275                 280                 285

Pro Ala Pro Glu Leu Leu Gly Gly Pro Ser Val Phe Leu Phe Pro Pro
290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
            325                 330                 335

Tyr Val Asp Gly Val Glu Val His Asn Ala Lys Thr Lys Pro Arg Glu
        340                 345                 350

Glu Gln Tyr Ala Ser Thr Tyr Arg Val Val Ser Val Leu Thr Val Leu
    355                 360                 365

His Gln Asp Trp Leu Asn Gly Lys Glu Tyr Lys Cys Lys Val Ser Asn
370                 375                 380

Lys Ala Leu Pro Ala Pro Ile Glu Lys Thr Ile Ser Lys Ala Lys Gly
385                 390                 395                 400
```

-continued

```
Gln Pro Arg Glu Pro Gln Val Cys Thr Leu Pro Pro Ser Arg Asp Glu
                405                 410                 415
Leu Thr Lys Asn Gln Val Ser Leu Ser Cys Ala Val Lys Gly Phe Tyr
            420                 425                 430
Pro Ser Asp Ile Ala Val Glu Trp Glu Ser Asn Gly Gln Pro Glu Asn
        435                 440                 445
Asn Tyr Lys Thr Thr Pro Pro Val Leu Asp Ser Asp Gly Ser Phe Phe
    450                 455                 460
Leu Val Ser Lys Leu Thr Val Asp Lys Ser Arg Trp Gln Gln Gly Asn
465                 470                 475                 480
Val Phe Ser Cys Ser Val Met His Glu Ala Leu His Asn His Tyr Thr
                485                 490                 495
Gln Lys Ser Leu Ser Leu Ser Pro Gly Gly Gly Gly Ser Gly Gly
            500                 505                 510
Gly Gly Ser Gly Gly Gly Gly Ser Ala Pro Thr Ser Ser Ser Thr Lys
        515                 520                 525
Lys Thr Gln Leu Gln Leu Glu His Leu Leu Leu Asp Leu Gln Met Ile
    530                 535                 540
Leu Asn Gly Ile Asn Asn Tyr Lys Asn Pro Lys Leu Thr Arg Met Leu
545                 550                 555                 560
Thr Phe Lys Phe Tyr Met Pro Lys Lys Ala Thr Glu Leu Lys His Leu
                565                 570                 575
Gln Cys Leu Glu Glu Leu Lys Pro Leu Glu Val Leu Asn Leu
            580                 585                 590
Ala Gln Ser Lys Asn Phe His Leu Arg Pro Arg Asp Leu Ile Ser Asn
        595                 600                 605
Ile Asn Val Ile Val Leu Glu Leu Lys Gly Ser Glu Thr Thr Phe Met
    610                 615                 620
Cys Glu Tyr Ala Asp Glu Thr Ala Thr Ile Val Glu Phe Leu Asn Arg
625                 630                 635                 640
Trp Ile Thr Phe Cys Gln Ser Ile Ile Ser Thr Leu Thr
                645                 650
```

<210> SEQ ID NO 23
<211> LENGTH: 1959
<212> TYPE: DNA
<213> ORGANISM: Artificial Sequence
<220> FEATURE:
<223> OTHER INFORMATION: Synthetic sequence

<400> SEQUENCE: 23

```
caagttcaac tggtggaaag cggtggtggt ctggttcagc cgggcggtag cctgcgtctg    60
agctgcgcgg cgagcggtgg taccctggac tactatgcga tcggttggtt ccgtcaggcg   120
ccgggcaagg agcgtgaggc ggtgagctgc attagcagca gcgacggtag cacctactat   180
gcggatagcg ttaagggccg ttttaccatc agccgtgata acagcaaaaa cacccctgtac   240
ctgcaaatga acagcctgcg tgcggaagac accgcggtgt atcactgcgc gaccgatcgt   300
gcgtgcggta gcagctggct gggcgcggag agctgggcgc aaggcaccct ggttaccgtg   360
agcagcggtg gaggcggtag tggcggaggc ggttcaggcg gaggcggatc tcaagttcaa   420
ctggtggaaa gcggtggtgg tctggttcag ccgggcggta gcctgcgtct gagctgcgcg   480
gcgagcggtg gtaccctgga ctactatgcg atcggttggt tccgtcaggc gccgggcaag   540
gagcgtgagg cggtgagctg cattagcagc agcgacggta gcacctacta tgcggatagc   600
gttaagggcc gttttaccat cagccgtgat aacagcaaaa acaccctgta cctgcaaatg   660
```

```
aacagcctgc gtgcggaaga caccgcggtg tatcactgcg cgaccgatcg tgcgtgcggt    720
agcagctggc tgggcgcgga gagctgggcg caaggcaccc tggttaccgt gagcagcggt    780
ggaggcggta gtggcggagg cggttcaggc ggaggcggat ctgaacccaa gtcctgcgac    840
aagacccaca cctgtccccc ttgtcctgcc cctgaactgc tgggcggacc cagcgtgttc    900
ctgttccccc caaagcctaa ggacaccctg atgatctccc ggaccccccga agtgacctgc    960 gtggtggtgg atgtgtccca cgaggaccct gaagtgaagt tcaattggta cgtggacggc   1020
gtggaagtgc acaacgccaa gaccaagcct agagaggaac agtacgcctc cacctaccgg   1080
gtggtgtccg tgctgaccgt gctgcaccag gattggctga acggcaaaga gtacaagtgc   1140
aaggtgtcca acaaggccct gcctgccccc atcgaaaaga ccatctccaa ggccaagggc   1200
cagcccgggg aacccaggt gtgtacactg cccctagca gggacgagct gaccaagaac   1260
caggtgtccc tgtcctgtgc cgtgaaaggc ttctacccct ccgatatcgc cgtggaatgg   1320
gagtccaacg gccagcctga gaacaactat aagaccaccc cccctgtgct ggactccgac   1380
ggctcattct tcctggtgag caagctgaca gtggacaagt cccggtggca gcagggcaac   1440
gtgttctcct gctccgtgat gcacgaggcc ctgcacaacc actacaccca gaagtccctg   1500
tccctgagcc ccggcggtgg aggcggtagt ggcggaggcg gttcaggcgg aggcggatct   1560
gcacctactt caagttctac aaagaaaaca cagctacaac tggagcattt actgctggat   1620
ttacagatga ttttgaatgg aattaataat tacaagaatc ccaaactcac caggatgctc   1680
acatttaagt tttacatgcc caagaaggcc acagaactga acatcttca gtgtctagaa   1740 gaagaactca aacctctgga ggaagtgcta aatttagctc aaagcaaaaa ctttcacttc   1800
gaccccaggg acgtggtgag caatatcaac gtattcgttc tggaactaaa gggatctgaa   1860
acaacattca tgtgtgaata tgctgatgag acagcaacca ttgtagaatt tctgaacaga   1920
tggattacct tttgtcaaag catcatctca acactgact                          1959
```

```
<210> SEQ ID NO 24
<211> LENGTH: 653
<212> TYPE: PRT
<213> ORGANISM: Artificial Sequence
<220> FEATURE:
<223> OTHER INFORMATION: Synthetic sequence

<400> SEQUENCE: 24
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

```
Gly Gly Gly Ser Gly Gly Gly Ser Gln Val Gln Leu Val Glu Ser
    130             135             140
Gly Gly Gly Leu Val Gln Pro Gly Gly Ser Leu Arg Leu Ser Cys Ala
145             150             155                 160
Ala Ser Gly Gly Thr Leu Asp Tyr Tyr Ala Ile Gly Trp Phe Arg Gln
            165             170             175
Ala Pro Gly Lys Glu Arg Glu Ala Val Ser Cys Ile Ser Ser Ser Asp
            180             185             190
Gly Ser Thr Tyr Tyr Ala Asp Ser Val Lys Gly Arg Phe Thr Ile Ser
            195             200             205
Arg Asp Asn Ser Lys Asn Thr Leu Tyr Leu Gln Met Asn Ser Leu Arg
210             215             220
Ala Glu Asp Thr Ala Val Tyr His Cys Ala Thr Asp Arg Ala Cys Gly
225             230             235                 240
Ser Ser Trp Leu Gly Ala Glu Ser Trp Ala Gln Gly Thr Leu Val Thr
            245             250             255
Val Ser Ser Gly Gly Gly Ser Gly Gly Gly Ser Gly Gly Gly
            260             265             270
Gly Ser Glu Pro Lys Ser Cys Asp Lys Thr His Thr Cys Pro Pro Cys
    275             280             285
Pro Ala Pro Glu Leu Leu Gly Gly Pro Ser Val Phe Leu Phe Pro Pro
290             295             300
Lys Pro Lys Asp Thr Leu Met Ile Ser Arg Thr Pro Glu Val Thr Cys
305             310             315                 320
Val Val Val Asp Val Ser His Glu Asp Pro Glu Val Lys Phe Asn Trp
            325             330             335
Tyr Val Asp Gly Val Glu Val His Asn Ala Lys Thr Lys Pro Arg Glu
            340             345             350
Glu Gln Tyr Ala Ser Thr Tyr Arg Val Val Ser Val Leu Thr Val Leu
            355             360             365
His Gln Asp Trp Leu Asn Gly Lys Glu Tyr Lys Cys Lys Val Ser Asn
    370             375             380
Lys Ala Leu Pro Ala Pro Ile Glu Lys Thr Ile Ser Lys Ala Lys Gly
385             390             395                 400
Gln Pro Arg Glu Pro Gln Val Cys Thr Leu Pro Pro Ser Arg Asp Glu
            405             410             415
Leu Thr Lys Asn Gln Val Ser Leu Ser Cys Ala Val Lys Gly Phe Tyr
            420             425             430
Pro Ser Asp Ile Ala Val Glu Trp Glu Ser Asn Gly Gln Pro Glu Asn
            435             440             445
Asn Tyr Lys Thr Thr Pro Pro Val Leu Asp Ser Asp Gly Ser Phe Phe
    450             455             460
Leu Val Ser Lys Leu Thr Val Asp Lys Ser Arg Trp Gln Gln Gly Asn
465             470             475                 480
Val Phe Ser Cys Ser Val Met His Glu Ala Leu His Asn His Tyr Thr
            485             490             495
Gln Lys Ser Leu Ser Leu Ser Pro Gly Gly Gly Gly Ser Gly Gly
            500             505             510
Gly Gly Ser Gly Gly Gly Gly Ser Ala Pro Thr Ser Ser Ser Thr Lys
            515             520             525
Lys Thr Gln Leu Gln Leu Glu His Leu Leu Leu Asp Leu Gln Met Ile
    530             535             540
Leu Asn Gly Ile Asn Asn Tyr Lys Asn Pro Lys Leu Thr Arg Met Leu
```

```
              545                 550                 555                 560
Thr Phe Lys Phe Tyr Met Pro Lys Lys Ala Thr Glu Leu Lys His Leu
                565                 570                 575

Gln Cys Leu Glu Glu Glu Leu Lys Pro Leu Glu Val Leu Asn Leu
            580                 585                 590

Ala Gln Ser Lys Asn Phe His Phe Asp Pro Arg Asp Val Val Ser Asn
        595                 600                 605

Ile Asn Val Phe Val Leu Glu Leu Lys Gly Ser Glu Thr Thr Phe Met
    610                 615                 620

Cys Glu Tyr Ala Asp Glu Thr Ala Thr Ile Val Glu Phe Leu Asn Arg
625                 630                 635                 640

Trp Ile Thr Phe Cys Gln Ser Ile Ile Ser Thr Leu Thr
                645                 650

<210> SEQ ID NO 25
<211> LENGTH: 1959
<212> TYPE: DNA
<213> ORGANISM: Artificial Sequence
<220> FEATURE:
<223> OTHER INFORMATION: Synthetic sequence

<400> SEQUENCE: 25
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg ttttaccatc agccgtgata acagcaaaaa cacccctgtac    240 ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tcaagttcaa     420
ctggtggaaa gcggtggtgg tctggttcag ccgggcggta gcctgcgtct gagctgcgcg     480
gcgagcggtg gtaccctgga ctactatgcg atcggttggt tccgtcaggc gccgggcaag     540
gagcgtgagg cggtgagctg cattagcagc agcgacggta gcacctacta tgcggatagc     600
gttaagggcc gttttaccat cagccgtgat aacagcaaaa acaccctgta cctgcaaatg     660
aacagcctgc gtgcggaaga caccgcggtg tatcactgcg cgaccgatcg tgcgtgcggt     720
agcagctggc tgggcgcgga gagctgggcg caaggcaccc tggttaccgt gagcagcggt     780
ggaggcggta gtggcggagg cggttcaggc ggaggcggat ctgaacccaa gtcctgcgac     840
aagacccaca cctgtccccc ttgtcctgcc ctgaactgc tgggcggacc cagcgtgttc     900
ctgttccccc caaagcctaa ggacaccctg atgatctccc ggacccccga agtgacctgc     960
gtggtggtgg atgtgtccca cgaggaccct gaagtgaagt tcaattggta cgtggacggc    1020
gtggaagtgc acaacgccaa gaccaagcct agagaggaac agtacgcctc cacctaccgg    1080
gtggtgtccg tgctgaccgt gctgcaccag gattggctga acggcaaaga gtacaagtgc    1140
aaggtgtcca acaaggccct gcctgccccc atcgaaaaga ccatctccaa ggccaagggc    1200
cagccccggg aacccaggt gtacacactg ccccccttgca gggacgagct gaccaagaac    1260
caggtgtccc tgtggtgtct cgtgaaaggc ttctaccct ccgatatcgc cgtggaatgg    1320
gagtccaacg gccagcctga gaacaactat aagaccaccc ccctgtgct ggactccgac    1380 ggctcattct tcctgtacag caagctgaca gtggacaagt cccggtggca gcagggcaac    1440
gtgttctcct gctccgtgat gcacgaggcc ctgcacaacc actacaccca gaagtccctg    1500
```

-continued

```
tccctgagcc ccggcggtgg aggcggtagt ggcggaggcg gttcaggcgg aggcggatct    1560
gcacctactt caagttctac aaagaaaaca cagctacaac tggagcattt actgctggat    1620
ttacagatga ttttgaatgg aattaataat tacaagaatc ccaaactcac caggatgctc    1680
acatttaagt tttacatgcc caagaaggcc acagaactga acatcttca gtgtctagaa     1740 gaagaactca aacctctgga ggaagtgcta aatttagctc aaagcaaaaa ctttcactta    1800
agacccaggg acttaatcag caatatcaac gtaatagttc tggaactaaa gggatctgaa    1860
acaacattca tgtgtgaata tgctgatgag acagcaacca ttgtagaatt tctgaacaga    1920
tggattacct tttgtcaaag catcatctca acactgact                           1959
```

<210> SEQ ID NO 26
<211> LENGTH: 653
<212> TYPE: PRT
<213> ORGANISM: Artificial Sequence
<220> FEATURE:
<223> OTHER INFORMATION: Synthetic sequence

<400> SEQUENCE: 26

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Leu Val Thr Val Ser Ser Gly Gly Gly Gly Ser Gly
        115                 120                 125

Gly Gly Gly Ser Gly Gly Gly Ser Gln Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Gly Thr Leu Asp Tyr Tyr Ala Ile Gly Trp Phe Arg Gln
                165                 170                 175

Ala Pro Gly Lys Glu Arg Glu Ala Val Ser Cys Ile Ser Ser Ser Asp
            180                 185                 190

Gly Ser Thr Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
    210                 215                 220

Ala Glu Asp Thr Ala Val Tyr His Cys Ala Thr Asp Arg Ala Cys Gly
225                 230                 235                 240

Ser Ser Trp Leu Gly Ala Glu Ser Trp Ala Gln Gly Thr Leu Val Thr
                245                 250                 255

Val Ser Ser Gly Gly Gly Gly Ser Gly Gly Gly Gly Ser Gly Gly Gly
            260                 265                 270

Gly Ser Glu Pro Lys Ser Cys Asp Lys Thr His Thr Cys Pro Pro Cys
```

-continued

```
                    275                 280                 285
        Pro Ala Pro Glu Leu Leu Gly Gly Pro Ser Val Phe Leu Phe Pro Pro
                290                 295                 300
        Lys Pro Lys Asp Thr Leu Met Ile Ser Arg Thr Pro Glu Val Thr Cys
        305                 310                 315                 320
        Val Val Val Asp Val Ser His Glu Asp Pro Glu Val Lys Phe Asn Trp
                        325                 330                 335
        Tyr Val Asp Gly Val Glu Val His Asn Ala Lys Thr Lys Pro Arg Glu
                    340                 345                 350
        Glu Gln Tyr Ala Ser Thr Tyr Arg Val Val Ser Val Leu Thr Val Leu
                355                 360                 365
        His Gln Asp Trp Leu Asn Gly Lys Glu Tyr Lys Cys Lys Val Ser Asn
            370                 375                 380
        Lys Ala Leu Pro Ala Pro Ile Glu Lys Thr Ile Ser Lys Ala Lys Gly
        385                 390                 395                 400
        Gln Pro Arg Glu Pro Gln Val Tyr Thr Leu Pro Pro Cys Arg Asp Glu
                        405                 410                 415
        Leu Thr Lys Asn Gln Val Ser Leu Trp Cys Leu Val Lys Gly Phe Tyr
                    420                 425                 430
        Pro Ser Asp Ile Ala Val Glu Trp Glu Ser Asn Gly Gln Pro Glu Asn
                435                 440                 445
        Asn Tyr Lys Thr Thr Pro Pro Val Leu Asp Ser Asp Gly Ser Phe Phe
            450                 455                 460
        Leu Tyr Ser Lys Leu Thr Val Asp Lys Ser Arg Trp Gln Gln Gly Asn
        465                 470                 475                 480
        Val Phe Ser Cys Ser Val Met His Glu Ala Leu His Asn His Tyr Thr
                        485                 490                 495
        Gln Lys Ser Leu Ser Leu Ser Pro Gly Gly Gly Gly Ser Gly Gly
                    500                 505                 510
        Gly Gly Ser Gly Gly Gly Gly Ser Ala Pro Thr Ser Ser Ser Thr Lys
                515                 520                 525
        Lys Thr Gln Leu Gln Leu Glu His Leu Leu Leu Asp Leu Gln Met Ile
            530                 535                 540
        Leu Asn Gly Ile Asn Asn Tyr Lys Asn Pro Lys Leu Thr Arg Met Leu
        545                 550                 555                 560
        Thr Phe Lys Phe Tyr Met Pro Lys Lys Ala Thr Glu Leu Lys His Leu
                        565                 570                 575
        Gln Cys Leu Glu Glu Glu Leu Lys Pro Leu Glu Glu Val Leu Asn Leu
                    580                 585                 590
        Ala Gln Ser Lys Asn Phe His Leu Arg Pro Arg Asp Leu Ile Ser Asn
                595                 600                 605
        Ile Asn Val Ile Val Leu Glu Leu Lys Gly Ser Glu Thr Thr Phe Met
            610                 615                 620
        Cys Glu Tyr Ala Asp Glu Thr Ala Thr Ile Val Glu Phe Leu Asn Arg
        625                 630                 635                 640
        Trp Ile Thr Phe Cys Gln Ser Ile Ile Ser Thr Leu Thr
                        645                 650
```

<210> SEQ ID NO 27
<211> LENGTH: 1515
<212> TYPE: DNA
<213> ORGANISM: Artificial Sequence
<220> FEATURE:
<223> OTHER INFORMATION: Synthetic sequence

<400> SEQUENCE: 27

```
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg ttttaccatc agccgtgata acagcaaaaa caccctgtac     240
ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tcaagttcaa     420
ctggtggaaa gcggtggtgg tctggttcag ccgggcggta gcctgcgtct gagctgcgcg     480
gcgagcggtg gtaccctgga ctactatgcg atcggttggt tccgtcaggc gccgggcaag     540
gagcgtgagg cggtgagctg cattagcagc agcgacggta gcacctacta tgcggatagc     600
gttaagggcc gttttaccat cagccgtgat aacagcaaaa acaccctgta cctgcaaatg     660
aacagcctgc gtgcggaaga caccgcggtg tatcactgcg cgaccgatcg tgcgtgcggt     720
agcagctggc tgggcgcgga gagctgggcg caaggcaccc tggttaccgt gagcagcggt     780
ggaggcggta gtggcggagg cggttcaggc ggaggcggat ctgaacccaa gtcctgcgac     840
aagacccaca cctgtccccc ttgtcctgcc cctgaactgc tgggcggacc cagcgtgttc     900
ctgttccccc caaagcctaa ggacaccctg atgatctccc ggacccccga agtgacctgc     960
gtggtggtgg atgtgtccca cgaggaccct gaagtgaagt tcaattggta cgtggacggc    1020
gtggaagtgc acaacgccaa gaccaagcct agagaggaac agtacgcctc cacctaccgg    1080
gtggtgtccg tgctgaccgt gctgcaccag gattggctga acggcaaaga gtacaagtgc    1140
aaggtgtcca acaaggccct gcctgccccc atcgaaaaga ccatctccaa ggccaagggc    1200
cagccccggg aaccccaggt gtgtacactg cccctagca gggacgagct gaccaagaac    1260
caggtgtccc tgtcctgtgc cgtgaaaggc ttctacccct ccgatatcgc cgtggaatgg    1320
gagtccaacg gccagcctga gaacaactat aagaccaccc cccctgtgct ggactccgac    1380
ggctcattct cctggtgag caagctgaca gtggacaagt cccggtggca gcagggcaac    1440
gtgttctcct gctccgtgat gcacgaggcc ctgcacaacc actacaccca gaagtccctg    1500
tccctgagcc ccggc                                                      1515
```

<210> SEQ ID NO 28
<211> LENGTH: 505
<212> TYPE: PRT
<213> ORGANISM: Artificial Sequence
<220> FEATURE:
<223> OTHER INFORMATION: Synthetic sequence

<400> SEQUENCE: 28

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr His Cys
                 85                  90                  95
Ala Thr Asp Arg Ala Cys Gly Ser Ser Trp Leu Gly Ala Glu Ser Trp
            100                 105                 110
Ala Gln Gly Thr Leu Val Thr Val Ser Ser Gly Gly Gly Gly Ser Gly
        115                 120                 125
Gly Gly Gly Ser Gly Gly Gly Ser Gln Val Gln Leu Val Glu Ser
    130                 135                 140
Gly Gly Gly Leu Val Gln Pro Gly Gly Ser Leu Arg Leu Ser Cys Ala
145                 150                 155                 160
Ala Ser Gly Gly Thr Leu Asp Tyr Tyr Ala Ile Gly Trp Phe Arg Gln
            165                 170                 175
Ala Pro Gly Lys Glu Arg Glu Ala Val Ser Cys Ile Ser Ser Ser Asp
        180                 185                 190
Gly Ser Thr Tyr Tyr Ala Asp Ser Val Lys Gly Arg Phe Thr Ile Ser
    195                 200                 205
Arg Asp Asn Ser Lys Asn Thr Leu Tyr Leu Gln Met Asn Ser Leu Arg
210                 215                 220
Ala Glu Asp Thr Ala Val Tyr His Cys Ala Thr Asp Arg Ala Cys Gly
225                 230                 235                 240
Ser Ser Trp Leu Gly Ala Glu Ser Trp Ala Gln Gly Thr Leu Val Thr
            245                 250                 255
Val Ser Ser Gly Gly Gly Gly Ser Gly Gly Gly Gly Ser Gly Gly Gly
        260                 265                 270
Gly Ser Glu Pro Lys Ser Cys Asp Lys Thr His Thr Cys Pro Pro Cys
    275                 280                 285
Pro Ala Pro Glu Leu Leu Gly Gly Pro Ser Val Phe Leu Phe Pro Pro
290                 295                 300
Lys Pro Lys Asp Thr Leu Met Ile Ser Arg Thr Pro Glu Val Thr Cys
305                 310                 315                 320
Val Val Val Asp Val Ser His Glu Asp Pro Glu Val Lys Phe Asn Trp
            325                 330                 335
Tyr Val Asp Gly Val Glu Val His Asn Ala Lys Thr Lys Pro Arg Glu
        340                 345                 350
Glu Gln Tyr Ala Ser Thr Tyr Arg Val Val Ser Val Leu Thr Val Leu
    355                 360                 365
His Gln Asp Trp Leu Asn Gly Lys Glu Tyr Lys Cys Lys Val Ser Asn
    370                 375                 380
Lys Ala Leu Pro Ala Pro Ile Glu Lys Thr Ile Ser Lys Ala Lys Gly
385                 390                 395                 400
Gln Pro Arg Glu Pro Gln Val Cys Thr Leu Pro Pro Ser Arg Asp Glu
            405                 410                 415
Leu Thr Lys Asn Gln Val Ser Leu Ser Cys Ala Val Lys Gly Phe Tyr
        420                 425                 430
Pro Ser Asp Ile Ala Val Glu Trp Glu Ser Asn Gly Gln Pro Glu Asn
    435                 440                 445
Asn Tyr Lys Thr Thr Pro Pro Val Leu Asp Ser Asp Gly Ser Phe Phe
    450                 455                 460
Leu Val Ser Lys Leu Thr Val Asp Lys Ser Arg Trp Gln Gln Gly Asn
465                 470                 475                 480
Val Phe Ser Cys Ser Val Met His Glu Ala Leu His Asn His Tyr Thr
            485                 490                 495
Gln Lys Ser Leu Ser Leu Ser Pro Gly
```

<210> SEQ ID NO 29
<211> LENGTH: 1515
<212> TYPE: DNA
<213> ORGANISM: Artificial Sequence
<220> FEATURE:
<223> OTHER INFORMATION: Synthetic sequence

<400> SEQUENCE: 29

```
caagttcaac tggtggaaag cggtggtggt ctggttcagc cgggcggtag cctgcgtctg      60
agctgcgcgg cgagcggtgg taccctggac tactatgcga tcggttggtt ccgtcaggcg     120
ccgggcaagg agcgtgaggc ggtgagctgc attagcagca gcgacggtag cacctactat     180
gcggatagcg ttaagggccg ttttaccatc agccgtgata acagcaaaaa cacccctgtac    240
ctgcaaatga acagcctgcg tgcggaagac accgcggtgt atcactgcgc gaccgatcgt     300
gcgtgcggta gcagctggct gggcgcggag agctgggcgc aaggcaccct ggttaccgtg     360
agcagcggtg gaggcggtag tggcggaggc ggttcaggcg gaggcggatc tcaagttcaa    420
ctggtggaaa gcggtggtgg tctggttcag ccgggcggta gcctgcgtct gagctgcgcg     480
gcgagcggtg gtaccctgga ctactatgcg atcggttggt tccgtcaggc gccgggcaag     540
gagcgtgagg cggtgagctg cattagcagc agcgacggta gcacctacta tgcggatagc     600
gttaagggcc gttttaccat cagccgtgat aacagcaaaa acaccctgta cctgcaaatg     660
aacagcctgc gtgcggaaga caccgcggtg tatcactgcg cgaccgatcg tgcgtgcggt     720
agcagctggc tgggcgcgga gagctgggcg caaggcaccc tggttaccgt gagcagcggt     780
ggaggcggta gtggcggagg cggttcaggc ggaggcggat ctgaacccaa gtcctgcgac     840
aagacccaca cctgtccccc ttgtcctgcc cctgaactgc tgggcggacc cagcgtgttc     900
ctgttccccc caaagcctaa ggacaccctg atgatctccc ggaccccccga agtgacctgc    960
gtggtggtgg atgtgtccca cgaggaccct gaagtgaagt tcaattggta cgtggacggc    1020
gtggaagtgc acaacgccaa gaccaagcct agagaggaac agtacgcctc cacctaccgg    1080
gtggtgtccg tgctgaccgt gctgcaccag gattggctga acggcaaaga gtacaagtgc    1140
aaggtgtcca acaaggccct gcctgccccc atcgaaaaga ccatctccaa ggccaagggc    1200
cagccccggg aaccccaggt gtacacactg cccccctagca gggacgagct gaccaagaac    1260
caggtgtccc tgacctgtct cgtgaaaggc ttctacccct ccgatatcgc cgtggaatgg    1320
gagtccaacg gccagcctga gaacaactat aagaccaccc cccctgtgct ggactccgac    1380
ggctcattct tcctgtacag caagctgaca gtggacaagt cccggtggca gcagggcaac    1440
gtgttctcct gctccgtgat gcacgaggcc ctgcacaacc actacaccca gaagtccctg    1500
tccctgagcc ccggc                                                    1515
```

<210> SEQ ID NO 30
<211> LENGTH: 505
<212> TYPE: PRT
<213> ORGANISM: Artificial Sequence
<220> FEATURE:
<223> OTHER INFORMATION: Synthetic sequence

<400> SEQUENCE: 30

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Leu Asp Tyr Tyr
            20                  25                  30
```

```
Ala Ile Gly Trp Phe Arg Gln Ala Pro Gly Lys Glu Arg Glu Ala Val
         35                  40                  45

Ser Cys Ile Ser Ser Ser Asp Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Thr Asp Arg Ala Cys Gly Ser Ser Trp Leu Gly Ala Glu Ser Trp
                100                 105                 110

Ala Gln Gly Thr Leu Val Thr Val Ser Ser Gly Gly Gly Gly Ser Gly
            115                 120                 125

Gly Gly Gly Ser Gly Gly Gly Ser Gln Val Gln Leu Val Glu Ser
        130                 135                 140

Gly Gly Gly Leu Val Gln Pro Gly Gly Ser Leu Arg Leu Ser Cys Ala
145                 150                 155                 160

Ala Ser Gly Gly Thr Leu Asp Tyr Tyr Ala Ile Gly Trp Phe Arg Gln
                165                 170                 175

Ala Pro Gly Lys Glu Arg Glu Ala Val Ser Cys Ile Ser Ser Ser Asp
            180                 185                 190

Gly Ser Thr Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
    210                 215                 220

Ala Glu Asp Thr Ala Val Tyr His Cys Ala Thr Asp Arg Ala Cys Gly
225                 230                 235                 240

Ser Ser Trp Leu Gly Ala Glu Ser Trp Ala Gln Gly Thr Leu Val Thr
                245                 250                 255

Val Ser Ser Gly Gly Gly Gly Ser Gly Gly Gly Gly Ser Gly Gly Gly
            260                 265                 270

Gly Ser Glu Pro Lys Ser Cys Asp Lys Thr His Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Ala Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445
```

```
Asn Tyr Lys Thr Thr Pro Pro Val Leu Asp Ser Asp Gly Ser Phe Phe
450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly
                500             505

<210> SEQ ID NO 31
<211> LENGTH: 2655
<212> TYPE: DNA
<213> ORGANISM: Artificial Sequence
<220> FEATURE:
<223> OTHER INFORMATION: Synthetic sequence

<400> SEQUENCE: 31
```

| | |
|---|---|
| gaagtgcagc tggttgagtc cggcggcggc ctggtgcagc ctggcggttc tctgcggctg | 60 |
| tcttgcgccg tgagcggaaa tatctacaac cggaacttca tgggctggtt tcggcaggct | 120 |
| ccaggcaaag gactggaagg cgtgtccgcc atctacaccg gcacctctcg gacctactac | 180 |
| gccgactctg tcaaaggcag attcaccatc tcccgcgaca cagcaaaaa caccgtgtac | 240 |
| ctgcagatga acagcctgag agctgaagat acagctgtgt actattgcgc cgccgatctg | 300 |
| agagacggct tctgggacac aggcgtgtgg aacacctggg ccagggcac acttgtgacc | 360 |
| gtgtcctctg agtctaagta cggccctccc tgtcctcctt gccctgctcc tgagttcgag | 420 |
| ggcggcccct ccgtgtttct cttcccaccc aagcctaagg acaccctgat gatctccaga | 480 |
| acccctgagg tgacctgcgt ggtggttgac gtgtctcagg aggatcccga agtgcagttt | 540 |
| aattggtacg tggacggcgt cgaagtgcac aatgctaaaa ccaagcctcg ggaggaacag | 600 |
| ttcaatagca cctacagagt ggtgagcgtt ctgacagtgc tgcaccagga ctggctgaac | 660 |
| ggcaaagagt acaagtgcaa ggtgtccaac aagggcctgc catcctccat cgagaagacc | 720 |
| atctccaagg ccaagggaca acctagagag cctcaggtgt acaccctgcc tccctgtcag | 780 |
| gaggagatga ccaagaacca ggtgtctctg tggtgcctgg tgaagggctt ctacccttcc | 840 |
| gacatcgccg tggaatggga agcaacggc caacctgaga caactacaa gaccacccct | 900 |
| cctgtgctgg actccgatgg atctttcttc ctgtactctc ggctgaccgt cgacaagtct | 960 |
| agatggcagg agggcaacgt gttcagctgc tccgtcatgc acgaggccct gcataaccac | 1020 |
| tacacccaga gtccctgtc cttatctctg ggctcaggtg gaggcggtag tggcggaggc | 1080 |
| ggttcaggcg gaggcggatc tatttgggag ctgaagaaag acgtgtacgt ggtcgagctg | 1140 |
| gactggtacc ctgatgcccc aggcgagatg gtcgtgctga cctgcgatac accagaggaa | 1200 |
| gatggtatca cctggacact ggatcagtcc tcagaggtgc tgggctctgg taaaacactg | 1260 |
| accattcagg tgaaggagtt cggtgacgct ggacagtaca cttgtcataa gggcggggag | 1320 |
| gtgctgtctc actccctgct gctgctgcat aagaaggagg atggaatctg tccactgac | 1380 |
| atcctgaaag accagaagga gccaaagaac aaaaccttcc tgcgatgcga ggctaagaac | 1440 |
| tacagcggcc gctttacatg ctggtggctg acaaccatca gcaccgatct gaccttagc | 1500 |
| gtgaagtcat ccaggggcag ttcagaccct cagggagtca catgtggcgc cgcaaccctg | 1560 |
| tcagcagagc gagtgcgggg agacaataag gaatacgagt acagcgtcga gtgtcaggag | 1620 |
| gattccgcat gtccagctgc agaagaatcc ctgcctatcg aagtcatggt ggacgctgtg | 1680 |
| cataaactga agtacgagaa ttacaccagc agctttttca tccgggacat catcaagccc | 1740 |

```
gatccaccta agaatctgca gctgaagcct ctgaaaaata gccgacaggt cgaagtgtca    1800
tgggaatacc cagacacctg gtcaacacca cactcctact tctccctgac cttctgtgtg    1860
caggtccagg gaaaaagcaa gcgggaaaag aaagatcggg tgttcaccga caagaccagt    1920
gctacagtga tttgccggaa gaatgccagc atttctgtca gagctcagga ccggtactat    1980
agctcttcct ggagcgagtg ggcttcagtg ccatgttctg gaggcggtgg atctggcgga    2040
ggtggaagcg gaggcggtgg atctagaaac ctgcccgtcg caaccccctga tccagggatg    2100 ttccccctgtc tgcatcacag ccagaatctg ctgagggctg tctccaacat gctgcagaag    2160
gctcgacaga ccctggagtt ctacccatgt accagcgaag atcgacca cgaggatatc    2220 acaaaggata aaccagcac agtggaagca tgcctgcctc tggaactgac caagaatgag    2280
agctgcctga atagcaggga gacctccttc atcaccaacg gctcatgcct ggcttcaagg    2340
aagaccagct tcatgatggc tctgtgtctg agctctatct atgaggacct gaagatgtac    2400
caggtggagt tcaagaccat gaacgccaag ctgctgatgg atccaaagag gcagatcttc    2460
ctggatcaga atatgctggc agtgatcgat gagctgatgc aggccctgaa ttttaacagt    2520
gagacagtgc ctcagaagag ctctctggaa gagccagact tttacaaaac taagatcaag    2580
ctgtgcattc tgctgcacgc tttccgcatc agagctgtca ctatcgatag agtgatgagc    2640
tatctgaatg cctca                                                    2655
```

<210> SEQ ID NO 32
<211> LENGTH: 885
<212> TYPE: PRT
<213> ORGANISM: Artificial Sequence
<220> FEATURE:
<223> OTHER INFORMATION: Synthetic sequence

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Ala Pro Glu Phe Glu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser Gln Glu Asp Pro
                165                 170                 175

Glu Val Gln Phe Asn Trp Tyr Val Asp Gly Val Glu Val His Asn Ala
            180                 185                 190
```

```
Lys Thr Lys Pro Arg Glu Glu Gln Phe Asn Ser Thr Tyr Arg Val Val
            195                 200                 205

Ser Val Leu Thr Val Leu His Gln Asp Trp Leu Asn Gly Lys Glu Tyr
210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Cys Gln Glu Glu Met Thr Lys Asn Gln Val Ser Leu Trp Cys
            260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Val Leu Asp
290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Ser
            340                 345                 350

Gly Gly Gly Gly Ser Gly Gly Gly Gly Ser Gly Gly Gly Gly Ser Ile
            355                 360                 365

Trp Glu Leu Lys Lys Asp Val Tyr Val Val Glu Leu Asp Trp Tyr Pro
            370                 375                 380

Asp Ala Pro Gly Glu Met Val Val Leu Thr Cys Asp Thr Pro Glu Glu
385                 390                 395                 400

Asp Gly Ile Thr Trp Thr Leu Asp Gln Ser Ser Glu Val Leu Gly Ser
                405                 410                 415

Gly Lys Thr Leu Thr Ile Gln Val Lys Glu Phe Gly Asp Ala Gly Gln
            420                 425                 430

Tyr Thr Cys His Lys Gly Gly Glu Val Leu Ser His Ser Leu Leu Leu
            435                 440                 445

Leu His Lys Lys Glu Asp Gly Ile Trp Ser Thr Asp Ile Leu Lys Asp
450                 455                 460

Gln Lys Glu Pro Lys Asn Lys Thr Phe Leu Arg Cys Glu Ala Lys Asn
465                 470                 475                 480

Tyr Ser Gly Arg Phe Thr Cys Trp Trp Leu Thr Thr Ile Ser Thr Asp
                485                 490                 495

Leu Thr Phe Ser Val Lys Ser Ser Arg Gly Ser Ser Asp Pro Gln Gly
            500                 505                 510

Val Thr Cys Gly Ala Ala Thr Leu Ser Ala Glu Arg Val Arg Gly Asp
            515                 520                 525

Asn Lys Glu Tyr Glu Tyr Ser Val Glu Cys Gln Glu Asp Ser Ala Cys
530                 535                 540

Pro Ala Ala Glu Glu Ser Leu Pro Ile Glu Val Met Val Asp Ala Val
545                 550                 555                 560

His Lys Leu Lys Tyr Glu Asn Tyr Thr Ser Ser Phe Phe Ile Arg Asp
                565                 570                 575

Ile Ile Lys Pro Asp Pro Pro Lys Asn Leu Gln Leu Lys Pro Leu Lys
            580                 585                 590

Asn Ser Arg Gln Val Glu Val Ser Trp Glu Tyr Pro Asp Thr Trp Ser
            595                 600                 605

Thr Pro His Ser Tyr Phe Ser Leu Thr Phe Cys Val Gln Val Gln Gly
```

| | | | |
|---|---|---|---|
| | 610 | 615 | 620 |

Lys Ser Lys Arg Glu Lys Asp Arg Val Phe Thr Asp Lys Thr Ser
625                     630                     635                     640

Ala Thr Val Ile Cys Arg Lys Asn Ala Ser Ile Ser Val Arg Ala Gln
                    645                     650                     655

Asp Arg Tyr Tyr Ser Ser Trp Ser Glu Trp Ala Ser Val Pro Cys
                660                     665                     670

Ser Gly Gly Gly Ser Gly Gly Gly Ser Gly Gly Gly Ser
            675                     680                     685

Arg Asn Leu Pro Val Ala Thr Pro Asp Pro Gly Met Phe Pro Cys Leu
690                     695                     700

His His Ser Gln Asn Leu Leu Arg Ala Val Ser Asn Met Leu Gln Lys
705                     710                     715                     720

Ala Arg Gln Thr Leu Glu Phe Tyr Pro Cys Thr Ser Glu Glu Ile Asp
                    725                     730                     735

His Glu Asp Ile Thr Lys Asp Lys Thr Ser Thr Val Glu Ala Cys Leu
                740                     745                     750

Pro Leu Glu Leu Thr Lys Asn Glu Ser Cys Leu Asn Ser Arg Glu Thr
                755                     760                     765

Ser Phe Ile Thr Asn Gly Ser Cys Leu Ala Ser Arg Lys Thr Ser Phe
770                     775                     780

Met Met Ala Leu Cys Leu Ser Ser Ile Tyr Glu Asp Leu Lys Met Tyr
785                     790                     795                     800

Gln Val Glu Phe Lys Thr Met Asn Ala Lys Leu Leu Met Asp Pro Lys
                    805                     810                     815

Arg Gln Ile Phe Leu Asp Gln Asn Met Leu Ala Val Ile Asp Glu Leu
                820                     825                     830

Met Gln Ala Leu Asn Phe Asn Ser Glu Thr Val Pro Gln Lys Ser Ser
                835                     840                     845

Leu Glu Glu Pro Asp Phe Tyr Lys Thr Lys Ile Lys Leu Cys Ile Leu
850                     855                     860

Leu His Ala Phe Arg Ile Arg Ala Val Thr Ile Asp Arg Val Met Ser
865                     870                     875                     880

Tyr Leu Asn Ala Ser
            885

<210> SEQ ID NO 33
<211> LENGTH: 1500
<212> TYPE: DNA
<213> ORGANISM: Artificial Sequence
<220> FEATURE:
<223> OTHER INFORMATION: Synthetic sequence

<400> SEQUENCE: 33

```
gaagtgcagc tggttgagtc cggcggcggc ctggtgcagc ctggcggttc tctgcggctg      60
tcttgcgccg tgagcggaaa tatctacaac cggaacttca tgggctggtt tcggcaggct     120
ccaggcaaag gactggaagg cgtgtccgcc atctacaccg gcacctctcg gacctactac     180
gccgactctg tcaaaggcag attcaccatc tcccgcgaca cagcaaaaa caccgtgtac     240
ctgcagatga cagcctgag agctgaagat acagctgtgt actattgcgc cgccgatctg     300
agagacggct ctgggacac aggcgtgtgg aacacctggg gccagggcac acttgtgacc     360
gtgtcctctg agtctaagta cggccctccc tgtcctcctt gccctgctcc tgagttcgag     420
ggcggcccct ccgtgtttct cttcccaccc aagcctaagg acaccctgat gatctccaga     480
```

```
accccctgagg tgacctgcgt ggtggttgac gtgtctcagg aggatcccga agtgcagttt      540
aattggtacg tggacggcgt cgaagtgcac aatgctaaaa ccaagcctcg ggaggaacag      600
ttcaatagca cctacagagt ggtgagcgtt ctgacagtgc tgcaccagga ctggctgaac      660
ggcaaagagt acaagtgcaa ggtgtccaac aagggcctgc catcctccat cgagaagacc      720
atctccaagg ccaagggaca acctagagag cctcaggtgt gcaccctgcc tccctctcag      780
gaggagatga ccaagaacca ggtgtctctg tcctgcgctg tgaagggctt ctacccttcc      840
gacatcgccg tggaatggga agcaacggc caacctgaga caactacaa gaccaccct       900 cctgtgctgg actccgatgg atctttcttc ctggtttctc ggctgaccgt cgacaagtct      960
agatggcagg agggcaacgt gttcagctgc tccgtcatgc acgaggccct gcataaccac     1020
tacacccaga agtccctgtc cttatctctg ggctcaggtg gaggcggtag tggcggaggc     1080
ggttcaggcg gaggcggatc tgcacctact tcaagttcta caagaaaaac acagctacaa     1140
ctggagcatt tactgctgga tttacagatg attttgaatg gaattaataa ttacaagaat     1200
cccaaactca ccaggatgct cacatttaag ttttacatgc ccaagaaggc cacagaactg     1260
aaacatcttc agtgtctaga agaagaactc aaacctctgg aggaagtgct aaatttagct     1320
caaagcaaaa actttcactt aagacccagg gacttaatca gcaatatcaa cgtaatagtt     1380
ctggaactaa agggatctga acaacattc atgtgtgaat atgctgatga cagcaacc       1440 attgtagaat ttctgaacag atggattacc ttttgtcaaa gcatcatctc aacactgact     1500
```

<210> SEQ ID NO 34
<211> LENGTH: 500
<212> TYPE: PRT
<213> ORGANISM: Artificial Sequence
<220> FEATURE:
<223> OTHER INFORMATION: Synthetic sequence

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Glu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190
```

```
Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
        210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Cys Thr Leu
                245                 250                 255

Pro Pro Ser Gln Glu Glu Met Thr Lys Asn Gln Val Ser Leu Ser Cys
            260                 265                 270

Ala Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
        290                 295                 300

Ser Asp Gly Ser Phe Phe Leu Val Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Ser
            340                 345                 350

Gly Gly Gly Gly Ser Gly Gly Gly Gly Ser Gly Gly Gly Gly Ser Ala
        355                 360                 365

Pro Thr Ser Ser Ser Thr Lys Lys Thr Gln Leu Gln Leu Glu His Leu
        370                 375                 380

Leu Leu Asp Leu Gln Met Ile Leu Asn Gly Ile Asn Asn Tyr Lys Asn
385                 390                 395                 400

Pro Lys Leu Thr Arg Met Leu Thr Phe Lys Phe Tyr Met Pro Lys Lys
                405                 410                 415

Ala Thr Glu Leu Lys His Leu Gln Cys Leu Glu Glu Glu Leu Lys Pro
            420                 425                 430

Leu Glu Glu Val Leu Asn Leu Ala Gln Ser Lys Asn Phe His Leu Arg
        435                 440                 445

Pro Arg Asp Leu Ile Ser Asn Ile Asn Val Ile Val Leu Glu Leu Lys
        450                 455                 460

Gly Ser Glu Thr Thr Phe Met Cys Glu Tyr Ala Asp Glu Thr Ala Thr
465                 470                 475                 480

Ile Val Glu Phe Leu Asn Arg Trp Ile Thr Phe Cys Gln Ser Ile Ile
                485                 490                 495

Ser Thr Leu Thr
            500

<210> SEQ ID NO 35
<211> LENGTH: 1053
<212> TYPE: DNA
<213> ORGANISM: Artificial Sequence
<220> FEATURE:
<223> OTHER INFORMATION: Synthetic sequence

<400> SEQUENCE: 35
gaagtgcagc tggttgagtc cggcggcggc ctggtgcagc ctggcggttc tctgcggctg      60
tcttgcgccg tgagcggaaa tatctacaac cggaacttca tgggctggtt tcggcaggct    120
ccaggcaaag gactggaagg cgtgtccgcc atctacaccg gcacctctcg gacctactac    180
gccgactctg tcaaaggcag attcaccatc tcccgcgaca cagcaaaaaa caccgtgtac    240
```

```
ctgcagatga acagcctgag agctgaagat acagctgtgt actattgcgc cgccgatctg    300
agagacggct tctgggacac aggcgtgtgg aacacctggg gccagggcac acttgtgacc    360
gtgtcctctg agtctaagta cggccctccc tgtcctcctt gccctgctcc tgagttcgag    420
ggcggcccct ccgtgtttct cttcccaccc aagcctaagg acaccctgat gatctccaga    480
accctgaggt tgacctgcgt ggtggttgac gtgtctcagg aggatcccga agtgcagttt    540
aattggtacg tggacggcgt cgaagtgcac aatgctaaaa ccaagcctcg ggaggaacag    600
ttcaatagca cctacagagt ggtgagcgtt ctgacagtgc tgcaccagga ctggctgaac    660
ggcaaagagt acaagtgcaa ggtgtccaac aagggcctgc catcctccat cgagaagacc    720
atctccaagg ccaagggaca acctagagag cctcaggtgt gcaccctgcc tcctctcag    780 gaggagatga ccaagaacca ggtgtctctg tcctgcgctg tgaagggctt ctacccttcc    840
gacatcgccg tggaatggga aagcaacggc caacctgaga caactacaa gaccaccct    900 cctgtgctgg actccgatgg atctttcttc ctggtttctc ggctgaccgt cgacaagtct    960
agatggcagg agggcaacgt gttcagctgc tccgtcatgc acgaggccct gcataaccac    1020
tacacccaga agtccctgtc cttatctctg ggc                                1053
```

<210> SEQ ID NO 36
<211> LENGTH: 351
<212> TYPE: PRT
<213> ORGANISM: Artificial Sequence
<220> FEATURE:
<223> OTHER INFORMATION: Synthetic sequence

<400> SEQUENCE: 36

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Glu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
    210                 215                 220
```

```
Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Cys Thr Leu
                245                 250                 255

Pro Pro Ser Gln Glu Glu Met Thr Lys Asn Gln Val Ser Leu Ser Cys
            260                 265                 270

Ala Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
            290                 295                 300

Ser Asp Gly Ser Phe Phe Leu Val Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly
            340                 345                 350

<210> SEQ ID NO 37
<211> LENGTH: 1500
<212> TYPE: DNA
<213> ORGANISM: Artificial Sequence
<220> FEATURE:
<223> OTHER INFORMATION: Synthetic sequence

<400> SEQUENCE: 37
gaagtgcagc tggttgagtc cggcggcggc ctggtgcagc ctggcggttc tctgcggctg      60
tcttgcgccg tgagcggaaa tatctacaac cggaacttca tgggctggtt tcggcaggct     120
ccaggcaaag gactggaagg cgtgtccgcc atctacaccg gcacctctcg gacctactac     180
gccgactctg tcaaaggcag attcaccatc tcccgcgaca cagcaaaaa caccgtgtac      240 ctgcagatga acagcctgag agctgaagat acagctgtgt actattgcgc cgccgatctg     300
agagacggct tctgggacac aggcgtgtgg aacacctggg gccagggcac acttgtgacc     360
gtgtcctctg agtctaagta cggccctccc tgtcctcctt gccctgctcc tgagttcgag     420
ggcggcccct ccgtgtttct cttcccaccc aagcctaagg acaccctgat gatctccaga     480 accccctgagg tgacctgcgt ggtggttgac gtgtctcagg aggatcccga agtgcagttt     540
aattggtacg tggacggcgt cgaagtgcac aatgctaaaa ccaagcctcg ggaggaacag     600
ttcaatagca cctacagagt ggtgagcgtt ctgacagtgc tgcaccagga ctggctgaac     660
ggcaaagagt acaagtgcaa ggtgtccaac aagggcctgc catcctccat cgagaagacc     720
atctccaagg ccaagggaca acctagagag cctcaggtgt acaccctgcc tccctgtcag     780
gaggagatga ccaagaacca ggtgtctctg tggtgcctgg tgaagggctt ctaccctc     840 gacatcgccg tggaatggga aagcaacggc caacctgaga caactacaa gaccaccct      900 cctgtgctgg actccgatgg atctttcttc ctgtactctc ggctgaccgt cgacaagtct     960
agatggcagg agggcaacgt gttcagctgc tccgtcatgc acgaggccct gcataaccac    1020
tacacccaga gtccctgtc cttatctctg gctcaggtg gaggcggtag tggcggaggc      1080
ggttcaggcg gaggcggatc tgcacctact tcaagttcta caagaaaac acagctacaa    1140 ctggagcatt tactgctgga tttacagatg attttgaatg gaattaataa ttacaagaat    1200
cccaaactca ccaggatgct cacatttaag ttttacatgc caagaaggc cacagaactg     1260 aaacatcttc agtgtctaga agaagaactc aaacctctgg aggaagtgct aaatttagct    1320
```

```
caaagcaaaa actttcactt aagacccagg gacttaatca gcaatatcaa cgtaatagtt      1380
ctggaactaa agggatctga aacaacattc atgtgtgaat atgctgatga gacagcaacc      1440
attgtagaat ttctgaacag atggattacc ttttgtcaaa gcatcatctc aacactgact      1500
```

<210> SEQ ID NO 38
<211> LENGTH: 500
<212> TYPE: PRT
<213> ORGANISM: Artificial Sequence
<220> FEATURE:
<223> OTHER INFORMATION: Synthetic sequence

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Glu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Cys Gln Glu Glu Met Thr Lys Asn Gln Val Ser Leu Trp Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335
```

```
Leu His Asn His Tyr Thr Gln Lys Ser Leu Ser Leu Ser Leu Gly Ser
                340                 345                 350

Gly Gly Gly Gly Ser Gly Gly Gly Ser Gly Gly Gly Ser Ala
            355                 360                 365

Pro Thr Ser Ser Ser Thr Lys Lys Thr Gln Leu Gln Leu Glu His Leu
            370                 375                 380

Leu Leu Asp Leu Gln Met Ile Leu Asn Gly Ile Asn Asn Tyr Lys Asn
385                 390                 395                 400

Pro Lys Leu Thr Arg Met Leu Thr Phe Lys Phe Tyr Met Pro Lys Lys
                405                 410                 415

Ala Thr Glu Leu Lys His Leu Gln Cys Leu Glu Glu Glu Leu Lys Pro
            420                 425                 430

Leu Glu Glu Val Leu Asn Leu Ala Gln Ser Lys Asn Phe His Leu Arg
            435                 440                 445

Pro Arg Asp Leu Ile Ser Asn Ile Asn Val Ile Val Leu Glu Leu Lys
        450                 455                 460

Gly Ser Glu Thr Thr Phe Met Cys Glu Tyr Ala Asp Glu Thr Ala Thr
465                 470                 475                 480

Ile Val Glu Phe Leu Asn Arg Trp Ile Thr Phe Cys Gln Ser Ile Ile
                485                 490                 495

Ser Thr Leu Thr
            500

<210> SEQ ID NO 39
<211> LENGTH: 2658
<212> TYPE: DNA
<213> ORGANISM: Artificial Sequence
<220> FEATURE:
<223> OTHER INFORMATION: Synthetic sequence

<400> SEQUENCE: 39
gaggtgcagc tggtggaatc cggcggaggc ctggtccagc ctggcggctc tctgcggctg      60
tcctgcgccg cttctggcag aaccttcgtg acctacggca tgggctggtt ccggcaggct     120
cctggcaagg gcagagagtt cgtgtccgcc atctcctggt ccggctccat gacctcttac     180
ggcgactctg tgaagggcag attcaccatc agccgggata cgccaagaa cacactgtac     240 ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagtctaa gtacggcccc cctgtcctc cttgccctgc tcctgagttc     420
gagggcggcc cctccgtgtt tctcttccca cccaagccta aggacaccct gatgatctcc     480 agaaccctg aggtgacctg cgtggtggtt gacgtgtctc aggaggatcc cgaagtgcag     540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
accatctcca aggccaaggg acaacctaga gagcctcagg tgtacaccct gcctccctgt     780
caggaggaga tgaccaagaa ccaggtgtct ctgtggtgcc tggtgaaggg cttctaccct     840
tccgacatcg ccgtggaatg ggaaagcaac ggccaacctg agaacaacta caagaccacc     900
cctcctgtgc tggactccga tggatctttc ttcctgtact ctcggctgac cgtcgacaag     960
tctagatggc aggagggcaa cgtgttcagc tgctccgtca tgcacgaggc cctgcataac    1020
cactacaccc agaagtccct gtccttatct ctgggctcag gtgaggcgg tagtggcgga    1080
```

```
ggcggttcag gcggaggcgg atctatttgg gagctgaaga aagacgtgta cgtggtcgag      1140
ctggactggt accctgatgc cccaggcgag atggtcgtgc tgacctgcga tacaccagag      1200
gaagatggta tcacctggac actggatcag tcctcagagg tgctgggctc tggtaaaaca      1260
ctgaccattc aggtgaagga gttcggtgac gctggacagt acacttgtca taagggcggg      1320
gaggtgctgt ctcactccct gctgctgctg cataagaagg aggatggaat ctggtccact      1380
gacatcctga agaccagaa ggagccaaag aacaaaacct tcctgcgatg cgaggctaag       1440
aactacagcg ccgctttac atgctggtgg ctgacaacca tcagcaccga tctgaccttt       1500
agcgtgaagt catccagggg cagttcagac cctcagggag tcatatgtgg cgccgcaacc      1560
ctgtcagcag agcgagtgcg gggagacaat aaggaatacg agtacagcgt cgagtgtcag      1620
gaggattccg catgtccagc tgcagaagaa tccctgccta tcgaagtcat ggtgacgct       1680 gtgcataaac tgaagtacga gaattacacc agcagctttt tcatccggga catcatcaag      1740
cccgatccac ctaagaatct gcagctgaag cctctgaaaa atagccgaca ggtcgaagtg      1800
tcatgggaat acccagacac ctggtcaaca ccacactcct acttctccct gaccttctgt      1860
gtgcaggtcc agggaaaaag caagcgggaa aagaaagatc gggtgttcac cgacaagacc      1920
agtgctacag tgatttgccg gaagaatgcc agcatttctg tcagagctca ggaccggtac      1980
tatagctctt cctggagcga gtgggcttca gtgccatgtt ctggaggcgg tggatctggc      2040
ggaggtggaa gcggaggcgg tggatctaga acctgcccg tcgcaacccc tgatccaggg      2100
atgttcccct gtctgcatca cagccagaat ctgctgaggg ctgtctccaa catgctgcag      2160
aaggctcgac agaccctgga gttctaccca tgtaccagcg aagagatcga ccacgaggat      2220
atcacaaagg ataaaaccag cacagtggaa gcatgcctgc ctctggaact gaccaagaat      2280
gagagctgcc tgaatagcag ggagacctcc ttcatcacca acggctcatg cctggcttca      2340
aggaagacca gcttcatgat ggctctgtgt ctgagctcta tctatgagga cctgaagatg      2400
taccaggtgg agttcaagac catgaacgcc aagctgctga tggatccaaa gaggcagatc      2460
ttcctggatc agaatatgct ggcagtgatc gatgagctga tgcaggccct gaatttttaac     2520 agtgagacag tgcctcagaa gagctctctg aagagccag acttttacaa aactaagatc       2580
aagctgtgca ttctgctgca cgctttccgc atcagagctg tcactatcga tagagtgatg      2640
agctatctga atgcctca                                                    2658
```

<210> SEQ ID NO 40
<211> LENGTH: 886
<212> TYPE: PRT
<213> ORGANISM: Artificial Sequence
<220> FEATURE:
<223> OTHER INFORMATION: Synthetic sequence

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Met Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Pro Glu Asp Thr Ala Val Tyr Tyr Cys
                 85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
            115                 120                 125

Gly Pro Pro Cys Pro Pro Cys Pro Ala Pro Glu Phe Glu Gly Gly Pro
            130                 135                 140

Ser Val Phe Leu Phe Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
                180                 185                 190

Ala Lys Thr Lys Pro Arg Glu Glu Gln Phe Asn Ser Thr Tyr Arg Val
            195                 200                 205

Val Ser Val Leu Thr Val Leu His Gln Asp Trp Leu Asn Gly Lys Glu
            210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Cys Gln Glu Glu Met Thr Lys Asn Gln Val Ser Leu Trp
                260                 265                 270

Cys Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
            290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
                340                 345                 350

Ser Gly Gly Gly Gly Ser Gly Gly Gly Gly Ser Gly Gly Gly Gly Ser
            355                 360                 365

Ile Trp Glu Leu Lys Lys Asp Val Tyr Val Val Glu Leu Asp Trp Tyr
            370                 375                 380

Pro Asp Ala Pro Gly Glu Met Val Val Leu Thr Cys Asp Thr Pro Glu
385                 390                 395                 400

Glu Asp Gly Ile Thr Trp Thr Leu Asp Gln Ser Ser Glu Val Leu Gly
                405                 410                 415

Ser Gly Lys Thr Leu Thr Ile Gln Val Lys Glu Phe Gly Asp Ala Gly
            420                 425                 430

Gln Tyr Thr Cys His Lys Gly Gly Glu Val Leu Ser His Ser Leu Leu
            435                 440                 445

Leu Leu His Lys Lys Glu Asp Gly Ile Trp Ser Thr Asp Ile Leu Lys
450                 455                 460

Asp Gln Lys Glu Pro Lys Asn Lys Thr Phe Leu Arg Cys Glu Ala Lys
465                 470                 475                 480

Asn Tyr Ser Gly Arg Phe Thr Cys Trp Trp Leu Thr Thr Ile Ser Thr
                485                 490                 495

Asp Leu Thr Phe Ser Val Lys Ser Ser Arg Gly Ser Ser Asp Pro Gln
```

-continued

```
                500             505             510
Gly Val Thr Cys Gly Ala Ala Thr Leu Ser Ala Glu Arg Val Arg Gly
            515                 520                 525

Asp Asn Lys Glu Tyr Glu Tyr Ser Val Glu Cys Gln Glu Asp Ser Ala
        530                 535                 540

Cys Pro Ala Ala Glu Glu Ser Leu Pro Ile Glu Val Met Val Asp Ala
545                 550                 555                 560

Val His Lys Leu Lys Tyr Glu Asn Tyr Thr Ser Ser Phe Phe Ile Arg
                565                 570                 575

Asp Ile Ile Lys Pro Asp Pro Pro Lys Asn Leu Gln Leu Lys Pro Leu
            580                 585                 590

Lys Asn Ser Arg Gln Val Glu Val Ser Trp Glu Tyr Pro Asp Thr Trp
        595                 600                 605

Ser Thr Pro His Ser Tyr Phe Ser Leu Thr Phe Cys Val Gln Val Gln
    610                 615                 620

Gly Lys Ser Lys Arg Glu Lys Lys Asp Arg Val Phe Thr Asp Lys Thr
625                 630                 635                 640

Ser Ala Thr Val Ile Cys Arg Lys Asn Ala Ser Ile Ser Val Arg Ala
                645                 650                 655

Gln Asp Arg Tyr Tyr Ser Ser Ser Trp Ser Glu Trp Ala Ser Val Pro
            660                 665                 670

Cys Ser Gly Gly Gly Ser Gly Gly Gly Ser Gly Gly Gly Gly
        675                 680                 685

Ser Arg Asn Leu Pro Val Ala Thr Pro Asp Pro Gly Met Phe Pro Cys
    690                 695                 700

Leu His His Ser Gln Asn Leu Leu Arg Ala Val Ser Asn Met Leu Gln
705                 710                 715                 720

Lys Ala Arg Gln Thr Leu Glu Phe Tyr Pro Cys Thr Ser Glu Glu Ile
                725                 730                 735

Asp His Glu Asp Ile Thr Lys Asp Lys Thr Ser Thr Val Glu Ala Cys
            740                 745                 750

Leu Pro Leu Glu Leu Thr Lys Asn Glu Ser Cys Leu Asn Ser Arg Glu
        755                 760                 765

Thr Ser Phe Ile Thr Asn Gly Ser Cys Leu Ala Ser Arg Lys Thr Ser
    770                 775                 780

Phe Met Met Ala Leu Cys Leu Ser Ser Ile Tyr Glu Asp Leu Lys Met
785                 790                 795                 800

Tyr Gln Val Glu Phe Lys Thr Met Asn Ala Lys Leu Leu Met Asp Pro
                805                 810                 815

Lys Arg Gln Ile Phe Leu Asp Gln Asn Met Leu Ala Val Ile Asp Glu
            820                 825                 830

Leu Met Gln Ala Leu Asn Phe Asn Ser Glu Thr Val Pro Gln Lys Ser
        835                 840                 845

Ser Leu Glu Glu Pro Asp Phe Tyr Lys Thr Lys Ile Lys Leu Cys Ile
    850                 855                 860

Leu Leu His Ala Phe Arg Ile Arg Ala Val Thr Ile Asp Arg Val Met
865                 870                 875                 880

Ser Tyr Leu Asn Ala Ser
                885

<210> SEQ ID NO 41
<211> LENGTH: 1503
<212> TYPE: DNA
<213> ORGANISM: Artificial Sequence
```

<220> FEATURE:
<223> OTHER INFORMATION: Synthetic sequence

<400> SEQUENCE: 41

```
gaggtgcagc tggtggaatc cggcggaggc ctggtccagc ctggcggctc tctgcggctg      60
tcctgcgccg cttctggcag aaccttcgtg acctacggca tgggctggtt ccggcaggct     120
cctggcaagg gcagagagtt cgtgtccgcc atctcctggt ccggctccat gacctcttac     180
ggcgactctg tgaagggcag attcaccatc agccgggata cgccaagaa cacactgtac      240
ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagtctaa gtacggccct ccctgtcctc cttgccctgc tcctgagttc     420
gagggcggcc cctccgtgtt tctcttccca cccaagccta aggacaccct gatgatctcc     480
agaacccctg aggtgacctg cgtggtggtt gacgtgtctc aggaggatcc cgaagtgcag     540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
accatctcca aggccaaggg acaacctaga gagcctcagg tgtgcaccct gcctccctct     780
caggaggaga tgaccaagaa ccaggtgtct cgtcctgcg ctgtgaaggg cttctaccct     840
tccgacatcg ccgtggaatg ggaaagcaac ggccaacctg agaacaacta caagaccacc     900
cctcctgtgc tggactccga tggatctttc ttcctggttt ctcggctgac cgtcgacaag     960
tctagatggc aggagggcaa cgtgttcagc tgctccgtca tgcacgaggc cctgcataac    1020
cactacaccc agaagtccct gtccttatct ctgggctcag gtggaggcgg tagtggcgga    1080
ggcggttcag gcggaggcgg atctgcacct acttcaagtt ctacaaagaa aacacagcta    1140
caactggagc atttactgct ggatttacag atgattttga atggaattaa taattacaag    1200
aatcccaaac tcaccaggat gctcacattt aagttttaca tgcccaagaa ggccacagaa    1260
ctgaaacatc ttcagtgtct agaagaagaa ctcaaacctc tggaggaagt gctaaattta    1320
gctcaaagca aaaactttca cttaagaccc agggacttaa tcagcaatat caacgtaata    1380
gttctggaac taagggatc tgaaacaaca ttcatgtgtg aatatgctga tgagacagca    1440
accattgtag aatttctgaa cagatggatt acctttgtc aaagcatcat ctcaacactg    1500
act                                                                  1503
```

<210> SEQ ID NO 42
<211> LENGTH: 501
<212> TYPE: PRT
<213> ORGANISM: Artificial Sequence
<220> FEATURE:
<223> OTHER INFORMATION: Synthetic sequence

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Met Thr Ser Tyr Gly Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Ala Leu Gly Ala Val Val Tyr Thr Thr Arg Glu Pro Tyr Thr
                100                 105                 110

Tyr Trp Gly Gln Gly Thr Leu Val Thr Val Ser Ser Glu Ser Lys Tyr
                115                 120                 125

Gly Pro Pro Cys Pro Pro Cys Pro Ala Pro Glu Phe Glu Gly Gly Pro
            130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
                180                 185                 190

Ala Lys Thr Lys Pro Arg Glu Glu Gln Phe Asn Ser Thr Tyr Arg Val
                195                 200                 205

Val Ser Val Leu Thr Val Leu His Gln Asp Trp Leu Asn Gly Lys Glu
210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Cys Thr
                245                 250                 255

Leu Pro Pro Ser Gln Glu Glu Met Thr Lys Asn Gln Val Ser Leu Ser
                260                 265                 270

Cys Ala Val Lys Gly Phe Tyr Pro Ser Asp Ile Ala Val Glu Trp Glu
                275                 280                 285

Ser Asn Gly Gln Pro Glu Asn Asn Tyr Lys Thr Thr Pro Pro Val Leu
                290                 295                 300

Asp Ser Asp Gly Ser Phe Phe Leu Val Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
                340                 345                 350

Ser Gly Gly Gly Gly Ser Gly Gly Gly Ser Gly Gly Gly Gly Gly Ser
                355                 360                 365

Ala Pro Thr Ser Ser Ser Thr Lys Lys Thr Gln Leu Gln Leu Glu His
                370                 375                 380

Leu Leu Leu Asp Leu Gln Met Ile Leu Asn Gly Ile Asn Asn Tyr Lys
385                 390                 395                 400

Asn Pro Lys Leu Thr Arg Met Leu Thr Phe Lys Phe Tyr Met Pro Lys
                405                 410                 415

Lys Ala Thr Glu Leu Lys His Leu Gln Cys Leu Glu Glu Glu Leu Lys
                420                 425                 430

Pro Leu Glu Glu Val Leu Asn Leu Ala Gln Ser Lys Asn Phe His Leu
                435                 440                 445

Arg Pro Arg Asp Leu Ile Ser Asn Ile Asn Val Ile Val Leu Glu Leu
                450                 455                 460

Lys Gly Ser Glu Thr Thr Phe Met Cys Glu Tyr Ala Asp Glu Thr Ala
465                 470                 475                 480

Thr Ile Val Glu Phe Leu Asn Arg Trp Ile Thr Phe Cys Gln Ser Ile
```

Ile Ser Thr Leu Thr
            500

<210> SEQ ID NO 43
<211> LENGTH: 1056
<212> TYPE: DNA
<213> ORGANISM: Artificial Sequence
<220> FEATURE:
<223> OTHER INFORMATION: Synthetic sequence

<400> SEQUENCE: 43

```
gaggtgcagc tggtggaatc cggcggaggc ctggtccagc ctggcggctc tctgcggctg      60
tcctgcgccg cttctggcag aaccttcgtg acctacggca tgggctggtt ccggcaggct     120
cctggcaagg gcagagagtt cgtgtccgcc atctcctggt ccggctccat gacctcttac     180
ggcgactctg tgaagggcag attcaccatc agccgggata cgccaagaa cacactgtac      240
ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagtctaa gtacggcccc cctgtcctc cttgccctgc tcctgagttc      420
gagggcggcc cctccgtgtt tctcttccca cccaagccta aggacaccct gatgatctcc     480
agaaccctg aggtgacctg cgtggtggtt gacgtgtctc aggaggatcc cgaagtgcag      540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
accatctcca aggccaaggg acaacctaga gagcctcagg tgtgcaccct gcctcccctct    780
caggaggaga tgaccaagaa ccaggtgtct ctgtcctgcg ctgtgaaggg cttctaccct     840
tccgacatcg ccgtggaatg ggaaagcaac ggccaacctg agaacaacta caagaccacc    900
cctcctgtgc tggactccga tggatctttc ttcctggttt tccggctgac cgtcgacaag    960
tctagatggc aggagggcaa cgtgttcagc tgctccgtca tgcacgaggc cctgcataac    1020
cactacaccc agaagtccct gtccttatct ctgggc                             1056
```

<210> SEQ ID NO 44
<211> LENGTH: 352
<212> TYPE: PRT
<213> ORGANISM: Artificial Sequence
<220> FEATURE:
<223> OTHER INFORMATION: Synthetic sequence

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Met Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Cys Thr
                245                 250                 255

Leu Pro Pro Ser Gln Glu Glu Met Thr Lys Asn Gln Val Ser Leu Ser
            260                 265                 270

Cys Ala Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Val Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

<210> SEQ ID NO 45
<211> LENGTH: 1503
<212> TYPE: DNA
<213> ORGANISM: Artificial Sequence
<220> FEATURE:
<223> OTHER INFORMATION: Synthetic sequence

<400> SEQUENCE: 45
gaggtgcagc tggtggaatc cggcggaggc ctggtccagc tggcggctc tctgcggctg      60 tcctgcgccg cttctggcag aaccttcgtg acctacggca tgggctggtt ccggcaggct     120
cctggcaagg gcagagagtt cgtgtccgcc atctcctggt ccggctccat gacctcttac     180
ggcgactctg tgaagggcag attcaccatc agccgggata cgccaagaa cacactgtac     240 ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagtctaa gtacggcccc cctgtcctc cttgccctgc tcctgagttc     420
gagggcggcc cctccgtgtt tctcttccca cccaagccta aggacaccct gatgatctcc     480 agaaccctg aggtgacctg cgtggtggtt gacgtgtctc aggaggatcc cgaagtgcag     540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660

```
aacggcaaag agtacaagtg caaggtgtcc aacaagggcc tgccatcctc catcgagaag    720
accatctcca aggccaaggg acaacctaga gagcctcagg tgtacaccct gcctccctgt    780
caggaggaga tgaccaagaa ccaggtgtct ctgtggtgcc tggtgaaggg cttctaccct    840
tccgacatcg ccgtggaatg ggaaagcaac ggccaacctg agaacaacta caagaccacc    900
cctcctgtgc tggactccga tggatctttc ttcctgtact ctcggctgac cgtcgacaag    960
tctagatggc aggagggcaa cgtgttcagc tgctccgtca tgcacgaggc cctgcataac    1020
cactacaccc agaagtccct gtccttatct ctgggctcag gtggaggcgg tagtggcgga    1080
ggcggttcag gcggaggcgg atctgcacct acttcaagtt ctacaaagaa acacagcta    1140 caactggagc atttactgct ggatttacag atgatttga atggaattaa taattacaag    1200
aatcccaaac tcaccaggat gctcacattt aagttttaca tgcccaagaa ggccacagaa    1260
ctgaaacatc ttcagtgtct agaagaagaa ctcaaacctc tggaggaagt gctaaattta    1320
gctcaaagca aaactttca cttaagaccc agggacttaa tcagcaatat caacgtaata    1380
gttctggaac taagggatc tgaaacaaca ttcatgtgtg aatatgctga tgagacagca    1440
accattgtag aatttctgaa cagatggatt acctttttgtc aaagcatcat ctcaacactg    1500
act                                                                 1503

<210> SEQ ID NO 46
<211> LENGTH: 501
<212> TYPE: PRT
<213> ORGANISM: Artificial Sequence
<220> FEATURE:
<223> OTHER INFORMATION: Synthetic sequence

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Met Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205
```

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Cys Gln Glu Glu Met Thr Lys Asn Gln Val Ser Leu Trp
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Ser Gly Gly Gly Ser Gly Gly Gly Ser Gly Gly Gly Ser
        355                 360                 365

Ala Pro Thr Ser Ser Thr Lys Lys Thr Gln Leu Gln Leu Glu His
    370                 375                 380

Leu Leu Leu Asp Leu Gln Met Ile Leu Asn Gly Ile Asn Asn Tyr Lys
385                 390                 395                 400

Asn Pro Lys Leu Thr Arg Met Leu Thr Phe Lys Phe Tyr Met Pro Lys
                405                 410                 415

Lys Ala Thr Glu Leu Lys His Leu Gln Cys Leu Glu Glu Glu Leu Lys
            420                 425                 430

Pro Leu Glu Glu Val Leu Asn Leu Ala Gln Ser Lys Asn Phe His Leu
        435                 440                 445

Arg Pro Arg Asp Leu Ile Ser Asn Ile Asn Val Ile Val Leu Glu Leu
    450                 455                 460

Lys Gly Ser Glu Thr Thr Phe Met Cys Glu Tyr Ala Asp Glu Thr Ala
465                 470                 475                 480

Thr Ile Val Glu Phe Leu Asn Arg Trp Ile Thr Phe Cys Gln Ser Ile
                485                 490                 495

Ile Ser Thr Leu Thr
            500

<210> SEQ ID NO 47
<211> LENGTH: 2658
<212> TYPE: DNA
<213> ORGANISM: Artificial Sequence
<220> FEATURE:
<223> OTHER INFORMATION: Synthetic sequence

<400> SEQUENCE: 47
gaggtgcagc tggtggaatc cggcggaggc ctggtccagc ctggcggctc tctgcggctg    60
tcctgcgccg cttctggcag aaccttcgtg acctacggca tgggctggtt ccggcaggct   120
cctggcaagg gcagagagtt cgtgtccgcc atctcctggt ccggctccag cacctcttac   180
ggcgactctg tgaagggcag attcaccatc agccgggata cgccaagaa cacactgtac   240 ctgcagatga actccctgcg gcctgaggac accgccgtgt actactgcgc cgctgccctg   300
ggcgctgtcg tgtacaccac cagagaaccc tatacctact ggggacaggg caccctggtg   360

```
accgtgtcct ctgagtctaa gtacggccct ccctgtcctc cttgccctgc tcctgagttc    420
gagggcggcc cctccgtgtt tctcttccca cccaagccta aggacaccct gatgatctcc    480
agaacccctg aggtgacctg cgtggtggtt gacgtgtctc aggaggatcc cgaagtgcag    540
tttaattggt acgtggacgg cgtcgaagtg cacaatgcta aaaccaagcc tcgggaggaa    600
cagttcaata gcacctacag agtggtgagc gttctgacag tgctgcacca ggactggctg    660
aacggcaaag agtacaagtg caaggtgtcc aacaagggcc tgccatcctc catcgagaag    720
accatctcca aggccaaggg acaacctaga gagcctcagg tgtacaccct gcctccctgt    780
caggaggaga tgaccaagaa ccaggtgtct ctgtggtgcc tggtgaaggg cttctaccct    840
tccgacatcg ccgtggaatg gaaagcaac ggccaacctg agaacaacta caagaccacc    900
cctcctgtgc tggactccga tggatctttc ttcctgtact ctcggctgac cgtcgacaag    960
tctagatggc aggagggcaa cgtgttcagc tgctccgtca tgcacgaggc cctgcataac    1020
cactacaccc cagaagtccct gtccttatct ctgggctcag gtggaggcgg tagtggcgga    1080
ggcggttcag gcggaggcgg atctatttgg gagctgaaga agacgtgta cgtggtcgag    1140 ctggactggt accctgatgc cccaggcgag atggtcgtgc tgacctgcga taccagag    1200 gaagatggta tcacctggac actggatcag tcctcagagg tgctgggctc tggtaaaaca    1260
ctgaccattc aggtgaagga gttcggtgac gctggacagt acacttgtca taagggcggg    1320
gaggtgctgt ctcactccct gctgctgctg cataagaagg aggatggaat ctggtccact    1380
gacatcctga agaccagaa ggagccaaag aacaaaacct tcctgcgatg cgaggctaag    1440
aactacagcg ccgctttac atgctggtgg ctgacaacca tcagcaccga tctgaccttt    1500
agcgtgaagt catccagggg cagttcagac cctcagggag tcatgtgtgg cgccgcaacc    1560
ctgtcagcag agcgagtgcg gggagacaat aaggaatacg agtacagcgt cgagtgtcag    1620
gaggattccg catgtccagc tgcagaagaa tccctgccta tcgaagtcat ggtggacgct    1680
gtgcataaac tgaagtacga gaattacacc agcagctttt tcatccggga catcatcaag    1740
cccgatccac ctaagaatct gcagctgaag cctctgaaaa atagccgaca ggtcgaagtg    1800
tcatgggaat acccagacac ctggtcaaca ccacactcct acttctccct gaccttctgt    1860
gtgcaggtcc agggaaaaag caagcgggaa aagaaagatc gggtgttcac cgacaagacc    1920
agtgctacag tgatttgccg gaagaatgcc agcatttctg tcagagctca ggaccggtac    1980
tatagctctt cctggagcga gtgggcttca gtgccatgtt ctggaggcgg tggatctggc    2040
ggaggtggaa gcggaggcgg tggatctaga aacctgcccg tcgcaacccc tgatccaggg    2100
atgttcccct gtctgcatca cagccagaat ctgctgaggg ctgtctccaa catgctgcag    2160
aaggctcgac agaccctgga gttctaccca tgtaccagcg aagagatcga ccacgaggat    2220
atcacaaagg ataaaaccag cacagtggaa gcatgcctgc ctctggaact gaccaagaat    2280
gagagctgcc tgaatagcag ggagacctcc ttcatcacca acggctcatg cctggcttca    2340
aggaagacca gcttcatgat ggctctgtgt ctgagctcta tctatgagga cctgaagatg    2400
taccaggtgg agttcaagac catgaacgcc aagctgctga tggatccaaa gaggcagatc    2460
ttcctggatc agaatatgct ggcagtgatc gatgagctga tgcaggccct gaattttaac    2520
agtgagacag tgcctcagaa gagctctctg gaagagccag acttttacaa aactaagatc    2580
aagctgtgca ttctgctgca cgctttccgc atcagagctg tcactatcga tagagtgatg    2640
agctatctga atgcctca                                                   2658
```

```
<210> SEQ ID NO 48
<211> LENGTH: 886
<212> TYPE: PRT
<213> ORGANISM: Artificial Sequence
<220> FEATURE:
<223> OTHER INFORMATION: Synthetic sequence

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Ser Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Cys Gln Glu Glu Met Thr Lys Asn Gln Val Ser Leu Trp
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Ser Gly Gly Gly Gly Ser Gly Gly Gly Gly Ser Gly Gly Gly Gly Ser
        355                 360                 365
```

```
Ile Trp Glu Leu Lys Lys Asp Val Tyr Val Glu Leu Asp Trp Tyr
    370             375             380

Pro Asp Ala Pro Gly Glu Met Val Val Leu Thr Cys Asp Thr Pro Glu
385             390             395             400

Glu Asp Gly Ile Thr Trp Thr Leu Asp Gln Ser Ser Glu Val Leu Gly
                405             410             415

Ser Gly Lys Thr Leu Thr Ile Gln Val Lys Glu Phe Gly Asp Ala Gly
            420             425             430

Gln Tyr Thr Cys His Lys Gly Glu Val Leu Ser His Ser Leu Leu
        435             440             445

Leu Leu His Lys Lys Glu Asp Gly Ile Trp Ser Thr Asp Ile Leu Lys
    450             455             460

Asp Gln Lys Glu Pro Lys Asn Lys Thr Phe Leu Arg Cys Glu Ala Lys
465             470             475             480

Asn Tyr Ser Gly Arg Phe Thr Cys Trp Trp Leu Thr Thr Ile Ser Thr
                485             490             495

Asp Leu Thr Phe Ser Val Lys Ser Ser Arg Gly Ser Ser Asp Pro Gln
            500             505             510

Gly Val Thr Cys Gly Ala Ala Thr Leu Ser Ala Glu Arg Val Arg Gly
        515             520             525

Asp Asn Lys Glu Tyr Glu Tyr Ser Val Glu Cys Gln Glu Asp Ser Ala
530             535             540

Cys Pro Ala Ala Glu Glu Ser Leu Pro Ile Glu Val Met Val Asp Ala
545             550             555             560

Val His Lys Leu Lys Tyr Glu Asn Tyr Thr Ser Ser Phe Phe Ile Arg
                565             570             575

Asp Ile Ile Lys Pro Asp Pro Lys Asn Leu Gln Leu Lys Pro Leu
            580             585             590

Lys Asn Ser Arg Gln Val Glu Val Ser Trp Glu Tyr Pro Asp Thr Trp
        595             600             605

Ser Thr Pro His Ser Tyr Phe Ser Leu Thr Phe Cys Val Gln Val Gln
    610             615             620

Gly Lys Ser Lys Arg Glu Lys Lys Asp Arg Val Phe Thr Asp Lys Thr
625             630             635             640

Ser Ala Thr Val Ile Cys Arg Lys Asn Ala Ser Ile Ser Val Arg Ala
                645             650             655

Gln Asp Arg Tyr Tyr Ser Ser Ser Trp Ser Glu Trp Ala Ser Val Pro
            660             665             670

Cys Ser Gly Gly Gly Ser Gly Gly Gly Ser Gly Gly Gly
        675             680             685

Ser Arg Asn Leu Pro Val Ala Thr Pro Asp Pro Gly Met Phe Pro Cys
    690             695             700

Leu His His Ser Gln Asn Leu Leu Arg Ala Val Ser Asn Met Leu Gln
705             710             715             720

Lys Ala Arg Gln Thr Leu Glu Phe Tyr Pro Cys Thr Ser Glu Glu Ile
                725             730             735

Asp His Glu Asp Ile Thr Lys Asp Lys Thr Ser Thr Val Glu Ala Cys
            740             745             750

Leu Pro Leu Glu Leu Thr Lys Asn Glu Ser Cys Leu Asn Ser Arg Glu
        755             760             765

Thr Ser Phe Ile Thr Asn Gly Ser Cys Leu Ala Ser Arg Lys Thr Ser
    770             775             780

Phe Met Met Ala Leu Cys Leu Ser Ser Ile Tyr Glu Asp Leu Lys Met
```

| | | | | |
|---|---|---|---|---|
| 785 | 790 | 795 | 800 | |

Tyr Gln Val Glu Phe Lys Thr Met Asn Ala Lys Leu Leu Met Asp Pro
                 805                  810                  815

Lys Arg Gln Ile Phe Leu Asp Gln Asn Met Leu Ala Val Ile Asp Glu
            820                  825                  830

Leu Met Gln Ala Leu Asn Phe Asn Ser Glu Thr Val Pro Gln Lys Ser
                835                  840                  845

Ser Leu Glu Glu Pro Asp Phe Tyr Lys Thr Lys Ile Lys Leu Cys Ile
    850                  855                  860

Leu Leu His Ala Phe Arg Ile Arg Ala Val Thr Ile Asp Arg Val Met
865                  870                  875                  880

Ser Tyr Leu Asn Ala Ser
                885

<210> SEQ ID NO 49
<211> LENGTH: 1503
<212> TYPE: DNA
<213> ORGANISM: Artificial Sequence
<220> FEATURE:
<223> OTHER INFORMATION: Synthetic sequence

<400> SEQUENCE: 49

```
gaggtgcagc tggtggaatc cggcggaggc ctggtccagc ctggcggctc tctgcggctg      60
tcctgcgccg cttctggcag aaccttcgtg acctacggca tgggctggtt ccggcaggct     120
cctggcaagg gcagagagtt cgtgtccgcc atctcctggt ccggctccag cacctcttac     180
ggcgactctg tgaagggcag attcaccatc agccgggata cgccaagaa cacactgtac      240
ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagtctaa gtacggccct cctgtcctc cttgccctgc tcctgagttc      420
gagggcggcc cctccgtgtt tctcttccca cccaagccta aggacaccct gatgatctcc     480
agaaccctg aggtgacctg cgtggtggtt gacgtgtctc aggaggatcc cgaagtgcag      540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
accatctcca aggccaaggg acaacctaga gagcctcagg tgtgcaccct gcctccctct     780
caggaggaga tgaccaagaa ccaggtgtct ctgtcctgcg ctgtgaaggg cttctaccct     840
tccgacatcg ccgtggaatg ggaaagcaac ggccaacctg agaacaacta caagaccacc     900
cctcctgtgc tggactccga tggatctttc ttcctggttt ctcggctgac cgtcgacaag     960
tctagatggc aggagggcaa cgtgttcagc tgctccgtca tgcacgaggc cctgcataac    1020
cactacaccc agaagtccct gtccttatct ctgggctcag gtggaggcgg tagtggcgga    1080
ggcggttcag gcggaggcgg atctgcacct acttcaagtt ctacaaagaa acacagcta    1140
caactggagc atttactgct ggatttacag atgatttga atggaattaa taattacaag    1200
aatcccaaac tcaccaggat gctcacattt aagttttaca tgcccaagaa ggccacagaa    1260
ctgaaacatc ttcagtgtct agaagaagaa ctcaaacctc tggaggaagt gctaaattta    1320
gctcaaagca aaaactttca cttaagaccc agggacttaa tcagcaatat caacgtaata    1380
gttctggaac taaagggatc tgaaacaaca ttcatgtgtg aatatgctga tgagacagca    1440
accattgtag aatttctgaa cagatggatt accttttgtc aaagcatcat ctcaacactg    1500
``` act                                                                          1503

<210> SEQ ID NO 50
<211> LENGTH: 501
<212> TYPE: PRT
<213> ORGANISM: Artificial Sequence
<220> FEATURE:
<223> OTHER INFORMATION: Synthetic sequence

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Ser Thr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Cys Thr
                245                 250                 255

Leu Pro Pro Ser Gln Glu Glu Met Thr Lys Asn Gln Val Ser Leu Ser
            260                 265                 270

Cys Ala Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Val Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

```
Ser Gly Gly Gly Gly Ser Gly Gly Gly Ser Gly Gly Gly Ser
        355                 360                 365

Ala Pro Thr Ser Ser Thr Lys Thr Gln Leu Gln Leu Glu His
    370                 375                 380

Leu Leu Leu Asp Leu Gln Met Ile Leu Asn Gly Ile Asn Asn Tyr Lys
385                 390                 395                 400

Asn Pro Lys Leu Thr Arg Met Leu Thr Phe Lys Phe Tyr Met Pro Lys
                405                 410                 415

Lys Ala Thr Glu Leu Lys His Leu Gln Cys Leu Glu Glu Glu Leu Lys
                420                 425                 430

Pro Leu Glu Glu Val Leu Asn Leu Ala Gln Ser Lys Asn Phe His Leu
                435                 440                 445

Arg Pro Arg Asp Leu Ile Ser Asn Ile Asn Val Ile Val Leu Glu Leu
                450                 455                 460

Lys Gly Ser Glu Thr Thr Phe Met Cys Glu Tyr Ala Asp Glu Thr Ala
465                 470                 475                 480

Thr Ile Val Glu Phe Leu Asn Arg Trp Ile Thr Phe Cys Gln Ser Ile
                485                 490                 495

Ile Ser Thr Leu Thr
            500

<210> SEQ ID NO 51
<211> LENGTH: 1056
<212> TYPE: DNA
<213> ORGANISM: Artificial Sequence
<220> FEATURE:
<223> OTHER INFORMATION: Synthetic sequence

<400> SEQUENCE: 51
gaggtgcagc tggtggaatc cggcggaggc ctggtccagc ctggcggctc tctgcggctg      60
tcctgcgccg cttctggcag aaccttcgtg acctacggca tgggctggtt ccggcaggct     120
cctggcaagg gcagagagtt cgtgtccgcc atctcctggt ccggctccag cacctcttac     180
ggcgactctg tgaagggcag attcaccatc agccgggata cgccaagaa cacactgtac      240
ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagtctaa gtacggcccc cctgtcctcc ttgccctgc tcctgagttc      420
gagggcggcc cctccgtgtt tctcttccca cccaagccta aggacaccct gatgatctcc     480
agaacccctg aggtgacctg cgtggtggtt gacgtgtctc aggaggatcc cgaagtgcag     540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
accatctcca aggccaaggg acaacctaga gagcctcagg tgtgcaccct gcctccctct     780
caggaggaga tgaccaagaa ccaggtgtct ctgtcctgcg ctgtgaaggg cttctaccct     840
tccgacatcg ccgtggaatg ggaaagcaac ggccaacctg agaacaacta caagaccacc     900
cctcctgtgc tggactccga tggatctttc ttcctggttt ctcggctgac cgtcgacaag     960
tctagatggc aggagggcaa cgtgttcagc tgctccgtca tgcacgaggc cctgcataac    1020
cactacaccc agaagtccct gtccttatct ctgggc                              1056

<210> SEQ ID NO 52
<211> LENGTH: 352
```

<212> TYPE: PRT
<213> ORGANISM: Artificial Sequence
<220> FEATURE:
<223> OTHER INFORMATION: Synthetic sequence

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Cys Thr
                245                 250                 255

Leu Pro Pro Ser Gln Glu Glu Met Thr Lys Asn Gln Val Ser Leu Ser
            260                 265                 270

Cys Ala Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Val Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

<210> SEQ ID NO 53
<211> LENGTH: 1503
<212> TYPE: DNA
<213> ORGANISM: Artificial Sequence
<220> FEATURE:

<223> OTHER INFORMATION: Synthetic sequence

<400> SEQUENCE: 53

```
gaggtgcagc tggtggaatc cggcggaggc ctggtccagc ctggcggctc tctgcggctg     60
tcctgcgccg cttctggcag aaccttcgtg acctacggca tgggctggtt ccggcaggct    120
cctggcaagg gcagagagtt cgtgtccgcc atctcctggt ccggctccag cacctcttac    180
ggcgactctg tgaagggcag attcaccatc agccgggata cgccaagaa cacactgtac    240
ctgcagatga actccctgcg gcctgaggac accgccgtgt actactgcgc cgctgccctg    300
ggcgctgtcg tgtacaccac cagagaaccc tatacctact ggggacaggg caccctggtg    360
accgtgtcct ctgagtctaa gtacggccct ccctgtcctc cttgccctgc tcctgagttc    420
gagggcggcc cctccgtgtt tctcttccca cccaagccta aggacaccct gatgatctcc    480
agaacccctg aggtgacctg cgtggtggtt gacgtgtctc aggaggatcc cgaagtgcag    540
tttaattggt acgtggacgg cgtcgaagtg cacaatgcta aaaccaagcc tcgggaggaa    600
cagttcaata gcacctacag agtggtgagc gttctgacag tgctgcacca ggactggctg    660
aacggcaaag agtacaagtg caaggtgtcc aacaagggcc tgccatcctc catcgagaag    720
accatctcca aggccaaggg acaacctaga gagcctcagg tgtacaccct gcctccctgt    780
caggaggaga tgaccaagaa ccaggtgtct ctgtggtgcc tggtgaaggg cttctaccct    840
tccgacatcg ccgtggaatg ggaaagcaac ggccaacctg agaacaacta caagaccacc    900
cctcctgtgc tggactccga tggatctttc ttcctgtact ctcggctgac cgtcgacaag    960
tctagatggc aggagggcaa cgtgttcagc tgctccgtca tgcacgaggc cctgcataac   1020
cactacaccc agaagtccct gtccttatct ctgggctcag gtggaggcgg tagtggcgga   1080
ggcggttcag gcggaggcgg atctgcacct acttcaagtt ctacaaagaa aacacagcta   1140
caactggagc atttactgct ggatttacag atgatttga atggaattaa taattacaag   1200
aatcccaaac tcaccaggat gctcacattt aagttttaca tgcccaagaa ggccacagaa   1260
ctgaaacatc ttcagtgtct agaagaagaa ctcaaacctc tggaggaagt gctaaattta   1320
gctcaaagca aaaactttca cttaagaccc agggacttaa tcagcaatat caacgtaata   1380
gttctggaac taaagggatc tgaaacaaca ttcatgtgtg aatatgctga tgagacagca   1440
accattgtag aatttctgaa cagatggatt accttttgtc aaagcatcat ctcaacactg   1500
act                                                                 1503
```

<210> SEQ ID NO 54
<211> LENGTH: 501
<212> TYPE: PRT
<213> ORGANISM: Artificial Sequence
<220> FEATURE:
<223> OTHER INFORMATION: Synthetic sequence

<400> SEQUENCE: 54

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Val Thr Tyr
             20                  25                  30

Gly Met Gly Trp Phe Arg Gln Ala Pro Gly Lys Gly Arg Glu Phe Val
         35                  40                  45

Ser Ala Ile Ser Trp Ser Gly Ser Ser Thr Ser Tyr Gly Asp Ser Val
     50                  55                  60

Lys Gly Arg Phe Thr Ile Ser Arg Asp Asn Ala Lys Asn Thr Leu Tyr
```

```
                65                  70                  75                  80
Leu Gln Met Asn Ser Leu Arg Pro Glu Asp Thr Ala Val Tyr Tyr Cys
                    85                  90                  95
Ala Ala Ala Leu Gly Ala Val Val Tyr Thr Thr Arg Glu Pro Tyr Thr
                   100                 105                 110
Tyr Trp Gly Gln Gly Thr Leu Val Thr Val Ser Ser Glu Ser Lys Tyr
            115                 120                 125
Gly Pro Pro Cys Pro Pro Cys Pro Ala Pro Glu Phe Glu Gly Gly Pro
        130                 135                 140
Ser Val Phe Leu Phe Pro Pro Lys Pro Lys Asp Thr Leu Met Ile Ser
145                 150                 155                 160
Arg Thr Pro Glu Val Thr Cys Val Val Val Asp Val Ser Gln Glu Asp
                165                 170                 175
Pro Glu Val Gln Phe Asn Trp Tyr Val Asp Gly Val Glu Val His Asn
            180                 185                 190
Ala Lys Thr Lys Pro Arg Glu Glu Gln Phe Asn Ser Thr Tyr Arg Val
        195                 200                 205
Val Ser Val Leu Thr Val Leu His Gln Asp Trp Leu Asn Gly Lys Glu
    210                 215                 220
Tyr Lys Cys Lys Val Ser Asn Lys Gly Leu Pro Ser Ser Ile Glu Lys
225                 230                 235                 240
Thr Ile Ser Lys Ala Lys Gly Gln Pro Arg Glu Pro Gln Val Tyr Thr
                245                 250                 255
Leu Pro Pro Cys Gln Glu Glu Met Thr Lys Asn Gln Val Ser Leu Trp
            260                 265                 270
Cys Leu Val Lys Gly Phe Tyr Pro Ser Asp Ile Ala Val Glu Trp Glu
        275                 280                 285
Ser Asn Gly Gln Pro Glu Asn Asn Tyr Lys Thr Thr Pro Pro Val Leu
    290                 295                 300
Asp Ser Asp Gly Ser Phe Phe Leu Tyr Ser Arg Leu Thr Val Asp Lys
305                 310                 315                 320
Ser Arg Trp Gln Glu Gly Asn Val Phe Ser Cys Ser Val Met His Glu
                325                 330                 335
Ala Leu His Asn His Tyr Thr Gln Lys Ser Leu Ser Leu Ser Leu Gly
            340                 345                 350
Ser Gly Gly Gly Gly Ser Gly Gly Gly Ser Gly Gly Gly Gly Ser
        355                 360                 365
Ala Pro Thr Ser Ser Ser Thr Lys Lys Thr Gln Leu Gln Leu Glu His
    370                 375                 380
Leu Leu Leu Asp Leu Gln Met Ile Leu Asn Gly Ile Asn Asn Tyr Lys
385                 390                 395                 400
Asn Pro Lys Leu Thr Arg Met Leu Thr Phe Lys Phe Tyr Met Pro Lys
                405                 410                 415
Lys Ala Thr Glu Leu Lys His Leu Gln Cys Leu Glu Glu Glu Leu Lys
            420                 425                 430
Pro Leu Glu Glu Val Leu Asn Leu Ala Gln Ser Lys Asn Phe His Leu
        435                 440                 445
Arg Pro Arg Asp Leu Ile Ser Asn Ile Asn Val Ile Val Leu Glu Leu
    450                 455                 460
Lys Gly Ser Glu Thr Thr Phe Met Cys Glu Tyr Ala Asp Glu Thr Ala
465                 470                 475                 480
Thr Ile Val Glu Phe Leu Asn Arg Trp Ile Thr Phe Cys Gln Ser Ile
                485                 490                 495
```

Ile Ser Thr Leu Thr
            500

<210> SEQ ID NO 55
<211> LENGTH: 2658
<212> TYPE: DNA
<213> ORGANISM: Artificial Sequence
<220> FEATURE:
<223> OTHER INFORMATION: Synthetic sequence

<400> SEQUENCE: 55

| | | | | | |
|---|---|---|---|---|---|
| gaggtgcagc | tggtggaatc | cggcggaggc | ctggtgcagc | ctggcggctc | tctgagactg | 60 |
| tcctgcgccg | cttctggccg | gaccttcatc | acctacgcca | tcggctggtt | cagacaggcc | 120 |
| cctggcaagg | gcagagagtt | cgtgtccgcc | atctcctggt | ccggctctat | gaccagctac | 180 |
| gccgactctg | tgaagggcag | attcaccatc | tcccgggata | acgccaagaa | caccctgtac | 240 |
| ctgcagatga | attccctgag | acctgaggac | acagctgtgt | attactgcgc | cgctcaccgg | 300 |
| ggcgccatcg | ctcccatcgc | tcagagcgtg | tacaccaact | ggggcagggg | aaccctggtc | 360 |
| accgtgtcca | gcgagtctaa | gtacggcccc | ccctgtcctc | cttgccctgc | tcctgagttc | 420 |
| gagggcggcc | cctccgtgtt | tctcttccca | cccaagccta | aggacaccct | gatgatctcc | 480 |
| agaaccctg | aggtgacctg | cgtggtggtt | gacgtgtctc | aggaggatcc | cgaagtgcag | 540 |
| tttaattggt | acgtggacgg | cgtcgaagtg | cacaatgcta | aaaccaagcc | tcgggaggaa | 600 |
| cagttcaata | gcacctacag | agtggtgagc | gttctgacag | tgctgcacca | ggactggctg | 660 |
| aacggcaaag | agtacaagtg | caaggtgtcc | aacaagggcc | tgccatcctc | catcgagaag | 720 |
| accatctcca | aggccaaggg | acaacctaga | gagcctcagg | tgtacaccct | gcctccctgt | 780 |
| caggaggaga | tgaccaagaa | ccaggtgtct | ctgtggtgcc | tggtgaaggg | cttctaccct | 840 |
| tccgacatcg | ccgtggaatg | ggaaagcaac | ggccaacctg | agaacaacta | caagaccacc | 900 |
| cctcctgtgc | tggactccga | tggatctttc | ttcctgtact | ctcggctgac | cgtcgacaag | 960 |
| tctagatggc | aggagggcaa | cgtgttcagc | tgctccgtca | tgcacgaggc | cctgcataac | 1020 |
| cactacaccc | agaagtccct | gtccttatct | ctgggctcag | gtggaggcgg | tagtggcgga | 1080 |
| ggcggttcag | gcggaggcgg | atctatttgg | gagctgaaga | agacgtgta | cgtggtcgag | 1140 |
| ctggactggt | accctgatgc | cccaggcgag | atggtcgtgc | tgacctgcga | taccagag | 1200 |
| gaagatggta | tcacctggac | actggatcag | tcctcagagg | tgctgggctc | tggtaaaaca | 1260 |
| ctgaccattc | aggtgaagga | gttcggtgac | gctggacagt | acacttgtca | taagggcggg | 1320 |
| gaggtgctgt | ctcactccct | gctgctgctg | cataagaagg | aggatggaat | ctggtccact | 1380 |
| gacatcctga | agaccagaa | ggagccaaag | aacaaaacct | tcctgcgatg | cgaggctaag | 1440 |
| aactacagcg | ccgctttac | atgctggtgg | ctgacaacca | tcagcaccga | tctgacctt | 1500 |
| agcgtgaagt | catccagggg | cagttcagac | cctcagggag | tcatgtgtgg | cgccgcaacc | 1560 |
| ctgtcagcag | agcgagtgcg | gggagacaat | aaggaatacg | agtacagcgt | cgagtgtcag | 1620 |
| gaggattccg | catgtccagc | tgcagaagaa | tccctgccta | tcgaagtcat | ggtggacgct | 1680 |
| gtgcataaac | tgaagtacga | gaattacacc | agcagctttt | tcatccggga | catcatcaag | 1740 |
| cccgatccac | ctaagaatct | gcagctgaag | cctctgaaaa | atagccgaca | ggtcgaagtg | 1800 |
| tcatgggaat | acccagacac | ctggtcaaca | ccacactcct | acttctccct | gaccttctgt | 1860 |
| gtgcaggtcc | agggaaaaag | caagcgggaa | aagaaagatc | gggtgttcac | cgacaagacc | 1920 |
| agtgctacag | tgatttgccg | gaagaatgcc | agcatttctg | tcagagctca | ggaccggtac | 1980 |

-continued

```
tatagctctt cctggagcga gtgggcttca gtgccatgtt ctggaggcgg tggatctggc    2040
ggaggtggaa gcggaggcgg tggatctaga aacctgcccg tcgcaacccc tgatccaggg    2100
atgttcccct gtctgcatca cagccagaat ctgctgaggg ctgtctccaa catgctgcag    2160
aaggctcgac agaccctgga gttctaccca tgtaccagcg aagagatcga ccacgaggat    2220
atcacaaagg ataaaaccag cacagtggaa gcatgcctgc ctctggaact gaccaagaat    2280
gagagctgcc tgaatagcag ggagacctcc ttcatcacca acggctcatg cctggcttca    2340
aggaagacca gcttcatgat ggctctgtgt ctgagctcta tctatgagga cctgaagatg    2400
taccaggtgg agttcaagac catgaacgcc aagctgctga tggatccaaa gaggcagatc    2460
ttcctggatc agaatatgct ggcagtgatc gatgagctga tgcaggccct gaattttaac    2520
agtgagacag tgcctcagaa gagctctctg gaagagccag acttttacaa aactaagatc    2580
aagctgtgca ttctgctgca cgctttccgc atcagagctg tcactatcga tagagtgatg    2640
agctatctga atgcctca                                                   2658
```

<210> SEQ ID NO 56
<211> LENGTH: 886
<212> TYPE: PRT
<213> ORGANISM: Artificial Sequence
<220> FEATURE:
<223> OTHER INFORMATION: Synthetic sequence

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240
```

```
Thr Ile Ser Lys Ala Lys Gly Gln Pro Arg Glu Pro Gln Val Tyr Thr
            245                 250                 255

Leu Pro Pro Cys Gln Glu Glu Met Thr Lys Asn Gln Val Ser Leu Trp
            260                 265                 270

Cys Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
            290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
                340                 345                 350

Ser Gly Gly Gly Ser Gly Gly Gly Ser Gly Gly Gly Gly Ser
            355                 360                 365

Ile Trp Glu Leu Lys Lys Asp Val Tyr Val Val Glu Leu Asp Trp Tyr
            370                 375                 380

Pro Asp Ala Pro Gly Glu Met Val Val Leu Thr Cys Asp Thr Pro Glu
385                 390                 395                 400

Glu Asp Gly Ile Thr Trp Thr Leu Asp Gln Ser Ser Glu Val Leu Gly
                405                 410                 415

Ser Gly Lys Thr Leu Thr Ile Gln Val Lys Glu Phe Gly Asp Ala Gly
                420                 425                 430

Gln Tyr Thr Cys His Lys Gly Gly Glu Val Leu Ser His Ser Leu Leu
                435                 440                 445

Leu Leu His Lys Lys Glu Asp Gly Ile Trp Ser Thr Asp Ile Leu Lys
            450                 455                 460

Asp Gln Lys Glu Pro Lys Asn Lys Thr Phe Leu Arg Cys Glu Ala Lys
465                 470                 475                 480

Asn Tyr Ser Gly Arg Phe Thr Cys Trp Trp Leu Thr Thr Ile Ser Thr
                485                 490                 495

Asp Leu Thr Phe Ser Val Lys Ser Ser Arg Gly Ser Ser Asp Pro Gln
            500                 505                 510

Gly Val Thr Cys Gly Ala Ala Thr Leu Ser Ala Glu Arg Val Arg Gly
            515                 520                 525

Asp Asn Lys Glu Tyr Glu Tyr Ser Val Glu Cys Gln Glu Asp Ser Ala
530                 535                 540

Cys Pro Ala Ala Glu Glu Ser Leu Pro Ile Glu Val Met Val Asp Ala
545                 550                 555                 560

Val His Lys Leu Lys Tyr Glu Asn Tyr Thr Ser Ser Phe Phe Ile Arg
                565                 570                 575

Asp Ile Ile Lys Pro Asp Pro Pro Lys Asn Leu Gln Leu Lys Pro Leu
            580                 585                 590

Lys Asn Ser Arg Gln Val Glu Val Ser Trp Glu Tyr Pro Asp Thr Trp
            595                 600                 605

Ser Thr Pro His Ser Tyr Phe Ser Leu Thr Phe Cys Val Gln Val Gln
            610                 615                 620

Gly Lys Ser Lys Arg Glu Lys Lys Asp Arg Val Phe Thr Asp Lys Thr
625                 630                 635                 640

Ser Ala Thr Val Ile Cys Arg Lys Asn Ala Ser Ile Ser Val Arg Ala
                645                 650                 655
```

```
Gln Asp Arg Tyr Tyr Ser Ser Ser Trp Ser Glu Trp Ala Ser Val Pro
                660                 665                 670

Cys Ser Gly Gly Gly Ser Gly Gly Gly Ser Gly Gly Gly Gly
        675                 680                 685

Ser Arg Asn Leu Pro Val Ala Thr Pro Asp Pro Gly Met Phe Pro Cys
690                 695                 700

Leu His His Ser Gln Asn Leu Leu Arg Ala Val Ser Asn Met Leu Gln
705                 710                 715                 720

Lys Ala Arg Gln Thr Leu Glu Phe Tyr Pro Cys Thr Ser Glu Glu Ile
                725                 730                 735

Asp His Glu Asp Ile Thr Lys Asp Lys Thr Ser Thr Val Glu Ala Cys
                740                 745                 750

Leu Pro Leu Glu Leu Thr Lys Asn Glu Ser Cys Leu Asn Ser Arg Glu
                755                 760                 765

Thr Ser Phe Ile Thr Asn Gly Ser Cys Leu Ala Ser Arg Lys Thr Ser
770                 775                 780

Phe Met Met Ala Leu Cys Leu Ser Ser Ile Tyr Glu Asp Leu Lys Met
785                 790                 795                 800

Tyr Gln Val Glu Phe Lys Thr Met Asn Ala Lys Leu Leu Met Asp Pro
                805                 810                 815

Lys Arg Gln Ile Phe Leu Asp Gln Asn Met Leu Ala Val Ile Asp Glu
                820                 825                 830

Leu Met Gln Ala Leu Asn Phe Asn Ser Glu Thr Val Pro Gln Lys Ser
                835                 840                 845

Ser Leu Glu Glu Pro Asp Phe Tyr Lys Thr Lys Ile Lys Leu Cys Ile
850                 855                 860

Leu Leu His Ala Phe Arg Ile Arg Ala Val Thr Ile Asp Arg Val Met
865                 870                 875                 880

Ser Tyr Leu Asn Ala Ser
                885

<210> SEQ ID NO 57
<211> LENGTH: 1503
<212> TYPE: DNA
<213> ORGANISM: Artificial Sequence
<220> FEATURE:
<223> OTHER INFORMATION: Synthetic sequence

<400> SEQUENCE: 57
gaggtgcagc tggtggaatc cggcggaggc ctggtgcagc ctggcggctc tctgagactg      60
tcctgcgccg cttctggccg gaccttcatc acctacgcca tcggctggtt cagacaggcc     120
cctggcaagg gcagagagtt cgtgtccgcc atctcctggt ccggctctat gaccagctac     180
gccgactctg tgaagggcag attcaccatc tcccgggata cgccaagaa caccctgtac     240 ctgcagatga attccctgag acctgaggac acagctgtgt attactgcgc cgctcaccgg     300
ggcgccatcg ctcccatcgc tcagagcgtg tacaccaact ggggccaggg aaccctggtc     360
accgtgtcca gcgagtctaa gtacggccct cctgtcctc ttgccctgc tcctgagttc      420 gagggcggcc cctccgtgtt tctcttccca cccaagccta ggacaccct gatgatctcc      480 agaaccctg aggtgacctg cgtggtggtt gacgtgtctc aggaggatcc cgaagtgcag     540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
```

```
accatctcca aggccaaggg acaacctaga gagcctcagg tgtgcaccct gcctccctct    780
caggaggaga tgaccaagaa ccaggtgtct ctgtcctgcg ctgtgaaggg cttctaccct    840
tccgacatcg ccgtggaatg ggaaagcaac ggccaacctg agaacaacta caagaccacc    900
cctcctgtgc tggactccga tggatctttc ttcctggttt ctcggctgac cgtcgacaag    960
tctagatggc aggagggcaa cgtgttcagc tgctccgtca tgcacgaggc cctgcataac   1020
cactacaccc agaagtccct gtccttatct ctgggctcag gtggaggcgg tagtggcgga   1080
ggcggttcag gcggaggcgg atctgcacct acttcaagtt ctacaaagaa aacacagcta   1140
caactggagc atttactgct ggatttacag atgattttga atggaattaa taattacaag   1200
aatcccaaac tcaccaggat gctcacattt aagttttaca tgcccaagaa ggccacagaa   1260
ctgaaacatc ttcagtgtct agaagaagaa ctcaaacctc tggaggaagt gctaaattta   1320
gctcaaagca aaaactttca cttaagaccc agggacttaa tcagcaatat caacgtaata   1380
gttctggaac taagggatc tgaaacaaca ttcatgtgtg aatatgctga tgagacagca   1440
accattgtag aatttctgaa cagatggatt accttttgtc aaagcatcat ctcaacactg   1500
act                                                                 1503

<210> SEQ ID NO 58
<211> LENGTH: 501
<212> TYPE: PRT
<213> ORGANISM: Artificial Sequence
<220> FEATURE:
<223> OTHER INFORMATION: Synthetic sequence

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220
```

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Cys Thr
            245                 250                 255

Leu Pro Pro Ser Gln Glu Glu Met Thr Lys Asn Gln Val Ser Leu Ser
        260                 265                 270

Cys Ala Val Lys Gly Phe Tyr Pro Ser Asp Ile Ala Val Glu Trp Glu
    275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Val Ser Arg Leu Thr Val Asp Lys
305                 310                 315                 320

Ser Arg Trp Gln Glu Gly Asn Val Phe Ser Cys Ser Val Met His Glu
            325                 330                 335

Ala Leu His Asn His Tyr Thr Gln Lys Ser Leu Ser Leu Ser Leu Gly
        340                 345                 350

Ser Gly Gly Gly Gly Ser Gly Gly Gly Gly Ser Gly Gly Gly Gly Ser
    355                 360                 365

Ala Pro Thr Ser Ser Thr Lys Lys Thr Gln Leu Gln Leu Glu His
370                 375                 380

Leu Leu Leu Asp Leu Gln Met Ile Leu Asn Gly Ile Asn Asn Tyr Lys
385                 390                 395                 400

Asn Pro Lys Leu Thr Arg Met Leu Thr Phe Lys Phe Tyr Met Pro Lys
            405                 410                 415

Lys Ala Thr Glu Leu Lys His Leu Gln Cys Leu Glu Glu Leu Lys
        420                 425                 430

Pro Leu Glu Glu Val Leu Asn Leu Ala Gln Ser Lys Asn Phe His Leu
    435                 440                 445

Arg Pro Arg Asp Leu Ile Ser Asn Ile Asn Val Ile Val Leu Glu Leu
450                 455                 460

Lys Gly Ser Glu Thr Thr Phe Met Cys Glu Tyr Ala Asp Glu Thr Ala
465                 470                 475                 480

Thr Ile Val Glu Phe Leu Asn Arg Trp Ile Thr Phe Cys Gln Ser Ile
            485                 490                 495

Ile Ser Thr Leu Thr
            500

<210> SEQ ID NO 59
<211> LENGTH: 1056
<212> TYPE: DNA
<213> ORGANISM: Artificial Sequence
<220> FEATURE:
<223> OTHER INFORMATION: Synthetic sequence

<400> SEQUENCE: 59
gaggtgcagc tggtggaatc cggcggaggc ctggtgcagc ctggcggctc tctgagactg      60
tcctgcgccg cttctggccg gaccttcatc acctacgcca tcggctggtt cagacaggcc     120
cctggcaagg gcagagagtt cgtgtccgcc atctcctggt ccggctctat gaccagctac     180
gccgactctg tgaagggcag attcaccatc tcccgggata cgccaagaa cccctgtac      240 ctgcagatga attccctgag acctgaggac acagctgtgt attactgcgc cgctcaccgg     300
ggcgccatcg ctcccatcgc tcagagcgtg tacaccaact ggggccaggg aaccctggtc     360
accgtgtcca gcgagtctaa gtacggccct cctgtcctc cttgccctgc tcctgagttc     420

```
gagggcggcc cctccgtgtt tctcttccca cccaagccta aggacaccct gatgatctcc    480 agaaccctg aggtgacctg cgtggtggtt gacgtgtctc aggaggatcc cgaagtgcag     540
tttaattggt acgtggacgg cgtcgaagtg cacaatgcta aaaccaagcc tcgggaggaa    600
cagttcaata gcacctacag agtggtgagc gttctgacag tgctgcacca ggactggctg    660
aacggcaaag agtacaagtg caaggtgtcc aacaagggcc tgccatcctc catcgagaag    720
accatctcca aggccaaggg acaacctaga gagcctcagg tgtgcaccct gcctccctct    780
caggaggaga tgaccaagaa ccaggtgtct ctgtcctgcg ctgtgaaggg cttctaccct    840
tccgacatcg ccgtggaatg ggaaagcaac ggccaacctg agaacaacta caagaccacc    900
cctcctgtgc tggactccga tggatctttc ttcctggttt ctcggctgac cgtcgacaag    960
tctagatggc aggagggcaa cgtgttcagc tgctccgtca tgcacgaggc cctgcataac   1020
cactacaccc agaagtccct gtccttatct ctgggc                             1056
```

<210> SEQ ID NO 60
<211> LENGTH: 352
<212> TYPE: PRT
<213> ORGANISM: Artificial Sequence
<220> FEATURE:
<223> OTHER INFORMATION: Synthetic sequence

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Cys Thr
                245                 250                 255
```

Leu Pro Pro Ser Gln Glu Glu Met Thr Lys Asn Gln Val Ser Leu Ser
                260                 265                 270

Cys Ala Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
        290                 295                 300

Asp Ser Asp Gly Ser Phe Phe Leu Val Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
                340                 345                 350

<210> SEQ ID NO 61
<211> LENGTH: 1503
<212> TYPE: DNA
<213> ORGANISM: Artificial Sequence
<220> FEATURE:
<223> OTHER INFORMATION: Synthetic sequence

<400> SEQUENCE: 61
gaggtgcagc tggtggaatc cggcggaggc ctggtgcagc ctggcggctc tctgagactg      60
tcctgcgccg cttctggccg gaccttcatc acctacgcca tcggctggtt cagacaggcc     120
cctggcaagg gcagagagtt cgtgtccgcc atctcctggt ccggctctat gaccagctac     180
gccgactctg tgaagggcag attcaccatc tcccgggata cgccaagaa caccctgtac      240 ctgcagatga attccctgag acctgaggac acagctgtgt attactgcgc cgctcaccgg     300
ggcgccatcg ctcccatcgc tcagagcgtg tacaccaact ggggccaggg aaccctggtc     360
accgtgtcca gcgagtctaa gtacggccct cctgtcctc ttgccctgc tcctgagttc      420 gagggcggcc cctccgtgtt tctcttccca cccaagccta aggacaccct gatgatctcc     480 agaaccctg aggtgacctg cgtggtggtt gacgtgtctc aggaggatcc cgaagtgcag      540
tttaattggt acgtggacgg cgtcgaagtg cacaatgcta aaaccaagcc tcgggaggaa     600
cagttcaata gcacctacag agtggtgagc gttctgacag tgctgcacca ggactggctg     660
aacggcaaag agtacaagtg caaggtgtcc aacaagggcc tgccatcctc catcgagaag     720
accatctcca aggccaaggg acaacctaga gagcctcagg tgtacaccct gcctccctgt     780
caggaggaga tgaccaagaa ccaggtgtct ctgtggtgcc tggtgaaggg cttctaccct     840
tccgacatcg ccgtggaatg ggaaagcaac ggccaacctg agaacaacta caagaccacc     900
cctcctgtgc tggactccga tggatctttc ttcctgtact ctcggctgac cgtcgacaag     960
tctagatggc aggagggcaa cgtgttcagc tgctccgtca tgcacgaggc cctgcataac    1020
cactacaccc agaagtccct gtccttatct ctgggctcag gtggaggcgg tagtggcgga    1080
ggcggttcag gcggaggcgg atctgcacct acttcaagtt ctacaaagaa aacacagcta    1140
caactggagc atttactgct ggatttacag atgattttga atggaattaa taattacaag    1200
aatcccaaac tcaccaggat gctcacattt aagttttaca tgcccaagaa ggccacagaa    1260
ctgaaacatc ttcagtgtct agaagaagaa ctcaaacctc tggaggaagt gctaaattta    1320
gctcaaagca aaaactttca cttaagaccc agggacttaa tcagcaatat caacgtaata    1380
gttctggaac taaagggatc tgaaacaaca ttcatgtgtg aatatgctga tgagacagca    1440
accattgtag aatttctgaa cagatggatt accttttgtc aaagcatcat ctcaacactg    1500
act 1503

<210> SEQ ID NO 62
<211> LENGTH: 501
<212> TYPE: PRT
<213> ORGANISM: Artificial Sequence
<220> FEATURE:
<223> OTHER INFORMATION: Synthetic sequence

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Cys Gln Glu Glu Met Thr Lys Asn Gln Val Ser Leu Trp
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Ser Gly Gly Gly Gly Ser Gly Gly Gly Gly Ser Gly Gly Gly Gly Ser

```
                355                 360                 365
Ala Pro Thr Ser Ser Thr Lys Lys Thr Gln Leu Gln Leu Glu His
    370                 375                 380

Leu Leu Leu Asp Leu Gln Met Ile Leu Asn Gly Ile Asn Asn Tyr Lys
385                 390                 395                 400

Asn Pro Lys Leu Thr Arg Met Leu Thr Phe Lys Phe Tyr Met Pro Lys
                405                 410                 415

Lys Ala Thr Glu Leu Lys His Leu Gln Cys Leu Glu Glu Glu Leu Lys
            420                 425                 430

Pro Leu Glu Glu Val Leu Asn Leu Ala Gln Ser Lys Asn Phe His Leu
            435                 440                 445

Arg Pro Arg Asp Leu Ile Ser Asn Ile Asn Val Ile Val Leu Glu Leu
        450                 455                 460

Lys Gly Ser Glu Thr Thr Phe Met Cys Glu Tyr Ala Asp Glu Thr Ala
465                 470                 475                 480

Thr Ile Val Glu Phe Leu Asn Arg Trp Ile Thr Phe Cys Gln Ser Ile
                485                 490                 495

Ile Ser Thr Leu Thr
            500

<210> SEQ ID NO 63
<211> LENGTH: 1056
<212> TYPE: DNA
<213> ORGANISM: Artificial Sequence
<220> FEATURE:
<223> OTHER INFORMATION: Synthetic sequence

<400> SEQUENCE: 63
gaagtgcagc tggttgagtc cggcggcggc ctggtgcagc ctggcggttc tctgcggctg      60
tcttgcgccg tgagcggaaa tatctacaac cggaacttca tgggctggtt tcggcaggct     120
ccaggcaaag gactggaagg cgtgtccgcc atctacaccg gcacctctcg gacctactac     180
gccgactctg tcaaaggcag attcaccatc tcccgcgaca cagcaaaaa caccgtgtac     240 ctgcagatga acagcctgag agctgaagat cagctgtgt actattgcgc cgccgatctg     300
agagacggct tctgggacac aggcgtgtgg aacacctggg ccagggcac acttgtgacc     360 gtgtcctctg agagcaagta cggaccacct tgcccaccat gtccagctcc tgagtttgag     420
ggaggaccat ccgtgttcct gtttcctcca agcctaagg acaccctgat gatcagccgg     480
acacctgagg tgacctgcgt ggtggtggac gtgtctcagg aggatccaga ggtgcagttc     540
aactggtacg tggatggcgt ggaggtgcac aatgctaaga ccaagccaag agaggagcag     600
tttaattcca cataccgcgt ggtgagcgtg ctgaccgtgc tgcatcagga ttggctgaac     660
ggcaaggagt ataagtgcaa ggtgtccaat aagggcctgc cagctctat cgagaagaca     720 atcagcaagg ctaagggaca gcctagggag ccacaggtgt acaccctgcc cccttctcag     780
gaggagatga caaagaacca ggtgtccctg acctgtctgg tgaagggctt ctatccaagc     840
gacatcgctg tggagtggga gtctaatggc cagcccgaga caattacaa gaccacacca     900 cccgtgctgg actctgatgg ctccttcttt ctgtattcta ggctgacagt ggataagtcc     960
cggtggcagg agggcaacgt gtttagctgc tctgtgatgc acgaggccct gcacaatcat    1020
tatacccaga agtccctgag cctgtctctg ggcaag                              1056

<210> SEQ ID NO 64
<211> LENGTH: 352
<212> TYPE: PRT
```

<213> ORGANISM: Artificial Sequence
<220> FEATURE:
<223> OTHER INFORMATION: Synthetic sequence

<400> SEQUENCE: 64

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Val | Ser | Gly | Asn | Ile | Tyr | Asn | Arg | Asn |
| | | | 20 | | | | | 25 | | | | | 30 | | |
| Phe | Met | Gly | Trp | Phe | Arg | Gln | Ala | Pro | Gly | Lys | Gly | Leu | Glu | Gly | Val |
| | | 35 | | | | | 40 | | | | | 45 | | | |
| Ser | Ala | Ile | Tyr | Thr | Gly | Thr | Ser | Arg | Thr | Tyr | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Val | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Ala | Asp | Leu | Arg | Asp | Gly | Phe | Trp | Asp | Thr | Gly | Val | Trp | Asn | Thr |
| | | | 100 | | | | | 105 | | | | | 110 | | |
| Trp | Gly | Gln | Gly | Thr | Leu | Val | Thr | Val | Ser | Ser | Glu | Ser | Lys | Tyr | Gly |
| | | 115 | | | | | 120 | | | | | 125 | | | |
| Pro | Pro | Cys | Pro | Pro | Cys | Pro | Ala | Pro | Glu | Phe | Glu | Gly | Gly | Pro | Ser |
| 130 | | | | | 135 | | | | | 140 | | | | | |
| Val | Phe | Leu | Phe | Pro | Pro | Lys | Pro | Lys | Asp | Thr | Leu | Met | Ile | Ser | Arg |
| 145 | | | | | 150 | | | | | 155 | | | | | 160 |
| Thr | Pro | Glu | Val | Thr | Cys | Val | Val | Val | Asp | Val | Ser | Gln | Glu | Asp | Pro |
| | | | | 165 | | | | | 170 | | | | | 175 | |
| Glu | Val | Gln | Phe | Asn | Trp | Tyr | Val | Asp | Gly | Val | Glu | Val | His | Asn | Ala |
| | | | 180 | | | | | 185 | | | | | 190 | | |
| Lys | Thr | Lys | Pro | Arg | Glu | Glu | Gln | Phe | Asn | Ser | Thr | Tyr | Arg | Val | Val |
| | | 195 | | | | | 200 | | | | | 205 | | | |
| Ser | Val | Leu | Thr | Val | Leu | His | Gln | Asp | Trp | Leu | Asn | Gly | Lys | Glu | Tyr |
| 210 | | | | | 215 | | | | | 220 | | | | | |
| Lys | Cys | Lys | Val | Ser | Asn | Lys | Gly | Leu | Pro | Ser | Ser | Ile | Glu | Lys | Thr |
| 225 | | | | | 230 | | | | | 235 | | | | | 240 |
| Ile | Ser | Lys | Ala | Lys | Gly | Gln | Pro | Arg | Glu | Pro | Gln | Val | Tyr | Thr | Leu |
| | | | | 245 | | | | | 250 | | | | | 255 | |
| Pro | Pro | Ser | Gln | Glu | Glu | Met | Thr | Lys | Asn | Gln | Val | Ser | Leu | Thr | Cys |
| | | | 260 | | | | | 265 | | | | | 270 | | |
| Leu | Val | Lys | Gly | Phe | Tyr | Pro | Ser | Asp | Ile | Ala | Val | Glu | Trp | Glu | Ser |
| | | 275 | | | | | 280 | | | | | 285 | | | |
| Asn | Gly | Gln | Pro | Glu | Asn | Asn | Tyr | Lys | Thr | Thr | Pro | Pro | Val | Leu | Asp |
| 290 | | | | | 295 | | | | | 300 | | | | | |
| Ser | Asp | Gly | Ser | Phe | Phe | Leu | Tyr | Ser | Arg | Leu | Thr | Val | Asp | Lys | Ser |
| 305 | | | | | 310 | | | | | 315 | | | | | 320 |
| Arg | Trp | Gln | Glu | Gly | Asn | Val | Phe | Ser | Cys | Ser | Val | Met | His | Glu | Ala |
| | | | | 325 | | | | | 330 | | | | | 335 | |
| Leu | His | Asn | His | Tyr | Thr | Gln | Lys | Ser | Leu | Ser | Leu | Ser | Leu | Gly | Lys |
| | | | 340 | | | | | 345 | | | | | 350 | | |

<210> SEQ ID NO 65
<211> LENGTH: 1059
<212> TYPE: DNA
<213> ORGANISM: Artificial Sequence
<220> FEATURE:
<223> OTHER INFORMATION: Synthetic sequence

<400> SEQUENCE: 65

```
gaggtgcagc tggtggaatc cggcggaggc ctggtccagc ctggcggctc tctgcggctg     60
tcctgcgccg cttctggcag aaccttcgtg acctacggca tgggctggtt ccggcaggct    120
cctggcaagg gcagagagtt cgtgtccgcc atctcctggt ccggctccat gacctcttac    180
ggcgactctg tgaagggcag attcaccatc agccgggata cgccaagaa cacactgtac     240
ctgcagatga actccctgcg gcctgaggac accgccgtgt actactgcgc cgctgccctg    300
ggcgctgtcg tgtacaccac cagagaaccc tatacctact ggggacaggg caccctggtg    360
accgtgtcct ctgagagcaa gtacggacca ccttgcccac catgtccagc tcctgagttt    420
gagggaggac catccgtgtt cctgtttcct ccaaagccta aggacaccct gatgatcagc    480
cggacacctg aggtgacctg cgtggtggtg gacgtgtctc aggaggatcc agaggtgcag    540
ttcaactggt acgtggatgg cgtggaggtg cacaatgcta agaccaagcc aagagaggag    600
cagtttaatt ccacataccg cgtggtgagc gtgctgaccg tgctgcatca ggattggctg    660
aacggcaagg agtataagtg caaggtgtcc aataagggcc tgcccagctc tatcgagaag    720
acaatcagca aggctaaggg acagcctagg gagccacagg tgtacaccct gcccccttct    780
caggaggaga tgacaaagaa ccaggtgtcc ctgacctgtc tggtgaaggg cttctatcca    840
agcgacatcg ctgtggagtg ggagtctaat ggccagcccg agaacaatta caagaccaca    900
ccacccgtgc tggactctga tggctccttc tttctgtatt ctaggctgac agtggataag    960
tcccggtggc aggagggcaa cgtgtttagc tgctctgtga tgcacgaggc cctgcacaat   1020
cattataccc agaagtccct gagcctgtct ctgggcaag                          1059
```

<210> SEQ ID NO 66
<211> LENGTH: 353
<212> TYPE: PRT
<213> ORGANISM: Artificial Sequence
<220> FEATURE:
<223> OTHER INFORMATION: Synthetic sequence

<400> SEQUENCE: 66

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Val Thr Tyr
             20                  25                  30

Gly Met Gly Trp Phe Arg Gln Ala Pro Gly Lys Gly Arg Glu Phe Val
         35                  40                  45

Ser Ala Ile Ser Trp Ser Gly Ser Met Thr Ser Tyr Gly Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160
```

```
Arg Thr Pro Glu Val Thr Cys Val Val Asp Val Ser Gln Glu Asp
            165                 170                 175
Pro Glu Val Gln Phe Asn Trp Tyr Val Asp Gly Val Glu Val His Asn
        180                 185                 190
Ala Lys Thr Lys Pro Arg Glu Glu Gln Phe Asn Ser Thr Tyr Arg Val
    195                 200                 205
Val Ser Val Leu Thr Val Leu His Gln Asp Trp Leu Asn Gly Lys Glu
210                 215                 220
Tyr Lys Cys Lys Val Ser Asn Lys Gly Leu Pro Ser Ser Ile Glu Lys
225                 230                 235                 240
Thr Ile Ser Lys Ala Lys Gly Gln Pro Arg Glu Pro Gln Val Tyr Thr
                245                 250                 255
Leu Pro Pro Ser Gln Glu Glu Met Thr Lys Asn Gln Val Ser Leu Thr
            260                 265                 270
Cys Leu Val Lys Gly Phe Tyr Pro Ser Asp Ile Ala Val Glu Trp Glu
        275                 280                 285
Ser Asn Gly Gln Pro Glu Asn Asn Tyr Lys Thr Thr Pro Pro Val Leu
    290                 295                 300
Asp Ser Asp Gly Ser Phe Phe Leu Tyr Ser Arg Leu Thr Val Asp Lys
305                 310                 315                 320
Ser Arg Trp Gln Glu Gly Asn Val Phe Ser Cys Ser Val Met His Glu
                325                 330                 335
Ala Leu His Asn His Tyr Thr Gln Lys Ser Leu Ser Leu Ser Leu Gly
            340                 345                 350
Lys

<210> SEQ ID NO 67
<211> LENGTH: 1059
<212> TYPE: DNA
<213> ORGANISM: Artificial Sequence
<220> FEATURE:
<223> OTHER INFORMATION: Synthetic sequence

<400> SEQUENCE: 67
gaggtgcagc tggtggaatc cggcggaggc ctggtccagc ctggcggctc tctgcggctg      60
tcctgcgccg cttctggcag aaccttcgtg acctacggca tgggctggtt ccggcaggct     120
cctggcaagg gcagagagtt cgtgtccgcc atctcctggt ccggctccag cacctcttac     180
ggcgactctg tgaagggcag attcaccatc agccgggata cgccaagaa cacactgtac      240 ctgcagatga actccctgcg gcctgaggac accgccgtgt actactgcgc cgctgccctg     300
ggcgctgtcg tgtacaccac cagagaaccc tatacctact ggggacaggg caccctggtg     360
accgtgtcct ctgagagcaa gtacggacca ccttgcccac catgtccagc tcctgagttt     420
gagggaggac catccgtgtt cctgtttcct ccaaagccta aggacaccct gatgatcagc     480
cggacacctg aggtgacctg cgtggtggtg gacgtgtctc aggaggatcc agaggtgcag     540
ttcaactggt acgtggatgg cgtggaggtg cacaatgcta agaccaagcc aagagaggag     600
cagtttaatt ccacataccg cgtggtgagc gtgctgaccg tgctgcatca ggattggctg     660
aacggcaagg agtataagtg caaggtgtcc aataagggcc tgcccagctc tatcgagaag     720
acaatcagca aggctaaggg acagcctagg gagccacagg tgtacaccct gcccccttct     780
caggaggaga tgacaaagaa ccaggtgtcc ctgacctgtc tggtgaaggg cttctatcca     840
agcgacatcg ctgtggagtg ggagtctaat ggccagccg agaacaatta caagaccaca      900
ccacccgtgc tggactctga tggctccttc tttctgtatt ctaggctgac agtggataag     960
```
tcccggtggc aggagggcaa cgtgtttagc tgctctgtga tgcacgaggc cctgcacaat   1020
cattataccc agaagtccct gagcctgtct ctgggcaag                          1059

<210> SEQ ID NO 68
<211> LENGTH: 353
<212> TYPE: PRT
<213> ORGANISM: Artificial Sequence
<220> FEATURE:
<223> OTHER INFORMATION: Synthetic sequence

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Glu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly

Lys

<210> SEQ ID NO 69
<211> LENGTH: 1059
<212> TYPE: DNA
<213> ORGANISM: Artificial Sequence
<220> FEATURE:
<223> OTHER INFORMATION: Synthetic sequence

<400> SEQUENCE: 69

```
gaggtgcagc tggtggaatc cggcggaggc ctggtgcagc ctggcggctc tctgagactg      60
tcctgcgccg cttctggccg gaccttcatc acctacgcca tcggctggtt cagacaggcc     120
cctggcaagg gcagagagtt cgtgtccgcc atctcctggt ccggctctat gaccagctac     180
gccgactctg tgaagggcag attcaccatc tcccgggata cgccaagaa caccctgtac      240
ctgcagatga attccctgag acctgaggac acagctgtgt attactgcgc cgctcaccgg     300
ggcgccatcg ctcccatcgc tcagagcgtg tacaccaact ggggcaggg aaccctggtc      360
accgtgtcca gcgagagcaa gtacggacca ccttgcccac catgtccagc tcctgagttt     420
gagggaggac catccgtgtt cctgtttcct ccaaagccta aggacaccct gatgatcagc     480
cggacacctg aggtgacctg cgtggtggtg gacgtgtctc aggaggatcc agaggtgcag     540
ttcaactggt acgtggatgg cgtggaggtg cacaatgcta agaccaagcc aagagaggag     600
cagtttaatt ccacataccg cgtggtgagc gtgctgaccg tgctgcatca ggattggctg     660
aacggcaagg agtataagtg caaggtgtcc aataagggcc tgcccagctc tatcgagaag     720
acaatcagca aggctaaggg acagcctagg gagccacagg tgtacaccct gcccccttct     780
caggaggaga tgacaaagaa ccaggtgtcc ctgacctgtc tggtgaaggg cttctatcca     840
agcgacatcg ctgtggagtg ggagtctaat ggccagcccg agaacaatta caagaccaca     900
ccacccgtgc tggactctga tggctccttc tttctgtatt ctaggctgac agtggataag     960
tcccggtggc aggagggcaa cgtgtttagc tgctctgtga tgcacgaggc cctgcacaat    1020
cattataccc agaagtccct gagcctgtct ctgggcaag                           1059
```

<210> SEQ ID NO 70
<211> LENGTH: 353
<212> TYPE: PRT
<213> ORGANISM: Artificial Sequence
<220> FEATURE:
<223> OTHER INFORMATION: Synthetic sequence

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr

```
            100                 105                 110
Asn Trp Gly Gln Gly Thr Leu Val Thr Val Ser Ser Glu Ser Lys Tyr
        115                 120                 125
Gly Pro Pro Cys Pro Pro Cys Pro Ala Pro Glu Phe Glu Gly Gly Pro
    130                 135                 140
Ser Val Phe Leu Phe Pro Lys Pro Lys Asp Thr Leu Met Ile Ser
145                 150                 155                 160
Arg Thr Pro Glu Val Thr Cys Val Val Val Asp Val Ser Gln Glu Asp
                165                 170                 175
Pro Glu Val Gln Phe Asn Trp Tyr Val Asp Gly Val Glu Val His Asn
            180                 185                 190
Ala Lys Thr Lys Pro Arg Glu Glu Gln Phe Asn Ser Thr Tyr Arg Val
        195                 200                 205
Val Ser Val Leu Thr Val Leu His Gln Asp Trp Leu Asn Gly Lys Glu
    210                 215                 220
Tyr Lys Cys Lys Val Ser Asn Lys Gly Leu Pro Ser Ser Ile Glu Lys
225                 230                 235                 240
Thr Ile Ser Lys Ala Lys Gly Gln Pro Arg Glu Pro Gln Val Tyr Thr
                245                 250                 255
Leu Pro Pro Ser Gln Glu Glu Met Thr Lys Asn Gln Val Ser Leu Thr
            260                 265                 270
Cys Leu Val Lys Gly Phe Tyr Pro Ser Asp Ile Ala Val Glu Trp Glu
        275                 280                 285
Ser Asn Gly Gln Pro Glu Asn Asn Tyr Lys Thr Thr Pro Pro Val Leu
    290                 295                 300
Asp Ser Asp Gly Ser Phe Phe Leu Tyr Ser Arg Leu Thr Val Asp Lys
305                 310                 315                 320
Ser Arg Trp Gln Glu Gly Asn Val Phe Ser Cys Ser Val Met His Glu
                325                 330                 335
Ala Leu His Asn His Tyr Thr Gln Lys Ser Leu Ser Leu Ser Leu Gly
            340                 345                 350
Lys

<210> SEQ ID NO 71
<211> LENGTH: 123
<212> TYPE: PRT
<213> ORGANISM: Artificial Sequence
<220> FEATURE:
<223> OTHER INFORMATION: Synthetic sequence

<400> SEQUENCE: 71

Glu Val Gln Leu Val Glu Ser Gly Gly Gly Leu Val Gln Pro Gly Gly
1               5                   10                  15
Ser Leu Arg Leu Ser Cys Ala Val Ser Gly Asn Ile Tyr Asn Arg Asn
            20                  25                  30
Phe Met Gly Trp Phe Arg Gln Ala Pro Gly Lys Gly Leu Glu Gly Val
        35                  40                  45
Ser Ala Ile Tyr Thr Gly Thr Ser Arg Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Val Tyr Tyr Cys
                85                  90                  95
Ala Ala Asp Leu Arg Asp Gly Phe Trp Asp Thr Gly Val Trp Asn Thr
            100                 105                 110
```

```
Trp Gly Gln Gly Thr Leu Val Thr Val Ser Ser
        115                 120
```

<210> SEQ ID NO 72
<211> LENGTH: 124
<212> TYPE: PRT
<213> ORGANISM: Artificial Sequence
<220> FEATURE:
<223> OTHER INFORMATION: Synthetic sequence

<400> SEQUENCE: 72

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Met Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser
        115                 120
```

<210> SEQ ID NO 73
<211> LENGTH: 124
<212> TYPE: PRT
<213> ORGANISM: Artificial Sequence
<220> FEATURE:
<223> OTHER INFORMATION: Synthetic sequence

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Val Thr Tyr
            20                  25                  30

Gly Met Gly Trp Phe Arg Gln Ala Pro Gly Lys Gly Arg Glu Phe Val
        35                  40                  45

Ser Ala Ile Ser Trp Ser Gly Ser Ser Thr Ser Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ala Leu Gly Ala Val Val Tyr Thr Thr Arg Glu Pro Tyr Thr
            100                 105                 110

Tyr Trp Gly Gln Gly Thr Leu Val Thr Val Ser Ser
        115                 120
```

<210> SEQ ID NO 74
<211> LENGTH: 124
<212> TYPE: PRT
<213> ORGANISM: Artificial Sequence
<220> FEATURE:
<223> OTHER INFORMATION: Synthetic sequence

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ile Thr Tyr
            20                  25                  30

Ala Ile Gly Trp Phe Arg Gln Ala Pro Gly Lys Gly Arg Glu Phe Val
        35                  40                  45

Ser Ala Ile Ser Trp Ser Gly Ser Met Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Gly Ala Ile Ala Pro Ile Ala Gln Ser Val Tyr Thr
            100                 105                 110

Asn Trp Gly Gln Gly Thr Leu Val Thr Val Ser Ser
        115                 120

<210> SEQ ID NO 75
<211> LENGTH: 5
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(4)
<223> OTHER INFORMATION: sequence can be repeated 1 to 3 times

<400> SEQUENCE: 75

Gly Gly Gly Gly Ser
1               5

<210> SEQ ID NO 76
<211> LENGTH: 12
<212> TYPE: PRT
<213> ORGANISM: Artificial Sequence
<220> FEATURE:
<223> OTHER INFORMATION: linker sequence

<400> SEQUENCE: 76

Lys Arg Val Ala Pro Glu Leu Leu Gly Gly Pro Ser
1               5                   10

<210> SEQ ID NO 77
<211> LENGTH: 5
<212> TYPE: PRT
<213> ORGANISM: Artificial Sequence
<220> FEATURE:
<223> OTHER INFORMATION: linker sequence

<400> SEQUENCE: 77

Ala Ser Thr Lys Gly
1               5

```
<210> SEQ ID NO 78
<211> LENGTH: 6
<212> TYPE: PRT
<213> ORGANISM: Artificial Sequence
<220> FEATURE:
<223> OTHER INFORMATION: linker sequence

<400> SEQUENCE: 78

Asn Ser Pro Pro Ala Ala
1               5
```